US011492616B2

(12) United States Patent
Wen et al.

(10) Patent No.: US 11,492,616 B2
(45) Date of Patent: Nov. 8, 2022

(54) METHOD FOR MODIFYING AMINO ACID ATTENUATOR AND USE OF SAME IN PRODUCTION

(71) Applicant: Institute of Microbiology, Chinese Academy of Sciences, Beijing (CN)

(72) Inventors: Tingyi Wen, Beijing (CN); Shuwen Liu, Beijing (CN); Yun Zhang, Beijing (CN); Xiuling Shang, Beijing (CN); Haihan Xiao, Beijing (CN)

(73) Assignee: Institute of Microbiology, Chinese Academy of Sciences, Beijing (CN)

( * ) Notice: Subject to any disclaimer, the term of this patent is extended or adjusted under 35 U.S.C. 154(b) by 698 days.

(21) Appl. No.: 16/345,669

(22) PCT Filed: Oct. 24, 2017

(86) PCT No.: PCT/CN2017/107453
§ 371 (c)(1),
(2) Date: Apr. 26, 2019

(87) PCT Pub. No.: WO2018/077159
PCT Pub. Date: May 3, 2018

(65) Prior Publication Data
US 2019/0338282 A1 Nov. 7, 2019

(30) Foreign Application Priority Data

| Oct. 27, 2016 | (CN) | 201610958301.4 |
| Oct. 27, 2016 | (CN) | 201610958369.2 |
| Nov. 9, 2016 | (CN) | 201610987080.3 |
| Nov. 9, 2016 | (CN) | 201611035232.6 |
| May 27, 2017 | (CN) | 201710388772.0 |
| May 27, 2017 | (CN) | 201710388774.X |
| May 27, 2017 | (CN) | 201710388810.2 |
| Jun. 1, 2017 | (CN) | 201710403398.7 |
| Jun. 1, 2017 | (CN) | 201710403515.X |

(51) Int. Cl.
*C12N 15/113* (2010.01)
*C12N 15/63* (2006.01)
*C12P 13/06* (2006.01)
*C12P 13/22* (2006.01)

(52) U.S. Cl.
CPC ........... *C12N 15/113* (2013.01); *C12N 15/63* (2013.01); *C12P 13/06* (2013.01); *C12P 13/22* (2013.01)

(58) Field of Classification Search
CPC ............... A61K 39/025; A61K 48/005; C12N 15/1089; C12N 2830/15; C12Q 1/689; C12Q 1/6809
USPC ............. 435/6.1, 91.1, 91.31, 455, 458; 514/44 R; 536/23.1
See application file for complete search history.

(56) References Cited

FOREIGN PATENT DOCUMENTS

| CN | 104204189 A | * 12/2014 | ........... C07K 14/245 |
| CN | 104204189 A | 12/2014 | |
| CN | 107058323 A | 8/2017 | |
| CN | 107236738 A | 10/2017 | |
| WO | WO 03/097839 A1 | 11/2003 | |

OTHER PUBLICATIONS

C. L. Turnbough Jr. (Microbiol. And Molec. Biol. Reviews, vol. 83, No. 3, pp. 1-24 (2019)) (Year: 2019).*
International Search Report, in PCT/CN2017/107453, dated Jan. 24, 2018.
Lin, Weiping et al., "Construction and Expression of Trp Operon Gene Mutant of E.coil", Chinese Journal of Biologicals, 23(7), Jul. 20, 2010 pp. 711-713.
Roesser, Jr. et al., "The Effects of Leader Peptide Sequence and Length on Attenuation Control of the trp Operon of E. coil", Nucleic Acids Research, 19)4), Feb. 25, 1991, pp. 795-800.

* cited by examiner

*Primary Examiner* — Jane J Zara
(74) *Attorney, Agent, or Firm* — Knobbe, Martens, Olson & Bear, LLP

(57) ABSTRACT

The present invention discloses a method for modifying an amino acid attenuator, a class of amino acid attenuator mutants, engineered bacteria created on the basis of the amino acid attenuator mutants, and use of the engineered bacteria. The present invention protects a method for relieving the attenuation regulation of an amino acid operon gene, which is modification of the amino acid operon gene by: removing a gene coding for a leader peptide and an anterior reverse complementary palindromic sequence in the terminator stem-loop structure, and maintaining a posterior reverse complementary palindromic sequence in the terminator. The amino acid operon particularly can be histidine operon, tryptophan operon, phenylalanine operon, alanine operon, threonine operon and etc. The present invention can be used for the production of amino acids and derivatives thereof in fermentation by bacteria, providing a novel method for improving the production of amino acids in fermentation.

10 Claims, 1 Drawing Sheet
Specification includes a Sequence Listing.

SEQUENCE LISTING

<160> NUMBER OF SEQ ID NOS: 258

<210> SEQ ID NO 1
<211> LENGTH: 2305
<212> TYPE: DNA

<213> ORGANISM: E.coli

<400> SEQUENCE: 1

```
cgttaatgaa atatcgccag ttccacatcc atgcgcaatc agcggtactc agtgatagtg      60
cggtcatggc aatgcttaag cagaaataat cgtgtcacca ttggtgggta ctaaacctga     120
agttcagccc accgggatga gaaaaaatcg cctacgcccc cacatacgcc agattcagca     180
acggatacgg tttccccaaa tcgtccacct cagagcgtcc cgtaaacctta aaacccacct    240
tcttatagaa cccaaccgcc tgctcatttt gctcattaac gttggttgtc agttccggtg     300
ccatcgagag cgcatgctcc accagcaccc gacctacgcc gcagccgcgc acatcaggat     360
cgataaacag cgcatccata tgctgcccac ttagcaacat aaatccaacc ggctgatccc     420
gctcattaac cgcgacccac aacggcgctt ccggcaggaa ggaacgaact aggtcctcca     480
gctcggtccg atactctgct gatagaaaat cgtgagtggc atcgacagaa cgacaccaaa     540
tcgcaacgag ttcctcccct tcctcatgcc gtgagcggcg aatactaata accatttttct   600
ctccttttag tcattcttat attctaacgt agtcttttcc ttgaaacttt ctcaccttca     660
acatgcaggc tcgacattgg caaattttct ggttatcttc agctatctgg atgtctaaac     720
gtataagcgt atgtagtgag gtaatcaggt tatgccgatt cgtgtgccgg acgagctacc     780
cgccgtcaat ttcttgcgtg aagaaaacgt cttgtgatg acaacttctc gtgcgtctgg      840
tcaggaaatt cgtccactta aggttctgat ccttaacctg atgccgaaga agattgaaac     900
tgaaaatcag tttctgcgcc tgctttcaaa ctcacctttg caggtcgata ttcagctgtt     960
gcgcatcgat tcccgtgaat cgcgcaacac gcccgcagag catctgaaca acttctactg    1020
taactttgaa gatattcagg atcagaactt tgacggtttg attgtaactg gtgcgccgct    1080
gggcctggtg gagtttaatg atgtcgctta ctggccgcag atcaaacagg tgctggagtg    1140
gtcgaaagat cacgtcacct cgacgctgtt tgtctgctgg gcggtacagg ccgcgctcaa    1200
tatcctctac ggcattccta agcaaactcg caccgaaaaa ctctctggcg tttacgagca    1260
tcatattctc catcctcatg cgcttctgac gcgtggcttt gatgattcat tcctggcacc    1320
gcattcgcgc tatgctgact ttccggcagc gttgattcgt gattacaccg atctggaaat    1380
tctggcagag acggaagaag gggatgcata tctgtttgcc agtaaagata gcgcattgc     1440
ctttgtgacg ggccatcccg aatatgatgc gcaaacgctg gcgcaggaat ttttccgcga    1500
tgtggaagcc ggactagacc cggatgtacc gtataactat ttcccgcaca atgatccgca    1560
aaatacaccg cgagcgagct ggcgtagtca cggtaattta ctgtttacca actggctcaa    1620
ctattacgtc taccagatca cgccatacga tctacggcac atgaatccaa cgctggatta    1680
atcttctgtg atagtcgatc gttaagcgat tcagcacctt acctcaggca ccttcgggtg    1740
cctttttttat ttccgaaacg tacctcagca ggtgaataaa ttttattcat attgttatca   1800
acaagttatc aagtattttt aattaaaatg gaaattgttt ttgattttgc attttaaatg    1860
agtagtctta gttgtgctga acgaaaagag cacaacgatc cttcgttcac agtggggaag    1920
ttttcggatc catgacgagg agctgcacga tgactgaaca ggcaacaaca accgatgaac    1980
tggcttttcac aaggccgtat ggcgagcagg agaagcaaat tcttactgcc gaagcggtag   2040
aatttctgac tgagctggtg acgcatttta cgccacaacg caataaactt ctggcagcgc    2100
gcattcagca gcagcaagat attgataacg aacgttgcc tgatttttatt tcggaaacag    2160
cttccattcg cgatgctgat tggaaaattc gcgggattcc tgcggactta gaagaccgcc    2220
gcgtagagat aactggcccg gtagagcgca agatggtgat caacgcgctc aacgccaatg    2280
```
tgaaagtctt tatggccgat ttcga                                              2305

<210> SEQ ID NO 2
<211> LENGTH: 309
<212> TYPE: PRT
<213> ORGANISM: E.coli

<400> SEQUENCE: 2

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
            245                 250                 255

Pro Asp Val Pro Tyr Asn Tyr Phe Pro His Asn Asp Pro Gln Asn Thr
        260                 265                 270

Pro Arg Ala Ser Trp Arg Ser His Gly Asn Leu Leu Phe Thr Asn Trp
    275                 280                 285

Leu Asn Tyr Tyr Val Tyr Gln Ile Thr Pro Tyr Asp Leu Arg His Met
    290                 295                 300

Asn Pro Thr Leu Asp
305

<210> SEQ ID NO 3
<211> LENGTH: 2889
<212> TYPE: DNA
<213> ORGANISM: E.coli

<400> SEQUENCE: 3

| | |
|---|---:|
| atggctgtat ccgctcgctg gaacacgcct acagcaaaga cggcggcctg gcggtgctct | 60 |
| acggtaactt tgcggaaaac ggctgcatcg tgaaaacggc aggcgtcgat gacagcatcc | 120 |
| tcaaattcac cggcccggcg aaagtgtacg aaagccagga cgatgcggta aagcgattc | 180 |
| tcggcggtaa agttgtcgcc ggagatgtgg tagtaattcg ctatgaaggc ccgaaaggcg | 240 |
| gtccggggat gcaggaaatg ctctacccaa ccagcttcct gaaatcaatg ggtctcggca | 300 |
| aagcctgtgc gctgatcacc gacggtcgtt tctctggtgg cacctctggt ctttccatcg | 360 |
| gccacgtctc accggaagcg gcaagcggcg gcagcattgg cctgattgaa gatggtgacc | 420 |
| tgatcgctat cgacatcccg aaccgtgcga ttcagttaca ggtaagcgat gccgaactgg | 480 |
| cggcgcgtcg tgaagcgcag gacgctcgag gtgacaaagc ctggacgccg aaaaatcgtg | 540 |
| aacgtcaggt ctcctttgcc ctgcgtgctt atgccagcct ggcaaccagc gccgacaaag | 600 |
| gcgcggtgcg cgataaatcg aaactggggg gttaataatg gctgactcgc aaccctgtc | 660 |
| cggtgctccg gaaggtgccg aatatttaag agcagtgctg cgcgcgccgg tttacgaggc | 720 |
| ggcgcaggtt acgccgctac aaaaaatgga aaaactgtcg tcgcgtcttg ataacgtcat | 780 |
| tctggtgaag cgcgaagatc gccagccagt gcacagcttt aagctgcgcg gcgcatacgc | 840 |
| catgatggcg ggcctgacgg aagaacagaa agcgcacggc gtgatcactg cttctgcggg | 900 |
| taaccacgcg cagggcgtcg cgttttcttc tgcgcggtta ggcgtgaagg ccctgatcgt | 960 |
| tatgccaacc gccaccgccg acatcaaagt cgacgcggtg cgcggcttcg gcggcgaagt | 1020 |
| gctgctccac ggcgcgaact ttgatgaagc gaaagccaaa gcgatcgaac tgtcacagca | 1080 |
| gcaggggttc acctgggtgc cgccgttcga ccatccgatg gtgattgccg ggcaaggcac | 1140 |
| gctggcgctg aactgctcc agcaggacgc ccatctcgac cgcgtatttg tgccagtcgg | 1200 |
| cggcggcggt ctggctgctg gcgtggcggt gctgatcaaa caactgatgc cgcaaatcaa | 1260 |
| agtgatcgcc gtagaagcgg aagactccgc ctgcctgaaa gcagcgctgg atgcgggtca | 1320 |
| tccggttgat ctgccgcgcg tagggctatt tgctgaaggc gtagcggtaa aacgcatcgg | 1380 |
| tgacgaaacc ttccgtttat gccaggagta tctcgacgac atcatcaccg tcgatagcga | 1440 |
| tgcgatctgt gcggcgatga aggatttatt cgaagatgtg cgcgcggtgg cggaaccctc | 1500 |
| tggcgcgctg gcgctggcgg gaatgaaaaa atatatcgcc ctgcacaaca ttcgcggcga | 1560 |
| acggctggcg catattcttt ccggtgccaa cgtgaacttc cacggcctgc gctacgtctc | 1620 |
| agaacgctgc gaactgggcg aacagcgtga agcgttgttg gcggtgacca ttccggaaga | 1680 |
| aaaaggcagc ttcctcaaat tctgccaact gcttggcggg cgttcggtca ccgagttcaa | 1740 |
| ctaccgtttt gccgatgcca aaaacgcctg catctttgtc ggtgtgcgcc tgagccgcgg | 1800 |
| cctcgaagag cgcaaagaaa ttttgcagat gctcaacgac ggcggctaca gcgtggttga | 1860 |
| tctctccgac gacgaaatgg cgaagctaca cgtgcgctat atggtcggcg gacgtccatc | 1920 |
| gcatccgttg caggaacgcc tctacagctt cgaattcccg gaatcaccgg gcgcgctgct | 1980 |
| gcgcttcctc aacacgctgg gtacgtactg gaacatttct tgttccact atcgcagcca | 2040 |
| tggcaccgac tacgggcgcg tactggcggc gttcgaactt ggcgaccatg aaccggattt | 2100 |
| cgaaacccgc tgaatgagc tgggctacga ttgccacgac gaaaccaata cccggcgtt | 2160 |
| caggttcttt ttggcgggtt agggaaaaat gcctgatagc gcttcgctta tcaggcctac | 2220 |
| ccgcgcgaca acgtcatttg tggttcggca aaatcttcca gaatgcctca attagcggct | 2280 |
| catgtagccg ctttttctgc gcacacacgc ccagctcaaa cggcgttttc tcatcgctgc | 2340 |
| gctctaaaat catcacgcgg ttacgcaccg gttcggggct gttttccagc accacttccg | 2400 |

-continued

```
gcaacaatgc cacgccacag ccgagtgcca ccatcgatac catcgcttca tgcccgccaa      2460
ccgtggcgta atcatcgggt tactgattt tattgcgtcg aaaccacagt tcaatgcggc      2520
ggcgtaccgg ccctgatcg gccataataa acggcaccgt tgaccagtcc ggcttctcta       2580
ccgacacctg attacgcacc gggcagggca gcgcgggggc aatcagcact actgccagat      2640
tctccagcat cgaaaacgcc actgcgccgg gcaaggtttc cggtttaccc gcaatcgcca      2700
gatccgcttc accagtgacc accttttcca tcgcatctgc cgcatcacca gtagtaagtt      2760
taatctccac cgacgggtgt tccgcgcgga agcgatccag aatcggcggc agatggctgt      2820
aggcagcggt caccgagcag aagatatgta attcgccaga gagcgacggc ccttgctgat      2880
cgatggtgt                                                              2889
```

<210> SEQ ID NO 4
<211> LENGTH: 514
<212> TYPE: PRT
<213> ORGANISM: E.coli

<400> SEQUENCE: 4

```
Met Ala Asp Ser Gln Pro Leu Ser Gly Ala Pro Glu Gly Ala Glu Tyr
1               5                   10                  15

Leu Arg Ala Val Leu Arg Ala Pro Val Tyr Glu Ala Ala Gln Val Thr
            20                  25                  30

Pro Leu Gln Lys Met Glu Lys Leu Ser Ser Arg Leu Asp Asn Val Ile
        35                  40                  45

Leu Val Lys Arg Glu Asp Arg Gln Pro Val His Ser Phe Lys Leu Arg
    50                  55                  60

Gly Ala Tyr Ala Met Met Ala Gly Leu Thr Glu Glu Gln Lys Ala His
65                  70                  75                  80

Gly Val Ile Thr Ala Ser Ala Gly Asn His Ala Gln Gly Val Ala Phe
                85                  90                  95

Ser Ser Ala Arg Leu Gly Val Lys Ala Leu Ile Val Met Pro Thr Ala
            100                 105                 110

Thr Ala Asp Ile Lys Val Asp Ala Val Arg Gly Phe Gly Gly Glu Val
        115                 120                 125

Leu Leu His Gly Ala Asn Phe Asp Glu Ala Lys Ala Lys Ala Ile Glu
    130                 135                 140

Leu Ser Gln Gln Gln Gly Phe Thr Trp Val Pro Pro Phe Asp His Pro
145                 150                 155                 160

Met Val Ile Ala Gly Gln Gly Thr Leu Ala Leu Glu Leu Leu Gln Gln
                165                 170                 175

Asp Ala His Leu Asp Arg Val Phe Val Pro Val Gly Gly Gly Gly Leu
            180                 185                 190

Ala Ala Gly Val Ala Val Leu Ile Lys Gln Leu Met Pro Gln Ile Lys
        195                 200                 205

Val Ile Ala Val Glu Ala Glu Asp Ser Ala Cys Leu Lys Ala Ala Leu
    210                 215                 220

Asp Ala Gly His Pro Val Asp Leu Pro Arg Val Gly Leu Phe Ala Glu
225                 230                 235                 240

Gly Val Ala Val Lys Arg Ile Gly Asp Glu Thr Phe Arg Leu Cys Gln
                245                 250                 255

Glu Tyr Leu Asp Asp Ile Ile Thr Val Asp Ser Asp Ala Ile Cys Ala
            260                 265                 270

Ala Met Lys Asp Leu Phe Glu Asp Val Arg Ala Val Ala Glu Pro Ser
```

```
                    275                 280                 285
Gly Ala Leu Ala Leu Ala Gly Met Lys Lys Tyr Ile Ala Leu His Asn
                290                 295                 300
Ile Arg Gly Glu Arg Leu Ala His Ile Leu Ser Gly Ala Asn Val Asn
305                 310                 315                 320
Phe His Gly Leu Arg Tyr Val Ser Glu Arg Cys Glu Leu Gly Glu Gln
                325                 330                 335
Arg Glu Ala Leu Leu Ala Val Thr Ile Pro Glu Glu Lys Gly Ser Phe
            340                 345                 350
Leu Lys Phe Cys Gln Leu Leu Gly Gly Arg Ser Val Thr Glu Phe Asn
            355                 360                 365
Tyr Arg Phe Ala Asp Ala Lys Asn Ala Cys Ile Phe Val Gly Val Arg
        370                 375                 380
Leu Ser Arg Gly Leu Glu Glu Arg Lys Glu Ile Leu Gln Met Leu Asn
385                 390                 395                 400
Asp Gly Gly Tyr Ser Val Val Asp Leu Ser Asp Glu Met Ala Lys
                405                 410                 415
Leu His Val Arg Tyr Met Val Gly Gly Arg Pro Ser His Pro Leu Gln
                420                 425                 430
Glu Arg Leu Tyr Ser Phe Glu Phe Pro Glu Ser Pro Gly Ala Leu Leu
            435                 440                 445
Arg Phe Leu Asn Thr Leu Gly Thr Tyr Trp Asn Ile Ser Leu Phe His
450                 455                 460
Tyr Arg Ser His Gly Thr Asp Tyr Gly Arg Val Leu Ala Ala Phe Glu
465                 470                 475                 480
Leu Gly Asp His Glu Pro Asp Phe Glu Thr Arg Leu Asn Glu Leu Gly
                485                 490                 495
Tyr Asp Cys His Asp Glu Thr Asn Asn Pro Ala Phe Arg Phe Phe Leu
                500                 505                 510
Ala Gly

<210> SEQ ID NO 5
<211> LENGTH: 2565
<212> TYPE: DNA
<213> ORGANISM: E.coli

<400> SEQUENCE: 5
gtaacacaca cacttcatct aaagagagta attcggtacg ttctgttccc gcaggcgtat      60
ggagcgtttc agtgagtcct aaatcatgac gctgggccga gagccactct tcaagtagcg     120
gtgattcctg gggcacgata tttaagctga catcgggata acgtgccaga aagggttgca     180
ggagctgcgg taaaaagat tgcgaaaaga ccggcaggca ggcaatagac agttctccct      240
ggcgaaactc gcgcagactt tctgcggcgc tgacaatgcg atccagtccg taccaggatc     300
gttgcacttc ttcaaacaga cgcagtcctt gcacggtagg atgtaatcgc ccacgtacgc     360
gctcaaacaa tttcagcccg atcaccttct caaagcgcgc aagttcgcgg ctgacggttg     420
gctgtgaggt gtgtagcagg tgtgccgcct cagtcaggct tccggcggtc attaccgcat     480
gaaaaatttc aatatgacgt aagttaacgg cggccattag cgctctctcg caatccggta     540
atccatatca tttttgcata gactcgacat aaatcgatat ttttttattct ttttatgatg     600
tggcgtaatc ataaaaaagc acttatctgg agtttgttat gccacattca ctgttcagca     660
ccgataccga tctcaccgcc gaaaatctgc tgcgtttgcc cgctgaattt ggctgccgg      720
tgtgggtcta cgatgcgcaa attattcgtc ggcagattgc agcgctgaaa cagtttgatg     780
```

```
tggtgcgctt tgcacagaaa gcctgttcca atattcatat tttgcgctta atgcgtgagc      840
agggcgtgaa agtggattcc gtctcgttag gcgaaataga gcgtgcgttg gcggcgggtt      900
acaatccgca aacgcacccc gatgatattg tttttacggc agatgttatc gatcaggcga      960
cgcttgaacg cgtcagtgaa ttgcaaattc cggtgaatgc gggttctgtt gatatgctcg     1020
accaactggg ccaggtttcg ccagggcatc gggtatggct gcgcgttaat ccggggtttg     1080
gtcacggaca tagccaaaaa accaataccg gtggcgaaaa cagcaagcac ggtatctggt     1140
acaccgatct gcccgccgca ctggacgtga taacgtca tcatctgcag ctggtcggca     1200
ttcacatgca cattggttct ggcgttgatt atgcccatct ggaacaggtg tgtggtgcta     1260
tggtgcgtca ggtcatcgaa ttcggtcagg atttacaggc tatttctgcg ggcggtgggc     1320
tttctgttcc ttatcaacag ggtgaagagg cggttgatac cgaacattat tatggtctgt     1380
ggaatgccgc gcgtgagcaa atcgcccgcc atttgggcca ccctgtgaaa ctggaaattg     1440
aaccgggtcg cttcctggta gcgcagtctg gcgtattaat tactcaggtg cggagcgtca     1500
aacaaatggg gagccgccac tttgtgctgg ttgatgccgg gttcaacgat ctgatgcgcc     1560
cggcaatgta cggtagttac caccatatca gtgccctggc agctgatggt cgttctctgg     1620
aacacgcgcc aacggtggaa accgtcgtcg ccggaccgtt atgtgaatcg ggcgatgtct     1680 tacccagca ggaaggggga aatgttgaaa cccgcgcctt gccggaagtg aaggcaggtg     1740
attatctggt actgcatgat acaggggcat atggcgcatc aatgtcatcc aactacaata     1800
gccgtccgct gttaccagaa gttctgtttg ataatggtca ggcgcggttg attcgccgtc     1860
gccagaccat cgaagaatta ctggcgctgg aattgcttta actgcggtta gtcgctggtt     1920
gcatgatgac ttgcctccag cgacggagtt gacactgaat gacgcgtac cagcgtcgga     1980 ctaaagacat tagtgatttc cgggagaggg cgattatccg ccagcgccaa agccagttcg     2040
gcagcctggg tcgccatcgt cacgattggg taacgcacgg tggtcaggcg cggacgcaca     2100
tagcgtgaca ccagcacatc atcaaagcca attaacgaaa tctcacccgg tacatcaata     2160
ccattatcat tgagaacgcc catcgcaccc gccgccattg aatcgttata acaggctacc     2220
gcagtgaaat ttcttcctcg tcccaaaagc tcggtcattg cctgttcgcc gccgctttcg     2280
tctggttcgc caaatgtcac cagccggtca ttggccgcaa taccactttc agcaagggca     2340
tcgtaatacc cttgcagacg atcttcggcg tcagaaatag agtggttaga gcacagataa     2400
ccaatgcggg tatgaccttg ctgaattaaa tgacgcgttg ccagccaggc accgtaacga     2460
tcgtccagag caatacaacg gttttcaaag ccaggcagga tacggttgat cagcaccata     2520
ccgggcattt gtttcattaa tgaggctaaa tcagcatccg ggatc                   2565
```

<210> SEQ ID NO 6
<211> LENGTH: 420
<212> TYPE: PRT
<213> ORGANISM: E.coli

<400> SEQUENCE: 6

Met Pro His Ser Leu Phe Ser Thr Asp Thr Asp Leu Thr Ala Glu Asn
1               5                   10                  15

Leu Leu Arg Leu Pro Ala Glu Phe Gly Cys Pro Val Trp Val Tyr Asp
            20                  25                  30

Ala Gln Ile Ile Arg Arg Gln Ile Ala Ala Leu Lys Gln Phe Asp Val
        35                  40                  45

Val Arg Phe Ala Gln Lys Ala Cys Ser Asn Ile His Ile Leu Arg Leu

```
                    50                  55                  60
Met Arg Glu Gln Gly Val Lys Val Asp Ser Val Ser Leu Gly Glu Ile
 65                  70                  75                  80

Glu Arg Ala Leu Ala Ala Gly Tyr Asn Pro Gln Thr His Pro Asp Asp
                 85                  90                  95

Ile Val Phe Thr Ala Asp Val Ile Asp Gln Ala Thr Leu Glu Arg Val
            100                 105                 110

Ser Glu Leu Gln Ile Pro Val Asn Ala Gly Ser Val Asp Met Leu Asp
            115                 120                 125

Gln Leu Gly Gln Val Ser Pro Gly His Arg Val Trp Leu Arg Val Asn
130                 135                 140

Pro Gly Phe Gly His Gly His Ser Gln Lys Thr Asn Thr Gly Gly Glu
145                 150                 155                 160

Asn Ser Lys His Gly Ile Trp Tyr Thr Asp Leu Pro Ala Ala Leu Asp
                165                 170                 175

Val Ile Gln Arg His His Leu Gln Leu Val Gly Ile His Met His Ile
            180                 185                 190

Gly Ser Gly Val Asp Tyr Ala His Leu Glu Gln Val Cys Gly Ala Met
            195                 200                 205

Val Arg Gln Val Ile Glu Phe Gly Gln Asp Leu Gln Ala Ile Ser Ala
210                 215                 220

Gly Gly Gly Leu Ser Val Pro Tyr Gln Gln Gly Glu Glu Ala Val Asp
225                 230                 235                 240

Thr Glu His Tyr Tyr Gly Leu Trp Asn Ala Ala Arg Glu Gln Ile Ala
                245                 250                 255

Arg His Leu Gly His Pro Val Lys Leu Glu Ile Glu Pro Gly Arg Phe
            260                 265                 270

Leu Val Ala Gln Ser Gly Val Leu Ile Thr Gln Val Arg Ser Val Lys
            275                 280                 285

Gln Met Gly Ser Arg His Phe Val Leu Val Asp Ala Gly Phe Asn Asp
290                 295                 300

Leu Met Arg Pro Ala Met Tyr Gly Ser Tyr His His Ile Ser Ala Leu
305                 310                 315                 320

Ala Ala Asp Gly Arg Ser Leu Glu His Ala Pro Thr Val Glu Thr Val
                325                 330                 335

Val Ala Gly Pro Leu Cys Glu Ser Gly Asp Val Phe Thr Gln Gln Glu
            340                 345                 350

Gly Gly Asn Val Glu Thr Arg Ala Leu Pro Glu Val Lys Ala Gly Asp
            355                 360                 365

Tyr Leu Val Leu His Asp Thr Gly Ala Tyr Gly Ala Ser Met Ser Ser
370                 375                 380

Asn Tyr Asn Ser Arg Pro Leu Leu Pro Glu Val Leu Phe Asp Asn Gly
385                 390                 395                 400

Gln Ala Arg Leu Ile Arg Arg Arg Gln Thr Ile Glu Glu Leu Leu Ala
                405                 410                 415

Leu Glu Leu Leu
            420

<210> SEQ ID NO 7
<211> LENGTH: 2460
<212> TYPE: DNA
<213> ORGANISM: E.coli

<400> SEQUENCE: 7
```

```
gctatgccaa caacgatatg caggagctgg aagcacgtct gaaagaagcg cgtgaagccg      60
gtgcgcgtca tgtgctgatc gccaccgatg gtgtgttctc aatggacggc gtgattgcca     120
acctgaaggg cgtttgcgat ctggcagata aatatgatgc cctggtgatg gtagacgact     180
cccacgcggt cggttttgtc ggtgaaaatg gtcgtggttc ccatgaatac tgcgatgtga     240
tgggccgggt cgatattatc accggtacgc ttggtaaagc gctgggcggg gcttctggtg     300
gttataccgc ggcgcgcaaa gaagtggttg agtggctgcg ccagcgttct cgtccgtacc     360
tgttctccaa ctcgctggca ccggccattg ttgccgcgtc catcaaagta ctggagatgg     420
tcgaagcggg cagcgaactg cgtgaccgtc tgtgggcgaa cgcgcgtcag ttccgtgagc     480
aaatgtcggc ggcgggcttt accctggcgg gagccgatca cgccattatt ccggtcatgc     540
ttggtgatgc ggtagtggcg cagaaatttg cccgtgagct gcaaaaagag gcatttacg      600 ttaccggttt cttctatccg gtcgttccga aaggtcaggc gcgtattcgt acccagatgt     660
ctgcggcgca taccctgag  caaattacgc gtgcagtaga agcatttacg cgtattggta     720
aacaactggg cgttatcgcc tgaggatgtg agatgaaagc gttatccaaa ctgaaagcgg     780
aagagggcat ctggatgacc gacgttcctg taccggaact cgggcataac gatctgctga     840
ttaaaatccg taaaacagcc atctgcggga ctgacgttca catctataac tgggatgagt     900
ggtcgcaaaa aaccatcccg gtgccgatgg tcgtgggcca tgaatatgtc ggtgaagtgg     960
taggtattgg tcaggaagtg aaaggcttca agatcggcga tcgcgtttct ggcgaaggcc    1020
atatcacctg tggtcattgc cgcaactgtc gtggtggtcg tacccatttg tgccgcaaca    1080
cgataggcgt tggtgttaat cgcccgggct gctttgccga atatctggtg atcccggcat    1140
tcaacgcctt caaaatcccc gacaatattt ccgatgactt agccgcaatt tttgatccct    1200
tcggtaacgc cgtgcatacc gcgctgtcgt ttgatctggt gggcgaagat gtgctggttt    1260
ctggtgcagg cccgattggt attatggcag cggcggtggc gaaacacgtt ggtgcacgca    1320
atgtggtgat cactgatgtt aacgaatacc gccttgagct ggcgcgtaaa atgggtatca    1380
cccgtgcggt taacgtcgcc aaagaaaatc tcaatgacgt gatggcggag ttaggcatga    1440
ccgaaggttt tgatgtcggt ctggaaatgt ccggtgcgcc gccagcgttt cgtaccatgc    1500
ttgacaccat gaatcacggc ggccgtattg cgatgctggg tattccgccg tctgatatgt    1560
ctatcgactg gaccaaagtg atctttaaag gcttgttcat taaaggtatt tacggtcgtg    1620
agatgtttga aacctggtac aagatggcgg cgctgattca gtctggcctc gatctttcgc    1680
cgatcattac ccatcgtttc tctatcgatg atttccagaa gggctttgac gctatgcgtt    1740
cgggccagtc cgggaaagtt attctgagct gggattaaca cgaacaaggg ctggtattcc    1800
agccctttta tctgaggata atctgttaaa tatgtaaaat cctgtcagtg taataaagag    1860
ttcgtaattg tgctgatctc ttatatagct gctctcatta tctctctacc ctgaagtgac    1920
tctctcacct gtaaaaataa tatctcacag gcttaatagt ttcttaatac aaagcctgta    1980
aaacgtcagg ataacttcag aggtcgtcgg taatttatga tgaacagcac caataaactt    2040
agtgttatta ttccgttata taatgcgggc gatgatttcc gcacttgtat ggaatcttta    2100
attacgcaaa cctggactgc tctggaaatc attattatta cgatggttc  aacggataat    2160 tctgttgaaa tagcaaagta ttacgcagaa aactatccgc acgttcgttt gttgcatcag    2220
gcgaatgctg gcgcatcggt ggcgcgtaat cgtgggattg aagtggcaac gggcaaatat    2280
gtcgcttttg tcgatgctga cgatgaagtc tatcccacca tgtacgaaac gctgatgacc    2340
atggcgttag aggacgacct cgacgtggcg cagtgcaacg ctgactggtg ttttcgtgaa    2400
```
acgggagaaa cctggcaatc catccccacc gatcgccttc gctcaaccgg cgtattaacc    2460

<210> SEQ ID NO 8
<211> LENGTH: 341
<212> TYPE: PRT
<213> ORGANISM: E.coli

<400> SEQUENCE: 8

Met Lys Ala Leu Ser Lys Leu Lys Ala Glu Glu Gly Ile Trp Met Thr
1               5                   10                  15

Asp Val Pro Val Pro Glu Leu Gly His Asn Asp Leu Leu Ile Lys Ile
            20                  25                  30

Arg Lys Thr Ala Ile Cys Gly Thr Asp Val His Ile Tyr Asn Trp Asp
        35                  40                  45

Glu Trp Ser Gln Lys Thr Ile Pro Val Pro Met Val Val Gly His Glu
    50                  55                  60

Tyr Val Gly Glu Val Val Gly Ile Gly Gln Glu Val Lys Gly Phe Lys
65                  70                  75                  80

Ile Gly Asp Arg Val Ser Gly Glu Gly His Ile Thr Cys Gly His Cys
                85                  90                  95

Arg Asn Cys Arg Gly Gly Arg Thr His Leu Cys Arg Asn Thr Ile Gly
            100                 105                 110

Val Gly Val Asn Arg Pro Gly Cys Phe Ala Glu Tyr Leu Val Ile Pro
        115                 120                 125

Ala Phe Asn Ala Phe Lys Ile Pro Asp Asn Ile Ser Asp Asp Leu Ala
    130                 135                 140

Ala Ile Phe Asp Pro Phe Gly Asn Ala Val His Thr Ala Leu Ser Phe
145                 150                 155                 160

Asp Leu Val Gly Glu Asp Val Leu Val Ser Gly Ala Gly Pro Ile Gly
                165                 170                 175

Ile Met Ala Ala Ala Val Ala Lys His Val Gly Ala Arg Asn Val Val
            180                 185                 190

Ile Thr Asp Val Asn Glu Tyr Arg Leu Glu Leu Ala Arg Lys Met Gly
        195                 200                 205

Ile Thr Arg Ala Val Asn Val Ala Lys Glu Asn Leu Asn Asp Val Met
    210                 215                 220

Ala Glu Leu Gly Met Thr Glu Gly Phe Asp Val Gly Leu Glu Met Ser
225                 230                 235                 240

Gly Ala Pro Pro Ala Phe Arg Thr Met Leu Asp Thr Met Asn His Gly
                245                 250                 255

Gly Arg Ile Ala Met Leu Gly Ile Pro Pro Ser Asp Met Ser Ile Asp
            260                 265                 270

Trp Thr Lys Val Ile Phe Lys Gly Leu Phe Ile Lys Gly Ile Tyr Gly
        275                 280                 285

Arg Glu Met Phe Glu Thr Trp Tyr Lys Met Ala Ala Leu Ile Gln Ser
    290                 295                 300

Gly Leu Asp Leu Ser Pro Ile Ile Thr His Arg Phe Ser Ile Asp Asp
305                 310                 315                 320

Phe Gln Lys Gly Phe Asp Ala Met Arg Ser Gly Gln Ser Gly Lys Val
                325                 330                 335

Ile Leu Ser Trp Asp
            340

<210> SEQ ID NO 9

<211> LENGTH: 2732
<212> TYPE: DNA
<213> ORGANISM: E.coli

<400> SEQUENCE: 9

| | | | | | |
|---|---|---|---|---|---|
| gatgccaaaa | ggtgcgccaa | aatccaaagt | agcggcaacg | tgcgactact | ccgcagaagt | 60 |
| cgttctgcat | ggtgataact | tcaacgacac | tatcgctaaa | gtgagcgaaa | ttgtcgaaat | 120 |
| ggaaggccgt | atttttatcc | caccttacga | tgatccgaaa | gtgattgctg | ccagggaac | 180 |
| gattggtctg | gaaattatgg | aagatctcta | tgatgtcgat | aacgtgattg | tgccaattgg | 240 |
| tggtggcggt | ttaattgctg | gtattgcggt | ggcaattaaa | tctattaacc | cgaccattcg | 300 |
| tgttattggc | gtacagtctg | aaaacgttca | cggcatggcg | gcttcttcc | actccggaga | 360 |
| aataaccacg | caccgaacta | ccggcaccct | ggcggatggt | tgtgatgtct | cccgcccggg | 420 |
| taatttaact | tacgaaatcg | ttcgtgaatt | agtcgatgac | atcgtgctgg | tcagcgaaga | 480 |
| cgaaatcaga | aacagtatga | ttgccttaat | tcagcgcaat | aaagtcgtca | ccgaaggcgc | 540 |
| aggcgctctg | gcatgtgctg | cattattaag | cggtaaatta | gaccaatata | ttcaaaacag | 600 |
| aaaaaccgtc | agtattattt | ccggcggcaa | tatcgatctt | tctcgcgtct | ctcaaatcac | 660 |
| cggtttcgtt | gacgcttaat | taattcgttg | aggataggat | atgagtactt | cagatagcat | 720 |
| tgtatccagc | cagacaaaac | aatcgtcctg | gcgtaaatca | gataccacat | ggacgttagg | 780 |
| cttgtttggt | acggcaatcg | gcgccggggt | gctgttcttc | cctatccgcg | caggttttgg | 840 |
| cggactgatc | ccgattcttc | tgatgttggt | attggcatac | cccatcgcgt | tttattgcca | 900 |
| ccgggcgctg | gcgcgtctgt | gtctttctgg | ctctaaccct | tccggcaaca | ttacggaaac | 960 |
| ggtggaagag | cattttggta | aaactggcgg | cgtggttatc | acgttcctgt | acttcttcgc | 1020 |
| gatttgccca | ctgctgtgga | tttatggcgt | tactattacc | aatacctta | tgacgttctg | 1080 |
| ggaaaaccag | ctcggctttg | caccgctgaa | tcgcggcttt | gtggcgctgt | tcctgttgct | 1140 |
| gctgatggct | ttcgtcatct | ggtttggtaa | ggatctgatg | gttaaagtga | tgagctacct | 1200 |
| ggtatggccg | tttatcgcca | gcctggtgct | gatttctttg | tcgctgatcc | cttactggaa | 1260 |
| ctctgcagtt | atcgaccagg | ttgacctcgg | ttcgctgtcg | ttaaccggtc | atgacggtat | 1320 |
| cctgatcact | gtctggctgg | ggatttccat | catggttttc | tcctttaact | tctcgccaat | 1380 |
| cgtctcttcc | ttcgtggttt | ctaagcgtga | agagtatgag | aaagacttcg | gtcgcgactt | 1440 |
| caccgaacgt | aaatgttccc | aaatcatttc | tcgtgccagc | atgctgatgg | ttgcagtggt | 1500 |
| gatgttctt | gcctttagct | gcctgtttac | tctgtctccg | gccaacatgg | cggaagccaa | 1560 |
| agcgcagaat | attccagtgc | tttcttatct | ggctaaccac | tttgcgtcca | tgaccggtac | 1620 |
| caaaacaacg | ttcgcgatta | cactggaata | tgcggcttcc | atcatcgcac | tcgtggctat | 1680 |
| cttcaaatct | ttcttcggtc | actatctggg | aacgctggaa | ggtctgaatg | gcctggtcct | 1740 |
| gaagtttggt | tataaaggcg | acaaaactaa | agtgtcgctg | ggtaaactga | acactatcag | 1800 |
| catgatcttc | atcatgggct | ccacctgggt | tgttgcctac | gccaacccga | acatccttga | 1860 |
| cctgattgaa | gccatgggcg | caccgattat | cgcatccctg | ctgtgcctgt | tgccgatgta | 1920 |
| tgccatccgt | aaagcgccgt | ctctggcgaa | ataccgtggt | cgtctggata | cgtgtttgt | 1980 |
| taccgtgatt | ggtctgctga | ccatcctgaa | catcgtatac | aaactgtttt | aatccgtaac | 2040 |
| tcaggatgag | aaaagagatg | aatgaatttc | cggttgtttt | ggttattaac | tgtggttcgt | 2100 |
| cttcgattaa | gttttccgtg | ctcgatgcca | gcgactgtga | agtattaatg | tcaggtattg | 2160 |
| ccgacggtat | taactcggaa | aatgcattct | tatccgtaaa | tgggggagag | ccagcaccgc | 2220 |

-continued

```
tggctcacca cagctacgaa ggtgcattga aggcaattgc atttgaactg gaaaaacgga    2280
atttaaatga cagtgtggcc ttaattggcc accgcatcgc tcacggcggc agtattttta    2340
ccgagtccgc cattattacc gatgaagtca ttgataatat ccgtcgcgtt tctccactgg    2400 caccccctgca taattacgcc aatttaagtg gtattgaatc ggcgcagcaa ttatttccgg    2460
gcgtaactca ggtggcggta tttgatacca gtttccacca gacgatggct ccggaagctt    2520
atttatacgg cctgccgtgg aaatattatg aagagttagg tgtacgccgt tatggttttcc    2580 acggcacgtc gcaccgctat gtttcccagc gcgcacattc gctgctgaat ctggcggaag    2640
atgactccgg cctggttgtg gcgcatcttg gcaatggcgc gtcaatctgc gcggttcgca    2700
acggtcagag tgttgatacc tcaatgggaa tg                                   2732
```

```
<210> SEQ ID NO 10
<211> LENGTH: 443
<212> TYPE: PRT
<213> ORGANISM: E.coli

<400> SEQUENCE: 10
```

```
Met Ser Thr Ser Asp Ser Ile Val Ser Ser Gln Thr Lys Gln Ser Ser
1               5                   10                  15

Trp Arg Lys Ser Asp Thr Thr Trp Thr Leu Gly Leu Phe Gly Thr Ala
            20                  25                  30

Ile Gly Ala Gly Val Leu Phe Phe Pro Ile Arg Ala Gly Phe Gly Gly
        35                  40                  45

Leu Ile Pro Ile Leu Leu Met Leu Val Leu Ala Tyr Pro Ile Ala Phe
    50                  55                  60

Tyr Cys His Arg Ala Leu Ala Arg Leu Cys Leu Ser Gly Ser Asn Pro
65                  70                  75                  80

Ser Gly Asn Ile Thr Glu Thr Val Glu Glu His Phe Gly Lys Thr Gly
                85                  90                  95

Gly Val Val Ile Thr Phe Leu Tyr Phe Phe Ala Ile Cys Pro Leu Leu
            100                 105                 110

Trp Ile Tyr Gly Val Thr Ile Thr Asn Thr Phe Met Thr Phe Trp Glu
        115                 120                 125

Asn Gln Leu Gly Phe Ala Pro Leu Asn Arg Gly Phe Val Ala Leu Phe
    130                 135                 140

Leu Leu Leu Leu Met Ala Phe Val Ile Trp Phe Gly Lys Asp Leu Met
145                 150                 155                 160

Val Lys Val Met Ser Tyr Leu Val Trp Pro Phe Ile Ala Ser Leu Val
                165                 170                 175

Leu Ile Ser Leu Ser Leu Ile Pro Tyr Trp Asn Ser Ala Val Ile Asp
            180                 185                 190

Gln Val Asp Leu Gly Ser Leu Ser Leu Thr Gly His Asp Gly Ile Leu
        195                 200                 205

Ile Thr Val Trp Leu Gly Ile Ser Ile Met Val Phe Ser Phe Asn Phe
    210                 215                 220

Ser Pro Ile Val Ser Ser Phe Val Val Ser Lys Arg Glu Glu Tyr Glu
225                 230                 235                 240

Lys Asp Phe Gly Arg Asp Phe Thr Glu Arg Lys Cys Ser Gln Ile Ile
                245                 250                 255

Ser Arg Ala Ser Met Leu Met Val Ala Val Val Met Phe Phe Ala Phe
            260                 265                 270

Ser Cys Leu Phe Thr Leu Ser Pro Ala Asn Met Ala Glu Ala Lys Ala
```

```
            275                 280                 285
Gln Asn Ile Pro Val Leu Ser Tyr Leu Ala Asn His Phe Ala Ser Met
        290                 295                 300
Thr Gly Thr Lys Thr Thr Phe Ala Ile Thr Leu Glu Tyr Ala Ala Ser
305                 310                 315                 320
Ile Ile Ala Leu Val Ala Ile Phe Lys Ser Phe Phe Gly His Tyr Leu
                325                 330                 335
Gly Thr Leu Glu Gly Leu Asn Gly Leu Val Leu Lys Phe Gly Tyr Lys
            340                 345                 350
Gly Asp Lys Thr Lys Val Ser Leu Gly Lys Leu Asn Thr Ile Ser Met
            355                 360                 365
Ile Phe Ile Met Gly Ser Thr Trp Val Val Ala Tyr Ala Asn Pro Asn
        370                 375                 380
Ile Leu Asp Leu Ile Glu Ala Met Gly Ala Pro Ile Ile Ala Ser Leu
385                 390                 395                 400
Leu Cys Leu Leu Pro Met Tyr Ala Ile Arg Lys Ala Pro Ser Leu Ala
                405                 410                 415
Lys Tyr Arg Gly Arg Leu Asp Asn Val Phe Val Thr Val Ile Gly Leu
            420                 425                 430
Leu Thr Ile Leu Asn Ile Val Tyr Lys Leu Phe
            435                 440

<210> SEQ ID NO 11
<211> LENGTH: 2645
<212> TYPE: DNA
<213> ORGANISM: E.coli

<400> SEQUENCE: 11
atagcattcc ggctatcttc gccgtgacca ctgacccgtt cattgtgctg acctcaaacc      60
tgtttgcgat cctcggcctg cgtgcgatgt atttcctgct ggcgggcgta gcagagcgtt     120
tctcgatgct caaatatggc ctggcggtga ttctggtgtt tatcggtatc aagatgctga     180
ttgtcgactt ctaccatatt ccaatcgccg tctcgctggg cgtggtgttt ggcattctgg     240
tgatgacgtt tattatcaac gcctgggtga attatcggca tgataagcag cggggtggat     300
aatttttaat ctgcctaagc cgtgtaccct gtcattaaca tgagcaccgt tttctccctc     360
tcccttccag ggagagggtc ggggtgaggg taattttttcg caccgatgct ggcctgttcc     420
cctcacccta accctctccc caaacggggc gaggggactg accgagtcct tttttgatgt     480
tgtcatcagt ctggaagccg cacgttggct ttatttttat gtcaaagaaa tgtaaccatt     540
aagtttcaaa atatgaccct tctttaaaat ccagcatttt tcgcttcccg aagctgtaac     600
tttccttata ctcgaccttg caaacacttt gttacatcct gaaagatgcg tcgacagaac     660
gcaccaggga tgtgcgacaa cacaatgaaa ggatcgaaaa atgactacgc aacgttcacc     720
ggggctattc cggcgtctgg ctcatggcag cctggtaaaa caaatcctgg tcggccttgt     780
tctggggatt cttctggcat ggatctcaaa acccgcggcg aagctgttg gtctgttagg     840 tactttgttc gtcggcgcac tgaaagccgt tgcccccatc ctggtgttga tgctggtgat     900
ggcatctatt gctaaccacc agcacgggca gaaaaccaat atccgcccta ttttgttcct     960
ctatctactg ggcaccttct ctgctgctct ggccgcagta gtcttcagct ttgccttccc    1020 ttctacccctg catttatcca gtagcgcggg tgatatttcg ccgccgtcag gcattgtcga    1080
agtgatgcgc gggctggtaa tgagcatggt ttccaacccc atcgacgcgc tgctgaaagg    1140
taactacatc gggattctgg tgtgggcgat cggcctcggc ttcgcactgc gtcacggtaa    1200
```

```
cgagaccacc aaaaacctgg ttaacgatat gtcgaatgcc gttaccttta tggtgaaact    1260
ggtcattcgc ttcgcaccga ttggtatttt tgggctggtt tcttctaccc tggcaaccac    1320
cggtttctcc acactgtggg gctacgcgca actgctggtc gtgctggttg ctgtatgtt     1380 actggtggcg ctggtggtta acccattgct ggtgtggtgg aaaattcgtc gtaacccgtt    1440
cccgctggtg ctgctgtgcc tgcgcgaaag cggtgtgtat gccttcttca cccgcagctc    1500
tgcagcgaac attccggtga atatggcgct gtgtgaaaag ctgaatctgg atcgcgatac    1560
ctattccgtt tctattccgc tgggagccac catcaatatg gcgggcgcag caatcactat    1620
taccgtgttg acgctggctg cggttaatac gctgggtatt ccgtcgatc tgcccacggc     1680 gctgctgttg agcgtggtgg cttctctgtg tgcctgtggc catccggcg tggcgggggg     1740 gtctctgctg ctgatcccac tggcctgtaa tatgttcggt atttcgaacg atatcgccat    1800
gcaggtggtt gccgtcggct ttatcatcgg cgtattgcag gactcttgcg aaaccgcgct    1860
gaactcttca actgacgtgc tgttcactgc ggcagcttgc caggcagaag acgatcgtct    1920
ggcaaatagc gccctgcgta attaattgtt taacccctt cgtctacggc ggaagggggtt    1980 ttctcaactt taaacggatc aattcccctt ttctgcatcc gccagaaacg aatgatattc    2040
aggccattca taagcagaaa actaccctca atcatcgtgc cgcctatcga ccccgcccag    2100
aagttgtgaa tcacccagca acacgttgaa aaccacatta cgcagcgcat ggtcagccct    2160
ttacagcaga atagcgccca ggtactgaca atcgtgccga taaccggcaa tagttcgaca    2220
ggatgatgga acttcgcgag gccaattccg ccagtcagca aataaaaaat cgccattacc    2280
cataagctgc gcgtgcgtaa ggtaatcaat gtacgaatgg cattaaggat ggcactggca    2340
ccagcgggat aggtgcccag aagaaaaaaa tgtacgccaa taacggcgct atagaccgaa    2400
agctgctttt tgaagcgacg ttcgtcacga ttgaaaaatg ttgtgatacc aatcagaaag    2460
gcgatgacac ccacgccctg gccagccaa tacgcggtca tgataaatcc ttagcaggta     2520
tggaaaagca aacggcgctt cacattatga aacgccgttt tttattaaca actcatttcg    2580
actttatagc gttacgccgc ttttgaagat cgccagttcg cggaagtcgt tacgctcgtt    2640
acagg                                                                2645
```

<210> SEQ ID NO 12
<211> LENGTH: 414
<212> TYPE: PRT
<213> ORGANISM: E.coli

<400> SEQUENCE: 12

```
Met Thr Thr Gln Arg Ser Pro Gly Leu Phe Arg Arg Leu Ala His Gly
1               5                   10                  15

Ser Leu Val Lys Gln Ile Leu Val Gly Leu Val Gly Ile Leu Leu
            20                  25                  30

Ala Trp Ile Ser Lys Pro Ala Ala Glu Ala Val Gly Leu Leu Gly Thr
        35                  40                  45

Leu Phe Val Gly Ala Leu Lys Ala Val Ala Pro Ile Leu Val Leu Met
    50                  55                  60

Leu Val Met Ala Ser Ile Ala Asn His Gln His Gly Gln Lys Thr Asn
65                  70                  75                  80

Ile Arg Pro Ile Leu Phe Leu Tyr Leu Leu Gly Thr Phe Ser Ala Ala
                85                  90                  95

Leu Ala Ala Val Val Phe Ser Phe Ala Phe Pro Ser Thr Leu His Leu
            100                 105                 110
```

Ser Ser Ser Ala Gly Asp Ile Ser Pro Ser Gly Ile Val Glu Val
            115                 120                 125

Met Arg Gly Leu Val Met Ser Met Val Ser Asn Pro Ile Asp Ala Leu
        130                 135                 140

Leu Lys Gly Asn Tyr Ile Gly Ile Leu Val Trp Ala Ile Gly Leu Gly
145                 150                 155                 160

Phe Ala Leu Arg His Gly Asn Glu Thr Thr Lys Asn Leu Val Asn Asp
                165                 170                 175

Met Ser Asn Ala Val Thr Phe Met Val Lys Leu Val Ile Arg Phe Ala
            180                 185                 190

Pro Ile Gly Ile Phe Gly Leu Val Ser Ser Thr Leu Ala Thr Thr Gly
        195                 200                 205

Phe Ser Thr Leu Trp Gly Tyr Ala Gln Leu Leu Val Val Leu Val Gly
    210                 215                 220

Cys Met Leu Leu Val Ala Leu Val Val Asn Pro Leu Val Trp Trp
225                 230                 235                 240

Lys Ile Arg Arg Asn Pro Phe Pro Leu Val Leu Cys Leu Arg Glu
                245                 250                 255

Ser Gly Val Tyr Ala Phe Phe Thr Arg Ser Ser Ala Ala Asn Ile Pro
            260                 265                 270

Val Asn Met Ala Leu Cys Glu Lys Leu Asn Leu Asp Arg Asp Thr Tyr
        275                 280                 285

Ser Val Ser Ile Pro Leu Gly Ala Thr Ile Asn Met Ala Gly Ala Ala
    290                 295                 300

Ile Thr Ile Thr Val Leu Thr Leu Ala Ala Val Asn Thr Leu Gly Ile
305                 310                 315                 320

Pro Val Asp Leu Pro Thr Ala Leu Leu Leu Ser Val Val Ala Ser Leu
                325                 330                 335

Cys Ala Cys Gly Ala Ser Gly Val Ala Gly Gly Ser Leu Leu Leu Ile
            340                 345                 350

Pro Leu Ala Cys Asn Met Phe Gly Ile Ser Asn Asp Ile Ala Met Gln
        355                 360                 365

Val Val Ala Val Gly Phe Ile Ile Gly Val Leu Gln Asp Ser Cys Glu
    370                 375                 380

Thr Ala Leu Asn Ser Ser Thr Asp Val Leu Phe Thr Ala Ala Ala Cys
385                 390                 395                 400

Gln Ala Glu Asp Asp Arg Leu Ala Asn Ser Ala Leu Arg Asn
                405                 410

<210> SEQ ID NO 13
<211> LENGTH: 162
<212> TYPE: DNA
<213> ORGANISM: Artificial Sequence
<220> FEATURE:
<223> OTHER INFORMATION: promoter sequence

<400> SEQUENCE: 13
caattccgac gtctaagaaa ccattattat catgacatta acctataaaa ataggcgtat      60
cacgaggccc tttcgtcttc acctcgagtc cctatcagtg atagagattg acatccctat     120
cagtgataga gatactgagc acatcagcag gacgcactga cc                        162

<210> SEQ ID NO 14
<211> LENGTH: 5020
<212> TYPE: DNA
<213> ORGANISM: Artificial Sequence
<220> FEATURE:
<223> OTHER INFORMATION: DNA moleucule A

<400> SEQUENCE: 14

```
agcttttcat tctgactgca acgggcaata tgtctctgtg tggattaaaa aaagagtgtc      60
tgatagcagc ttctgaactg gttacctgcc gtgagtaaat taaaattttta ttgacttagg     120
tcactaaata ctttaaccaa tataggcata gcgcacagac agataaaaat tacagagtac     180
acaacatcca tgaaacgcat tagcaccacc attaccacca ccatcaccat taccacaggt     240
aacggtgcgg gctgacgcgt acaggaaaca cagaaaaaag cccgcacctg acagtgcggg     300
ctttttttt cgaccaaagg taacgaggta caaccatgc gagtgttgaa gttcggcggt       360
acatcagtgg caaatgcaga acgttttctg cgtgttgccg atattctgga agcaatgcc     420
aggcaggggc aggtggccac cgtcctctct gcccccgcca aaatcaccaa ccacctggtg    480
gcgatgattg aaaaaaccat tagcggccag gatgctttac ccaatatcag cgatgccgaa    540
cgtattttg ccgaactttt gacgggactc gccgccgcc agccgggggt cccgctggcg      600
caattgaaaa ctttcgtcga tcaggaattt gcccaaataa acatgtcct gcatggcatt     660
agtttgttgg ggcagtgccc ggatagcatc aacgctgcgc tgatttgccg tggcgagaaa   720
atgtcgatcg ccattatggc cggcgtatta aagcgcgcg gtcacaacgt tactgttatc    780
gatccggtcg aaaaactgct ggcagtgggg cattacctcg aatctaccgt cgatattgct  840
gagtccaccc gccgtattgc ggcaagccgc attccggctg atcacatggt gctgatggca 900
ggtttcaccg ccggtaatga aaaggcgaa ctggtggtgc ttggacgcaa cggttccgac   960
tactctgctg cggtgctggc tgcctgttta cgcgccgatt gttgcgagat ttggacggac  1020
gttgacgggg tctatacctg cgacccgcgt caggtgcccg atgcgaggtt gttgaagtcg 1080
atgtcctacc aggaagcgat ggagctttcc tacttcggcg ctaaagttct tcaccccgc  1140
accattaccc ccatcgccca gttccagatc ccttgcctga ttaaaaatac cggaaatcct  1200
caagcaccag gtacgctcat tggtgccagc cgtgatgaag acgaattacc ggtcaagggc 1260
atttccaatc tgaataacat ggcaatgttc agcgtttctg gtccggggat gaaagggatg 1320
gtcggcatgg cggcgcgcgt ctttgcagcg atgtcacgcg cccgtatttc cgtggtgctg 1380
attacgcaat catcttccga atacagcatc agtttctgcg ttccacaaag cgactgtgtg 1440
cgagctgaac gggcaatgca ggaagagttc tacctggaac tgaaagaagg cttactggag 1500
ccgctggcag tgacggaacg gctggccatt atctcggtgg taggtgatgg tatcgcacc  1560
ttgcgtggga tctcggcgaa atctttgcc gcactggccc gcgccaatat caacattgtc  1620
gccattgctc agggatcttc tgaacgctca atctctgtcg tggtaaataa cgatgatgcg  1680
accactggcg tgcgcgttac tcatcagatg ctgttcaata ccgatcaggt tatcgaagtg 1740
tttgtgattg gcgtcggtgg cgttggcggt gcgctgctgg agcaactgaa gcgtcagcaa 1800
agctggctga gaataaaca tatcgactta cgtgtctgcg gtgttgccaa ctcgaaggct   1860
ctgctcacca atgtacatgg ccttaatctg gaaaactggc aggaagaact ggcgcaagcc 1920
aaagagccgt ttaatctcgg gcgcttaatt cgcctcgtga agaatatca tctgctgaac   1980
ccggtcattg ttgactgcac ttccagccag gcagtggcgc atcaatatgc cgacttcctg 2040
cgcgaaggtt ccacgttgt cacgccgaac aaaaaggcca cacctcgtc gatggattac  2100
taccatcagt tgcgttatgc ggcggaaaaa tcgcggcgta aattcctcta tgacaccaac 2160
gttggggctg gattaccggt tattgagaac ctgcaaaatc tgctcaatgc aggtgatgaa 2220
```

```
ttgatgaagt tctccggcat tctttctggt tcgctttctt atatcttcgg caagttagac      2280
gaaggcatga gttctccga ggcgaccacg ctggcgcggg aaatgggtta taccgaaccg       2340
gacccgcgag atgatctttc tggtatggat gtggcgcgta aactattgat tctcgctcgt      2400
gaaacgggac gtgaactgga gctggcggat attgaaattg aacctgtgct gcccgcagag      2460
tttaacgccg agggtgatgt tgccgctttt atggcgaatc tgtcacaact cgacgatctc     2520
tttgccgcgc gcgtggcgaa ggcccgtgat gaaggaaaag ttttgcgcta tgttggcaat      2580
attgatgaag atggcgtctg ccgcgtgaag attgccgaag tggatggtaa tgatccgctg     2640
ttcaaagtga aaaatggcga aaacgccctg gccttctata gccactatta tcagccgctg      2700
ccgttggtac tgcgcggata tggtgcgggc aatgacgtta cagctgccgg tgtctttgct     2760
gatctgctac gtaccctctc atggaagtta ggagtctgac atggttaaag tttatgcccc      2820
ggcttccagt gccaatatga gcgtcgggtt tgatgtgctc ggggcggcgg tgacacctgt     2880
tgatggtgca ttgctcggag atgtagtcac ggttgaggcg gcagagacat tcagtctcaa      2940
caacctcgga cgctttgccg ataagctgcc gtcagaacca cgggaaaata tcgtttatca      3000
gtgctgggag cgttttgcc aggaactggg taagcaaatt ccagtggcga tgaccctgga      3060
aaagaatatg ccgatcggtt cgggcttagg ctccagtgcc tgttcggtgg tcgcggcgct     3120
gatggcgatg aatgaacact gcggcaagcc gcttaatgac actcgtttgc tggctttgat     3180
gggcgagctg gaaggccgta tctccggcag cattcattac gacaacgtgg caccgtgttt     3240
tctcggtggt atgcagttga tgatcgaaga aaacgacatc atcagccagc aagtgccagg     3300
gtttgatgag tggctgtggg tgctggcgta tccggggatt aaagtctcga cggcagaagc      3360
cagggctatt ttaccggcgc agtatcgccg ccaggattgc attgcgcacg gcgacatct      3420 ggcaggcttc attcacgcct gctattcccg tcagcctgag cttgccgcga agctgatgaa     3480
agatgttatc gctgaaccct accgtgaacg gttactgcca ggcttccggc aggcgcggca      3540
ggcggtcgcg gaaatcggcg cggtagcgag cggtatctcc ggctccggcc cgaccttgtt     3600
cgctctgtgt gacaagccgg aaaccgccca gcgcgttgcc gactggttgg gtaagaacta     3660
cctgcaaaat caggaaggtt ttgttcatat ttgccggctg gatacggcgg gcgcacgagt     3720
actggaaaac taaatgaaac tctacaatct gaaagatcac aacgagcagg tcagctttgc     3780
gcaagccgta acccaggggt tgggcaaaaa tcaggggctg ttttttccgc acgacctgcc      3840
ggaattcagc ctgactgaaa ttgatgagat gctgaagctg gattttgtca cccgcagtgc     3900
gaagatcctc tcggcgttta ttggtgatga aatcccacag gaaatcctgg aagagcgcgt      3960
gcgcgcggcg tttgccttcc cggctccggt cgccaatgtt gaaagcgatg tcggttgtct     4020
ggaattgttc cacgggccaa cgctggcatt taaagatttc ggcggtcgct ttatggcaca      4080
aatgctgacc catattgcgg gtgataagcc agtgaccatt ctgaccgcga cctccggtga     4140
taccggagcg gcagtggctc atgctttcta cggtttaccg aatgtgaaag tggttatcct      4200
ctatccacga ggcaaaatca gtccactgca agaaaaactg ttctgtacat tgggcggcaa     4260
tatcgaaact gttgccatcg acggcgattt cgatgcctgt caggcgctgg tgaagcaggc     4320
gtttgatgat gaagaactga agtggcgct agggttaaac tcggctaact cgattaacat     4380
cagccgtttg ctggcgcaga tttgctacta cttttgaagct gttgcgcagc tgccgcagga     4440
gacgcgcaac cagctggttg tctcggtgcc aagcggaaac ttcggcgatt tgacggcggg      4500
tctgctggcg aagtcactcg gtctgccggt gaaacgtttt attgctgcga ccaacgtgaa     4560
cgataccgtg ccacgttccc tgcacgacgg tcagtggtca cccaaagcga ctcaggcgac     4620
```

```
gttatccaac gcgatggacg tgagtcagcc gaacaactgg ccgcgtgtgg aagagttgtt    4680
ccgccgcaaa atctggcaac tgaaagagct gggttatgca gccgtggatg atgaaaccac    4740
gcaacagaca atgcgtgagt taaaagaact gggctacact tcggagccgc acgctgccgt    4800
agcttatcgt gcgctgcgtg atcagttgaa tccaggcgaa tatggcttgt tcctcggcac    4860
cgcgcatccg gcgaaattta aagagagcgt ggaagcgatt ctcggtgaaa cgttggatct    4920
gccaaaagag ctggcagaac gtgctgattt acccttgctt tcacataatc tgcccgccga    4980
ttttgctgcg ttgcgtaaat tgatgatgaa tcatcagtaa                          5020

<210> SEQ ID NO 15
<211> LENGTH: 3113
<212> TYPE: DNA
<213> ORGANISM: Artificial Sequence
<220> FEATURE:
<223> OTHER INFORMATION: lacZ sequence

<400> SEQUENCE: 15
atgaccatga ttacggattc actggccgtc gttttacaac gtcgtgactg ggaaaaccct      60
ggcgttaccc aacttaatcg ccttgcagca catccccctt tcgccagctg gcgtaatagc     120
gaagaggccc gcaccgatcg cccttcccaa cagttgcgca gcctgaatgg cgaatggcgc     180
tttgcctggt ttccggcacc agaagcggtg ccggaaagct ggctggagtg cgatcttcct     240
gaggccgata ctgtcgtcgt cccctcaaac tggcagatgc acggttacga tgcgcccatc     300
tacaccaacg tgacctatcc cattacggtc aatccgccgt ttgttcccac ggagaatccg     360
acgggttgtt actcgctcac atttaatgtt gatgaaagct ggctacagga aggccagacg     420
cgaattattt ttgatggcgt taactcggcg tttcatctgt ggtgcaacgg gcgctgggtc     480
ggttacggcc aggacagtcg tttgccgtct gaatttgacc tgagcgcatt tttacgcgcc     540
ggagaaaacc gcctcgcggt gatggtgctg cgctggagtg acggcagtta tctggaagat     600
caggatatgt ggcggatgag cggcattttc cgtgacgtct cgttgctgca taaaccgact     660
acacaaatca gcgatttcca tgttgccact cgctttaatg atgatttcag ccgcgctgta     720
ctggaggctg aagttcagat gtgcggcgag ttgcgtgact acctacgggt aacagtttct     780
ttatggcagg gtgaaacgca ggtcgccagc ggcaccgcgc ctttcggcgg tgaaattatc     840
gatgagcgtg gtggttatgc cgatcgcgtc acactacgtc tgaacgtcga aaacccgaaa     900
ctgtggagcg ccgaaatccc gaatctctat cgtgcggtgg ttgaactgca caccgccgac     960
ggcacgctga ttgaagcaga agcctgcgat gtcggtttcc gcgaggtgcg gattgaaaat    1020
ggtctgctgc tgctgaacgg caagccgttg ctgattcgag gcgttaaccg tcacgagcat    1080
catcctctgc atggtcaggt catggatgag cagacgatgg tgcaggatat cctgctgatg    1140
aagcagaaca actttaacgc cgtgcgctgt tcgcattatc cgaaccatcc gctgtggtac    1200
acgctgtgcg accgctacgg cctgtatgtg gtggatgaag ccaatattga acccacggc     1260 atggtgccaa tgaatcgtct gaccgatgat ccgcgctggc taccggcgat gagcgaacgc    1320
gtaacgcgaa tggtgcagcg cgatcgtaat cacccgagtg tgatcatctg gtcgctgggg    1380
aatgaatcag gccacggcgc taatcacgac gcgctgtatc gctggatcaa atctgtcgat    1440
ccttcccgcc cggtgcagta tgaaggcggc ggagccgaca ccacggccac cgatattatt    1500
tgcccgatgt acgcgcgcgt ggatgaagac cagcccttcc cggctgtgcc gaaatggtcc    1560
atcaaaaaat ggcttttcgct acctggagag acgcgcccgc tgatcctttg cgaatacgcc    1620
```

```
cacgcgatgg gtaacagtct tggcggtttc gctaaatact ggcaggcgtt tcgtcagtat   1680
ccccgtttac agggcggctt cgtctgggac tgggtggatc agtcgctgat taaatatgat   1740
gaaaacggca acccgtggtc ggcttacggc ggtgattttg gcgatacgcc gaacgatcgc   1800
cagttctgta tgaacggtct ggtctttgcc gaccgcacgc cgcatccagc gctgacggaa   1860
gcaaaacacc agcagcagtt tttccagttc cgtttatccg gcaaaccat cgaagtgacc    1920 agcgaatacc tgttccgtca tagcgataac gagctcctgc actggatggt ggcgctggat   1980
ggtaagccgc tggcaagcgg tgaagtgcct ctggatgtcg ctccacaagg taaacagttg   2040
attgaactgc ctgaactacc gcagccggag agcgccgggc aactctggct cacagtacgc   2100
gtagtgcaac cgaacgcgac cgcatggtca gaagccgggc acatcagcgc ctggcagcag   2160
tggcgtctgg cggaaaacct cagtgtgacg ctccccgccg cgtcccacgc catcccgcat   2220
ctgaccacca gcgaaatgga tttttgcatc gagctgggta ataagcgttg gcaatttaac   2280
cgccagtcag gctttctttc acagatgtgg attggcgata aaaacaact gctgacgccg    2340 ctgcgcgatc agttcacccg tgcaccgctg ataacgaca ttggcgtaag tgaagcgacc    2400
cgcattgacc ctaacgcctg ggtcgaacgc tggaaggcgg cgggccatta ccaggccgaa   2460
gcagcgttgt tgcagtgcac ggcagataca cttgctgatg cggtgctgat tacgaccgct   2520
cacgcgtggc agcatcaggg gaaaaccta tttatcagcc ggaaaaccta ccggattgat    2580
ggtagtggtc aaatggcgat taccgttgat gttgaagtgg cgagcgatac accgcatccg   2640
gcgcggattg gcctgaactg ccagctggcg caggtagcag agcgggtaaa ctggctcgga   2700
ttagggccgc aagaaaacta tcccgaccgc cttactgccg cctgttttga ccgctgggat   2760
ctgccattgt cagacatgta taccccgtac gtcttcccga gcgaaaacgg tctgcgctgc   2820
gggacgcgcg aattgaatta tggcccacac cagtggcgcg cgacttcca gttcaacatc    2880 agccgctaca gtcaacagca actgatggaa accagccatc gccatctgct gcacgcggaa   2940
gaaggcacat ggctgaatat cgacggtttc catatgggga ttggtggcga cgactcctgg   3000
agcccgtcag tatcggcgga attccagctg agcgccggtc gctaccatta ccagttggtc   3060
tggtgtcaaa aataataata accgggcagg ccatgtctgc ccgtatttcg cgt           3113
```

<210> SEQ ID NO 16
<211> LENGTH: 717
<212> TYPE: DNA
<213> ORGANISM: Artificial Sequence
<220> FEATURE:
<223> OTHER INFORMATION: gfp sequence

<400> SEQUENCE: 16

```
atgagtaaag gagaagaact tttcactgga gttgtcccaa ttcttgttga attagatggt     60
gatgttaatg ggcacaaatt ttctgtcagt ggagagggtg aaggtgatgc aacatacgga   120
aaacttaccc ttaaatttat ttgcactact ggaaaactac ctgttccatg gccaacactt   180
gtcactactt tcgggtatgg tgttcaatgc tttgcgagat acccagatca tatgaaacag   240
catgactttt tcaagagtgc catgcccgaa ggttatgtac aggaaagaac tatattttc    300 aaagatgacg ggaactacaa gacacgtgct gaagtcaagt ttgaaggtga tacccttgtt   360
aatagaatcg agttaaaagg tattgatttt aaagaagatg gaaacattct tggacacaaa   420
ttggaataca actataactc acacaatgta tacatcatgg cagacaaaca aaagaatgga   480
atcaaagtta acttcaaaat tagacacaac attgaagatg gaagcgttca actagcagac   540
cattatcaac aaaatactcc aattggcgat ggccctgtcc ttttaccaga caaccattac   600
```

```
ctgtccacac aatctgccct ttcgaaagat cccaacgaaa agagagacca catggtcctt      660
cttgagtttg taacagctgc tgggattaca catggcatgg atgaactata caaataa        717

<210> SEQ ID NO 17
<211> LENGTH: 1242
<212> TYPE: DNA
<213> ORGANISM: Artificial Sequence
<220> FEATURE:
<223> OTHER INFORMATION: recognition sequence

<400> SEQUENCE: 17
cacatataca ggaggagaca gatatgatca tagggttcc taaagagata aaaaacaatg       60
aaaaccgtgt cgcattaaca cccggggcg tttctcagct catttcaaac ggccaccggg      120
tgctggttga aacaggcgcg ggccttggaa gcggatttga aaatgaagcc tatgagtcag     180
caggagcgga aatcattgct gatccgaagc aggtctggga cgccgaaatg gtcatgaaag     240
taaaagaacc gctgccggaa gaatatgttt attttcgcaa aggacttgtg ctgtttacgt     300
accttcattt agcagctgag cctgagcttg cacaggcctt gaaggataaa ggagtaactg     360
ccatcgcata tgaaacggtc agtgaaggcc ggacattgcc tcttctgacg ccaatgtcag     420
aggttgcggg cagaatggca gcgcaaatcg gcgctcaatt cttagaaaag cctaaaggcg     480
gaaaaggcat tctgcttgcc ggggtgcctg gcgtttcccg cggaaaagta acaattatcg     540
gaggaggcgt tgtcgggaca aacgcggcga aaatggctgt cggcctcggt gcagatgtga     600
cgatcattga cttaaacgca gaccgcttgc gccagcttga tgacatcttc ggccatcaga     660
ttaaaacgtt aatttctaat ccggtcaata ttgctgatgc tgtggcggaa gcggatctcc     720
tcatttgcgc ggtattaatt ccgggtgcta aagctccgac tcttgtcact gaggaaatgg     780
taaaacaaat gaaacccggt tcagttattg ttgatgtagc gatcgaccaa ggcggcatcg     840
tcgaaactgt cgaccatatc acaacacatg atcagccaac atatgaaaaa cacggggttg     900
tgcattatgc tgtagcgaac atgccaggcg cagtccctcg tacatcaaca atcgccctga     960
ctaacgttac tgttccatac gcgctgcaaa tcgcgaacaa aggggcagta aaagcgctcg    1020
cagacaatac ggcactgaga gcgggtttaa acaccgcaaa cggacacgtg acctatgaag    1080
ctgtagcaag agatctaggc tatgagtatg ttcctgccga gaaagcttta caggatgaat    1140
catctgtggc gggtgcttaa ttcacaataa gcttgcagaa agatttctgc aggcttttt      1200 atttttaaa aggaaaaaag agaccatttc acgaattatg ac                        1242

<210> SEQ ID NO 18
<211> LENGTH: 1262
<212> TYPE: DNA
<213> ORGANISM: Artificial Sequence
<220> FEATURE:
<223> OTHER INFORMATION: recognition sequence

<400> SEQUENCE: 18
gtgcgggctt ttttttcga ccaaaggtaa cgaggtaaca accatgatca tagggttcc        60 taaagagata aaaaacaatg aaaaccgtgt cgcattaaca cccggggcg tttctcagct      120 catttcaaac ggccaccggg tgctggttga aacaggcgcg ggccttggaa gcggatttga    180
aaatgaagcc tatgagtcag caggagcgga aatcattgct gatccgaagc aggtctggga   240
cgccgaaatg gtcatgaaag taaaagaacc gctgccggaa gaatatgttt attttcgcaa   300
aggacttgtg ctgtttacgt accttcattt agcagctgag cctgagcttg cacaggcctt   360
```

-continued

```
gaaggataaa ggagtaactg ccatcgcata tgaaacggtc agtgaaggcc ggacattgcc    420
tcttctgacg ccaatgtcag aggttgcggg cagaatggca gcgcaaatcg gcgctcaatt    480
cttagaaaag cctaaaggcg gaaaaggcat tctgcttgcc ggggtgcctg gcgtttcccg    540
cggaaaagta acaattatcg gaggaggcgt tgtcgggaca aacgcggcga aaatggctgt    600
cggcctcggt gcagatgtga cgatcattga cttaaacgca gaccgcttgc gccagcttga    660
tgacatcttc ggccatcaga ttaaaacgtt aatttctaat ccggtcaata ttgctgatgc    720
tgtggcggaa gcggatctcc tcatttgcgc ggtattaatt ccgggtgcta aagctccgac    780
tcttgtcact gaggaaatgg taaaacaaat gaaacccggt tcagttattg ttgatgtagc    840
gatcgaccaa ggcggcatcg tcgaaactgt cgaccatatc acaacacatg atcagccaac    900
atatgaaaaa cacggggttg tgcattatgc tgtagcgaac atgccaggcg cagtccctcg    960
tacatcaaca atcgccctga ctaacgttac tgttccatac gcgctgcaaa tcgcgaacaa   1020
agggcagta aaagcgctcg cagacaatac ggcactgaga gcgggtttaa acaccgcaaa   1080
cggacacgtg acctatgaag ctgtagcaag agatctaggc tatgagtatg ttcctgccga   1140
gaaagcttta caggatgaat catctgtggc gggtgcttaa ttcacaataa gcttgcagaa   1200
agatttctgc aggctttttt attttttaaa aggaaaaaag agaccatttc acgaattatg   1260
ac                                                                  1262
```

<210> SEQ ID NO 19
<211> LENGTH: 378
<212> TYPE: PRT
<213> ORGANISM: Artificial Sequence
<220> FEATURE:
<223> OTHER INFORMATION: peptide sequence

<400> SEQUENCE: 19

```
Met Ile Ile Gly Val Pro Lys Glu Ile Lys Asn Asn Glu Asn Arg Val
1               5                   10                  15

Ala Leu Thr Pro Gly Gly Val Ser Gln Leu Ile Ser Asn Gly His Arg
            20                  25                  30

Val Leu Val Glu Thr Gly Ala Gly Leu Gly Ser Gly Phe Glu Asn Glu
        35                  40                  45

Ala Tyr Glu Ser Ala Gly Ala Glu Ile Ile Ala Asp Pro Lys Gln Val
    50                  55                  60

Trp Asp Ala Glu Met Val Met Lys Val Lys Glu Pro Leu Pro Glu Glu
65                  70                  75                  80

Tyr Val Tyr Phe Arg Lys Gly Leu Val Leu Phe Thr Tyr Leu His Leu
                85                  90                  95

Ala Ala Glu Pro Glu Leu Ala Gln Ala Leu Lys Asp Lys Gly Val Thr
            100                 105                 110

Ala Ile Ala Tyr Glu Thr Val Ser Glu Gly Arg Thr Leu Pro Leu Leu
        115                 120                 125

Thr Pro Met Ser Glu Val Ala Gly Arg Met Ala Ala Gln Ile Gly Ala
    130                 135                 140

Gln Phe Leu Glu Lys Pro Lys Gly Gly Lys Gly Ile Leu Leu Ala Gly
145                 150                 155                 160

Val Pro Gly Val Ser Arg Gly Lys Val Thr Ile Ile Gly Gly Gly Val
                165                 170                 175

Val Gly Thr Asn Ala Ala Lys Met Ala Val Gly Leu Gly Ala Asp Val
            180                 185                 190

Thr Ile Ile Asp Leu Asn Ala Asp Arg Leu Arg Gln Leu Asp Asp Ile
```

```
               195                 200                 205
Phe Gly His Gln Ile Lys Thr Leu Ile Ser Asn Pro Val Asn Ile Ala
    210                 215                 220
Asp Ala Val Ala Glu Ala Asp Leu Leu Ile Cys Ala Val Leu Ile Pro
225                 230                 235                 240
Gly Ala Lys Ala Pro Thr Leu Val Thr Glu Met Val Lys Gln Met
                245                 250                 255
Lys Pro Gly Ser Val Ile Val Asp Val Ala Ile Asp Gln Gly Gly Ile
            260                 265                 270
Val Glu Thr Val Asp His Ile Thr Thr His Asp Gln Pro Thr Tyr Glu
        275                 280                 285
Lys His Gly Val Val His Tyr Ala Val Ala Asn Met Pro Gly Ala Val
    290                 295                 300
Pro Arg Thr Ser Thr Ile Ala Leu Thr Asn Val Thr Val Pro Tyr Ala
305                 310                 315                 320
Leu Gln Ile Ala Asn Lys Gly Ala Val Lys Ala Leu Ala Asp Asn Thr
                325                 330                 335
Ala Leu Arg Ala Gly Leu Asn Thr Ala Asn Gly His Val Thr Tyr Glu
            340                 345                 350
Ala Val Ala Arg Asp Leu Gly Tyr Glu Tyr Val Pro Ala Glu Lys Ala
        355                 360                 365
Leu Gln Asp Glu Ser Ser Val Ala Gly Ala
    370                 375

<210> SEQ ID NO 20
<211> LENGTH: 5132
<212> TYPE: DNA
<213> ORGANISM: Artificial Sequence
<220> FEATURE:
<223> OTHER INFORMATION: nucleotide sequence

<400> SEQUENCE: 20
agcttttcat tctgactgca acgggcaata tgtctctgtg tggattaaaa aaagagtgtc     60
tgatagcagc ttctgaactg gttacctgcc gtgagtaaat taaaatttta ttgacttagg    120
tcactaaata ctttaaccaa tataggcata gcgcacagac agataaaaat tacagagtac    180
acaacatcca tgaaacgcat tagcaccacc attaccacca ccatcaccat taccacaggt    240
aacggtgcgg gctgacgcgt acaggaaaca cagaaaaaag cccgcacctg acagtgcggg    300 ctttttttt cgaccaaagg taacgaggta acaaccatgc gagtgttgaa gttcggcggt    360
acatcagtgg caaatgcaga acgttttctg cgtgttgccg atattctgga agcaatgcc    420 aggcaggggc aggtggccac cgtcctctct gccccgcca aaatcaccaa ccacctggtg    480
gcgatgattg aaaaaaccat tagcggccag gatgctttac caatatcag cgatgccgaa    540 cgtatttttg ccgaactttt gacgggactc gccgccgccc agccggggtt cccgctggcg    600
caattgaaaa ctttcgtcga tcaggaattt gcccaaataa acatgtcct gcatggcatt    660 agtttgttgg ggcagtgccc ggatagcatc aacgctgcgc tgatttgccg tggcgagaaa    720
atgtcgatcg ccattatggc cggcgtatta gaagcgcgcg tcacaacgt tactgttatc    780 gatccggtcg aaaaactgct ggcagtgggg cattacctcg aatctaccgt cgatattgct    840
gagtccaccc gccgtattgc ggcaagccgc attccggctg atcacatggt gctgatggca    900
ggtttcaccg ccgtaatga aaaaggcgaa ctggtggtgc ttggacgcaa cggttccgac    960
tactctgctg cggtgctggc tgcctgttta cgcgccgatt gttgcgagat tggacggac   1020
```

```
gttgacgggg tctatacctg cgacccgcgt caggtgcccg atgcgaggtt gttgaagtcg    1080
atgtcctacc agcatgcgat ggagctttcc tacttcggcg ctaaagttct tcacccccgc    1140
accattaccc ccatcgccca gttccagatc ccttgcctga ttaaaaatac cggaaatcct    1200
caagcaccag gtacgctcat tggtgccagc cgtgatgaag acgaattacc ggtcaagggc    1260
atttccaatc tgaataacat ggcaatgttc agcgtttctg gtccggggat gaaagggatg    1320
gtcggcatgg cggcgcgcgt ctttgcagcg atgtcacgcg cccgtatttc cgtggtgctg    1380
attacgcaat catcttccga atacagcatc agtttctgcg ttccacaaag cgactgtgtg    1440
cgagctgaac gggcaatgca ggaagagttc tacctggaac tgaaagaagg cttactggag    1500
ccgctggcag tgacggaacg gctggccatt atctcggtgg taggtgatgg tatgcgcacc    1560
ttgcgtggga tctcggcgaa attctttgcc gcactggccc gcgccaatat caacattgtc    1620
gccattgctc agggatcttc tgaacgctca atctctgtcg tggtaaataa cgatgatgcg    1680
accactggcg tgcgcgttac tcatcagatg ctgttcaata ccgatcaggt tatcgaagtg    1740
tttgtgattg gcgtcggtgg cgttggcggt gcgctgctgg agcaactgaa gcgtcagcaa    1800
agctggctga agaataaaca tatcgactta cgtgtctgcg gtgttgccaa ctcgaaggct    1860
ctgctcacca atgtacatgg ccttaatctg gaaaactggc aggaagaact ggcgcaagcc    1920
aaagagccgt ttaatctcgg gcgcttaatt cgcctcgtga agaatatca tctgctgaac    1980 ccggtcattg ttgactgcac ttccagccag gcagtggcgg atcaatatgc cgacttcctg    2040
cgcgaaggtt tccacgttgt cacgccgaac aaaaaggcca cacctcgtc gatggattac    2100 taccatcagt tgcgttatgc ggcggaaaaa tcgcggcgta aattcctcta tgacaccaac    2160
gttggggctg gattaccggt tattgagaac ctgcaaaatc tgctcaatgc aggtgatgaa    2220
ttgatgaagt tctccggcat tctttctggt tcgctttctt atatcttcgg caagttagac    2280
gaaggcatga gtttctccga ggcgaccacg ctggcgcggg aaatgggtta taccgaaccg    2340
gacccgcgag atgatctttc tggtatggat gtggcgcgta actattgat tctcgctcgt    2400 gaaacgggac gtgaactgga gctggcggat attgaaattg aacctgtgct gcccgcagag    2460
tttaacgccg agggtgatgt tgccgctttt atggcgaatc tgtcacaact cgacgatctc    2520
tttgccgcgc gcgtggcgaa ggcccgtgat gaaggaaaag ttttgcgcta tgttggcaat    2580
attgatgaag atggcgtctg ccgcgtgaag attgccgaag tggatggtaa tgatccgctg    2640
ttcaaagtga aaaatggcga aaacgccctg gccttctata gccactatta tcagccgctg    2700
ccgttggtac tgcgcggata tggtgcgggc aatgacgtta cagctgccgg tgtcttttgct    2760 gatctgctac gtaccctctc atggaagtta ggagtctgac atggttaaag tttatgcccc    2820
ggcttccagt gccaatatga gcgtcgggtt tgatgtgctc ggggcggcgg tgacacctgt    2880
tgatggtgca ttgctcggag atgtagtcac ggttgaggcg gcagagacat tcagtctcaa    2940
caacctcgga cgctttgccg ataagctgcc gtcagaacca cgggaaaata tcgtttatca    3000
gtgctgggag cgttttgcc aggaactggg taagcaaatt ccagtggcga tgaccctgga    3060
aaagaatatg ccgatcggtt cgggcttagg ctccagtgcc tgttcggtgg tcgcggcgct    3120
gatggcgatg aatgaacact gcggcaagcc gcttaatgac actcgtttgc tggctttgat    3180
gggcgagctg gaaggccgta tctccggcag cattcattac gacaacgtgg caccgtgttt    3240
tctcggtggt atgcagttga tgatcgaaga aaacgacatc atcagccagc aagtgccagg    3300
gtttgatgag tggctgtggg tgctggcgta tccggggatt aaagtctcga cggcagaagc    3360
cagggctatt ttaccggcgc agtatcgccg ccaggattgc attgcgcacg ggcgacatct    3420
```

-continued

```
ggcaggcttc attcacgcct gctattcccg tcagcctgag cttgccgcga agctgatgaa    3480
agatgttatc gctgaacect accgtgaacg gttactgcca ggcttccggc aggcgcggca    3540
ggcggtcgcg gaaatcggcg cggtagcgag cggtatctcc ggctccggcc cgaccttgtt    3600
cgctctgtgt gacaagccgg aaaccgccca gcgcgttgcc gactggttgg gtaagaacta    3660
cctgcaaaat caggaaggtt ttgttcatat ttgccggctg gatacggcgg cgcacgagt    3720
actgaaaac taaatgaaac tctacaatct gaaagatcac aacgagcagg tcagctttgc    3780
gcaagccgta acccaggggt tgggcaaaaa tcagggctg ttttttccgc acgacctgcc    3840
ggaattcagc ctgactgaaa ttgatgagat gctgaagctg gattttgtca cccgcagtgc    3900
gaagatcctc tcggcgttta ttggtgatga atcccacag gaaatcctgg aagagcgcgt    3960
gcgcgcggcg tttgccttcc cggctccggt cgccaatgtt gaaagcgatg tcggttgtct    4020
ggaattgttc cacgggccaa cgctggcatt taaagatttc ggcggtcgct ttatggcaca    4080
aatgctgacc catattgcgg gtgataagcc agtgaccatt ctgaccgcga cctccggtga    4140
taccggagcg gcagtggctc atgctttcta cggtttaccg aatgtgaaag tggttatcct    4200
ctatccacga ggcaaaatca gtccactgca agaaaaactg ttctgtacat gggcggcaa    4260
tatcgaaact gttgccatcg acggcgattt cgatgcctgt caggcgctgg tgaagcaggc    4320
gtttgatgat gaagaactga agtggcgct agggttaaac tcggctaact cgattaacat    4380
cagccgtttg ctggcgcaga tttgctacta ctttgaagct gttgcgcagc tgccgcagga    4440
gacgcgcaac cagctggttg tctcggtgcc aagcggaaac ttcggcgatt tgacggcggg    4500
tctgctggcg aagtcactcg gtctgccggt gaaacgtttt attgctgcga ccaacgtgaa    4560
cgataccgtg ccacgtttcc tgcacgacgg tcagtggtca cccaaagcga ctcaggcgac    4620
gttatccaac gcgatggacg tgagtcagcc gaacaactgg ccgcgtgtgg aagagttgtt    4680
ccgccgcaaa atctggcaac tgaaagagct gggttatgca gccgtggatg atgaaaccac    4740
gcaacagaca atgcgtgagt aaaagaact gggctacact tcggagccgc acgctgccgt    4800
agcttatcgt gcgctgcgtg atcagttgaa tccaggcgaa tatggcttgt tcctcggcac    4860
cgcgcatccg gcgaaattta agagagcgt ggaagcgatt ctcggtgaaa cgttggatct    4920
gccaaaagag ctggcagaac gtgctgattt acccttgctt tcacataatc tgcccgccga    4980
ttttgctgcg ttgcgtaaat tgatgatgaa tcatcagtaa aatctattca ttatctcaat    5040
caggccgggt ttgcttttat gcagcccggc tttttatga gaaattatg gagaaaaatg    5100
acagggaaaa aggagaaatt ctcaataaat gc                                 5132
```

<210> SEQ ID NO 21
<211> LENGTH: 820
<212> TYPE: PRT
<213> ORGANISM: Artificial Sequence
<220> FEATURE:
<223> OTHER INFORMATION: peptide sequence

<400> SEQUENCE: 21

Met Arg Val Leu Lys Phe Gly Gly Thr Ser Val Ala Asn Ala Glu Arg
1               5                   10                  15

Phe Leu Arg Val Ala Asp Ile Leu Glu Ser Asn Ala Arg Gln Gly Gln
            20                  25                  30

Val Ala Thr Val Leu Ser Ala Pro Ala Lys Ile Thr Asn His Leu Val
        35                  40                  45

Ala Met Ile Glu Lys Thr Ile Ser Gly Gln Asp Ala Leu Pro Asn Ile

```
                50                  55                  60
Ser Asp Ala Glu Arg Ile Phe Ala Glu Leu Leu Thr Gly Leu Ala Ala
 65                  70                  75                  80

Ala Gln Pro Gly Phe Pro Leu Ala Gln Leu Lys Thr Phe Val Asp Gln
                     85                  90                  95

Glu Phe Ala Gln Ile Lys His Val Leu His Gly Ile Ser Leu Leu Gly
                100                 105                 110

Gln Cys Pro Asp Ser Ile Asn Ala Ala Leu Ile Cys Arg Gly Glu Lys
                115                 120                 125

Met Ser Ile Ala Ile Met Ala Gly Val Leu Glu Ala Arg Gly His Asn
130                 135                 140

Val Thr Val Ile Asp Pro Val Glu Lys Leu Leu Ala Val Gly His Tyr
145                 150                 155                 160

Leu Glu Ser Thr Val Asp Ile Ala Glu Ser Thr Arg Arg Ile Ala Ala
                165                 170                 175

Ser Arg Ile Pro Ala Asp His Met Val Leu Met Ala Gly Phe Thr Ala
                180                 185                 190

Gly Asn Glu Lys Gly Glu Leu Val Val Leu Gly Arg Asn Gly Ser Asp
                195                 200                 205

Tyr Ser Ala Ala Val Leu Ala Ala Cys Leu Arg Ala Asp Cys Cys Glu
210                 215                 220

Ile Trp Thr Asp Val Asp Gly Val Tyr Thr Cys Asp Pro Arg Gln Val
225                 230                 235                 240

Pro Asp Ala Arg Leu Leu Lys Ser Met Ser Tyr Gln His Ala Met Glu
                245                 250                 255

Leu Ser Tyr Phe Gly Ala Lys Val Leu His Pro Arg Thr Ile Thr Pro
                260                 265                 270

Ile Ala Gln Phe Gln Ile Pro Cys Leu Ile Lys Asn Thr Gly Asn Pro
                275                 280                 285

Gln Ala Pro Gly Thr Leu Ile Gly Ala Ser Arg Asp Glu Asp Glu Leu
                290                 295                 300

Pro Val Lys Gly Ile Ser Asn Leu Asn Asn Met Ala Met Phe Ser Val
305                 310                 315                 320

Ser Gly Pro Gly Met Lys Gly Met Val Gly Met Ala Ala Arg Val Phe
                325                 330                 335

Ala Ala Met Ser Arg Ala Arg Ile Ser Val Val Leu Ile Thr Gln Ser
                340                 345                 350

Ser Ser Glu Tyr Ser Ile Ser Phe Cys Val Pro Gln Ser Asp Cys Val
                355                 360                 365

Arg Ala Glu Arg Ala Met Gln Glu Glu Phe Tyr Leu Glu Leu Lys Glu
                370                 375                 380

Gly Leu Leu Glu Pro Leu Ala Val Thr Glu Arg Leu Ala Ile Ile Ser
385                 390                 395                 400

Val Val Gly Asp Gly Met Arg Thr Leu Arg Gly Ile Ser Ala Lys Phe
                405                 410                 415

Phe Ala Ala Leu Ala Arg Ala Asn Ile Asn Ile Val Ala Ile Ala Gln
                420                 425                 430

Gly Ser Ser Glu Arg Ser Ile Ser Val Val Val Asn Asn Asp Asp Ala
                435                 440                 445

Thr Thr Gly Val Arg Val Thr His Gln Met Leu Phe Asn Thr Asp Gln
                450                 455                 460

Val Ile Glu Val Phe Val Ile Gly Val Gly Val Gly Gly Ala Leu
465                 470                 475                 480
```

```
Leu Glu Gln Leu Lys Arg Gln Gln Ser Trp Leu Lys Asn Lys His Ile
            485                 490                 495
Asp Leu Arg Val Cys Gly Val Ala Asn Ser Lys Ala Leu Leu Thr Asn
            500                 505                 510
Val His Gly Leu Asn Leu Glu Asn Trp Gln Glu Glu Leu Ala Gln Ala
            515                 520                 525
Lys Glu Pro Phe Asn Leu Gly Arg Leu Ile Arg Leu Val Lys Glu Tyr
            530                 535                 540
His Leu Leu Asn Pro Val Ile Val Asp Cys Thr Ser Ser Gln Ala Val
545                 550                 555                 560
Ala Asp Gln Tyr Ala Asp Phe Leu Arg Glu Gly Phe His Val Val Thr
                565                 570                 575
Pro Asn Lys Lys Ala Asn Thr Ser Ser Met Asp Tyr Tyr His Gln Leu
            580                 585                 590
Arg Tyr Ala Ala Glu Lys Ser Arg Arg Lys Phe Leu Tyr Asp Thr Asn
            595                 600                 605
Val Gly Ala Gly Leu Pro Val Ile Glu Asn Leu Gln Asn Leu Leu Asn
            610                 615                 620
Ala Gly Asp Glu Leu Met Lys Phe Ser Gly Ile Leu Ser Gly Ser Leu
625                 630                 635                 640
Ser Tyr Ile Phe Gly Lys Leu Asp Glu Gly Met Ser Phe Ser Glu Ala
                645                 650                 655
Thr Thr Leu Ala Arg Glu Met Gly Tyr Thr Glu Pro Asp Pro Arg Asp
            660                 665                 670
Asp Leu Ser Gly Met Asp Val Ala Arg Lys Leu Leu Ile Leu Ala Arg
            675                 680                 685
Glu Thr Gly Arg Glu Leu Glu Leu Ala Asp Ile Glu Ile Glu Pro Val
            690                 695                 700
Leu Pro Ala Glu Phe Asn Ala Glu Gly Asp Val Ala Ala Phe Met Ala
705                 710                 715                 720
Asn Leu Ser Gln Leu Asp Asp Leu Phe Ala Ala Arg Val Ala Lys Ala
                725                 730                 735
Arg Asp Glu Gly Lys Val Leu Arg Tyr Val Gly Asn Ile Asp Glu Asp
            740                 745                 750
Gly Val Cys Arg Val Lys Ile Ala Glu Val Asp Gly Asn Asp Pro Leu
            755                 760                 765
Phe Lys Val Lys Asn Gly Glu Asn Ala Leu Ala Phe Tyr Ser His Tyr
            770                 775                 780
Tyr Gln Pro Leu Pro Leu Val Leu Arg Gly Tyr Gly Ala Gly Asn Asp
785                 790                 795                 800
Val Thr Ala Ala Gly Val Phe Ala Asp Leu Leu Arg Thr Leu Ser Trp
                805                 810                 815
Lys Leu Gly Val
            820
```

<210> SEQ ID NO 22
<211> LENGTH: 310
<212> TYPE: PRT
<213> ORGANISM: Artificial Sequence
<220> FEATURE:
<223> OTHER INFORMATION: peptide sequence

<400> SEQUENCE: 22

```
Met Val Lys Val Tyr Ala Pro Ala Ser Ser Ala Asn Met Ser Val Gly
1               5                   10                  15
```

```
Phe Asp Val Leu Gly Ala Ala Val Thr Pro Val Asp Gly Ala Leu Leu
            20                  25                  30

Gly Asp Val Thr Val Glu Ala Glu Thr Phe Ser Leu Asn Asn
        35                  40                  45

Leu Gly Arg Phe Ala Asp Lys Leu Pro Ser Glu Pro Arg Glu Asn Ile
 50                  55                  60

Val Tyr Gln Cys Trp Glu Arg Phe Cys Gln Glu Leu Gly Lys Gln Ile
 65                  70                  75                  80

Pro Val Ala Met Thr Leu Glu Lys Asn Met Pro Ile Gly Ser Gly Leu
                85                  90                  95

Gly Ser Ser Ala Cys Ser Val Val Ala Ala Leu Met Ala Met Asn Glu
                100                 105                 110

His Cys Gly Lys Pro Leu Asn Asp Thr Arg Leu Leu Ala Leu Met Gly
            115                 120                 125

Glu Leu Glu Gly Arg Ile Ser Gly Ser Ile His Tyr Asp Asn Val Ala
130                 135                 140

Pro Cys Phe Leu Gly Gly Met Gln Leu Met Ile Glu Glu Asn Asp Ile
145                 150                 155                 160

Ile Ser Gln Gln Val Pro Gly Phe Asp Glu Trp Leu Trp Val Leu Ala
                165                 170                 175

Tyr Pro Gly Ile Lys Val Ser Thr Ala Glu Ala Arg Ala Ile Leu Pro
            180                 185                 190

Ala Gln Tyr Arg Arg Gln Asp Cys Ile Ala His Gly Arg His Leu Ala
            195                 200                 205

Gly Phe Ile His Ala Cys Tyr Ser Arg Gln Pro Glu Leu Ala Ala Lys
210                 215                 220

Leu Met Lys Asp Val Ile Ala Glu Pro Tyr Arg Glu Arg Leu Leu Pro
225                 230                 235                 240

Gly Phe Arg Gln Ala Arg Gln Ala Val Ala Glu Ile Gly Ala Val Ala
                245                 250                 255

Ser Gly Ile Ser Gly Ser Gly Pro Thr Leu Phe Ala Leu Cys Asp Lys
            260                 265                 270

Pro Glu Thr Ala Gln Arg Val Ala Asp Trp Leu Gly Lys Asn Tyr Leu
            275                 280                 285

Gln Asn Gln Glu Gly Phe Val His Ile Cys Arg Leu Asp Thr Ala Gly
290                 295                 300

Ala Arg Val Leu Glu Asn
305                 310

<210> SEQ ID NO 23
<211> LENGTH: 428
<212> TYPE: PRT
<213> ORGANISM: Artificial Sequence
<220> FEATURE:
<223> OTHER INFORMATION: peptide sequence

<400> SEQUENCE: 23

Met Lys Leu Tyr Asn Leu Lys Asp His Asn Glu Gln Val Ser Phe Ala
1                5                  10                  15

Gln Ala Val Thr Gln Gly Leu Gly Lys Asn Gln Gly Leu Phe Phe Pro
            20                  25                  30

His Asp Leu Pro Glu Phe Ser Leu Thr Glu Ile Asp Glu Met Leu Lys
        35                  40                  45

Leu Asp Phe Val Thr Arg Ser Ala Lys Ile Leu Ser Ala Phe Ile Gly
 50                  55                  60
```

Asp Glu Ile Pro Gln Glu Ile Leu Glu Arg Val Arg Ala Ala Phe
65                  70                  75                  80

Ala Phe Pro Ala Pro Val Ala Asn Val Glu Ser Asp Val Gly Cys Leu
            85                  90                  95

Glu Leu Phe His Gly Pro Thr Leu Ala Phe Lys Asp Phe Gly Gly Arg
            100                 105                 110

Phe Met Ala Gln Met Leu Thr His Ile Ala Gly Asp Lys Pro Val Thr
            115                 120                 125

Ile Leu Thr Ala Thr Ser Gly Asp Thr Gly Ala Ala Val Ala His Ala
130                 135                 140

Phe Tyr Gly Leu Pro Asn Val Lys Val Ile Leu Tyr Pro Arg Gly
145                 150                 155                 160

Lys Ile Ser Pro Leu Gln Glu Lys Leu Phe Cys Thr Leu Gly Gly Asn
                165                 170                 175

Ile Glu Thr Val Ala Ile Asp Gly Asp Phe Asp Ala Cys Gln Ala Leu
                180                 185                 190

Val Lys Gln Ala Phe Asp Asp Glu Glu Leu Lys Val Ala Leu Gly Leu
            195                 200                 205

Asn Ser Ala Asn Ser Ile Asn Ile Ser Arg Leu Leu Ala Gln Ile Cys
210                 215                 220

Tyr Tyr Phe Glu Ala Val Ala Gln Leu Pro Gln Glu Thr Arg Asn Gln
225                 230                 235                 240

Leu Val Val Ser Val Pro Ser Gly Asn Phe Gly Asp Leu Thr Ala Gly
                245                 250                 255

Leu Leu Ala Lys Ser Leu Gly Leu Pro Val Lys Arg Phe Ile Ala Ala
                260                 265                 270

Thr Asn Val Asn Asp Thr Val Pro Arg Phe Leu His Asp Gly Gln Trp
            275                 280                 285

Ser Pro Lys Ala Thr Gln Ala Thr Leu Ser Asn Ala Met Asp Val Ser
290                 295                 300

Gln Pro Asn Asn Trp Pro Arg Val Glu Glu Leu Phe Arg Arg Lys Ile
305                 310                 315                 320

Trp Gln Leu Lys Glu Leu Gly Tyr Ala Ala Val Asp Asp Glu Thr Thr
                325                 330                 335

Gln Gln Thr Met Arg Glu Leu Lys Glu Leu Gly Tyr Thr Ser Glu Pro
            340                 345                 350

His Ala Ala Val Ala Tyr Arg Ala Leu Arg Asp Gln Leu Asn Pro Gly
            355                 360                 365

Glu Tyr Gly Leu Phe Leu Gly Thr Ala His Pro Ala Lys Phe Lys Glu
370                 375                 380

Ser Val Glu Ala Ile Leu Gly Glu Thr Leu Asp Leu Pro Lys Glu Leu
385                 390                 395                 400

Ala Glu Arg Ala Asp Leu Pro Leu Ser His Asn Leu Pro Ala Asp
            405                 410                 415

Phe Ala Ala Leu Arg Lys Leu Met Met Asn His Gln
            420                 425

<210> SEQ ID NO 24
<211> LENGTH: 3275
<212> TYPE: DNA
<213> ORGANISM: Artificial Sequence
<220> FEATURE:
<223> OTHER INFORMATION: nucleotide sequence

<400> SEQUENCE: 24

```
atggctgact cgcaacccct gtccggtgct ccggaaggtg ccgaatattt aagagcagtg      60
ctgcgcgcgc cggtttacga ggcggcgcag gttacgccgc tacaaaaaat ggaaaaactg     120
tcgtcgcgtc ttgataacgt cattctggtg aagcgcgaag atcgccagcc agtgcacagc     180
tttaagctgc gcggcgcata cgccatgatg gcgggcctga cggaagaaca gaaagcgcac     240
ggcgtgatca ctgcttctgc gggtaaccac gcgcagggcg tcgcgttttc ttctgcgcgg     300
ttaggcgtga aggccctgat cgttatgcca accgccaccg ccgacatcaa agtcgacgcg     360
gtgcgcggct cggcggcga agtgctgctc cacggcgcga actttgatga agcgaaagcc     420
aaagcgatcg aactgtcaca gcagcagggg ttcacctggg tgccgccgtt cgaccatccg     480
atggtgattg ccgggcaagg cacgctggcg ctggaactgc tccagcagga cgcccatctc     540
gaccgcgtat ttgtgccagt cggcggcggc ggtctggctg ctggcgtggc ggtgctgatc     600
aaacaactga tgccgcaaat caaagtgatc gccgtagaag cggaagactc cgcctgcctg     660
aaagcagcgc tggatgcggg tcatccggtt gatctgccgc gcgtagggct atttgctgaa     720
ggcgtagcgg taaaacgcat cggtgacgaa accttccgtt tatgccagga gtatctcgac     780
gacatcatca ccgtcgatag cgatgcgatc tgtgcggcga tgaaggattt attcgaagat     840
gtgcgcgcgg tggcggaacc ctctggcgcg ctggcgctgg cgggaatgaa aaaatatatc     900
gccctgcaca acattcgcgg cgaacggctg gcgcatattc tttccggtgc caacgtgaac     960
ttccacggcc tgcgctacgt ctcagaacgc tgcgaactgg gcgaacagcg tgaagcgttg    1020
ttggcggtga ccattccgga agaaaaaggc agcttcctca aattctgcca actgcttggc    1080
gggcgttcgg tcaccgagtt caactaccgt tttgccgatg ccaaaaacgc ctgcatcttt    1140
gtcggtgtgc gcctgagccg cggcctcgaa gagcgcaaag aaattttgca gatgctcaac    1200
gacggcggct acagcgtggt tgatctctcc gacgacgaaa tggcgaagct acacgtgcgc    1260
tatatggtcg gcgacgtcc atcgcatccg ttgcaggaac gcctctacag cttcgaattc    1320
ccggaatcac cgggcgcgtt tctgcgcttc gccaacacgc tgggtacgta ctggaacatt    1380
tctttgttcc actatcgcag ccatggcacc gactacgggc gcgtactggc ggcgttcgaa    1440
cttggcgacc atgaaccgga tttcgaaacc cggctgaatg agctgggcta cgattgccac    1500
gacgaaacca ataacccggc gttcaggttc tttttggcgg gttagggaaa aatgcctgat    1560
agcgcttcgc ttatcaggcc tacccgcgcg acaacgtcat ttgtggttcg gcaaaatctt    1620
ccagaatgcc ccgcaataaa tttcctgtca tatagtgaat tcaatctcgc aaacgcgaac    1680
cgaacaataa gaagcacaac atcacgagga atcaccatgg ctaactactt caatacactg    1740
aatctgcgcc agcagctggc acagctgggc aaatgtcgct ttatgggccg cgatgaattc    1800
gccgatggcg cgagctacct tcagggtaaa aaagtagtca tcgtcggctg tggcgcacag    1860
ggtctgaacc agggcctgaa catgcgtgat tctggtctcg atatctccta cgctctgcgt    1920
aaagaagcga ttgccgagaa gcgcgcgtcc tggcgtaaag cgaccgaaaa tggttttaaa    1980
gtgggtactt acgaagaact gatcccacag gcggatctgg tgattaacct gacgccggac    2040
aagcagcact ctgatgtagt gcgcaccgta cagccactga tgaaagacgg cgcggcgctg    2100
ggctactcgc acgtttcaa catcgtcgaa gtgggcgagc agatccgtaa agatatcacc    2160
gtagtgatgg ttgcgccgaa atgcccaggc accgaagtgc gtgaagagta caacgtggg    2220 ttcggcgtac cgacgctgat tgccgttcac ccggaaaacg atccgaaagg cgaaggcatg    2280
gcgattgcca aagcctgggc ggctgcaacc ggtggtcacc gtgcgggtgt gctggaatcg    2340
```

```
tccttcgttg cggaagtgaa atctgacctg atgggcgagc aaaccatcct gtgcggtatg    2400
ttgcaggctg gctctctgct gtgcttcgac aagctggtgg aagaaggtac cgatccagca    2460
tacgcagaaa aactgattca gttcggttgg gaaaccatca ccgaagcact gaaacagggc    2520
ggcatcaccc tgatgatgga ccgtctctct aacccggcga actgcgtgc ttatgcgctt     2580 tctgaacagc tgaaagagat catggcaccc ctgttccaga acatatgga cgacatcatc    2640 tccggcgaat tctcttccgg tatgatggcg gactgggcca acgatgataa gaaactgctg    2700
acctggcgtg aagagaccgg caaaaccgcg tttgaaaccg cgccgcagta tgaaggcaaa    2760
atcggcgagc aggagtactt cgataaaggc gtactgatga ttgcgatggt gaaagcgggc    2820
gttgaactgg cgttcgaaac catggtcgat tccggcatca ttgaagagtc tgcatattat    2880
gaatcactgc acgagctgcc gctgattgcc aacaccatcg cccgtaagcg tctgtacgaa    2940
atgaacgtgg ttatctctga taccgctgag tacggtaact atctgttctc ttacgcttgt    3000
gtgccgttgc tgaaaccgtt tatggcagag ctgcaaccgg gcgacctggg taaagctatt    3060
ccggaaggcg cggtagataa cggcaactg cgtgatgtga cgaagcgat tcgcagccat      3120 gcgattgagc aggtaggtaa gaaactgcgc ggctatatga cagatatgaa acgtattgct    3180
gttgcgggtt aagtgcgcgc tgatgccctc accccgaccc tctcccacag ggagagggag    3240
aaaacactca aggccttctc ctggagaagg ccttg                               3275
```

<210> SEQ ID NO 25
<211> LENGTH: 514
<212> TYPE: PRT
<213> ORGANISM: E.coli

<400> SEQUENCE: 25

```
Met Ala Asp Ser Gln Pro Leu Ser Gly Ala Pro Glu Gly Ala Glu Tyr
1               5                   10                  15

Leu Arg Ala Val Leu Arg Ala Pro Val Tyr Glu Ala Ala Gln Val Thr
            20                  25                  30

Pro Leu Gln Lys Met Glu Lys Leu Ser Ser Arg Leu Asp Asn Val Ile
        35                  40                  45

Leu Val Lys Arg Glu Asp Arg Gln Pro Val His Ser Phe Lys Leu Arg
    50                  55                  60

Gly Ala Tyr Ala Met Met Ala Gly Leu Thr Glu Glu Gln Lys Ala His
65                  70                  75                  80

Gly Val Ile Thr Ala Ser Ala Gly Asn His Ala Gln Gly Val Ala Phe
                85                  90                  95

Ser Ser Ala Arg Leu Gly Val Lys Ala Leu Ile Val Met Pro Thr Ala
            100                 105                 110

Thr Ala Asp Ile Lys Val Asp Ala Val Arg Gly Phe Gly Gly Glu Val
        115                 120                 125

Leu Leu His Gly Ala Asn Phe Asp Glu Ala Lys Ala Lys Ala Ile Glu
    130                 135                 140

Leu Ser Gln Gln Gln Gly Phe Thr Trp Val Pro Phe Asp His Pro
145                 150                 155                 160

Met Val Ile Ala Gly Gln Gly Thr Leu Ala Leu Glu Leu Leu Gln Gln
                165                 170                 175

Asp Ala His Leu Asp Arg Val Phe Val Pro Val Gly Gly Gly Gly Leu
            180                 185                 190

Ala Ala Gly Val Ala Val Leu Ile Lys Gln Leu Met Pro Gln Ile Lys
        195                 200                 205
```

-continued

```
Val Ile Ala Val Glu Ala Glu Asp Ser Ala Cys Leu Lys Ala Ala Leu
            210                 215                 220
Asp Ala Gly His Pro Val Asp Leu Pro Arg Val Gly Leu Phe Ala Glu
225                 230                 235                 240
Gly Val Ala Val Lys Arg Ile Gly Asp Glu Thr Phe Arg Leu Cys Gln
                245                 250                 255
Glu Tyr Leu Asp Asp Ile Ile Thr Val Asp Ser Asp Ala Ile Cys Ala
            260                 265                 270
Ala Met Lys Asp Leu Phe Glu Asp Val Arg Ala Val Ala Glu Pro Ser
        275                 280                 285
Gly Ala Leu Ala Leu Ala Gly Met Lys Lys Tyr Ile Ala Leu His Asn
    290                 295                 300
Ile Arg Gly Glu Arg Leu Ala His Ile Leu Ser Gly Ala Asn Val Asn
305                 310                 315                 320
Phe His Gly Leu Arg Tyr Val Ser Glu Arg Cys Glu Leu Gly Glu Gln
                325                 330                 335
Arg Glu Ala Leu Leu Ala Val Thr Ile Pro Glu Glu Lys Gly Ser Phe
            340                 345                 350
Leu Lys Phe Cys Gln Leu Leu Gly Gly Arg Ser Val Thr Glu Phe Asn
        355                 360                 365
Tyr Arg Phe Ala Asp Ala Lys Asn Ala Cys Ile Phe Val Gly Val Arg
    370                 375                 380
Leu Ser Arg Gly Leu Glu Arg Lys Glu Ile Leu Gln Met Leu Asn
385                 390                 395                 400
Asp Gly Gly Tyr Ser Val Val Asp Leu Ser Asp Asp Glu Met Ala Lys
                405                 410                 415
Leu His Val Arg Tyr Met Val Gly Gly Arg Pro Ser His Pro Leu Gln
            420                 425                 430
Glu Arg Leu Tyr Ser Phe Glu Phe Pro Glu Ser Pro Gly Ala Leu Leu
        435                 440                 445
Arg Phe Leu Asn Thr Leu Gly Thr Tyr Trp Asn Ile Ser Leu Phe His
    450                 455                 460
Tyr Arg Ser His Gly Thr Asp Tyr Gly Arg Val Leu Ala Ala Phe Glu
465                 470                 475                 480
Leu Gly Asp His Glu Pro Asp Phe Glu Thr Arg Leu Asn Glu Leu Gly
                485                 490                 495
Tyr Asp Cys His Asp Glu Thr Asn Asn Pro Ala Phe Arg Phe Phe Leu
            500                 505                 510
Ala Gly

<210> SEQ ID NO 26
<211> LENGTH: 491
<212> TYPE: PRT
<213> ORGANISM: E.coli

<400> SEQUENCE: 26

Met Ala Asn Tyr Phe Asn Thr Leu Asn Leu Arg Gln Gln Leu Ala Gln
1               5                   10                  15
Leu Gly Lys Cys Arg Phe Met Gly Arg Asp Glu Phe Ala Asp Gly Ala
            20                  25                  30
Ser Tyr Leu Gln Gly Lys Lys Val Val Ile Val Gly Cys Gly Ala Gln
        35                  40                  45
Gly Leu Asn Gln Gly Leu Asn Met Arg Asp Ser Gly Leu Asp Ile Ser
    50                  55                  60
```

```
Tyr Ala Leu Arg Lys Glu Ala Ile Ala Glu Lys Arg Ala Ser Trp Arg
 65                  70                  75                  80

Lys Ala Thr Glu Asn Gly Phe Lys Val Gly Thr Tyr Glu Glu Leu Ile
                 85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
            115                 120                 125

Gly Tyr Ser His Gly Phe Asn Ile Val Glu Val Gly Glu Gln Ile Arg
            130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Thr Gly Gly His Arg Ala Gly Val Leu Glu Ser
            195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
            275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
            355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
            435                 440                 445

Pro Glu Gly Ala Val Asp Asn Gly Gln Leu Arg Asp Val Asn Glu Ala
            450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
```

<210> SEQ ID NO 27
<211> LENGTH: 6556
<212> TYPE: DNA
<213> ORGANISM: Artificial Sequence
<220> FEATURE:
<223> OTHER INFORMATION: nucleotide sequence

<400> SEQUENCE: 27

```
atgacagccc ttctacgagt gattagcctg gtcgtgatta gcgtggtggt gattattatc     60
ccaccgtgcg gggctgcact tggacgagga aaggcttaga gatcaagcct taacgaacta    120
agaccccgc accgaaaggt ccgggggttt tttttgacct taaaaacata accgaggagc     180
agacaatgaa taacagcaca aaattctgtt tctcaagatt caggacgggg aactaactat    240
gaatggcgca cagtgggtgg tacatgcgtt gcgggcacag ggtgtgaaca ccgttttcgg    300
ttatccgggt ggcgcaatta tgccggttta cgatgcattg tatgacgcg gcgtggagca     360
cttgctatgc cgacatgagc agggtgcggc aatggcggct atcggttatg ctcgtgctac    420
cggcaaaact ggcgtatgta tcgccacgtc tggtccgggc gcaaccaacc tgataaccgg    480
gcttgcggac gcactgttag attccatccc tgttgttgcc atcaccggtc aagtgtccgc    540
accgtttatc ggcactgacg catttcagga agtggatgtc ctgggattgt cgttagcctg    600
taccaagcac agctttctgg tgcagtcgct ggaagagttg ccgcgcatca tggctgaagc    660
attcgacgtt gcctgctcag gtcgtcctgg tccggttctg gtcgatatcc caaaagatat    720
ccagttagcc agcggtgacc tggaaccgtg gttcaccacc gttgaaaacg aagtgacttt    780
cccacatgcc gaagttgagc aagcgcgcca gatgctggca aaagcgcaaa accgatgct     840
gtacgttggc ggtggcgtgg gtatggcgca ggcagttccg gctttgcgtg aatttctcgc    900
tgccacaaaa atgcctgcca cctgtacgct gaaagggctg ggcgcagtag aagcagatta    960
tccgtactat ctgggcatgc tgggaatgca tggcaccaaa gcggcgaact tcgcggtgca   1020
ggagtgcgac ttgctgatcg ccgtgggtgc acgttttgat gaccgggtga ccggcaaact   1080
gaacaccttc gcaccacacg ccagtgttat ccatatggat atcgacccgg cagaaatgaa   1140
caagctgcgt caggcacatg tggcattaca aggtgattta aatgctctgt taccagcatt   1200
acagcagccg ttaaatatca atgactggca gctacactgc gcgcagctgc gtgatgaaca   1260
tgcctggcgt tacgaccatc ccggtgacgc tatctacgcg ccgttgttgt taaaacaact   1320
gtcagatcgt aaacctgcgg attgcgtcgt gaccacagat gtggggcagc accagatgtg   1380
ggctgcgcag cacatcgccc acactcgccc ggaaaatttc atcacctcca gcggcttagg   1440
caccatgggg tttggtttac cggcggcggt tggcgcgcaa gtcgcgcgac caaacgatac   1500
cgtcgtctgt atctccggtg acggctcttt catgatgaat gtgcaagagc tgggcaccgt   1560
aaaacgcaag cagttaccgt tgaaaatcgt cttactcgat aaccacggt tagggatggt    1620
tcgacaatgg cagcaactgt ttttccagga acgatatagc gaaaccaccc ttaccgataa    1680
ccccgatttc ctcatgttag ccagcgcctt cggcatccct ggccaacaca tcacccgtaa    1740
agaccaggtt gaagcggcac tcgacaccat gctgaacagt gatgggccat acctgcttca    1800
tgtctcaatc gacgaacttg agaacgtctg gccgctggtg ccgcctggtg ccagtaattc    1860
agaaatgttg gagaaattat catgatgcaa catcaggtca atgtatcggc tcgcttcaat    1920
ccagaaacct tagaacgtgt tttacgcgtg gtgcgtcatc gtggtttcca cgtctgctca    1980
atgaatatgg ccgccgccag cgatgcacaa aatataaata tcgaattgac cgttgccagc    2040
```

```
ccacggtcgg tcgacttact gtttagtcag ttaaataaac tggtggacgt cgcacacgtt   2100
gccatctgcc agagcacaac cacatcacaa caaatccgcg cctgagcgca aaaggaatat   2160
aaaaatgacc acgaagaaag ctgattacat ttggttcaat ggggagatgg ttcgctggga   2220
agacgcgaag gtgcatgtga tgtcgcacgc gctgcactat ggcacttcgg tttttgaagg   2280
catccgttgc tacgactcgc acaaaggacc ggttgtattc cgccatcgtg agcatatgca   2340
gcgtctgcat gactccgcca aaatctatcg cttcccggtt tcgcagagca ttgatgagct   2400
gatggaagct tgtcgtgacg tgatccgcaa aaacaatctc accagcgcct atatccgtcc   2460
gctgatcttc gtcggtgatg ttggcatggg agtaaacccg ccagcgggat actcaaccga   2520
cgtgattatc gctgctttcc cgtggggagc gtatctgggc gcagaagcgc tggagcaggg   2580
gatcgatgcg atggtttcct cctggaaccg cgcagcacca acaccatcc cgacggcggc    2640 aaaagccggt ggtaactacc tctcttccct gctggtgggt agcgaagcgc gccgccacgg   2700
ttatcaggaa ggtatcgcgc tggatgtgaa cggttatatc tctgaaggcg caggcgaaaa   2760
cctgtttgaa gtgaaagatg gtgtgctgtt caccccaccg ttcacctcct ccgcgctgcc   2820
gggtattacc cgtgatgcca tcatcaaact ggcgaaagag ctgggaattg aagtacgtga   2880
gcaggtgctg tcgcgcgaat ccctgtacct ggcggatgaa gtgtttatgt ccggtacggc   2940
ggcagaaatc acgccagtgc gcagcgtaga cggtattcag gttggcgaag ccgttgtgg    3000 cccggttacc aaacgcattc agcaagcctt cttcggcctc ttcactggcg aaaccgaaga   3060 taatgggc tggttagatc aagttaatca ataaatacaa aaaatgggac ggcacgcacc     3120 gtcccatttta cgagacagac actgggagta aataaagtat gcctaagtac cgttccgcca   3180
ccaccactca tggtcgtaat atggcgggtg ctcgtgcgct gtggcgcgcc accggaatga   3240
ccgacgccga tttcggtaag ccgattatcg cggttgtgaa ctcgttcacc caatttgtac   3300
cgggtcacgt ccatctgcgc gatctcggta aactggtcgc cgaacaaatt gaagcggctg   3360
gcggcgttgc caaagagttc aacaccattg cggtggatga tgggattgcc atgggccacg   3420
gggggatgct ttattcactg ccatctcgcg aactgatcgc tgattccgtt gagtatatgg   3480
tcaacgccca ctgcgccgac gccatggtct gcatctctaa ctgcgacaaa atcaccccgg   3540
ggatgctgat ggcttccctg cgcctgaata ttccggtgat ctttgtttcc ggcggcccga   3600
tggaggccga gaaaaccaaa ctttccgatc agatcatcaa gctcgatctg ttgatgcga    3660 tgatccaggg cgcagacccg aaagtatctg actcccagag cgatcaggtt gaacgttccg   3720
cgtgtccgac ctgcggttcc tgctccggga tgtttaccgc taactcaatg aactgcctga   3780
ccgaagcgct gggcctgtcg cagccgggca acggctcgct gctggcaacc cacgccgacc   3840
gtaagcagct gttccttaat gctggtaaac gcattgttga attgaccaaa cgttattacg   3900
agcaaaacga cgaaagtgca ctgccgcgta atatcgccag taaggcggcg tttgaaaacg   3960
ccatgacgct ggatatcgcg atgggtggat cgactaacac cgtacttcac ctgctggcg    4020 cggcgcagga agcggaaatc gacttcacca tgagtgatat cgataagctt tcccgcaagg   4080
ttccacagct gtgtaaagtt gcgccgagca cccagaaata ccatatggaa gatgttcacc   4140
gtgctggtgg tgttatcggt attctcggcg aactggatcg cgcggggtta ctgaaccgtg   4200
atgtgaaaaa cgtacttggc ctgacgttgc cgcaaacgct ggaacaatac gacgttatgc   4260
tgacccagga tgacgcggta aaaaatatgt tccgcgcagg tcctgcaggc attcgtacca   4320
cacaggcatt ctcgcaagat tgccgttggg atacgctgga cgacgatcgc gccaatggct   4380
```

```
gtatccgctc gctggaacac gcctacagca aagacggcgg cctggcggtg ctctacggta    4440
actttgcgga aaacggctgc atcgtgaaaa cggcaggcgt cgatgacagc atcctcaaat    4500
tcaccggccc ggcgaaagtg tacgaaagcc aggacgatgc ggtagaagcg attctcggcg    4560
gtaaagttgt cgccggagat gtggtagtaa ttcgctatga aggcccgaaa ggcggtccgg    4620
ggatgcagga aatgctctac ccaaccagct tcctgaaatc aatgggtctc ggcaaagcct    4680
gtgcgctgat caccgacggt cgtttctctg gtggcacctc tggtctttcc atcggccacg    4740
tctcaccgga agcggcaagc ggcggcagca ttggcctgat tgaagatggt gacctgatcg    4800
ctatcgacat cccgaaccgt ggcattcagt tacaggtaag cgatgccgaa ctggcggcgc    4860
gtcgtgaagc gcaggacgct cgaggtgaca aagcctggac gccgaaaaat cgtgaacgtc    4920
aggtctcctt tgccctgcgt gcttatgcca gcctggcaac cagcgccgac aaaggcgcgg    4980
tgcgcgataa atcgaaactg ggggttaat aatggctgac tcgcaacccc tgtccggtgc    5040
tccggaaggt gccgaatatt taagagcagt gctgcgcgcg ccggtttacg aggcggcgca    5100
ggttacgccg ctacaaaaaa tggaaaaact gtcgtcgcgt cttgataacg tcattctggt    5160
gaagcgcgaa gatcgccagc cagtgcacag ctttaagctg cgcggcgcat acgccatgat    5220
ggcgggcctg acgaagaac agaaagcgca cggcgtgatc actgcttctg cgggtaacca    5280
cgcgcagggc gtcgcgtttt cttctgcgcg gttaggcgtg aaggccctga tcgttatgcc    5340
aaccgccacc gccgacatca agtcgacgc ggtgcgcggc ttcggcggcg aagtgctgct    5400
ccacggcgcg aactttgatg aagcgaaagc caaagcgatc gaactgtcac agcagcaggg    5460
gttcacctgg gtgccgccgt tcgaccatcc gatggtgatt gccgggcaag gcacgctggc    5520
gctggaactg ctccagcagg acgcccatct cgaccgcgta tttgtgccag tcggcggcgg    5580
cggtctggct gctggcgtgg cggtgctgat caaacaactg atgccgcaaa tcaaagtgat    5640
cgccgtagaa gcggaagact ccgcctgcct gaaagcagcg ctggatgcgg tcatccggt     5700
tgatctgccg cgcgtagggc tatttgctga aggcgtagcg gtaaaacgca tcggtgacga    5760
aaccttccgt ttatgccagg agtatctcga cgacatcatc accgtcgata gcgatgcgat    5820
ctgtgcggca atgaaggatt tattcgaaga tgtgcgcgcg gtggcggaac cctctggcgc    5880
gctggcgctg gcgggaatga aaaatatat cgccctgcac aacattcgcg gcgaacggct    5940
ggcgcatatt ctttccggtg ccaacgtgaa cttccacggc ctgcgctacg tctcagaacg    6000
ctgcgaactg ggcgaacagc gtgaagcgtt gttggcggtg accattccgg aagaaaaagg    6060
cagcttcctc aaattctgcc aactgcttgg cgggcgttcg gtcaccgagt tcaactaccg    6120
ttttgccgat gccaaaaacg cctgcatctt tgtcggtgtg cgcctgagcc gcggcctcga    6180
agagcgcaaa gaattttgc agatgctcaa cgacggcggc tacagcgtgg ttgatctctc    6240
cgacgacgaa atggcgaagc tacacgtgcg ctatatggtc ggcggacgtc catcgcatcc    6300
gttgcaggaa cgcctctaca gcttcgaatt cccggaatca ccgggcgcgc tgctgcgctt    6360
cctcaacacg ctgggtacgt actggaacat ttctttgttc cactatcgca gccatggcac    6420
cgactacggg cgcgtactgg cggcgttcga acttggcgac catgaaccgg atttcgaaac    6480
ccggctgaat gagctgggct acgattgcca cgacgaaacc aataacccgg cgttcaggtt    6540
cttttttggcg ggttag                                                  6556
```

<210> SEQ ID NO 28
<211> LENGTH: 1000
<212> TYPE: DNA
<213> ORGANISM: E.coli

<400> SEQUENCE: 28

```
aatcagtaaa aggttgtgcc cgccagcagc ggtaatttcc agtcctcgct ttccttgttc      60
ctgaccgata acatcactga gatcatgttg tagcgcccgg gatactgcat cagttggttt     120
cgggcgttcg agagcgtgct taccttccag aaacgcacag acagcttgca gatgatcggc     180
tatcaggcat ccttcaccgt taattagccc cacttcatct tcgttatctt tcgcgacgat     240
aattttctg cccgacttaa tagcttcagt tgcactggag attgcgccgg gaacgccacg      300
cagagcgcct gtaagcgcca gttctccgac taattcatat tcatctaact tattggctgt     360
aagctgttct gaggccgcca gcaacgcaat ggcgatagga aaatcatatc gtcccccttc     420
ttttggcaga tcagctggag ccaggttgat ggtgattttt ttcgccggat attcatatcc     480
gctattgata atggcgctgc gcacgcgatc gcgagcttct tttaccgttg tttctggtaa     540
gcccaccatc gttaagccgg gtagacccttt actgatatgt acctcaacag tgatcggggg    600
cgcatttact cccagggctg cgcgggtatg aacaattgac agtgacataa gccctccttg     660
agtcaccatt atgtgcataa gatatcgctg ctgtagcccg ctaattcgtg aattttagtg     720
gctgattcct gtttatttgt gcaagtgaag ttgagttgtt ctggcggtgg aatgatgctc     780
gcaaaaatgc agcggacaaa ggatgaacta cgaggaaggg aacaacattc atactgaaat     840
tgaattttt tcactcacta ttttatttt aaaaaacaac aatttatatt gaaattatta      900
aacgcatcat aaaaatcggc caaaaatat cttgtactat ttacaaaacc tatggtaact      960
ctttaggcat tccttcgaac aagatgcaag aaaagacaaa                           1000
```

<210> SEQ ID NO 29
<211> LENGTH: 192
<212> TYPE: DNA
<213> ORGANISM: E.coli

<400> SEQUENCE: 29

```
gcttttcatt ctgactgcaa cgggcaatat gtctctgtgt ggattaaaaa aagagtgtct      60
gatagcagct tctgaactgg ttacctgccg tgagtaaatt aaaattttat tgacttaggt     120
cactaaatac tttaaccaat ataggcatag cgcacagaca gttgacaatt aatcatccgg     180
ctcgtataat gt                                                          192
```

<210> SEQ ID NO 30
<211> LENGTH: 717
<212> TYPE: DNA
<213> ORGANISM: Artificial Sequence
<220> FEATURE:
<223> OTHER INFORMATION: nucleotide sequence

<400> SEQUENCE: 30

```
atgagtaaag gagaagaact tttcactgga gttgtcccaa ttcttgttga attagatggt      60
gatgttaatg ggcacaaatt ttctgtcagt ggagagggtg aaggtgatgc aacatacgga     120
aaacttaccc ttaaatttat ttgcactact ggaaaactac ctgttccatg gccaacactt     180
gtcactactt tctcttatgg tgttcaatgc ttttcccgtt atccggatca tatgaaacgg     240
catgactttt tcaagagtgc catgcccgaa ggttatgtac aggaacgcac tatatctttc     300
aaagatgacg ggaactacaa gacgcgtgct gaagtcaagt ttgaaggtga tacccttgtt     360
aatcgtatcg agttaaaagg tattgatttt aagaagatg gaaacattct cggacacaaa     420
ctcgagtaca actataactc acacaatgta tacatcacgg cagacaaaca aaagaatgga     480
```

```
atcaaagcta acttcaaaat tcgccacaac attgaagatg gatccgttca actagcagac    540
cattatcaac aaaatactcc aattggcgat ggccctgtcc ttttaccaga caaccattac    600
ctgtcgacac aatctgccct tcgaaagat cccaacgaaa agcgtgacca catggtcctt    660
cttgagtttg taactgctgc tgggattaca catggcatgg atgagctcta caaataa      717

<210> SEQ ID NO 31
<211> LENGTH: 1645
<212> TYPE: DNA
<213> ORGANISM: E.coli

<400> SEQUENCE: 31
atgaatggcg cacagtgggt ggtacatgcg ttgcgggcac agggtgtgaa caccgttttc     60
ggttatccgg gtggcgcaat tatgccggtt tacgatgcat tgtatgacgg cggcgtggag    120
cacttgctat gccgacatga gcagggtgcg gcaatggcgg ctatcggtta tgctcgtgct    180
accggcaaaa ctggcgtatg tatcgccacg tctggtccgg gcgcaaccaa cctgataacc    240
gggcttgcgg acgcactgtt agattccatc cctgttgttg ccatcaccgg tcaagtgtcc    300
gcaccgttta tcggcactga cgcatttcag gaagtggatg tcctgggatt gtcgttagcc    360
tgtaccaagc acagctttct ggtgcagtcg ctggaagagt gccgcgcat catggctgaa    420 gcattcgacg ttgcctgctc aggtcgtcct ggtccggttc tggtcgatat cccaaaagat    480
atccagttag ccagcggtga cctggaaccg tggttcacca ccgttgaaaa cgaagtgact    540
ttcccacatg ccgaagttga gcaagcgcgc agatgctgg caaaagcgca aaaccgatg    600 ctgtacgttg gcggtggcgt gggtatggcg caggcagttc cggctttgcg tgaatttctc    660
gctgccacaa aaatgcctgc cacctgtacg ctgaaagggc tgggcgcagt agaagcagat    720
tatccgtact atctgggcat gctggggatg cacggcacca aagcggcaaa cttcgcggtg    780
caggagtgtg acctgctgat cgccgtgggc gcacgttttg atgaccgggt gaccggcaaa    840
ctgaacacct tcgcgccaca cgccagtgtt atccatatgg atatcgaccc ggcagaaatg    900
aacaagctgc gtcaggcaca tgtggcatta aaggtgatt taaatgctct gttaccagca    960
ttacagcagc cgttaaatca atgactggca gcaacactgc gcgcagctgc gtgatgaaca   1020
ttcctggcgt tacgaccatc ccggtgacgc tatctacgcg ccgttgttgt taaaacaact   1080
gtcggatcgt aaacctgcgg attgcgtcgt gaccacagat gtgggcagc accagatgtg   1140 ggctgcgcag cacatcgccc acactcgccc ggaaaatttc atcacctcca gcggtttagg   1200
taccatgggt tttggtttac cggcggcggt tggcgcacaa gtcgcgcgac cgaacgatac   1260
cgttgtctgt atctccggtg acggctcttt catgatgaat gtgcaagagc tgggcaccgt   1320
aaaacgcaag cagttaccgt tgaaaatcgt cttactcgat aaccaacggt tagggatggt   1380
tcgacaatgg cagcaactgt tttttcagga acgatacagc gaaaccaccc ttactgataa   1440
ccccgatttc ctcatgttag ccagcgcctt cggcatccat ggccaacaca tcacccggaa   1500
agaccaggtt gaagcggcac tcgacaccat gctgaacagt gatgggccat acctgcttca   1560
tgtctcaatc gacgaacttg agaacgtctg gccgctggtg ccgcctggcg ccagtaattc   1620
agaaatgttg gagaaattat catga                                         1645

<210> SEQ ID NO 32
<211> LENGTH: 16
<212> TYPE: PRT
<213> ORGANISM: E.coli

<400> SEQUENCE: 32
```

```
Met Asn Asn Ser Thr Lys Phe Cys Phe Ser Arg Phe Arg Thr Gly Asn
1               5                   10                  15

<210> SEQ ID NO 33
<211> LENGTH: 548
<212> TYPE: PRT
<213> ORGANISM: E.coli

<400> SEQUENCE: 33

Met Asn Gly Ala Gln Trp Val Val His Ala Leu Arg Ala Gln Gly Val
1               5                   10                  15

Asn Thr Val Phe Gly Tyr Pro Gly Gly Ala Ile Met Pro Val Tyr Asp
                20                  25                  30

Ala Leu Tyr Asp Gly Gly Val Glu His Leu Leu Cys Arg His Glu Gln
            35                  40                  45

Gly Ala Ala Met Ala Ala Ile Gly Tyr Ala Arg Ala Thr Gly Lys Thr
        50                  55                  60

Gly Val Cys Ile Ala Thr Ser Gly Pro Gly Ala Thr Asn Leu Ile Thr
65                  70                  75                  80

Gly Leu Ala Asp Ala Leu Leu Asp Ser Ile Pro Val Val Ala Ile Thr
                85                  90                  95

Gly Gln Val Ser Ala Pro Phe Ile Gly Thr Asp Ala Phe Gln Glu Val
            100                 105                 110

Asp Val Leu Gly Leu Ser Leu Ala Cys Thr Lys His Ser Phe Leu Val
        115                 120                 125

Gln Ser Leu Glu Glu Leu Pro Arg Ile Met Ala Glu Ala Phe Asp Val
130                 135                 140

Ala Cys Ser Gly Arg Pro Gly Pro Val Leu Val Asp Ile Pro Lys Asp
145                 150                 155                 160

Ile Gln Leu Ala Ser Gly Asp Leu Glu Pro Trp Phe Thr Thr Val Glu
                165                 170                 175

Asn Glu Val Thr Phe Pro His Ala Glu Val Glu Gln Ala Arg Gln Met
            180                 185                 190

Leu Ala Lys Ala Gln Lys Pro Met Leu Tyr Val Gly Gly Gly Val Gly
        195                 200                 205

Met Ala Gln Ala Val Pro Ala Leu Arg Glu Phe Leu Ala Ala Thr Lys
210                 215                 220

Met Pro Ala Thr Cys Thr Leu Lys Gly Leu Gly Ala Val Glu Ala Asp
225                 230                 235                 240

Tyr Pro Tyr Tyr Leu Gly Met Leu Gly Met His Gly Thr Lys Ala Ala
                245                 250                 255

Asn Phe Ala Val Gln Glu Cys Asp Leu Leu Ile Ala Val Gly Ala Arg
            260                 265                 270

Phe Asp Asp Arg Val Thr Gly Lys Leu Asn Thr Phe Ala Pro His Ala
        275                 280                 285

Ser Val Ile His Met Asp Ile Asp Pro Ala Glu Met Asn Lys Leu Arg
290                 295                 300

Gln Ala His Val Ala Leu Gln Gly Asp Leu Asn Ala Leu Leu Pro Ala
305                 310                 315                 320

Leu Gln Gln Pro Leu Asn Ile Asn Asp Trp Gln Leu His Cys Ala Gln
                325                 330                 335

Leu Arg Asp Glu His Ala Trp Arg Tyr Asp His Pro Gly Asp Ala Ile
            340                 345                 350

Tyr Ala Pro Leu Leu Leu Lys Gln Leu Ser Asp Arg Lys Pro Ala Asp
```

```
                355                 360                 365
Cys Val Val Thr Thr Asp Val Gly Gln His Gln Met Trp Ala Ala Gln
        370                 375                 380

His Ile Ala His Thr Arg Pro Glu Asn Phe Ile Thr Ser Ser Gly Leu
385                 390                 395                 400

Gly Thr Met Gly Phe Gly Leu Pro Ala Ala Val Gly Ala Gln Val Ala
                405                 410                 415

Arg Pro Asn Asp Thr Val Val Cys Ile Ser Gly Asp Gly Ser Phe Met
        420                 425                 430

Met Asn Val Gln Glu Leu Gly Thr Val Lys Arg Lys Gln Leu Pro Leu
                435                 440                 445

Lys Ile Val Leu Leu Asp Asn Gln Arg Leu Gly Met Val Arg Gln Trp
        450                 455                 460

Gln Gln Leu Phe Phe Gln Glu Arg Tyr Ser Glu Thr Thr Leu Thr Asp
465                 470                 475                 480

Asn Pro Asp Phe Leu Met Leu Ala Ser Ala Phe Gly Ile Pro Gly Gln
                485                 490                 495

His Ile Thr Arg Lys Asp Gln Val Glu Ala Ala Leu Asp Thr Met Leu
                500                 505                 510

Asn Ser Asp Gly Pro Tyr Leu Leu His Val Ser Ile Asp Glu Leu Glu
                515                 520                 525

Asn Val Trp Pro Leu Val Pro Pro Gly Ala Ser Asn Ser Glu Met Leu
        530                 535                 540

Glu Lys Leu Ser
545

<210> SEQ ID NO 34
<211> LENGTH: 87
<212> TYPE: PRT
<213> ORGANISM: E.coli

<400> SEQUENCE: 34

Met Met Gln His Gln Val Asn Val Ser Ala Arg Phe Asn Pro Glu Thr
1               5                   10                  15

Leu Glu Arg Val Leu Arg Val Val Arg His Arg Gly Phe His Val Cys
                20                  25                  30

Ser Met Asn Met Ala Ala Ala Ser Asp Ala Gln Asn Ile Asn Ile Glu
        35                  40                  45

Leu Thr Val Ala Ser Pro Arg Ser Val Asp Leu Leu Phe Ser Gln Leu
    50                  55                  60

Asn Lys Leu Val Asp Val Ala His Val Ala Ile Cys Gln Ser Thr Thr
65                  70                  75                  80

Thr Ser Gln Gln Ile Arg Ala
                85

<210> SEQ ID NO 35
<211> LENGTH: 309
<212> TYPE: PRT
<213> ORGANISM: E.coli

<400> SEQUENCE: 35

Met Thr Thr Lys Lys Ala Asp Tyr Ile Trp Phe Asn Gly Glu Met Val
1               5                   10                  15

Arg Trp Glu Asp Ala Lys Val His Val Met Ser His Ala Leu His Tyr
                20                  25                  30

Gly Thr Ser Val Phe Glu Gly Ile Arg Cys Tyr Asp Ser His Lys Gly
```

```
                    35                  40                  45
Pro Val Val Phe Arg His Arg Glu His Met Gln Arg Leu His Asp Ser
 50                  55                  60

Ala Lys Ile Tyr Arg Phe Pro Val Ser Gln Ser Ile Asp Glu Leu Met
 65                  70                  75                  80

Glu Ala Cys Arg Asp Val Ile Arg Lys Asn Asn Leu Thr Ser Ala Tyr
                 85                  90                  95

Ile Arg Pro Leu Ile Phe Val Gly Asp Val Gly Met Gly Val Asn Pro
                100                 105                 110

Pro Ala Gly Tyr Ser Thr Asp Val Ile Ile Ala Ala Phe Pro Trp Gly
                115                 120                 125

Ala Tyr Leu Gly Ala Glu Ala Leu Glu Gln Gly Ile Asp Ala Met Val
130                 135                 140

Ser Ser Trp Asn Arg Ala Ala Pro Asn Thr Ile Pro Thr Ala Ala Lys
145                 150                 155                 160

Ala Gly Gly Asn Tyr Leu Ser Ser Leu Leu Val Gly Ser Glu Ala Arg
                165                 170                 175

Arg His Gly Tyr Gln Glu Gly Ile Ala Leu Asp Val Asn Gly Tyr Ile
                180                 185                 190

Ser Glu Gly Ala Gly Glu Asn Leu Phe Glu Val Lys Asp Gly Val Leu
                195                 200                 205

Phe Thr Pro Pro Phe Thr Ser Ser Ala Leu Pro Gly Ile Thr Arg Asp
                210                 215                 220

Ala Ile Ile Lys Leu Ala Lys Glu Leu Gly Ile Glu Val Arg Glu Gln
225                 230                 235                 240

Val Leu Ser Arg Glu Ser Leu Tyr Leu Ala Asp Glu Val Phe Met Ser
                245                 250                 255

Gly Thr Ala Ala Glu Ile Thr Pro Val Arg Ser Val Asp Gly Ile Gln
                260                 265                 270

Val Gly Glu Gly Arg Cys Gly Pro Val Thr Lys Arg Ile Gln Gln Ala
                275                 280                 285

Phe Phe Gly Leu Phe Thr Gly Glu Thr Glu Asp Lys Trp Gly Trp Leu
                290                 295                 300

Asp Gln Val Asn Gln
305

<210> SEQ ID NO 36
<211> LENGTH: 616
<212> TYPE: PRT
<213> ORGANISM: E.coli

<400> SEQUENCE: 36

Met Pro Lys Tyr Arg Ser Ala Thr Thr Thr His Gly Arg Asn Met Ala
 1                   5                  10                  15

Gly Ala Arg Ala Leu Trp Arg Ala Thr Gly Met Thr Asp Ala Asp Phe
                 20                  25                  30

Gly Lys Pro Ile Ile Ala Val Val Asn Ser Phe Thr Gln Phe Val Pro
                 35                  40                  45

Gly His Val His Leu Arg Asp Leu Gly Lys Leu Val Ala Glu Gln Ile
                 50                  55                  60

Glu Ala Ala Gly Gly Val Ala Lys Glu Phe Asn Thr Ile Ala Val Asp
 65                  70                  75                  80

Asp Gly Ile Ala Met Gly His Gly Gly Met Leu Tyr Ser Leu Pro Ser
                 85                  90                  95
```

-continued

```
Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Val Ile Gly Ile Leu
                325                 330                 335

Gly Glu Leu Asp Arg Ala Gly Leu Leu Asn Arg Asp Val Lys Asn Val
            340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
    370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Ala Val Glu Ala
    450                 455                 460

Ile Leu Gly Gly Lys Val Val Ala Gly Asp Val Val Ile Arg Tyr
465                 470                 475                 480

Glu Gly Pro Lys Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
            500                 505                 510

Asp Gly Arg Phe Ser Gly Gly Thr Ser Gly Leu Ser Ile Gly His Val
```

```
            515                 520                 525
Ser Pro Glu Ala Ala Ser Gly Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
                595                 600                 605

Arg Asp Lys Ser Lys Leu Gly Gly
            610                 615

<210> SEQ ID NO 37
<211> LENGTH: 514
<212> TYPE: PRT
<213> ORGANISM: E.coli

<400> SEQUENCE: 37

Met Ala Asp Ser Gln Pro Leu Ser Gly Ala Pro Glu Gly Ala Glu Tyr
1               5                   10                  15

Leu Arg Ala Val Leu Arg Ala Pro Val Tyr Glu Ala Ala Gln Val Thr
                20                  25                  30

Pro Leu Gln Lys Met Glu Lys Leu Ser Ser Arg Leu Asp Asn Val Ile
            35                  40                  45

Leu Val Lys Arg Glu Asp Arg Gln Pro Val His Ser Phe Lys Leu Arg
    50                  55                  60

Gly Ala Tyr Ala Met Met Ala Gly Leu Thr Glu Glu Gln Lys Ala His
65                  70                  75                  80

Gly Val Ile Thr Ala Ser Ala Gly Asn His Ala Gln Gly Val Ala Phe
                85                  90                  95

Ser Ser Ala Arg Leu Gly Val Lys Ala Leu Ile Val Met Pro Thr Ala
            100                 105                 110

Thr Ala Asp Ile Lys Val Asp Ala Val Arg Gly Phe Gly Gly Glu Val
        115                 120                 125

Leu Leu His Gly Ala Asn Phe Asp Glu Ala Lys Ala Lys Ala Ile Glu
    130                 135                 140

Leu Ser Gln Gln Gln Gly Phe Thr Trp Val Pro Pro Phe Asp His Pro
145                 150                 155                 160

Met Val Ile Ala Gly Gln Gly Thr Leu Ala Leu Glu Leu Leu Gln Gln
                165                 170                 175

Asp Ala His Leu Asp Arg Val Phe Val Pro Val Gly Gly Gly Gly Leu
            180                 185                 190

Ala Ala Gly Val Ala Val Leu Ile Lys Gln Leu Met Pro Gln Ile Lys
        195                 200                 205

Val Ile Ala Val Glu Ala Glu Asp Ser Ala Cys Leu Lys Ala Ala Leu
    210                 215                 220

Asp Ala Gly His Pro Val Asp Leu Pro Arg Val Gly Leu Phe Ala Glu
225                 230                 235                 240

Gly Val Ala Val Lys Arg Ile Gly Asp Glu Thr Phe Arg Leu Cys Gln
                245                 250                 255

Glu Tyr Leu Asp Asp Ile Ile Thr Val Asp Ser Asp Ala Ile Cys Ala
            260                 265                 270
```

Ala Met Lys Asp Leu Phe Glu Asp Val Arg Ala Val Ala Glu Pro Ser
          275                 280                 285

Gly Ala Leu Ala Leu Ala Gly Met Lys Lys Tyr Ile Ala Leu His Asn
        290                 295                 300

Ile Arg Gly Glu Arg Leu Ala His Ile Leu Ser Gly Ala Asn Val Asn
305                 310                 315                 320

Phe His Gly Leu Arg Tyr Val Ser Glu Arg Cys Glu Leu Gly Glu Gln
                325                 330                 335

Arg Glu Ala Leu Leu Ala Val Thr Ile Pro Glu Glu Lys Gly Ser Phe
            340                 345                 350

Leu Lys Phe Cys Gln Leu Leu Gly Gly Arg Ser Val Thr Glu Phe Asn
        355                 360                 365

Tyr Arg Phe Ala Asp Ala Lys Asn Ala Cys Ile Phe Val Gly Val Arg
    370                 375                 380

Leu Ser Arg Gly Leu Glu Glu Arg Lys Glu Ile Leu Gln Met Leu Asn
385                 390                 395                 400

Asp Gly Gly Tyr Ser Val Val Asp Leu Ser Asp Glu Met Ala Lys
                405                 410                 415

Leu His Val Arg Tyr Met Val Gly Gly Arg Pro Ser His Pro Leu Gln
            420                 425                 430

Glu Arg Leu Tyr Ser Phe Glu Phe Pro Glu Ser Pro Gly Ala Leu Leu
        435                 440                 445

Arg Phe Leu Asn Thr Leu Gly Thr Tyr Trp Asn Ile Ser Leu Phe His
    450                 455                 460

Tyr Arg Ser His Gly Thr Asp Tyr Gly Arg Val Leu Ala Ala Phe Glu
465                 470                 475                 480

Leu Gly Asp His Glu Pro Asp Phe Glu Thr Arg Leu Asn Glu Leu Gly
                485                 490                 495

Tyr Asp Cys His Asp Glu Thr Asn Asn Pro Ala Phe Arg Phe Phe Leu
            500                 505                 510

Ala Gly

<210> SEQ ID NO 38
<211> LENGTH: 5057
<212> TYPE: DNA
<213> ORGANISM: Artificial Sequence
<220> FEATURE:
<223> OTHER INFORMATION: nucleotide sequence

<400> SEQUENCE: 38
atgacagccc ttctacgagt gattagcctg gtcgtgatta gcgtggtggt gattattatc    60
ccaccgtgcg gggctgcact tggacgagga aaggcttaga gatcaagcct taacgaacta   120 agaccccgc accgaaaggt ccgggggttt tttttgacct taaaaacata accgaggagc   180
agacaatgaa taacagcaca aaattctgtt tctcaagatt caggacgggg aactaactat   240
gaatggcgca cagtgggtgg tacatgcgtt gcgggcacag ggtgtgaaca ccgttttcgg   300
ttatccgggt ggcgcaatta tgccggttta cgatgcattg tatgacggcg cgtggagca    360 cttgctatgc cgacatgagc agggtgcggc aatggcggct atcggttatg ctcgtgctac   420
cggcaaaact ggcgtatgta tcgccacgtc tggtccgggc gcaaccaacc tgataaccgg   480
gcttgcggac gcactgttag attccatccc tgttgttgcc atcaccggtc aagtgtccgc   540
accgtttatc ggcactgacg catttcagga agtggatgtc ctgggattgt cgttagcctg   600
taccaagcac agctttctgg tgcagtcgct ggaagagttg ccgcgcatca tggctgaagc   660

```
attcgacgtt gcctgctcag gtcgtcctgg tccggttctg gtcgatatcc caaaagatat    720
ccagttagcc agcggtgacc tggaaccgtg gttcaccacc gttgaaaacg aagtgacttt    780
cccacatgcc gaagttgagc aagcgcgcca gatgctggca aaagcgcaaa aaccgatgct    840
gtacgttggc ggtggcgtgg gtatggcgca ggcagttccg gctttgcgtg aatttctcgc    900
tgccacaaaa atgcctgcca cctgtacgct gaaagggctg ggcgcagtag aagcagatta    960
tccgtactat ctgggcatgc tgggaatgca tggcaccaaa gcggcgaact tcgcggtgca   1020
ggagtgcgac ttgctgatcg ccgtgggtgc acgttttgat gaccgggtga ccggcaaact   1080
gaacaccttc gcaccacacg ccagtgttat ccatatggat atcgacccgg cagaaatgaa   1140
caagctgcgt caggcacatg tggcattaca aggtgattta aatgctctgt taccagcatt   1200
acagcagccg ttaaatatca atgactggca gctacactgc gcgcagctgc gtgatgaaca   1260
tgcctggcgt tacgaccatc ccggtgacgc tatctacgcg ccgttgttgt taaaacaact   1320
gtcagatcgt aaacctgcgg attgcgtcgt gaccacagat gtggggcagc accagatgtg   1380
ggctgcgcag cacatcgccc acactcgccc ggaaaatttc atcacctcca gcggcttagg   1440
caccatgggt tttggtttac cggcggcggt tggcgcgcaa gtcgcgcgac caaacgatac   1500
cgtcgtctgt atctccggtg acggctcttt catgatgaat gtgcaagagc tgggcaccgt   1560
aaaacgcaag cagttaccgt tgaaaatcgt cttactcgat aaccaacggt tagggatggt   1620
tcgacaatgg cagcaactgt ttttccagga acgatatagc gaaaccaccc ttaccgataa   1680
ccccgatttc ctcatgttag ccagcgcctt cggcatccct ggccaacaca tcacccgtaa   1740
agaccaggtt gaagcggcac tcgacaccat gctgaacagt gatgggccat acctgcttca   1800
tgtctcaatc gacgaacttg agaacgtctg gccgctggtg ccgcctggtg ccagtaattc   1860
agaaatgttg gagaaattat catgatgcaa catcaggtca atgtatcggc tcgcttcaat   1920
ccagaaacct agaacgtgt tttacgcgtg gtgcgtcatc gtggtttcca cgtctgctca   1980
atgaatatgg ccgccgccag cgatgcacaa aatataaata tcgaattgac cgttgccagc   2040
ccacggtcgg tcgacttact gtttagtcag ttaaataaac tggtggacgt cgcacacgtt   2100
gccatctgcc agagcacaac cacatcacaa caaatccgcg cctgagcgca aaaggaatat   2160
aaaaatgacc acgaagaaag ctgattacat ttggttcaat ggggagatgg ttcgctggga   2220
agacgcgaag gtgcatgtga tgtcgcacgc gctgcactat ggcacttcgg tttttgaagg   2280
catccgttgc tacgactcgc acaaaggacc ggttgtattc cgccatcgtg agcatatgca   2340
gcgtctgcat gactccgcca aaatctatcg cttcccggtt tcgcagagca ttgatgagct   2400
gatggaagct tgtcgtgacg tgatccgcaa aaacaatctc accagcgcct atatccgtcc   2460
gctgatcttc gtcggtgatg ttggcatggg agtaaacccg ccagcgggat actcaaccga   2520
cgtgattatc gctgctttcc cgtggggagc gtatctgggc gcagaagcgc tggagcaggg   2580
gatcgatgcg atggtttcct cctggaaccg cgcagcacca acaccatccc gacggcggc   2640
aaaagccggt ggtaactacc tctcttccct gctggtgggt agcgaagcgc gccgccacgg   2700
ttatcaggaa ggtatcgcgc tggatgtgaa cggttatatc tctgaaggcg caggcgaaaa   2760
cctgtttgaa gtgaaagatg gtgtgctgtt caccccaccg ttcacctcct ccgcgctgcc   2820
gggtattacc cgtgatgcca tcatcaaact ggcgaaagag ctgggaattg aagtacgtga   2880
gcaggtgctg tcgcgcgaat ccctgtacct ggcggatgaa gtgtttatgt ccggtacggc   2940
ggcagaaatc acgccagtgc gcagcgtaga cggtattcag gttggcgaag ccgttgtgg   3000
cccggttacc aaacgcattc agcaagcctt cttcggcctc ttcactggcg aaaccgaaga   3060
```

-continued

```
taaatggggc tggttagatc aagttaatca ataaatacaa aaatgggac ggcacgcacc      3120
gtcccattta cgagacagac actgggagta aataaagtat gcctaagtac cgttccgcca      3180
ccaccactca tggtcgtaat atggcgggtg ctcgtgcgct gtggcgcgcc accggaatga      3240
ccgacgccga tttcggtaag ccgattatcg cggttgtgaa ctcgttcacc caatttgtac      3300
cgggtcacgt ccatctgcgc gatctcggta aactggtcgc cgaacaaatt gaagcggctg      3360
gcggcgttgc caaagagttc aacaccattg cggtggatga tgggattgcc atgggccacg      3420
gggggatgct ttattcactg ccatctcgcg aactgatcgc tgattccgtt gagtatatgg      3480
tcaacgccca ctgcgccgac gccatggtct gcatctctaa ctgcgacaaa tcaccccgg       3540
ggatgctgat ggcttccctg cgcctgaata ttccggtgat cttttgtttcc ggcggcccga     3600
tggaggccgg gaaaaccaaa ctttccgatc agatcatcaa gctcgatctg ttgatgcga      3660
tgatccaggg cgcagacccg aaagtatctg actcccagag cgatcaggtt gaacgttccg      3720
cgtgtccgac ctgcggttcc tgctccggga tgtttaccgc taactcaatg aactgcctga     3780
ccgaagcgct gggcctgtcg cagccgggca acggctcgct gctggcaacc cacgccgacc      3840
gtaagcagct gttccttaat gctggtaaac gcattgttga attgaccaaa cgttattacg      3900
agcaaaacga cgaaagtgca ctgccgcgta atatcgccag taaggcggcg tttgaaaacg      3960
ccatgacgct ggatatcgcg atgggtggat cgactaacac cgtacttcac ctgctggcgg      4020
cggcgcagga agcggaaatc gacttcacca tgagtgatat cgataagctt tcccgcaagg      4080
ttccacagct gtgtaaagtt gcgccgagca cccagaaata ccatatggaa gatgttcacc      4140
gtgctggtgg tgttatcggt attctcggcg aactggatcg cgcggggtta ctgaaccgtg      4200
atgtgaaaaa cgtacttggc ctgacgttgc cgcaaacgct ggaacaatac gacgttatgc      4260
tgacccagga tgacgcggta aaaaatatgt tccgcgcagg cctgcaggc attcgtacca      4320
cacaggcatt ctcgcaagat tgccgttggg atacgctgga cgacgatcgc gccaatggct      4380
gtatccgctc gctggaacac gcctacagca aagacggcgg cctggcggtg ctctacggta      4440
actttgcgga aaacggctgc atcgtgaaaa cggcaggcgt cgatgacagc atcctcaaat      4500
tcaccggccc ggcgaaagtg tacgaaagcc aggacgatgg ggtagaagcg attctcggcg      4560
gtaaagttgt cgccggagat gtggtagtaa ttcgctatga aggcccgaaa ggcggtccgg      4620
ggatgcagga aatgctctac ccaaccagct tcctgaaatc aatgggtctc ggcaaagcct      4680
gtgcgctgat caccgacggt cgtttctctg gtggcacctc tggtctttcc atcggccacg      4740
tctcaccgga agcggcaagc ggcggcagca ttggcctgat tgaagatggt gacctgatcg      4800
ctatcgacat cccgaaccgt ggcattcagt tacaggtaag cgatgccgaa ctggcggcgc      4860
gtcgtgaagc gcaggacgct cgaggtgaca aagcctggac gccgaaaaat cgtgaacgtc      4920
aggtctcctt tgccctgcgt gcttatgcca gcctggcaac cagcgccgac aaaggcgcgg      4980
tgcgcgataa atcgaaactg gggggttaac tagcataacc ccttgggggcc tctaaacggg      5040
tcttgagggg tttttttg                                                    5057
```

<210> SEQ ID NO 39
<211> LENGTH: 162
<212> TYPE: DNA
<213> ORGANISM: Artificial Sequence
<220> FEATURE:
<223> OTHER INFORMATION: nucleotide sequence

<400> SEQUENCE: 39

| | |
|---|---:|
| caattccgac gtctaagaaa ccattattat catgacatta acctataaaa ataggcgtat | 60 |
| cacgaggccc tttcgtcttc acctcgagtc cctatcagtg atagagattg acctccctat | 120 |
| cagtgataga gatactgagc acatcagcag gacgcactga cc | 162 |

<210> SEQ ID NO 40
<211> LENGTH: 6865
<212> TYPE: DNA
<213> ORGANISM: E.coli

<400> SEQUENCE: 40

| | |
|---|---:|
| acgtaaaaag ggtatcgaca atgaaagcaa ttttcgtact gaaaggttgg tggcgcactt | 60 |
| cctgaaacgg gcagtgtatt caccatgcgt aaagcaatca gatacccagc ccgcctaatg | 120 |
| agcgggcttt ttttgaaca aaattagaga ataacaatgc aaacacaaaa accgactctc | 180 |
| gaactgctaa cctgcgaagg cgcttatcgc gacaatccca ccgcgctttt tcaccagttg | 240 |
| tgtggggatc gtccggcaac gctgctgctg gaatccgcag atatcgacag caaagatgat | 300 |
| ttaaaaagcc tgctgctggt agacagtgcg ctgcgcatta cagctttagg tgacactgtc | 360 |
| acaatccagg cactttccgg caacggcgaa gccctcctgg cactactgga taacgccctg | 420 |
| cctgcgggtg tggaaagtga acaatcacca aactgccgtg tgctgcgctt ccccctgtc | 480 |
| agtccactgc tggatgaaga cgcccgctta tgctcccttt cggttttga cgctttccgt | 540 |
| ttattgcaga atctgttgaa tgtaccgaag gaagaacgag aagccatgtt cttcggcggc | 600 |
| ctgttctctt atgaccttgt ggcgggattt gaagatttac cgcaactgtc agcggaaaat | 660 |
| aactgccctg atttctgttt ttatctcgct gaaacgctga tggtgattga ccatcagaaa | 720 |
| aaaagcaccc gtattcaggc cagcctgttt gctccgaatg aagaagaaaa acaacgtctc | 780 |
| actgctcgcc tgaacgaact acgtcagcaa ctgaccgaag ccgcgccgcc gctgccagtg | 840 |
| gtttccgtgc cgcatatgcg ttgtgaatgt aatcagagcg atgaagagtt cggtggcgta | 900 |
| gtgcgtttgt tgcaaaaagc gattcgcgct ggagaaattt tccaggtggt gccatctcgc | 960 |
| cgtttctctc tgccctgccc gtcaccgctg gcggcctatt acgtgctgaa aaagagtaat | 1020 |
| cccagcccgt acacgttttt tatgcaggat aatgatttca ccctatttgg cgcgtcgccg | 1080 |
| gaaagctcgc tcaagtatga tgccaccagc cgccagattg agatctaccc gattgccgga | 1140 |
| acacgcccac gcggtcgtcg cgccgatggt tcactggaca gagatctcga cagccgtatt | 1200 |
| gaactggaaa tgcgtaccga tcataaagag ctgtctgaac atctgatgct ggttgatctc | 1260 |
| gcccgtaatg atctggcacg catttgcacc cccggcagcc gctacgtcgc cgatctcacc | 1320 |
| aaagttgacc gttattccta tgtgatgcac ctcgtctctc gcgtagtcgg cgaactgcgt | 1380 |
| cacgatcttg acgccctgca cgcttatcgc gcctgtatga atatggggac gttaagcggt | 1440 |
| gcgccgaaag tacgcgctat gcagttaatt gccgaggcgg aaggtcgtcg ccgcggcagc | 1500 |
| tacgcggcg cggtaggtta tttcaccgcg catggcgatc tcgacacctg cattgtgatc | 1560 |
| cgctcggcgc tggtggaaaa cggtatcgcc accgtgcaag cgggtgctgg tgtagtcctt | 1620 |
| gattctgttc cgcagtcgga agccgacgaa accgtaaca aagcccgcgc tgtactgcgc | 1680 |
| gctattgcca ccgcgcatca tgcacaggag actttctgat ggctgacatt ctgctgctcg | 1740 |
| ataatatcga ctctttttacg tacaacctgg cagatcagtt gcgcagcaat gggcataacg | 1800 |
| tggtgattta ccgcaaccat attccggcgc aaaccttaat tgaacgcctg gcgaccatga | 1860 |
| gcaatccggt gctgatgctt tctcctggcc ccggtgtgcc gagcgaagcc ggttgtatgc | 1920 |
| cggaactcct cacccgcttg cgtggcaagc tgcccattat tggcatttgc ctcggacatc | 1980 |

```
aggcgattgt cgaagcttac gggggctatg tcggtcaggc gggcgaaatt ctccacggta    2040
aagcctccag cattgaacat gacggtcagg cgatgtttgc cggattaaca aacccgctgc    2100
cggtggcgcg ttatcactcg ctggttggca gtaacattcc ggccggttta accatcaacg    2160
cccattttaa tggcatggtg atggcagtac gtcacgatgc ggatcgcgtt tgtggattcc    2220
agttccatcc ggaatccatt ctcaccaccc agggcgctcg cctgctggaa caaacgctgg    2280
cctgggcgca gcagaaacta gagccagcca acacgctgca accgattctg gaaaaactgt    2340
atcaggcgca gacgcttagc caacaagaaa gccaccagct gttttcagcg gtggtgcgtg    2400
gcgagctgaa gccggaacaa ctggcggcgg cgctggtgag catgaaaatt cgcggtgagc    2460
acccgaacga gatcgccggg gcagcaaccg cgctactgga aaacgcagcg ccgttcccgc    2520
gcccggatta tctgtttgct gatatcgtcg gtactggcgg tgacggcagc aacagtatca    2580
atatttctac cgccagtgcg tttgtcgccg cggcctgtgg gctgaaagtg gcgaaacacg    2640
gcaaccgtag cgtctccagt aaatctggtt cgtccgatct gctggcggcg ttcggtatta    2700
atcttgatat gaacgccgat aaatcgcgcc aggcgctgga tgagttaggt gtatgtttcc    2760
tctttgcgcc gaagtatcac accggattcc gccacgcgat gccggttcgc cagcaactga    2820
aaacccgcac cctgttcaat gtgctggggc cattgattaa cccggcgcat ccgccgctgg    2880
cgttaattgg tgtttatagt ccggaactgg tgctgccgat tgccgaaacc ttgcgcgtgc    2940
tggggtatca acgcgcggcg gtggtgcaca gcggcgggat ggatgaagtt tcattacacg    3000
cgccgacaat cgttgccgaa ctgcatgacg gcgaaattaa aagctatcag ctcaccgcag    3060
aagactttgg cctgacaccc taccaccagg agcaactggc aggcggaaca ccggaagaaa    3120
accgtgacat tttaacacgt ttgttacaag gtaaaggcga cgccgcccat gaagcagccg    3180
tcgctgcgaa cgtcgccatg ttaatgcgcc tgcatggcca tgaagatctg caagccaatg    3240
cgcaaaccgt tcttgaggta ctgcgcagtg gttccgctta cgacagagtc accgcactgg    3300
cggcacgagg gtaaatgatg caaaccgttt tagcgaaaat cgtcgcagac aaggcgattt    3360
gggtagaagc ccgcaaacag cagcaaccgc tggccagttt tcagaatgag gttcagccga    3420
gcacgcgaca ttttttatgat gcgctacagg gtgcgcgcac ggcgtttatt ctggagtgca    3480
agaaagcgtc gccgtcaaaa ggcgtgatcc gtgatgattt cgatccagca cgcattgccg    3540
ccatttataa acattacgct tcggcaattt cggtgctgac tgatgagaaa tatttccagg    3600
ggagctttaa tttcctcccc atcgtcagcc aaatcgcccc gcagccgatt ttatgtaaag    3660
acttcattat cgaccttac cagatctatc tggcgcgcta ttaccaggcc gatgcctgct    3720
tattaatgct ttcagtactg gatgacgacc aatatcgcca gcttgccgcc gtcgctcaca    3780
gtctggagat gggggtgctg accgaagtca gtaatgaaga ggaacaggag cgcgccattg    3840
cattgggagc aaaggtcgtt ggcatcaaca accgcgatct gcgtgatttg tcgattgatc    3900
tcaaccgtac ccgcgagctt gcgccgaaac tggggcacaa cgtgacggta atcagcgaat    3960
ccggcatcaa tacttacgct caggtgcgcg agttaagcca cttcgctaac ggttttctga    4020
ttggttcggc gttgatggcc catgacgatt gcacgccgcc cgtgcgccgg tgttgctgg    4080 gtgagaataa agtatgtggc ctgacgcgtg ggcaagatgc taaagcagct tatgacgcgg    4140
gcgcgattta cggtgggttg atttttgttg cgacatcacc gcgttgcgtc aacgttgaac    4200
aggcgcagga agtgatggct gcggcaccgt tgcagtatgt tggcgtgttc cgcaatcacg    4260
atattgccga tgtggtggac aaagctaagg tgttatcgct ggcggcagtg caactgcatg    4320
```

```
gtaatgaaga acagctgtat atcgatacgc tgcgtgaagc tctgccagca catgttgcca    4380
tctggaaagc attaagcgtc ggtgaaaccc tgcccgcccg cgagtttcag cacgttgata    4440
aatatgtttt agacaacggc cagggtggaa gcgggcaacg ttttgactgg tcactattaa    4500
atggtcaatc gcttggcaac gttctgctgg cgggggggctt aggcgcagat aactgcgtgg    4560
aagcggcaca aaccggctgc gccggacttg attttaattc tgctgtagag tcgcaaccgg    4620
gcatcaaaga cgcacgtctt ttggcctcgg ttttccagac gctgcgcgca tattaaggaa    4680
aggaacaatg acaacattac ttaaccccta ttttggtgag tttggcggca tgtacgtgcc    4740
acaaatcctg atgcctgctc tgcgccagct ggaagaagct tttgtcagtg cgcaaaaaga    4800
tcctgaattt caggctcagt tcaacgacct gctgaaaaac tatgccgggc gtccaaccgc    4860
gctgaccaaa tgccagaaca ttacagccgg acgaacacc acgctgtatc tcaagcgtga    4920
agatttgctg cacggcggcg cgcataaaac taaccaggtg ctggggcagg cgttgctggc    4980
gaagcggatg ggtaaaaccg aaatcatcgc cgaaaccggt gccggtcagc atggcgtggc    5040
gtcggccctt gccagcgccc tgctcggcct gaaatgccgt atttatatgg gtgccaaaga    5100
cgttgaacgc cagtcgccta acgttttttcg tatgcgctta atgggtgcgg aagtgatccc    5160
ggtgcatagc ggttccgcga cgctgaaaga tgcctgtaac gaggcgctgc gcgactggtc    5220
cggtagttac gaaaccgcgc actatatgct gggcaccgca gctggcccgc atccttatcc    5280
gaccattgtg cgtgagtttc agcggatgat ggcgaagaa accaaagcgc agattctgga    5340
aagagaaggt cgcctgccgg atgccgttat cgcctgtgtt ggcggcggtt cgaatgccat    5400
cggcatgttt gctgatttca tcaatgaaac caacgtcggc ctgattggtg tggagccagg    5460
tggtcacggt atcgaaactg gcgagcacgg cgcaccgcta aaacatggtc gcgtgggtat    5520
ctatttcggt atgaaagcgc cgatgatgca aaccgaagac gggcagattg aagaatctta    5580
ctccatctcc gccggactgg atttcccgtc tgtcggccca caacacgcgt atcttaacag    5640
cactggacgc gctgattacg tgtctattac cgatgatgaa gcccttgaag ccttcaaaac    5700
gctgtgcctg cacgaaggga tcatcccggc gctggaatcc tcccacgccc tggcccatgc    5760
gttgaaaatg atgcgcgaaa acccggataa agagcagcta ctggtggtta accttttccgg    5820 tcgcggcgat aaagacatct tcaccgttca cgatattttg aaagcacgag gggaaatctg    5880
atggaacgct acgaatctct gtttgcccag ttgaaggagc gcaaagaagg cgcattcgtt    5940
cctttcgtca cgctcggtga tccgggcatt gagcagtcat tgaaaattat cgatacgcta    6000
attgaagccg gtgctgacgc gctggagtta ggtatcccct ctccgacccc actggcggat    6060
ggcccgacga ttcaaaacgc cactctgcgc gcctttgcgg caggtgtgac tccggcacaa    6120
tgttttgaaa tgctggcact gattcgccag aaacacccga ccattcccat ggcctgttg    6180 atgtatgcca atctggtgtt taacaaaggc attgatgagt tttatgccca gtgcgaaaaa    6240
gtcggcgtcg attcggtgct ggttgccgat gtgccagttg aagagtccgc gcccttccgc    6300
caggccgcgt tgcgtcataa tgtcgcacct atcttcatct gcccgccaaa tgccgatgac    6360
gacctgctgc gccagatagc ctcttacggt cgtggttaca cctatttgct gtcacgagca    6420
ggcgtgaccg cgcagaaaaa ccgcgccgcg ttaccccctca atcatctggt tgcgaagctg    6480
aaagagtaca acgctgcacc tccattgcag ggatttggta tttccgcccc ggatcaggta    6540
aaagcagcga ttgatgcagg agctgcgggc gcgattctg gttcggccat tgttaaaatc    6600
atcgagcaac atattaatga gccagagaaa atgctggcgg cactgaaagt ttttgtacaa    6660
ccgatgaaag cggcgacgcg cagttaatcc cacagccgcc agttccgctg gcggcatttt    6720
```

```
aactttcttt aatgaagccg gaaaaatcct aaattcattt aatatttatc ttttaccgt    6780
ttcgcttacc ccggtcgaac gtcaacttac gtcattttc cgcccaacag taatataatc     6840
aaacaaatta atcccgcaac ataac                                          6865
```

<210> SEQ ID NO 41
<211> LENGTH: 1403
<212> TYPE: DNA
<213> ORGANISM: E.coli

<400> SEQUENCE: 41

```
atctcgtttt tcgcgacaat ctggcgtttt tcttgctaat tccaggatta atccgttcat      60
agtgtaaaac cccgtttaca cattctgacg gaagatatag attggaagta ttgcattcac     120
taagataagt atggcaacac tggaacagac atgaattatc agaacgacga tttacgcatc     180
aaagaaatca agagttact tcctcctgtc gcattgctgg aaaaattccc cgctactgaa      240
aatgccgcga atacggttgc ccatgcccga aaagcgatcc ataagatcct gaaaggtaat     300
gatgatcgcc tgttggttgt gattggccca tgctcaattc atgatcctgt cgcggcaaaa    360
gagtatgcca ctcgcttgct ggcgctgcgt gaagagctga agatgagct ggaaatcgta     420
atgcgcgtct attttgaaaa gccgcgtacc acggtgggct ggaaagggct gattaacgat    480
ccgcatatgg ataatagctt ccagatcaac gacggtctgc gtatagcccg taaattgctg    540
cttgatatta cgacagcgg tctgccagcg gcaggtgagt ttctcgatat gatcacccta    600
caatatctcg ctgacctgat gagctgggc gcaattggcg cacgtaccac cgaatcgcag    660
gtgcaccgcg aactggcatc agggctttct tgtccggtcg gcttcaaaaa tggcaccgac   720
ggtacgatta agtggctat cgatgccatt aatgccgccg gtgcgccgca ctgcttcctg    780
tccgtaacga aatgggggca ttcggcgatt gtgaatacca gcggtaacgg cgattgccat    840
atcattctgc gcggcggtaa agagcctaac tacagcgcga agcacgttgc tgaagtgaaa    900
gaagggctga acaaagcagg cctgccagca caggtgatga tcgatttcag ccatgctaac    960
tcgtccaaac aattcaaaaa gcagatggat gtttgtgctg acgtttgcca gcagattgcc   1020
ggtggcgaaa aggccattat tggcgtgatg gtggaaagcc atctggtgga aggcaatcag   1080
agcctcgaga gcggggagcc gctggcctac ggtaagagca tcaccgatgc ctgcatcggc   1140
tgggaagata ccgatgctct gttacgtcaa ctggcgaatg cagtaaaagc gcgtcgcggg   1200
taaggtttaa ttgtcggatg cgccgtcaga gtggcgtatc cgatgaatca ccacaggcct   1260
gataagtcgc gcagcgtcgc atcaggcaat gtgctccatt gttagcaaca aaaaagccga   1320
ctcacttgca gtcggctttc tcattttaaa cgaatgacgt ttacttcgct ttaccctggt   1380
ttgcaaccgc cgctgctttc gct                                           1403
```

<210> SEQ ID NO 42
<211> LENGTH: 350
<212> TYPE: PRT
<213> ORGANISM: E.coli

<400> SEQUENCE: 42

```
Met Asn Tyr Gln Asn Asp Asp Leu Arg Ile Lys Glu Ile Lys Glu Leu
1               5                   10                  15

Leu Pro Pro Val Ala Leu Leu Glu Lys Phe Pro Ala Thr Glu Asn Ala
            20                  25                  30

Ala Asn Thr Val Ala His Ala Arg Lys Ala Ile His Lys Ile Leu Lys
        35                  40                  45
```

Gly Asn Asp Asp Arg Leu Leu Val Val Ile Gly Pro Cys Ser Ile His
            50                  55                  60

Asp Pro Val Ala Ala Lys Glu Tyr Ala Thr Arg Leu Leu Ala Leu Arg
 65                  70                  75                  80

Glu Glu Leu Lys Asp Glu Leu Glu Ile Val Met Arg Val Tyr Phe Glu
                 85                  90                  95

Lys Pro Arg Thr Thr Val Gly Trp Lys Gly Leu Ile Asn Asp Pro His
            100                 105                 110

Met Asp Asn Ser Phe Gln Ile Asn Asp Gly Leu Arg Ile Ala Arg Lys
            115                 120                 125

Leu Leu Leu Asp Ile Asn Asp Ser Gly Leu Pro Ala Ala Gly Glu Phe
130                 135                 140

Leu Asp Met Ile Thr Leu Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
            195                 200                 205

Phe Leu Ser Val Thr Lys Trp Gly His Ser Ala Ile Val Asn Thr Ser
210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
            275                 280                 285

Ile Ala Gly Gly Glu Lys Ala Ile Ile Gly Val Met Val Glu Ser His
290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
            340                 345                 350

<210> SEQ ID NO 43
<211> LENGTH: 2342
<212> TYPE: DNA
<213> ORGANISM: E.coli

<400> SEQUENCE: 43
atccagagat tctgaagcg gcaaaaggat gttccatgta catgacgcgc ggcttgcggt       60
aaattgttgg caaattttcc ggcgtagccc aaaacgcgct gtcgtcaagt cgttaagggc    120
gtgcccttca tcatccgatc tggagtcaaa atgtcctcac gtaaagagct tgccaatgct    180
attcgtgcgc tgagcatgga cgcagtacag aaagccaaat ccggtcaccc gggtgcccct    240
atgggtatgg ctgacattgc cgaagtcctg tggcgtgatt tcctgaaaca caacccgcag    300
aatccgtcct gggctgaccg tgaccgcttc gtgctgtcca acggccacgg ctccatgctg    360
atctacagcc tgctgcacct caccggttac gatctgccga tggaagaact gaaaaacttc    420

-continued

```
cgtcagctgc actctaaaac tccgggtcac ccggaagtgg gttacaccgc tggtgtggaa      480
accaccaccg gtccgctggg tcagggtatt gccaacgcag tcggtatggc gattgcagaa      540
aaaacgctgg cggcgcagtt taaccgtccg ggccacgaca ttgtcgacca ctacacctac      600
gccttcatgg gcgacggctg catgatggaa ggcatctccc acgaagtttg ctctctggcg      660
ggtacgctga agctgggtaa actgattgca ttctacgatg acaacggtat ttctatcgat      720
ggtcacgttg aaggctggtt caccgacgac accgcaatgc gtttcgaagc ttacggctgg      780
cacgttattc gcgacatcga cggtcatgac gcggcatcta tcaaacgcgc agtagaagaa      840
gcgcgcgcag tgactgacaa accttccctg ctgatgtgca aaaccatcat cggtttcggt      900
tccccgaaca agccggtac ccacgactcc cacggtgcgc cgctgggcga cgctgaaatt      960
gccctgaccc cgaacaact gggctggaaa tatgcgccgt cgaaatcccc gtctgaaatc     1020
tatgctcagt gggatgcgaa agaagcaggc caggcgaaag aatccgcatg gaacgagaaa     1080
ttcgctgctt acgcgaaagc ttatccgcag gaagccgctg aatttacccg ccgtatgaaa     1140
ggcgaaatgc cgtctgactt cgacgctaaa gcgaaagagt tcatcgctaa actgcaggct     1200
aatccggcga aaatcgccag ccgtaaagcg tctcagaatg ctatcgaagc gttcggtccg     1260
ctgttgccgg aattcctcgg cggttctgct gacctggcgc cgtctaacct gacccctgtgg     1320 tctggttcta aagcaatcaa cgaagatgct gcgggtaact acatccacta cggtgttcgc     1380
gagttcggta tgaccgcgat tgctaacggt atctccctgc acggtggctt cctgccgtac     1440
acctccacct tcctgatgtt cgtggaatac gcacgtaacg ccgtacgtat ggctgcgctg     1500
atgaaacagc gtcaggtgat ggtttacacc cacgactcca tcggtctggg cgaagacggc     1560
ccgactcacc agccggttga gcaggtcgct tctctgcgcg taaccccgaa catgtctaca     1620
tggcgtccgt gtgaccaggt tgaatccgcg gtcgcgtgga atacggtgt tgagcgtcag     1680 gacggcccga ccgcactgat cctctcccgt cagaacctgg cgcagcagga acgaactgaa     1740
gagcaactgg caaacatcgc gcgcggtggt tatgtgctga aagactgcgc cggtcagccg     1800
gaactgattt tcatcgctac cggttcagaa gttgaactgg ctgttgctgc ctacgaaaaa     1860
ctgactgccg aaggcgtgaa agcgcgcgtg gtgtccatgc cgtctaccga cgcatttgac     1920
aagcaggatg ctgcttaccg tgaatccgta ctgccgaaag cggttactgc acgcgttgct     1980
gtagaagcgg gtattgctga ctactggtac aagtatgttg gcctgaacgg tgctatcgtc     2040
ggtatgacca ccttcggtga atctgctccg gcagagctgc tgtttgaaga gttcggcttc     2100
actgttgata cgttgttgc gaaagcaaaa gaactgctgt aattagcatt tcgggtaaaa     2160
aggtcgcttc ggcgaccttt tttattacct tgatatgtcc gtttgcggac aagcaataga     2220
taaggcgtgt tgtagatcac aaatatttat atgcaataaa tatcaattat gtaatatgca     2280
tcacgatatg cgtattgaca tttgttgtta tatctataac tcaatgttat ataagaaatt     2340
aa                                                                    2342
```

<210> SEQ ID NO 44
<211> LENGTH: 663
<212> TYPE: PRT
<213> ORGANISM: E.coli

<400> SEQUENCE: 44

```
Met Ser Ser Arg Lys Glu Leu Ala Asn Ala Ile Arg Ala Leu Ser Met
1               5                   10                  15

Asp Ala Val Gln Lys Ala Lys Ser Gly His Pro Gly Ala Pro Met Gly
```

```
                    20                  25                  30
Met Ala Asp Ile Ala Glu Val Leu Trp Arg Asp Phe Leu Lys His Asn
                35                  40                  45
Pro Gln Asn Pro Ser Trp Ala Asp Arg Asp Arg Phe Val Leu Ser Asn
            50                  55                  60
Gly His Gly Ser Met Leu Ile Tyr Ser Leu Leu His Leu Thr Gly Tyr
65                  70                  75                  80
Asp Leu Pro Met Glu Glu Leu Lys Asn Phe Arg Gln Leu His Ser Lys
                85                  90                  95
Thr Pro Gly His Pro Glu Val Gly Tyr Thr Ala Gly Val Glu Thr Thr
            100                 105                 110
Thr Gly Pro Leu Gly Gln Gly Ile Ala Asn Ala Val Gly Met Ala Ile
            115                 120                 125
Ala Glu Lys Thr Leu Ala Ala Gln Phe Asn Arg Pro Gly His Asp Ile
            130                 135                 140
Val Asp His Tyr Thr Tyr Ala Phe Met Gly Asp Gly Cys Met Met Glu
145                 150                 155                 160
Gly Ile Ser His Glu Val Cys Ser Leu Ala Gly Thr Leu Lys Leu Gly
                165                 170                 175
Lys Leu Ile Ala Phe Tyr Asp Asp Asn Gly Ile Ser Ile Asp Gly His
                180                 185                 190
Val Glu Gly Trp Phe Thr Asp Asp Thr Ala Met Arg Phe Glu Ala Tyr
            195                 200                 205
Gly Trp His Val Ile Arg Asp Ile Asp Gly His Asp Ala Ala Ser Ile
            210                 215                 220
Lys Arg Ala Val Glu Glu Ala Arg Ala Val Thr Asp Lys Pro Ser Leu
225                 230                 235                 240
Leu Met Cys Lys Thr Ile Ile Gly Phe Gly Ser Pro Asn Lys Ala Gly
                245                 250                 255
Thr His Asp Ser His Gly Ala Pro Leu Gly Asp Ala Glu Ile Ala Leu
                260                 265                 270
Thr Arg Glu Gln Leu Gly Trp Lys Tyr Ala Pro Phe Glu Ile Pro Ser
            275                 280                 285
Glu Ile Tyr Ala Gln Trp Asp Ala Lys Glu Ala Gly Gln Ala Lys Glu
            290                 295                 300
Ser Ala Trp Asn Glu Lys Phe Ala Ala Tyr Ala Lys Ala Tyr Pro Gln
305                 310                 315                 320
Glu Ala Ala Glu Phe Thr Arg Arg Met Lys Gly Glu Met Pro Ser Asp
                325                 330                 335
Phe Asp Ala Lys Ala Lys Glu Phe Ile Ala Lys Leu Gln Ala Asn Pro
                340                 345                 350
Ala Lys Ile Ala Ser Arg Lys Ala Ser Gln Asn Ala Ile Glu Ala Phe
            355                 360                 365
Gly Pro Leu Leu Pro Glu Phe Leu Gly Gly Ser Ala Asp Leu Ala Pro
            370                 375                 380
Ser Asn Leu Thr Leu Trp Ser Gly Ser Lys Ala Ile Asn Glu Asp Ala
385                 390                 395                 400
Ala Gly Asn Tyr Ile His Tyr Gly Val Arg Glu Phe Gly Met Thr Ala
                405                 410                 415
Ile Ala Asn Gly Ile Ser Leu His Gly Gly Phe Leu Pro Tyr Thr Ser
                420                 425                 430
Thr Phe Leu Met Phe Val Glu Tyr Ala Arg Asn Ala Val Arg Met Ala
            435                 440                 445
```

Ala Leu Met Lys Gln Arg Gln Val Met Val Tyr Thr His Asp Ser Ile
    450                 455                 460

Gly Leu Gly Glu Asp Gly Pro Thr His Gln Pro Val Glu Gln Val Ala
465                 470                 475                 480

Ser Leu Arg Val Thr Pro Asn Met Ser Thr Trp Arg Pro Cys Asp Gln
            485                 490                 495

Val Glu Ser Ala Val Ala Trp Lys Tyr Gly Val Glu Arg Gln Asp Gly
            500                 505                 510

Pro Thr Ala Leu Ile Leu Ser Arg Gln Asn Leu Ala Gln Gln Glu Arg
            515                 520                 525

Thr Glu Glu Gln Leu Ala Asn Ile Ala Arg Gly Gly Tyr Val Leu Lys
530                 535                 540

Asp Cys Ala Gly Gln Pro Glu Leu Ile Phe Ile Ala Thr Gly Ser Glu
545                 550                 555                 560

Val Glu Leu Ala Val Ala Ala Tyr Glu Lys Leu Thr Ala Glu Gly Val
            565                 570                 575

Lys Ala Arg Val Val Ser Met Pro Ser Thr Asp Ala Phe Asp Lys Gln
            580                 585                 590

Asp Ala Ala Tyr Arg Glu Ser Val Leu Pro Lys Ala Val Thr Ala Arg
    595                 600                 605

Val Ala Val Glu Ala Gly Ile Ala Asp Tyr Trp Tyr Lys Tyr Val Gly
610                 615                 620

Leu Asn Gly Ala Ile Val Gly Met Thr Thr Phe Gly Glu Ser Ala Pro
625                 630                 635                 640

Ala Glu Leu Leu Phe Glu Glu Phe Gly Phe Thr Val Asp Asn Val Val
            645                 650                 655

Ala Lys Ala Lys Glu Leu Leu
            660

<210> SEQ ID NO 45
<211> LENGTH: 520
<212> TYPE: PRT
<213> ORGANISM: E.coli

<400> SEQUENCE: 45

Met Gln Thr Gln Lys Pro Thr Leu Glu Leu Leu Thr Cys Glu Gly Ala
1               5                   10                  15

Tyr Arg Asp Asn Pro Thr Ala Leu Phe His Gln Leu Cys Gly Asp Arg
            20                  25                  30

Pro Ala Thr Leu Leu Leu Glu Ser Ala Asp Ile Asp Ser Lys Asp Asp
        35                  40                  45

Leu Lys Ser Leu Leu Leu Val Asp Ser Ala Leu Arg Ile Thr Ala Leu
    50                  55                  60

Gly Asp Thr Val Thr Ile Gln Ala Leu Ser Gly Asn Gly Glu Ala Leu
65                  70                  75                  80

Leu Ala Leu Leu Asp Asn Ala Leu Pro Ala Gly Val Glu Ser Glu Gln
                85                  90                  95

Ser Pro Asn Cys Arg Val Leu Arg Phe Pro Pro Val Ser Pro Leu Leu
            100                 105                 110

Asp Glu Asp Ala Arg Leu Cys Ser Leu Ser Val Phe Asp Ala Phe Arg
        115                 120                 125

Leu Leu Gln Asn Leu Leu Asn Val Pro Lys Glu Glu Arg Glu Ala Met
    130                 135                 140

Phe Phe Gly Gly Leu Phe Ser Tyr Asp Leu Val Ala Gly Phe Glu Asp

```
            145                 150                 155                 160
Leu Pro Gln Leu Ser Ala Glu Asn Asn Cys Pro Asp Phe Cys Phe Tyr
                165                 170                 175

Leu Ala Glu Thr Leu Met Val Ile Asp His Gln Lys Lys Ser Thr Arg
                180                 185                 190

Ile Gln Ala Ser Leu Phe Ala Pro Asn Glu Glu Lys Gln Arg Leu
                195                 200                 205

Thr Ala Arg Leu Asn Glu Leu Arg Gln Gln Leu Thr Glu Ala Ala Pro
        210                 215                 220

Pro Leu Pro Val Val Ser Val Pro His Met Arg Cys Glu Cys Asn Gln
225                 230                 235                 240

Ser Asp Glu Glu Phe Gly Gly Val Arg Leu Leu Gln Lys Ala Ile
                245                 250                 255

Arg Ala Gly Glu Ile Phe Gln Val Val Pro Ser Arg Arg Phe Ser Leu
                260                 265                 270

Pro Cys Pro Ser Pro Leu Ala Ala Tyr Tyr Val Leu Lys Lys Ser Asn
                275                 280                 285

Pro Ser Pro Tyr Thr Phe Phe Met Gln Asp Asn Asp Phe Thr Leu Phe
        290                 295                 300

Gly Ala Ser Pro Glu Ser Ser Leu Lys Tyr Asp Ala Thr Ser Arg Gln
305                 310                 315                 320

Ile Glu Ile Tyr Pro Ile Ala Gly Thr Arg Pro Arg Gly Arg Arg Ala
                325                 330                 335

Asp Gly Ser Leu Asp Arg Asp Leu Asp Ser Arg Ile Glu Leu Glu Met
                340                 345                 350

Arg Thr Asp His Lys Glu Leu Ser Glu His Leu Met Leu Val Asp Leu
        355                 360                 365

Ala Arg Asn Asp Leu Ala Arg Ile Cys Thr Pro Gly Ser Arg Tyr Val
        370                 375                 380

Ala Asp Leu Thr Lys Val Asp Arg Tyr Ser Tyr Val Met His Leu Val
385                 390                 395                 400

Ser Arg Val Val Gly Glu Leu Arg His Asp Leu Asp Ala Leu His Ala
                405                 410                 415

Tyr Arg Ala Cys Met Asn Met Gly Thr Leu Ser Gly Ala Pro Lys Val
                420                 425                 430

Arg Ala Met Gln Leu Ile Ala Glu Ala Glu Gly Arg Arg Arg Gly Ser
        435                 440                 445

Tyr Gly Gly Ala Val Gly Tyr Phe Thr Ala His Gly Asp Leu Asp Thr
        450                 455                 460

Cys Ile Val Ile Arg Ser Ala Leu Val Glu Asn Gly Ile Ala Thr Val
465                 470                 475                 480

Gln Ala Gly Ala Gly Val Val Leu Asp Ser Val Pro Gln Ser Glu Ala
                485                 490                 495

Asp Glu Thr Arg Asn Lys Ala Arg Ala Val Leu Arg Ala Ile Ala Thr
        500                 505                 510

Ala His His Ala Gln Glu Thr Phe
        515                 520

<210> SEQ ID NO 46
<211> LENGTH: 531
<212> TYPE: PRT
<213> ORGANISM: E.coli

<400> SEQUENCE: 46
```

```
Met Ala Asp Ile Leu Leu Asp Asn Ile Asp Ser Phe Thr Tyr Asn
1               5                   10                  15

Leu Ala Asp Gln Leu Arg Ser Asn Gly His Asn Val Val Ile Tyr Arg
            20                  25                  30

Asn His Ile Pro Ala Gln Thr Leu Ile Glu Arg Leu Ala Thr Met Ser
            35                  40                  45

Asn Pro Val Leu Met Leu Ser Pro Gly Pro Gly Val Pro Ser Glu Ala
        50                  55                  60

Gly Cys Met Pro Glu Leu Thr Arg Leu Arg Gly Lys Leu Pro Ile
65                  70                  75                  80

Ile Gly Ile Cys Leu Gly His Gln Ala Ile Val Glu Ala Tyr Gly Gly
                85                  90                  95

Tyr Val Gly Gln Ala Gly Glu Ile Leu His Gly Lys Ala Ser Ser Ile
            100                 105                 110

Glu His Asp Gly Gln Ala Met Phe Ala Gly Leu Thr Asn Pro Leu Pro
            115                 120                 125

Val Ala Arg Tyr His Ser Leu Val Gly Ser Asn Ile Pro Ala Gly Leu
            130                 135                 140

Thr Ile Asn Ala His Phe Asn Gly Met Val Met Ala Val Arg His Asp
145                 150                 155                 160

Ala Asp Arg Val Cys Gly Phe Gln Phe His Pro Glu Ser Ile Leu Thr
                165                 170                 175

Thr Gln Gly Ala Arg Leu Leu Glu Gln Thr Leu Ala Trp Ala Gln Gln
            180                 185                 190

Lys Leu Glu Pro Ala Asn Thr Leu Gln Pro Ile Leu Glu Lys Leu Tyr
            195                 200                 205

Gln Ala Gln Thr Leu Ser Gln Gln Glu Ser His Gln Leu Phe Ser Ala
            210                 215                 220

Val Val Arg Gly Glu Leu Lys Pro Glu Gln Leu Ala Ala Ala Leu Val
225                 230                 235                 240

Ser Met Lys Ile Arg Gly Glu His Pro Asn Glu Ile Ala Gly Ala Ala
                245                 250                 255

Thr Ala Leu Leu Glu Asn Ala Ala Pro Phe Pro Arg Pro Asp Tyr Leu
            260                 265                 270

Phe Ala Asp Ile Val Gly Thr Gly Gly Asp Gly Ser Asn Ser Ile Asn
            275                 280                 285

Ile Ser Thr Ala Ser Ala Phe Val Ala Ala Ala Cys Gly Leu Lys Val
            290                 295                 300

Ala Lys His Gly Asn Arg Ser Val Ser Ser Lys Ser Gly Ser Ser Asp
305                 310                 315                 320

Leu Leu Ala Ala Phe Gly Ile Asn Leu Asp Met Asn Ala Asp Lys Ser
                325                 330                 335

Arg Gln Ala Leu Asp Glu Leu Gly Val Cys Phe Leu Phe Ala Pro Lys
            340                 345                 350

Tyr His Thr Gly Phe Arg His Ala Met Pro Val Arg Gln Gln Leu Lys
            355                 360                 365

Thr Arg Thr Leu Phe Asn Val Leu Gly Pro Leu Ile Asn Pro Ala His
            370                 375                 380

Pro Pro Leu Ala Leu Ile Gly Val Tyr Ser Pro Glu Leu Val Leu Pro
385                 390                 395                 400

Ile Ala Glu Thr Leu Arg Val Leu Gly Tyr Gln Arg Ala Ala Val Val
                405                 410                 415

His Ser Gly Gly Met Asp Glu Val Ser Leu His Ala Pro Thr Ile Val
```

```
            420                 425                 430
Ala Glu Leu His Asp Gly Glu Ile Lys Ser Tyr Gln Leu Thr Ala Glu
                435                 440                 445
Asp Phe Gly Leu Thr Pro Tyr His Gln Glu Gln Leu Ala Gly Gly Thr
                450                 455                 460
Pro Glu Glu Asn Arg Asp Ile Leu Thr Arg Leu Leu Gln Gly Lys Gly
465                 470                 475                 480
Asp Ala Ala His Glu Ala Ala Val Ala Ala Asn Val Ala Met Leu Met
                485                 490                 495
Arg Leu His Gly His Glu Asp Leu Gln Ala Asn Ala Gln Thr Val Leu
                500                 505                 510
Glu Val Leu Arg Ser Gly Ser Ala Tyr Asp Arg Val Thr Ala Leu Ala
                515                 520                 525
Ala Arg Gly
    530

<210> SEQ ID NO 47
<211> LENGTH: 453
<212> TYPE: PRT
<213> ORGANISM: E.coli

<400> SEQUENCE: 47

Met Met Gln Thr Val Leu Ala Lys Ile Val Ala Asp Lys Ala Ile Trp
1               5                   10                  15
Val Glu Ala Arg Lys Gln Gln Pro Leu Ala Ser Phe Gln Asn Glu
                20                  25                  30
Val Gln Pro Ser Thr Arg His Phe Tyr Asp Ala Leu Gln Gly Ala Arg
                35                  40                  45
Thr Ala Phe Ile Leu Glu Cys Lys Lys Ala Ser Pro Ser Lys Gly Val
                50                  55                  60
Ile Arg Asp Asp Phe Asp Pro Ala Arg Ile Ala Ala Ile Tyr Lys His
65                  70                  75                  80
Tyr Ala Ser Ala Ile Ser Val Leu Thr Asp Glu Lys Tyr Phe Gln Gly
                85                  90                  95
Ser Phe Asn Phe Leu Pro Ile Val Ser Gln Ile Ala Pro Gln Pro Ile
                100                 105                 110
Leu Cys Lys Asp Phe Ile Ile Asp Pro Tyr Gln Ile Tyr Leu Ala Arg
                115                 120                 125
Tyr Tyr Gln Ala Asp Ala Cys Leu Leu Met Leu Ser Val Leu Asp Asp
                130                 135                 140
Asp Gln Tyr Arg Gln Leu Ala Ala Val Ala His Ser Leu Glu Met Gly
145                 150                 155                 160
Val Leu Thr Glu Val Ser Asn Glu Glu Glu Gln Glu Arg Ala Ile Ala
                165                 170                 175
Leu Gly Ala Lys Val Val Gly Ile Asn Asn Arg Asp Leu Arg Asp Leu
                180                 185                 190
Ser Ile Asp Leu Asn Arg Thr Arg Glu Leu Ala Pro Lys Leu Gly His
                195                 200                 205
Asn Val Thr Val Ile Ser Glu Ser Gly Ile Asn Thr Tyr Ala Gln Val
                210                 215                 220
Arg Glu Leu Ser His Phe Ala Asn Gly Phe Leu Ile Gly Ser Ala Leu
225                 230                 235                 240
Met Ala His Asp Asp Leu His Ala Ala Val Arg Arg Val Leu Leu Gly
                245                 250                 255
```

```
Glu Asn Lys Val Cys Gly Leu Thr Arg Gly Gln Asp Ala Lys Ala Ala
                260                 265                 270

Tyr Asp Ala Gly Ala Ile Tyr Gly Gly Leu Ile Phe Val Ala Thr Ser
            275                 280                 285

Pro Arg Cys Val Asn Val Glu Gln Ala Gln Glu Val Met Ala Ala Ala
        290                 295                 300

Pro Leu Gln Tyr Val Gly Val Phe Arg Asn His Asp Ile Ala Asp Val
305                 310                 315                 320

Val Asp Lys Ala Lys Val Leu Ser Leu Ala Ala Val Gln Leu His Gly
                325                 330                 335

Asn Glu Glu Gln Leu Tyr Ile Asp Thr Leu Arg Glu Ala Leu Pro Ala
            340                 345                 350

His Val Ala Ile Trp Lys Ala Leu Ser Val Gly Glu Thr Leu Pro Ala
        355                 360                 365

Arg Glu Phe Gln His Val Asp Lys Tyr Val Leu Asp Asn Gly Gln Gly
    370                 375                 380

Gly Ser Gly Gln Arg Phe Asp Trp Ser Leu Leu Asn Gly Gln Ser Leu
385                 390                 395                 400

Gly Asn Val Leu Leu Ala Gly Leu Gly Ala Asp Asn Cys Val Glu
                405                 410                 415

Ala Ala Gln Thr Gly Cys Ala Gly Leu Asp Phe Asn Ser Ala Val Glu
            420                 425                 430

Ser Gln Pro Gly Ile Lys Asp Ala Arg Leu Leu Ala Ser Val Phe Gln
        435                 440                 445

Thr Leu Arg Ala Tyr
    450

<210> SEQ ID NO 48
<211> LENGTH: 397
<212> TYPE: PRT
<213> ORGANISM: E.coli

<400> SEQUENCE: 48

Met Thr Thr Leu Leu Asn Pro Tyr Phe Gly Glu Phe Gly Gly Met Tyr
1               5                   10                  15

Val Pro Gln Ile Leu Met Pro Ala Leu Arg Gln Leu Glu Glu Ala Phe
            20                  25                  30

Val Ser Ala Gln Lys Asp Pro Glu Phe Gln Ala Gln Phe Asn Asp Leu
        35                  40                  45

Leu Lys Asn Tyr Ala Gly Arg Pro Thr Ala Leu Thr Lys Cys Gln Asn
    50                  55                  60

Ile Thr Ala Gly Thr Asn Thr Thr Leu Tyr Leu Lys Arg Glu Asp Leu
65                  70                  75                  80

Leu His Gly Gly Ala His Lys Thr Asn Gln Val Leu Gly Gln Ala Leu
                85                  90                  95

Leu Ala Lys Arg Met Gly Lys Thr Glu Ile Ile Ala Glu Thr Gly Ala
            100                 105                 110

Gly Gln His Gly Val Ala Ser Ala Leu Ala Ser Ala Leu Leu Gly Leu
        115                 120                 125

Lys Cys Arg Ile Tyr Met Gly Ala Lys Asp Val Glu Arg Gln Ser Pro
    130                 135                 140

Asn Val Phe Arg Met Arg Leu Met Gly Ala Glu Val Ile Pro Val His
145                 150                 155                 160

Ser Gly Ser Ala Thr Leu Lys Asp Ala Cys Asn Glu Ala Leu Arg Asp
                165                 170                 175
```

```
Trp Ser Gly Ser Tyr Glu Thr Ala His Tyr Met Leu Gly Thr Ala Ala
            180                 185                 190

Gly Pro His Pro Tyr Pro Thr Ile Val Arg Glu Phe Gln Arg Met Ile
        195                 200                 205

Gly Glu Glu Thr Lys Ala Gln Ile Leu Glu Arg Glu Gly Arg Leu Pro
    210                 215                 220

Asp Ala Val Ile Ala Cys Val Gly Gly Ser Asn Ala Ile Gly Met
225                 230                 235                 240

Phe Ala Asp Phe Ile Asn Glu Thr Asn Val Gly Leu Ile Gly Val Glu
                245                 250                 255

Pro Gly Gly His Gly Ile Glu Thr Gly Glu His Gly Ala Pro Leu Lys
        260                 265                 270

His Gly Arg Val Gly Ile Tyr Phe Gly Met Lys Ala Pro Met Met Gln
    275                 280                 285

Thr Glu Asp Gly Gln Ile Glu Glu Ser Tyr Ser Ile Ser Ala Gly Leu
290                 295                 300

Asp Phe Pro Ser Val Gly Pro Gln His Ala Tyr Leu Asn Ser Thr Gly
305                 310                 315                 320

Arg Ala Asp Tyr Val Ser Ile Thr Asp Asp Glu Ala Leu Glu Ala Phe
                325                 330                 335

Lys Thr Leu Cys Leu His Glu Gly Ile Ile Pro Ala Leu Glu Ser Ser
                340                 345                 350

His Ala Leu Ala His Ala Leu Lys Met Met Arg Glu Asn Pro Asp Lys
            355                 360                 365

Glu Gln Leu Leu Val Val Asn Leu Ser Gly Arg Gly Asp Lys Asp Ile
        370                 375                 380

Phe Thr Val His Asp Ile Leu Lys Ala Arg Gly Glu Ile
385                 390                 395

<210> SEQ ID NO 49
<211> LENGTH: 268
<212> TYPE: PRT
<213> ORGANISM: E.coli

<400> SEQUENCE: 49

Met Glu Arg Tyr Glu Ser Leu Phe Ala Gln Leu Lys Glu Arg Lys Glu
1               5                   10                  15

Gly Ala Phe Val Pro Phe Val Thr Leu Gly Asp Pro Gly Ile Glu Gln
            20                  25                  30

Ser Leu Lys Ile Ile Asp Thr Leu Ile Glu Ala Gly Ala Asp Ala Leu
        35                  40                  45

Glu Leu Gly Ile Pro Phe Ser Asp Pro Leu Ala Asp Gly Pro Thr Ile
    50                  55                  60

Gln Asn Ala Thr Leu Arg Ala Phe Ala Ala Gly Val Thr Pro Ala Gln
65                  70                  75                  80

Cys Phe Glu Met Leu Ala Leu Ile Arg Gln Lys His Pro Thr Ile Pro
                85                  90                  95

Ile Gly Leu Leu Met Tyr Ala Asn Leu Val Phe Asn Lys Gly Ile Asp
            100                 105                 110

Glu Phe Tyr Ala Gln Cys Glu Lys Val Gly Val Asp Ser Val Leu Val
        115                 120                 125

Ala Asp Val Pro Val Glu Glu Ser Ala Pro Phe Arg Gln Ala Ala Leu
    130                 135                 140

Arg His Asn Val Ala Pro Ile Phe Ile Cys Pro Pro Asn Ala Asp Asp
```

```
                145                 150                 155                 160
Asp Leu Leu Arg Gln Ile Ala Ser Tyr Gly Arg Gly Tyr Thr Tyr Leu
                165                 170                 175

Leu Ser Arg Ala Gly Val Thr Gly Ala Glu Asn Arg Ala Ala Leu Pro
            180                 185                 190

Leu Asn His Leu Val Ala Lys Leu Lys Glu Tyr Asn Ala Ala Pro Pro
        195                 200                 205

Leu Gln Gly Phe Gly Ile Ser Ala Pro Asp Gln Val Lys Ala Ala Ile
    210                 215                 220

Asp Ala Gly Ala Ala Gly Ala Ile Ser Gly Ser Ala Ile Val Lys Ile
225                 230                 235                 240

Ile Glu Gln His Ile Asn Glu Pro Glu Lys Met Leu Ala Ala Leu Lys
                245                 250                 255

Val Phe Val Gln Pro Met Lys Ala Ala Thr Arg Ser
            260                 265

<210> SEQ ID NO 50
<211> LENGTH: 162
<212> TYPE: DNA
<213> ORGANISM: Artificial Sequence
<220> FEATURE:
<223> OTHER INFORMATION: nucleotide sequence

<400> SEQUENCE: 50
caattccgac gtctaagaga ccattattat cgtgacatta acctataaga acaggcgtgt      60
cacgaggccc tttcgtcttc acctcgagtc cctatcagtg acagagattg acaccccctat    120 cagtgataga gatactgagc acatcagcag gacgcactga cc                        162

<210> SEQ ID NO 51
<211> LENGTH: 7230
<212> TYPE: DNA
<213> ORGANISM: Artificial Sequence
<220> FEATURE:
<223> OTHER INFORMATION: nucleotide sequence

<400> SEQUENCE: 51
atgacacgcg ttcaatttaa acaccaccat catcaccatc atcctgacta gtctttcagg      60
cgatgtgtgc tggaagacat tcagatcttc cagtggtgca tgaacgcatg agaaagcccc    120
cggaagatca ccttccgggg gcttttttat tgcgcggttg ataacggttc agacaggttt    180
aaagaggaat aacaaaatga cagacaaacac tcgtttacgc atagctatgc agaaatccgg    240
ccgtttaagt gatgactcac gcgaattgct ggcgcgctgt ggcattaaaa ttaatcttca    300
cacccagcgc ctgatcgcga tggcagaaaa catgccgatt gatattctgc gcgtgcgtga    360
cgacgacatt cccggtctgg taatggatgg cgtggtagac cttgggatta cggcgaaaa    420 cgtgctggaa gaagagctgc ttaaccgccg cgcccagggt gaagatccac gctactttac    480
cctgcgtcgt ctggatttcg gcggctgtcg tctttcgctg caacgccggt tgatgaagc    540 ctgggacggt ccgctctcct taaacggtaa acgtatcgcc acctcttatc ctcacctgct    600
caagcgttat ctcgaccaga aaggcatctc ttttaaatcc tgcttactga acggttctgt    660
tgaagtcgcc ccgcgtgccg gactggcgga tgcgatttgc gatctggttt ccaccggtgc    720
cacgctggaa gctaacggcc tgcgcgaagt cgaagttatc tatcgctcga aagcctgcct    780
gattcaacgc gatggcgaaa tgaagaatcc aaacagcaa ctgatcgaca aactgctgac    840
ccgtattcag ggtgtgatcc aggcgcgcga atcaaaatac atcatgatgc acgcaccgac    900
```

```
cgaacgtctg gatgaagtca tcgccctgct gccaggtgcc gaacgcccaa ctattctgcc    960
gctggcgggt gaccaacagc gcgtagcgat gcacatggtc agcagcaaaa ccctgttctg   1020
ggaaaccatg gaaaaactga aagcgctggg tgccagttca attctggtcc tgccgattga   1080
gaagatgatg gagtgatcgc catgagcttt aacacaatca ttgactggaa tagctgtact   1140
gcggagcaac aacgccagct gttaatgcgc ccggcgattt ccgcctctga aagcattacc   1200
cgcactgtta acgatattct cgataacgtg aaagcacgcg gcgatgaggc cctgcgggaa   1260
tacagcgcga agtttgataa aaccacggtt accgcgctga aggtgtctgc agaggagatc   1320
gccgccgcca gcgaacgcct gagcgacgag ctaaaacagg cgatggcggt ggcagtaaag   1380
aatattgaaa ccttccacac tgcgcaaaaa ctgccgccgg tagatgtaga aacgcagcca   1440
ggcgtgcgtt gccagcaggt cacgcgtccg gtagcttcag ttgggttgta tattcctggc   1500
ggctccgccc cgctcttctc aacggtatta atgctggcga ctccggcgag tattgcgggc   1560
tgtaaaaaag tggtgctgtg ctcaccgccg ccgattgccg atgagatcct ttatgcggcg   1620
cagctgtgcg gtgtgcagga cgtgtttaac gtcgcggcg cacaggccat tgccgcactg   1680
gcgtttggta cggaatctgt gccaaaagtg gacaaaatct tcgggccggg taacgccttt   1740
gtcaccgaag cgaaacgtca ggtgagccag cgtctgacg tgcggcgat cgatatgccc   1800
gcaggcccgt cggaagtgct ggtgattgct gacagcggcg ctacgccgga tttcgtggct   1860
tctgatttgc tctctcaggc tgaacacggc ccggactcac aggtgatttt actgacgccc   1920
gctgctgata tggcgcgtcg cgttgccgag gccgtcgaac gccaactggc agaactgccg   1980
cgtgccgaaa ccgccgcca ggcactgaac gccagccgcc tgatcgtgac taaagattta   2040
gcgcagtgcg tggagatctc caaccagtac ggcccggagc acctgatcat tcagacccgc   2100
aacgcccgtg aactggtcga tagcatcacc agcgccggtt cggtatttct tggtgactgg   2160
tcaccggaat cggcaggtga ttacgcctcc ggcaccaacc acgttctacc gacttacggt   2220
tacaccgcca cctgttccag cctcgggctg gcagatttcc agaagcgcat gaccgtacag   2280
gaactgtcga agagggggtt ctccgcgctg gcttcaacca tagaaacact ggccgccgcc   2340
gagcgcctga ccgcccacaa aaatgccgtt actttgcgtg ttaacgccct taaggagcaa   2400
gcatgagcac cgtgactatt accgatttag cgcgtgaaaa cgtccgcaac ctgacgccgt   2460
atcagtcggc gcgtcgtctg ggcggtaacg gcgatgtctg gctgaacgcc aacgaatacc   2520
ccactgccgt ggagtttcag cttactcagc aaacgctcaa ccgctacccg gaatgccagc   2580
cgaaagcgg gattgaaaat tacgcgcaat atgcaggcgt aaaaccggag caggtgctgg   2640
tcagccgtgg cgcggacgaa ggtattgaac tgctgattcg cgcttttttgc gaaccgggta   2700
aagacgccat cctctactgc ccgccaacgt acgcatgta cagcgtcagc gccgaaacga   2760
ttggcgtcga gtgccgcaca gtgccgacgc tggacaactg gcaactggac ttacagggca   2820
tttccgacaa gctggacggc gtaaaagtgg tttatgtttg cagccccaat aacccgaccg   2880
ggcaactgat caatccgcag gattttcgca ccctgctgga gttaacccgc ggtaaggcga   2940
ttgtggttgc cgatgaagcc tatatcgagt tttgcccgca ggcatcgctg ctggctggc   3000
tggcggaata tccgcacctg gctattttac gcacactgtc gaaagctttt gctctggcgg   3060
ggcttcgttg cggatttacg ctggcaaacg aagaagtcat caacctgctg atgaaagtga   3120
tcgcccccta cccgctctcg acgccggttg ccgacattgc ggcccaggcg ttaagcccac   3180
agggaatcgt cgccatgcgc gaacgggtag cgcaaattat tgcagaacgc gaatacctga   3240
ttgccgcact gaaagagatc ccctgcgtag agcaggtttt cgactctgaa accaactaca   3300
```

```
ttctggcgcg ctttaaagcc tccagtgcgg tgtttaaatc tttgtgggat cagggcatta   3360
tcttacgtga tcagaataaa caaccctctt taagcggctg cctgcgaatt accgtcggaa   3420
cccgtgaaga aagccagcgc gtcattgacg ccttacgtgc ggagcaagtt tgatgagtca   3480
gaagtatctt tttatcgatc gcgatggaac cctgattagc gaaccgccga gtgattttca   3540
ggtggaccgt tttgataaac tcgcctttga accgggcgtg atcccggaac tgctgaagct   3600
gcaaaaagcg ggctacaagc tggtgatgat cactaatcag gatggtcttg aacacaaag   3660
tttcccacag gcggatttcg atggcccgca caacctgatg atgcagatct tcacctcgca   3720
aggcgtacag tttgatgaag tgctgatttg tccgcacctg cccgccgatg agtgcgactg   3780
ccgtaagccg aaagtaaaac tggtggaacg ttatctggct gagcaagcga tggatcgcgc   3840
taacagttat gtgattggcg atcgcgcgac cgacattcaa ctggcggaaa acatgggcat   3900
tactggttta cgctacgacc gcgaaaccct gaactggcca atgattggcg agcaactcac   3960
cagacgtgac cgttacgctc acgtagtgcg taataccaaa gagacgcaga ttgacgttca   4020
ggtgtggctg atcgtgaag gtggcagcaa gattaacacc ggcgttggct ctttgatca   4080
tatgctggat cagatcgcta cccacggcgg tttccgcatg gaaatcaacg tcaaaggcga   4140
cctctatatc gacgatcacc acaccgtcga agataccggc ctggcgctgg gcgaagcgct   4200
aaaaatcgcc ctcggagaca aacgcggtat ttgccgcttt ggttttgtgc taccgatgga   4260
cgaatgcctt gcccgctgcg cgctggatat ctctggtcgc ccgcacctgg aatataaagc   4320
cgagtttacc taccagcgcg tgggcgatct cagcaccgaa atgatcgagc acttcttccg   4380
ttcgctctca tacaccatgg gcgtgacgct acacctgaaa accaaaggta aaacgatca   4440
tcaccgtgta gagagtctgt tcaaagcctt tggtcgcacc ctgcgccagg ccatccgcgt   4500
ggaaggcgat accctgccct cgtcgaaagg agtgctgtaa tgaacgtggt gatccttgat   4560
accggctgcg ccaacctgaa ctcggtgaag tctgccattg cgcgtcacgg ttatgaaccc   4620
aaagtcagcc gtgacccgga cgtcgtgttg ctggccgata aactgttttt acccggcgtt   4680
ggcactgcgc aagcggcgat ggatcaggta cgtgagcgcg agctgtttga tctcatcaaa   4740
gcctgtaccc aaccggtgct gggcatctgc ttagggatgc aactgctggg gcggcgcagc   4800
gaagagagca acggcgtcga cttgctgggc atcatcgacg aagacgtgcc gaaaatgacc   4860
gactttggtc tgccactgcc acatatgggc tggaaccgcg tttacccgca ggcaggcaac   4920
cgcctgtttc aggggattga agacggcgcg tactttttact ttgttcacag ctacgcaatg   4980
ccggtcaatc cgtggaccat cgcccagtgt aattacggcg aaccgttcac cgcggcggta   5040
caaaaagata acttctacgg cgtgcagttc cacccggagc gttctggtgc cgctggtgct   5100
aagttgctga aaaacttcct ggagatgtga tgattattcc ggcattagat ttaatcgacg   5160
gcactgtggt gcgtctccat cagggcgatt acggcaaaca gcgcgattac ggtaacgacc   5220
cgctgccgcg attgcaggat tacgccgcgc agggtgccga agtgctgcac ctggtggatc   5280
tgaccggggc aaaagatccg gctaaacgtc aaatcccgct gattaaaacc ctggtcgcgg   5340
gcgttaacgt tccggtgcag gttggcgcg gcgtgcgtag cgaagaagat gtggcggcgt   5400
tactggaagc gggcgttgcg cgcgtagtgg tcggctccac cgcggtgaaa tcacaagata   5460
tggtgaaagg ctggtttgaa cgcttcggtg ccgatgcctt agtgctggcg ctggatgtcc   5520
gtattgacga gcaaggcaac aagcaggtgg cagtcagcgg ctggcaagag aactcgggcg   5580
tttcactgga acaactggtg gaaacctatc tgcccgtcgg cctgaaacat gtgctgtgta   5640
```

| | |
|---|---|
| ccgatatctc gcgcgacggc acgctggcag gctctaacgt ctctttatat gaagaagtgt | 5700 |
| gcgccagata tccgcaggtg gcatttcagt cctccggcgg tattggcgac attgatgatg | 5760 |
| tggcggccct gcgtggcact ggtgtgcgcg gcgtaatagt tggtcgggca ttactggaag | 5820 |
| gtaaattcac cgtgaaggag gccatcgcat gctggcaaaa cgcataatcc catgtctcga | 5880 |
| cgttcgtgat ggtcaggtgg tgaaaggcgt acagtttcgc aaccatgaaa tcattggcga | 5940 |
| tatcgtgccg ctggcaaaac gctacgctga agaaggcgct gacgaactgg tgttctacga | 6000 |
| tatcaccgct tccagcgatg gccgtgtggt agataaaagc tgggtatctc gcgtggcgga | 6060 |
| agtgatcgac attccgtttt gtgtggcggg tgggattaag tctctggaag atgccgcgaa | 6120 |
| aattctttcc tttggcgcgg ataaaatttc catcaactct cctgcgctgg cagacccaac | 6180 |
| attaattact cgcctggccg atcgctttgg cgtgcagtgt attgtggtcg gtattgatac | 6240 |
| ctggtacgac gccgaaaccg gtaaatatca tgtgaatcaa tataccggcg atgaaagccg | 6300 |
| cacccgcgtc actcaatggg aaacgctcga ctgggtacag gaagtgcaaa acgcggtgc | 6360 |
| cggagaaatc gtcctcaata tgatgaatca ggacggcgtg cgtaacggtt acgacctcga | 6420 |
| acaactgaaa aaagtgcgtg aagtttgcca cgtcccgctg attgcctccg gtggcgcggg | 6480 |
| caccatggaa cacttcctcg aagccttccg cgatgccgac gttgacggcg cgctggcagc | 6540 |
| ttccgtattc cacaaacaaa taatcaatat tggtgaatta aaagcgtacc tggcaacaca | 6600 |
| gggcgtggag atcaggatat gttaacagaa caacaacgtc gcgaactgga ctgggaaaaa | 6660 |
| accgacggac ttatgccggt gattgtgcaa cacgcggtat ccggcgaagt gctaatgctg | 6720 |
| ggctatatga acccggaagc cttagacaaa accctcgaaa gcgcaaagt caccttcttc | 6780 |
| tcgcgcacta acagcgact gtggaccaaa ggcgaaacgt cgggcaattt cctcaacgta | 6840 |
| gtgagtattg ccccggactg cgacaacgac acgttactgg tgctggcgaa tcccatcggc | 6900 |
| ccgacctgcc acaaaggcac cagcagttgc ttcggcgaca ccgctcacca gtggctgttc | 6960 |
| ctgtatcaac tggaacaact gctcgccgag cgcaaatctg ccgatccgga aacctcctac | 7020 |
| accgccaaac tgtatgccag cggcaccaaa cgcattgcgc agaaagtggg tgaagaaggc | 7080 |
| gtggaaaccg cgctggcagc aacggtacat gaccgctttg agctgaccaa cgaggcgtct | 7140 |
| gatttgatgt atcacctgct ggtgttgttg caggatcagg ggctggattt aacgacggta | 7200 |
| attgagaacc tgcgtaaacg gcatcagtga | 7230 |

<210> SEQ ID NO 52
<211> LENGTH: 1691
<212> TYPE: DNA
<213> ORGANISM: E.coli

<400> SEQUENCE: 52

| | |
|---|---|
| cgcttatctg tttcctgcca gtacagataa tcgtcccatg attcctcaga ccagattagt | 60 |
| ttcactcaat gatgtccttt tccgttcctt tgcctgattt caggctatcg attgagtcca | 120 |
| tcaatctccg ggcgttagcg ggggagcgca gtagataagc cgtctcttcc agcgagttgt | 180 |
| attcttcgag tgacatcaga acacaagcct ctccattctg acgagtaata aggatcgggg | 240 |
| catgatcttc aacggctttc atcattgttg ccgacaaatt ctgacgcgct tcgctgtagc | 300 |
| taattgtacg catgtcaatc tcctcttttg tacagttcat tgtacaatga tgagcgttaa | 360 |
| ttaactattt attaattagt ttgtagatca aggtattgtc agtgagacga aaatccaggc | 420 |
| ttcgctattt ttggtgccat cagctaagag gacagtcctc ttagccccct cctttccccg | 480 |
| ctcattcatt aaacaaatcc attgccataa aatatataaa aaagcccttg ctttctaacg | 540 |

-continued

```
tgaaagtggt ttaggttaaa agacatcagt tgaataaaca ttcacagaga cttttatgac      600
acgcgttcaa tttaaacacc accatcatca ccatcatcct gactagtctt tcaggcgatg      660
tgtgctggaa gacattcaga tcttccagtg gtgcatgaac gcatgagaaa gcccccggaa      720
gatcaccttc cgggggcttt tttattgcgc ggttgataac ggttcagaca ggtttaaaga      780
ggaataacaa aatgacagac aacactcgtt tacgcatagc tatgcagaaa tccggccgtt      840
taagtgatga ctcacgcgaa ttgctggcgc gctgtggcat taaaattaat cttcacaccc      900
agcgcctgat cgcgatggca gaaaacatgc cgattgatat tctgcgcgtg cgtgacgacg      960
acattcccgg tctggtaatg gatggcgtgg tagaccttgg gattatcggc gaaaacgtgc     1020
tggaagaaga gctgcttaac cgccgcgccc agggtgaaga tccacgctac tttacccctgc     1080 gtcgtctgga tttcggcggc tgtcgtcttt cgctggcaac gccggttgat gaagcctggg     1140
acggtccgct ctccttaaac ggtaaacgta tcgccacctc ttatcctcac ctgctcaagc     1200
gttatctcga ccagaaaggc atctctttta aatcctgctt actgaacggt tctgttgaag     1260
tcgccccgcg tgccggactg gcggatgcga tttgcgatct ggtttccacc ggtgccacgc     1320
tggaagctaa cggcctgcgc gaagtcgaag ttatctatcg ctcgaaagcc tgcctgattc     1380
aacgcgatgg cgaaatggaa gaatccaaac agcaactgat cgacaaactg ctgacccgta     1440
ttcagggtgt gatccaggcg cgcgaatcaa aatacatcat gatgcacgca ccgaccgaac     1500
gtctggatga agtcatcgcc ctgctgccag gtgccgaacg cccaactatt ctgccgctgg     1560
cgggtgacca acagcgcgta gcgatgcaca tggtcagcag cgaaaccctg ttctgggaaa     1620
ccatggaaaa actgaaagcg ctgggtgcca gttcaattct ggtcctgccg attgagaaga     1680
tgatggagtg a                                                         1691
```

<210> SEQ ID NO 53
<211> LENGTH: 299
<212> TYPE: PRT
<213> ORGANISM: Artificial Sequence
<220> FEATURE:
<223> OTHER INFORMATION: peptide sequence

<400> SEQUENCE: 53

```
Met Thr Asp Asn Thr Arg Leu Arg Ile Ala Met Gln Lys Ser Gly Arg
1               5                   10                  15

Leu Ser Asp Asp Ser Arg Glu Leu Leu Ala Arg Cys Gly Ile Lys Ile
            20                  25                  30

Asn Leu His Thr Gln Arg Leu Ile Ala Met Ala Glu Asn Met Pro Ile
        35                  40                  45

Asp Ile Leu Arg Val Arg Asp Asp Ile Pro Gly Leu Val Met Asp
    50                  55                  60

Gly Val Val Asp Leu Gly Ile Ile Gly Glu Asn Val Leu Glu Glu Glu
65                  70                  75                  80

Leu Leu Asn Arg Arg Ala Gln Gly Glu Asp Pro Arg Tyr Phe Thr Leu
                85                  90                  95

Arg Arg Leu Asp Phe Gly Gly Cys Arg Leu Ser Leu Ala Thr Pro Val
            100                 105                 110

Asp Glu Ala Trp Asp Gly Pro Leu Ser Leu Asn Gly Lys Arg Ile Ala
        115                 120                 125

Thr Ser Tyr Pro His Leu Leu Lys Arg Tyr Leu Asp Gln Lys Gly Ile
    130                 135                 140

Ser Phe Lys Ser Cys Leu Leu Asn Gly Ser Val Glu Val Ala Pro Arg
```

```
                145                 150                 155                 160

Ala Gly Leu Ala Asp Ala Ile Cys Asp Leu Val Ser Thr Gly Ala Thr
                    165                 170                 175

Leu Glu Ala Asn Gly Leu Arg Glu Val Glu Val Ile Tyr Arg Ser Lys
                180                 185                 190

Ala Cys Leu Ile Gln Arg Asp Gly Glu Met Glu Ser Lys Gln Gln
        195                 200                 205

Leu Ile Asp Lys Leu Leu Thr Arg Ile Gln Gly Val Ile Gln Ala Arg
        210                 215                 220

Glu Ser Lys Tyr Ile Met Met His Ala Pro Thr Glu Arg Leu Asp Glu
    225                 230                 235                 240

Val Ile Ala Leu Leu Pro Gly Ala Glu Arg Pro Thr Ile Leu Pro Leu
                    245                 250                 255

Ala Gly Asp Gln Gln Arg Val Ala Met His Met Val Ser Ser Lys Thr
                260                 265                 270

Leu Phe Trp Glu Thr Met Glu Lys Leu Lys Ala Leu Gly Ala Ser Ser
                275                 280                 285

Ile Leu Val Leu Pro Ile Glu Lys Met Met Glu
        290                 295

<210> SEQ ID NO 54
<211> LENGTH: 299
<212> TYPE: PRT
<213> ORGANISM: E.coli

<400> SEQUENCE: 54

Met Thr Asp Asn Thr Arg Leu Arg Ile Ala Met Gln Lys Ser Gly Arg
    1               5                   10                  15

Leu Ser Asp Asp Ser Arg Glu Leu Leu Ala Arg Cys Gly Ile Lys Ile
                20                  25                  30

Asn Leu His Thr Gln Arg Leu Ile Ala Met Ala Glu Asn Met Pro Ile
                35                  40                  45

Asp Ile Leu Arg Val Arg Asp Asp Ile Pro Gly Leu Val Met Asp
        50                  55                  60

Gly Val Val Asp Leu Gly Ile Ile Gly Glu Asn Val Leu Glu Glu
    65                  70                  75                  80

Leu Leu Asn Arg Arg Ala Gln Gly Glu Asp Pro Arg Tyr Phe Thr Leu
                    85                  90                  95

Arg Arg Leu Asp Phe Gly Gly Cys Arg Leu Ser Leu Ala Thr Pro Val
                100                 105                 110

Asp Glu Ala Trp Asp Gly Pro Leu Ser Leu Asn Gly Lys Arg Ile Ala
            115                 120                 125

Thr Ser Tyr Pro His Leu Leu Lys Arg Tyr Leu Asp Gln Lys Gly Ile
        130                 135                 140

Ser Phe Lys Ser Cys Leu Leu Asn Gly Ser Val Glu Val Ala Pro Arg
    145                 150                 155                 160

Ala Gly Leu Ala Asp Ala Ile Cys Asp Leu Val Ser Thr Gly Ala Thr
                    165                 170                 175

Leu Glu Ala Asn Gly Leu Arg Glu Val Glu Val Ile Tyr Arg Ser Lys
                180                 185                 190

Ala Cys Leu Ile Gln Arg Asp Gly Glu Met Glu Ser Lys Gln Gln
        195                 200                 205

Leu Ile Asp Lys Leu Leu Thr Arg Ile Gln Gly Val Ile Gln Ala Arg
        210                 215                 220
```

```
Glu Ser Lys Tyr Ile Met Met His Ala Pro Thr Glu Arg Leu Asp Glu
225                 230                 235                 240

Val Ile Ala Leu Leu Pro Gly Ala Glu Arg Pro Thr Ile Leu Pro Leu
            245                 250                 255

Ala Gly Asp Gln Gln Arg Val Ala Met His Met Val Ser Ser Glu Thr
            260                 265                 270

Leu Phe Trp Glu Thr Met Glu Lys Leu Lys Ala Leu Gly Ala Ser Ser
            275                 280                 285

Ile Leu Val Leu Pro Ile Glu Lys Met Met Glu
            290                 295

<210> SEQ ID NO 55
<211> LENGTH: 434
<212> TYPE: PRT
<213> ORGANISM: E.coli

<400> SEQUENCE: 55

Met Ser Phe Asn Thr Ile Ile Asp Trp Asn Ser Cys Thr Ala Glu Gln
1               5                   10                  15

Gln Arg Gln Leu Leu Met Arg Pro Ala Ile Ser Ala Ser Glu Ser Ile
            20                  25                  30

Thr Arg Thr Val Asn Asp Ile Leu Asp Asn Val Lys Ala Arg Gly Asp
        35                  40                  45

Glu Ala Leu Arg Glu Tyr Ser Ala Lys Phe Asp Lys Thr Thr Val Thr
50                  55                  60

Ala Leu Lys Val Ser Ala Glu Glu Ile Ala Ala Ala Ser Glu Arg Leu
65                  70                  75                  80

Ser Asp Glu Leu Lys Gln Ala Met Ala Val Ala Val Lys Asn Ile Glu
                85                  90                  95

Thr Phe His Thr Ala Gln Lys Leu Pro Pro Val Asp Val Glu Thr Gln
            100                 105                 110

Pro Gly Val Arg Cys Gln Gln Val Thr Arg Pro Val Ala Ser Val Gly
        115                 120                 125

Leu Tyr Ile Pro Gly Gly Ser Ala Pro Leu Phe Ser Thr Val Leu Met
130                 135                 140

Leu Ala Thr Pro Ala Ser Ile Ala Gly Cys Lys Lys Val Val Leu Cys
145                 150                 155                 160

Ser Pro Pro Pro Ile Ala Asp Glu Ile Leu Tyr Ala Ala Gln Leu Cys
                165                 170                 175

Gly Val Gln Asp Val Phe Asn Val Gly Gly Ala Gln Ala Ile Ala Ala
            180                 185                 190

Leu Ala Phe Gly Thr Glu Ser Val Pro Lys Val Asp Lys Ile Phe Gly
        195                 200                 205

Pro Gly Asn Ala Phe Val Thr Glu Ala Lys Arg Gln Val Ser Gln Arg
210                 215                 220

Leu Asp Gly Ala Ala Ile Asp Met Pro Ala Gly Pro Ser Glu Val Leu
225                 230                 235                 240

Val Ile Ala Asp Ser Gly Ala Thr Pro Asp Phe Val Ala Ser Asp Leu
                245                 250                 255

Leu Ser Gln Ala Glu His Gly Pro Asp Ser Gln Val Ile Leu Leu Thr
            260                 265                 270

Pro Ala Ala Asp Met Ala Arg Arg Val Ala Glu Ala Val Glu Arg Gln
        275                 280                 285

Leu Ala Glu Leu Pro Arg Ala Glu Thr Ala Arg Gln Ala Leu Asn Ala
290                 295                 300
```

Ser Arg Leu Ile Val Thr Lys Asp Leu Ala Gln Cys Val Glu Ile Ser
305                 310                 315                 320

Asn Gln Tyr Gly Pro Glu His Leu Ile Ile Gln Thr Arg Asn Ala Arg
            325                 330                 335

Glu Leu Val Asp Ser Ile Thr Ser Ala Gly Ser Val Phe Leu Gly Asp
        340                 345                 350

Trp Ser Pro Glu Ser Ala Gly Asp Tyr Ala Ser Gly Thr Asn His Val
    355                 360                 365

Leu Pro Thr Tyr Gly Tyr Thr Ala Thr Cys Ser Ser Leu Gly Leu Ala
370                 375                 380

Asp Phe Gln Lys Arg Met Thr Val Gln Glu Leu Ser Lys Glu Gly Phe
385                 390                 395                 400

Ser Ala Leu Ala Ser Thr Ile Glu Thr Leu Ala Ala Glu Arg Leu
            405                 410                 415

Thr Ala His Lys Asn Ala Val Thr Leu Arg Val Asn Ala Leu Lys Glu
            420                 425                 430

Gln Ala

<210> SEQ ID NO 56
<211> LENGTH: 356
<212> TYPE: PRT
<213> ORGANISM: E.coli

<400> SEQUENCE: 56

Met Ser Thr Val Thr Ile Thr Asp Leu Ala Arg Glu Asn Val Arg Asn
1               5                   10                  15

Leu Thr Pro Tyr Gln Ser Ala Arg Arg Leu Gly Gly Asn Gly Asp Val
            20                  25                  30

Trp Leu Asn Ala Asn Glu Tyr Pro Thr Ala Val Glu Phe Gln Leu Thr
        35                  40                  45

Gln Gln Thr Leu Asn Arg Tyr Pro Glu Cys Gln Pro Lys Ala Val Ile
    50                  55                  60

Glu Asn Tyr Ala Gln Tyr Ala Gly Val Lys Pro Glu Gln Val Leu Val
65                  70                  75                  80

Ser Arg Gly Ala Asp Glu Gly Ile Glu Leu Leu Ile Arg Ala Phe Cys
                85                  90                  95

Glu Pro Gly Lys Asp Ala Ile Leu Tyr Cys Pro Pro Thr Tyr Gly Met
            100                 105                 110

Tyr Ser Val Ser Ala Glu Thr Ile Gly Val Glu Cys Arg Thr Val Pro
        115                 120                 125

Thr Leu Asp Asn Trp Gln Leu Asp Leu Gln Gly Ile Ser Asp Lys Leu
130                 135                 140

Asp Gly Val Lys Val Val Tyr Val Cys Ser Pro Asn Asn Pro Thr Gly
145                 150                 155                 160

Gln Leu Ile Asn Pro Gln Asp Phe Arg Thr Leu Leu Glu Leu Thr Arg
                165                 170                 175

Gly Lys Ala Ile Val Val Ala Asp Glu Ala Tyr Ile Glu Phe Cys Pro
            180                 185                 190

Gln Ala Ser Leu Ala Gly Trp Leu Ala Glu Tyr Pro His Leu Ala Ile
        195                 200                 205

Leu Arg Thr Leu Ser Lys Ala Phe Ala Leu Ala Gly Leu Arg Cys Gly
    210                 215                 220

Phe Thr Leu Ala Asn Glu Glu Val Ile Asn Leu Leu Met Lys Val Ile
225                 230                 235                 240

```
Ala Pro Tyr Pro Leu Ser Thr Pro Val Ala Asp Ile Ala Ala Gln Ala
            245                 250                 255

Leu Ser Pro Gln Gly Ile Val Ala Met Arg Glu Arg Val Ala Gln Ile
            260                 265                 270

Ile Ala Glu Arg Glu Tyr Leu Ile Ala Ala Leu Lys Glu Ile Pro Cys
            275                 280                 285

Val Glu Gln Val Phe Asp Ser Glu Thr Asn Tyr Ile Leu Ala Arg Phe
            290                 295                 300

Lys Ala Ser Ser Ala Val Phe Lys Ser Leu Trp Asp Gln Gly Ile Ile
305                 310                 315                 320

Leu Arg Asp Gln Asn Lys Gln Pro Ser Leu Ser Gly Cys Leu Arg Ile
            325                 330                 335

Thr Val Gly Thr Arg Glu Glu Ser Gln Arg Val Ile Asp Ala Leu Arg
            340                 345                 350

Ala Glu Gln Val
            355

<210> SEQ ID NO 57
<211> LENGTH: 355
<212> TYPE: PRT
<213> ORGANISM: E.coli

<400> SEQUENCE: 57

Met Ser Gln Lys Tyr Leu Phe Ile Asp Arg Asp Gly Thr Leu Ile Ser
1               5                   10                  15

Glu Pro Pro Ser Asp Phe Gln Val Asp Arg Phe Asp Lys Leu Ala Phe
            20                  25                  30

Glu Pro Gly Val Ile Pro Glu Leu Leu Lys Leu Gln Lys Ala Gly Tyr
            35                  40                  45

Lys Leu Val Met Ile Thr Asn Gln Asp Gly Leu Gly Thr Gln Ser Phe
50                  55                  60

Pro Gln Ala Asp Phe Asp Gly Pro His Asn Leu Met Met Gln Ile Phe
65                  70                  75                  80

Thr Ser Gln Gly Val Gln Phe Asp Glu Val Leu Ile Cys Pro His Leu
            85                  90                  95

Pro Ala Asp Glu Cys Asp Cys Arg Lys Pro Lys Val Lys Leu Val Glu
            100                 105                 110

Arg Tyr Leu Ala Glu Gln Ala Met Asp Arg Ala Asn Ser Tyr Val Ile
            115                 120                 125

Gly Asp Arg Ala Thr Asp Ile Gln Leu Ala Glu Asn Met Gly Ile Thr
130                 135                 140

Gly Leu Arg Tyr Asp Arg Glu Thr Leu Asn Trp Pro Met Ile Gly Glu
145                 150                 155                 160

Gln Leu Thr Arg Arg Asp Arg Tyr Ala His Val Val Arg Asn Thr Lys
            165                 170                 175

Glu Thr Gln Ile Asp Val Gln Val Trp Leu Asp Arg Glu Gly Gly Ser
            180                 185                 190

Lys Ile Asn Thr Gly Val Gly Phe Phe Asp His Met Leu Asp Gln Ile
            195                 200                 205

Ala Thr His Gly Gly Phe Arg Met Glu Ile Asn Val Lys Gly Asp Leu
            210                 215                 220

Tyr Ile Asp Asp His His Thr Val Glu Asp Thr Gly Leu Ala Leu Gly
225                 230                 235                 240

Glu Ala Leu Lys Ile Ala Leu Gly Asp Lys Arg Gly Ile Cys Arg Phe
```

```
                        245                 250                 255
Gly Phe Val Leu Pro Met Asp Glu Cys Leu Ala Arg Cys Ala Leu Asp
                260                 265                 270

Ile Ser Gly Arg Pro His Leu Glu Tyr Lys Ala Glu Phe Thr Tyr Gln
            275                 280                 285

Arg Val Gly Asp Leu Ser Thr Glu Met Ile Glu His Phe Phe Arg Ser
        290                 295                 300

Leu Ser Tyr Thr Met Gly Val Thr Leu His Leu Lys Thr Lys Gly Lys
305                 310                 315                 320

Asn Asp His His Arg Val Glu Ser Leu Phe Lys Ala Phe Gly Arg Thr
                325                 330                 335

Leu Arg Gln Ala Ile Arg Val Glu Gly Asp Thr Leu Pro Ser Ser Lys
                340                 345                 350

Gly Val Leu
        355
```

<210> SEQ ID NO 58
<211> LENGTH: 196
<212> TYPE: PRT
<213> ORGANISM: E.coli

<400> SEQUENCE: 58

```
Met Asn Val Val Ile Leu Asp Thr Gly Cys Ala Asn Leu Asn Ser Val
1               5                   10                  15

Lys Ser Ala Ile Ala Arg His Gly Tyr Glu Pro Lys Val Ser Arg Asp
            20                  25                  30

Pro Asp Val Val Leu Leu Ala Asp Lys Leu Phe Leu Pro Gly Val Gly
        35                  40                  45

Thr Ala Gln Ala Ala Met Asp Gln Val Arg Glu Arg Glu Leu Phe Asp
    50                  55                  60

Leu Ile Lys Ala Cys Thr Gln Pro Val Leu Gly Ile Cys Leu Gly Met
65                  70                  75                  80

Gln Leu Leu Gly Arg Arg Ser Glu Glu Ser Asn Gly Val Asp Leu Leu
                85                  90                  95

Gly Ile Ile Asp Glu Asp Val Pro Lys Met Thr Asp Phe Gly Leu Pro
            100                 105                 110

Leu Pro His Met Gly Trp Asn Arg Val Tyr Pro Gln Ala Gly Asn Arg
        115                 120                 125

Leu Phe Gln Gly Ile Glu Asp Gly Ala Tyr Phe Tyr Phe Val His Ser
    130                 135                 140

Tyr Ala Met Pro Val Asn Pro Trp Thr Ile Ala Gln Cys Asn Tyr Gly
145                 150                 155                 160

Glu Pro Phe Thr Ala Ala Val Gln Lys Asp Asn Phe Tyr Gly Val Gln
                165                 170                 175

Phe His Pro Glu Arg Ser Gly Ala Ala Gly Ala Lys Leu Leu Lys Asn
            180                 185                 190

Phe Leu Glu Met
        195
```

<210> SEQ ID NO 59
<211> LENGTH: 245
<212> TYPE: PRT
<213> ORGANISM: E.coli

<400> SEQUENCE: 59

```
Met Ile Ile Pro Ala Leu Asp Leu Ile Asp Gly Thr Val Val Arg Leu
```

```
              1               5                  10                 15
            His Gln Gly Asp Tyr Gly Lys Gln Arg Asp Tyr Gly Asn Asp Pro Leu
                            20                 25                 30

Pro Arg Leu Gln Asp Tyr Ala Ala Gln Gly Ala Glu Val Leu His Leu
                            35                 40                 45

Val Asp Leu Thr Gly Ala Lys Asp Pro Ala Lys Arg Gln Ile Pro Leu
             50                 55                 60

Ile Lys Thr Leu Val Ala Gly Val Asn Val Pro Val Gln Val Gly Gly
             65                 70                 75                 80

Gly Val Arg Ser Glu Glu Asp Val Ala Ala Leu Leu Glu Ala Gly Val
                            85                 90                 95

Ala Arg Val Val Val Gly Ser Thr Ala Val Lys Ser Gln Asp Met Val
                            100                105                110

Lys Gly Trp Phe Glu Arg Phe Gly Ala Asp Ala Leu Val Leu Ala Leu
                            115                120                125

Asp Val Arg Ile Asp Glu Gln Gly Asn Lys Gln Val Ala Val Ser Gly
                            130                135                140

Trp Gln Glu Asn Ser Gly Val Ser Leu Glu Gln Leu Val Glu Thr Tyr
             145                150                155                160

Leu Pro Val Gly Leu Lys His Val Leu Cys Thr Asp Ile Ser Arg Asp
                            165                170                175

Gly Thr Leu Ala Gly Ser Asn Val Ser Leu Tyr Glu Glu Val Cys Ala
                            180                185                190

Arg Tyr Pro Gln Val Ala Phe Gln Ser Ser Gly Gly Ile Gly Asp Ile
                            195                200                205

Asp Asp Val Ala Ala Leu Arg Gly Thr Gly Val Arg Gly Val Ile Val
                            210                215                220

Gly Arg Ala Leu Leu Glu Gly Lys Phe Thr Val Lys Glu Ala Ile Ala
             225                230                235                240

Cys Trp Gln Asn Ala
                            245

<210> SEQ ID NO 60
<211> LENGTH: 258
<212> TYPE: PRT
<213> ORGANISM: E.coli

<400> SEQUENCE: 60

Met Leu Ala Lys Arg Ile Ile Pro Cys Leu Asp Val Arg Asp Gly Gln
             1                  5                 10                 15

Val Val Lys Gly Val Gln Phe Arg Asn His Glu Ile Ile Gly Asp Ile
                            20                 25                 30

Val Pro Leu Ala Lys Arg Tyr Ala Glu Glu Gly Ala Asp Glu Leu Val
                            35                 40                 45

Phe Tyr Asp Ile Thr Ala Ser Ser Asp Gly Arg Val Val Asp Lys Ser
             50                 55                 60

Trp Val Ser Arg Val Ala Glu Val Ile Asp Ile Pro Phe Cys Val Ala
             65                 70                 75                 80

Gly Gly Ile Lys Ser Leu Glu Asp Ala Ala Lys Ile Leu Ser Phe Gly
                            85                 90                 95

Ala Asp Lys Ile Ser Ile Asn Ser Pro Ala Leu Ala Asp Pro Thr Leu
                            100                105                110

Ile Thr Arg Leu Ala Asp Arg Phe Gly Val Gln Cys Ile Val Val Gly
                            115                120                125
```

```
Ile Asp Thr Trp Tyr Asp Ala Glu Thr Gly Lys Tyr His Val Asn Gln
130                 135                 140

Tyr Thr Gly Asp Glu Ser Arg Thr Arg Val Thr Gln Trp Glu Thr Leu
145                 150                 155                 160

Asp Trp Val Gln Glu Val Gln Lys Arg Gly Ala Gly Glu Ile Val Leu
                165                 170                 175

Asn Met Met Asn Gln Asp Gly Val Arg Asn Gly Tyr Asp Leu Glu Gln
                180                 185                 190

Leu Lys Lys Val Arg Glu Val Cys His Val Pro Leu Ile Ala Ser Gly
                195                 200                 205

Gly Ala Gly Thr Met Glu His Phe Leu Glu Ala Phe Arg Asp Ala Asp
210                 215                 220

Val Asp Gly Ala Leu Ala Ala Ser Val Phe His Lys Gln Ile Ile Asn
225                 230                 235                 240

Ile Gly Glu Leu Lys Ala Tyr Leu Ala Thr Gln Gly Val Glu Ile Arg
                245                 250                 255

Ile Cys

<210> SEQ ID NO 61
<211> LENGTH: 203
<212> TYPE: PRT
<213> ORGANISM: E.coli

<400> SEQUENCE: 61

Met Leu Thr Glu Gln Gln Arg Arg Glu Leu Asp Trp Glu Lys Thr Asp
1                   5                   10                  15

Gly Leu Met Pro Val Ile Val Gln His Ala Val Ser Gly Glu Val Leu
                20                  25                  30

Met Leu Gly Tyr Met Asn Pro Glu Ala Leu Asp Lys Thr Leu Glu Ser
            35                  40                  45

Gly Lys Val Thr Phe Phe Ser Arg Thr Lys Gln Arg Leu Trp Thr Lys
        50                  55                  60

Gly Glu Thr Ser Gly Asn Phe Leu Asn Val Val Ser Ile Ala Pro Asp
65                  70                  75                  80

Cys Asp Asn Asp Thr Leu Leu Val Leu Ala Asn Pro Ile Gly Pro Thr
                85                  90                  95

Cys His Lys Gly Thr Ser Ser Cys Phe Gly Asp Thr Ala His Gln Trp
                100                 105                 110

Leu Phe Leu Tyr Gln Leu Glu Gln Leu Leu Ala Glu Arg Lys Ser Ala
            115                 120                 125

Asp Pro Glu Thr Ser Tyr Thr Ala Lys Leu Tyr Ala Ser Gly Thr Lys
        130                 135                 140

Arg Ile Ala Gln Lys Val Gly Glu Glu Gly Val Glu Thr Ala Leu Ala
145                 150                 155                 160

Ala Thr Val His Asp Arg Phe Glu Leu Thr Asn Glu Ala Ser Asp Leu
                165                 170                 175

Met Tyr His Leu Leu Val Leu Leu Gln Asp Gln Gly Leu Asp Leu Thr
                180                 185                 190

Thr Val Ile Glu Asn Leu Arg Lys Arg His Gln
            195                 200

<210> SEQ ID NO 62
<211> LENGTH: 1413
<212> TYPE: DNA
<213> ORGANISM: Artificial Sequence
<220> FEATURE:
```

<223> OTHER INFORMATION: nucleotide sequence

<400> SEQUENCE: 62

```
atgaaacaca taccgttttt cttcgcattc ttttttacct tcccctgaat gggaggcgtt      60
tcgtcgtgtg aaacagaatg cgaagacgaa caataaggcc tcccaaatcg ggggccttt     120
tttattgata acaaaaaggc aacactatga catcggaaaa cccgttactg gcgctgcgag    180
agaaaatcag cgcgctggat gaaaaattat tagcgttact ggcagaacgg cgcgaactgg    240
ccgtcgaggt gggaaaagcc aaactgctct cgcatcgccc ggtacgtgat attgatcgtg    300
aacgcgattt gctggaaaga ttaattacgc tcggtaaagc gcaccatctg gacgcccatt    360
acattactcg cctgttccag ctcatcattg aagattccgt attaactcag caggctttgc    420
tccaacaaca tctcaataaa attaatccgc actcagcacg catcgctttt ctcggcccca    480
aaggttctta ttcccatctt gcggcgcgcc agtatgctgc ccgtcacttt gagcaattca    540
ttgaaagtgg ctgcgccaaa tttgccgata tttttaatca ggtggaaacc ggccaggccg    600
actatgccgt cgtaccgatt gaaaatacca gctccggtgc cataaacgac gtttacgatc    660
tgctgcaaca taccagcttg tcgattgttg gcgagatgac gttaactatc gaccattgtt    720
tgttggtctc cggcactact gatttatcca ccatcaatac ggtctacagc catccgcagc    780
cattccagca atgcagcaaa ttccttaatc gttatccgca ctggaagatt gaatataccg    840
aaagtacgtc tgcggcaatg aaaaggttg cacaggcaaa atcaccgcat gttgctgcgt    900
tgggaagcga agctggcggc actttgtacg gtttgcaggt actggagcgt attgaagcaa    960
atcagcgaca aaacttcacc cgatttgtgg tgttggcgcg taaagccatt aacgtgtctg   1020
atcaggttcc ggcgaaaacc acgttgttaa tggcgaccgg gcaacaagcc tgtgcgctgg   1080
ttgaagcgtt gctggtactg cgcaaccaca atctgattat gacccgtctg aatcacgcc    1140
cgattcacgg taatccatgg aagagatgt tctatctgga tattcaggcc aatcttgaat   1200
cagcggaaat gcaaaaagca ttgaaagagt taggggaaat cacccgttca atgaaggtat   1260
tgggctgtta cccaagtgag aacgtagtgc ctgttgatcc aacctgatga aaaggtgccg   1320
gatgatgtga atcatccggc actggattat tactggcgat tgtcattcgc ctgacgcaat   1380
aacacgcggc tttcactctg aaaacgctgt gcg                                1413
```

<210> SEQ ID NO 63
<211> LENGTH: 386
<212> TYPE: PRT
<213> ORGANISM: E.coli

<400> SEQUENCE: 63

```
Met Thr Ser Glu Asn Pro Leu Leu Ala Leu Arg Glu Lys Ile Ser Ala
1               5                   10                  15

Leu Asp Glu Lys Leu Leu Ala Leu Leu Ala Glu Arg Arg Glu Leu Ala
            20                  25                  30

Val Glu Val Gly Lys Ala Lys Leu Leu Ser His Arg Pro Val Arg Asp
        35                  40                  45

Ile Asp Arg Glu Arg Asp Leu Leu Glu Arg Leu Ile Thr Leu Gly Lys
    50                  55                  60

Ala His His Leu Asp Ala His Tyr Ile Thr Arg Leu Phe Gln Leu Ile
65                  70                  75                  80

Ile Glu Asp Ser Val Leu Thr Gln Gln Ala Leu Leu Gln Gln His Leu
                85                  90                  95

Asn Lys Ile Asn Pro His Ser Ala Arg Ile Ala Phe Leu Gly Pro Lys
```

```
            100                 105                 110
Gly Ser Tyr Ser His Leu Ala Ala Arg Gln Tyr Ala Ala Arg His Phe
            115                 120                 125
Glu Gln Phe Ile Glu Ser Gly Cys Ala Lys Phe Ala Asp Ile Phe Asn
            130                 135                 140
Gln Val Glu Thr Gly Gln Ala Asp Tyr Ala Val Val Pro Ile Glu Asn
145                 150                 155                 160
Thr Ser Ser Gly Ala Ile Asn Asp Val Tyr Asp Leu Leu Gln His Thr
                165                 170                 175
Ser Leu Ser Ile Val Gly Glu Met Thr Leu Thr Ile Asp His Cys Leu
                180                 185                 190
Leu Val Ser Gly Thr Thr Asp Leu Ser Thr Ile Asn Thr Val Tyr Ser
                195                 200                 205
His Pro Gln Pro Phe Gln Gln Cys Ser Lys Phe Leu Asn Arg Tyr Pro
            210                 215                 220
His Trp Lys Ile Glu Tyr Thr Glu Ser Thr Ser Ala Ala Met Glu Lys
225                 230                 235                 240
Val Ala Gln Ala Lys Ser Pro His Val Ala Ala Leu Gly Ser Glu Ala
                245                 250                 255
Gly Gly Thr Leu Tyr Gly Leu Gln Val Leu Glu Arg Ile Glu Ala Asn
                260                 265                 270
Gln Arg Gln Asn Phe Thr Arg Phe Val Val Leu Ala Arg Lys Ala Ile
                275                 280                 285
Asn Val Ser Asp Gln Val Pro Ala Lys Thr Thr Leu Leu Met Ala Thr
            290                 295                 300
Gly Gln Gln Ala Gly Ala Leu Val Glu Ala Leu Leu Val Leu Arg Asn
305                 310                 315                 320
His Asn Leu Ile Met Thr Arg Leu Glu Ser Arg Pro Ile His Gly Asn
                325                 330                 335
Pro Trp Glu Glu Met Phe Tyr Leu Asp Ile Gln Ala Asn Leu Glu Ser
            340                 345                 350
Ala Glu Met Gln Lys Ala Leu Lys Glu Leu Gly Glu Ile Thr Arg Ser
            355                 360                 365
Met Lys Val Leu Gly Cys Tyr Pro Ser Glu Asn Val Val Pro Val Asp
370                 375                 380
Pro Thr
385

<210> SEQ ID NO 64
<211> LENGTH: 386
<212> TYPE: PRT
<213> ORGANISM: Artificial Sequence
<220> FEATURE:
<223> OTHER INFORMATION: peptide sequence

<400> SEQUENCE: 64

Met Thr Ser Glu Asn Pro Leu Leu Ala Leu Arg Glu Lys Ile Ser Ala
1               5                   10                  15
Leu Asp Glu Lys Leu Leu Ala Leu Leu Ala Glu Arg Arg Glu Leu Ala
            20                  25                  30
Val Glu Val Gly Lys Ala Lys Leu Ser His Arg Pro Val Arg Asp
            35                  40                  45
Ile Asp Arg Glu Arg Asp Leu Leu Glu Arg Leu Ile Thr Leu Gly Lys
        50                  55                  60
Ala His His Leu Asp Ala His Tyr Ile Thr Arg Leu Phe Gln Leu Ile
```

```
                65                  70                  75                  80
Ile Glu Asp Ser Val Leu Thr Gln Gln Ala Leu Leu Gln Gln His Leu
                        85                  90                  95

Asn Lys Ile Asn Pro His Ser Ala Arg Ile Ala Phe Leu Gly Pro Lys
                100                 105                 110

Gly Ser Tyr Ser His Leu Ala Ala Arg Gln Tyr Ala Ala Arg His Phe
                115                 120                 125

Glu Gln Phe Ile Glu Ser Gly Cys Ala Lys Phe Ala Asp Ile Phe Asn
            130                 135                 140

Gln Val Glu Thr Gly Gln Ala Asp Tyr Ala Val Val Pro Ile Glu Asn
145                 150                 155                 160

Thr Ser Ser Gly Ala Ile Asn Asp Val Tyr Asp Leu Leu Gln His Thr
                165                 170                 175

Ser Leu Ser Ile Val Gly Glu Met Thr Leu Thr Ile Asp His Cys Leu
                180                 185                 190

Leu Val Ser Gly Thr Thr Asp Leu Ser Thr Ile Asn Thr Val Tyr Ser
                195                 200                 205

His Pro Gln Pro Phe Gln Gln Cys Ser Lys Phe Leu Asn Arg Tyr Pro
            210                 215                 220

His Trp Lys Ile Glu Tyr Thr Glu Ser Thr Ser Ala Ala Met Glu Lys
225                 230                 235                 240

Val Ala Gln Ala Lys Ser Pro His Val Ala Ala Leu Gly Ser Glu Ala
                245                 250                 255

Gly Gly Thr Leu Tyr Gly Leu Gln Val Leu Glu Arg Ile Glu Ala Asn
                260                 265                 270

Gln Arg Gln Asn Phe Thr Arg Phe Val Val Leu Ala Arg Lys Ala Ile
            275                 280                 285

Asn Val Ser Asp Gln Val Pro Ala Lys Thr Thr Leu Leu Met Ala Thr
                290                 295                 300

Gly Gln Gln Ala Cys Ala Leu Val Glu Ala Leu Leu Val Leu Arg Asn
305                 310                 315                 320

His Asn Leu Ile Met Thr Arg Leu Glu Ser Arg Pro Ile His Gly Asn
                325                 330                 335

Pro Trp Glu Glu Met Phe Tyr Leu Asp Ile Gln Ala Asn Leu Glu Ser
                340                 345                 350

Ala Glu Met Gln Lys Ala Leu Lys Glu Leu Gly Glu Ile Thr Arg Ser
            355                 360                 365

Met Lys Val Leu Gly Cys Tyr Pro Ser Glu Asn Val Val Pro Val Asp
370                 375                 380

Pro Thr
385

<210> SEQ ID NO 65
<211> LENGTH: 1265
<212> TYPE: DNA
<213> ORGANISM: E.coli
<220> FEATURE:
<223> OTHER INFORMATION: nucleotide sequence

<400> SEQUENCE: 65
caaagcatag cggattgttt tcaaagggag tgtaaattta tctatacaga ggtaagggtt      60
gaaagcgcga ctaaattgcc tgtgtaaata aaaatgtacg aaatatggat tgaaaacttt     120
actttatgtg ttatcgttac gtcatcctcg ctgaggatca actatcgcaa acgagcataa     180
acaggatcgc catcatgcaa aaagacgcgc tgaataacgt acatattacc gacgaacagg     240
```

```
ttttaatgac tccggaacaa ctgaaggccg cttttccatt gagcctgcaa caagaagccc    300
agattgctga ctcgcgtaaa agcatttcag atattatcgc cgggcgcgat cctcgtctgc    360
tggtagtatg tggtccttgt tccattcatg atccggaaac tgctctggaa tatgctcgtc    420
gatttaaagc ccttgccgca gaggtcagcg atagcctcta tctggtaatg cgcgtctatt    480
ttgaaaaacc ccgtaccact gtcggctgga aagggttaat taacgatccc catatggatg    540
gctcttttga tgtagaagcc gggctgcaga tcgcgcgtaa attgctgctt gagctggtga    600
atatgggact gccactggcg acggaagcgt tagatccgaa tagcccgcaa tacctgggcg    660
atctgtttag ctggtcagca attggtgctc gtacaacgga atcgcaaact caccgtgaaa    720
tggcctccgg gctttccatg ccggttggtt ttaaaaacgg caccgacggc agtctggcaa    780
cagcaattaa cgctatgcgc gccgccgccc agccgcaccg ttttgttggc attaaccagg    840
cagggcaggt tgcgttgcta caaactcagg ggaatccgga cggccatgtg atcctgcgcg    900
gtggtaaagc gccgaactat agccctgcgg atgttgcgca atgtgaaaaa gagatggaac    960
aggcgggact gcgcccgtct ctgatggtag attgcagcca cggtaattcc aataaagatt   1020
atcgccgtca gcctgcggtg gcagaatccg tggttgctca aatcaaagat ggcaatcgct   1080
caattattgg tctgatgatc gaaagtaata tccacgaggg caatcagtct tccgagcaac   1140
cgcgcagtga aatgaaatac ggtgtatccg taaccgatgc ctgcattagc tgggaaatga   1200
ccgatgcctt gctgcgtgaa attcatcagg atctgaacgg gcagctgacg gctcgcgtgg   1260
cttaa                                                              1265
```

<210> SEQ ID NO 66
<211> LENGTH: 356
<212> TYPE: PRT
<213> ORGANISM: E.coli

<400> SEQUENCE: 66

```
Met Gln Lys Asp Ala Leu Asn Asn Val His Ile Thr Asp Glu Gln Val
1               5                   10                  15

Leu Met Thr Pro Glu Gln Leu Lys Ala Ala Phe Pro Leu Ser Leu Gln
            20                  25                  30

Gln Glu Ala Gln Ile Ala Asp Ser Arg Lys Ser Ile Ser Asp Ile Ile
        35                  40                  45

Ala Gly Arg Asp Pro Arg Leu Leu Val Val Cys Gly Pro Cys Ser Ile
    50                  55                  60

His Asp Pro Glu Thr Ala Leu Glu Tyr Ala Arg Arg Phe Lys Ala Leu
65                  70                  75                  80

Ala Ala Glu Val Ser Asp Ser Leu Tyr Leu Val Met Arg Val Tyr Phe
                85                  90                  95

Glu Lys Pro Arg Thr Thr Val Gly Trp Lys Gly Leu Ile Asn Asp Pro
            100                 105                 110

His Met Asp Gly Ser Phe Asp Val Glu Ala Gly Leu Gln Ile Ala Arg
        115                 120                 125

Lys Leu Leu Leu Glu Leu Val Asn Met Gly Leu Pro Leu Ala Thr Glu
    130                 135                 140

Ala Leu Asp Pro Asn Ser Pro Gln Tyr Leu Gly Asp Leu Phe Ser Trp
145                 150                 155                 160

Ser Ala Ile Gly Ala Arg Thr Thr Glu Ser Gln Thr His Arg Glu Met
                165                 170                 175

Ala Ser Gly Leu Ser Met Pro Val Gly Phe Lys Asn Gly Thr Asp Gly
```

```
            180                 185                 190
Ser Leu Ala Thr Ala Ile Asn Ala Met Arg Ala Ala Gln Pro His
            195                 200                 205

Arg Phe Val Gly Ile Asn Gln Ala Gly Gln Val Ala Leu Leu Gln Thr
            210                 215                 220

Gln Gly Asn Pro Asp Gly His Val Ile Leu Arg Gly Gly Lys Ala Pro
225                 230                 235                 240

Asn Tyr Ser Pro Ala Asp Val Ala Gln Cys Glu Lys Glu Met Glu Gln
            245                 250                 255

Ala Gly Leu Arg Pro Ser Leu Met Val Asp Cys Ser His Gly Asn Ser
            260                 265                 270

Asn Lys Asp Tyr Arg Arg Gln Pro Ala Val Ala Glu Ser Val Val Ala
            275                 280                 285

Gln Ile Lys Asp Gly Asn Arg Ser Ile Ile Gly Leu Met Ile Glu Ser
            290                 295                 300

Asn Ile His Glu Gly Asn Gln Ser Ser Glu Gln Pro Arg Ser Glu Met
305                 310                 315                 320

Lys Tyr Gly Val Ser Val Thr Asp Ala Cys Ile Ser Trp Glu Met Thr
            325                 330                 335

Asp Ala Leu Leu Arg Glu Ile His Gln Asp Leu Asn Gly Gln Leu Thr
            340                 345                 350

Ala Arg Val Ala
            355

<210> SEQ ID NO 67
<211> LENGTH: 18
<212> TYPE: DNA
<213> ORGANISM: Artificial Sequence
<220> FEATURE:
<223> OTHER INFORMATION: oligonucleotide

<400> SEQUENCE: 67
ggttctggtt ctggttct                                                     18

<210> SEQ ID NO 68
<211> LENGTH: 48
<212> TYPE: DNA
<213> ORGANISM: Artificial Sequence
<220> FEATURE:
<223> OTHER INFORMATION: oligonucleotide

<400> SEQUENCE: 68
ctagcataac cccttggggc tctaaacgg gtcttgaggg gttttttg                      48

<210> SEQ ID NO 69
<211> LENGTH: 30
<212> TYPE: DNA
<213> ORGANISM: Artificial Sequence
<220> FEATURE:
<223> OTHER INFORMATION: oligonucleotide

<400> SEQUENCE: 69
gcgtcgacat agaacccaac cgcctgctca                                         30

<210> SEQ ID NO 70
<211> LENGTH: 44
<212> TYPE: DNA
<213> ORGANISM: Artificial Sequence
<220> FEATURE:
<223> OTHER INFORMATION: oligonucleotide
```

<400> SEQUENCE: 70
aacgatcgac tatcacagaa gaaacctgat tacctcacta cata                44

<210> SEQ ID NO 71
<211> LENGTH: 44
<212> TYPE: DNA
<213> ORGANISM: Artificial Sequence
<220> FEATURE:
<223> OTHER INFORMATION: oligonucleotide

<400> SEQUENCE: 71
tatgtagtga ggtaatcagg tttcttctgt gatagtcgat cgtt                44

<210> SEQ ID NO 72
<211> LENGTH: 33
<212> TYPE: DNA
<213> ORGANISM: Artificial Sequence
<220> FEATURE:
<223> OTHER INFORMATION: oligonucleotide

<400> SEQUENCE: 72
attgcggccg cccgaaataa aatcaggcaa cgt                            33

<210> SEQ ID NO 73
<211> LENGTH: 20
<212> TYPE: DNA
<213> ORGANISM: Artificial Sequence
<220> FEATURE:
<223> OTHER INFORMATION: oligonucleotide

<400> SEQUENCE: 73
cgttaatgaa atatcgccag                                           20

<210> SEQ ID NO 74
<211> LENGTH: 20
<212> TYPE: DNA
<213> ORGANISM: Artificial Sequence
<220> FEATURE:
<223> OTHER INFORMATION: oligonucleotide

<400> SEQUENCE: 74
tcgaaatcgg ccataaagac                                           20

<210> SEQ ID NO 75
<211> LENGTH: 29
<212> TYPE: DNA
<213> ORGANISM: Artificial Sequence
<220> FEATURE:
<223> OTHER INFORMATION: oligonucleotide

<400> SEQUENCE: 75
cgcggatccg aaagtgtacg aaagccagg                                 29

<210> SEQ ID NO 76
<211> LENGTH: 40
<212> TYPE: DNA
<213> ORGANISM: Artificial Sequence
<220> FEATURE:
<223> OTHER INFORMATION: oligonucleotide

<400> SEQUENCE: 76
gcgctatcag gcatttttcc tattaacccc ccagtttcga                     40

<210> SEQ ID NO 77
<211> LENGTH: 40

```
<212> TYPE: DNA
<213> ORGANISM: Artificial Sequence
<220> FEATURE:
<223> OTHER INFORMATION: oligonucleotide

<400> SEQUENCE: 77
tcgaaactgg ggggttaata ggaaaaatgc ctgatagcgc                    40

<210> SEQ ID NO 78
<211> LENGTH: 31
<212> TYPE: DNA
<213> ORGANISM: Artificial Sequence
<220> FEATURE:
<223> OTHER INFORMATION: oligonucleotide

<400> SEQUENCE: 78
attgcggccg cgtgaagcgg atctggcgat t                             31

<210> SEQ ID NO 79
<211> LENGTH: 20
<212> TYPE: DNA
<213> ORGANISM: Artificial Sequence
<220> FEATURE:
<223> OTHER INFORMATION: oligonucleotide

<400> SEQUENCE: 79
atggctgtat ccgctcgctg                                          20

<210> SEQ ID NO 80
<211> LENGTH: 21
<212> TYPE: DNA
<213> ORGANISM: Artificial Sequence
<220> FEATURE:
<223> OTHER INFORMATION: oligonucleotide

<400> SEQUENCE: 80
acaccatcga tcagcaaggg c                                        21

<210> SEQ ID NO 81
<211> LENGTH: 29
<212> TYPE: DNA
<213> ORGANISM: Artificial Sequence
<220> FEATURE:
<223> OTHER INFORMATION: oligonucleotide

<400> SEQUENCE: 81
cgcggatccg gcacgatatt taagctgac                                29

<210> SEQ ID NO 82
<211> LENGTH: 40
<212> TYPE: DNA
<213> ORGANISM: Artificial Sequence
<220> FEATURE:
<223> OTHER INFORMATION: oligonucleotide

<400> SEQUENCE: 82
caaccagcga ctaaccgcag aacaaactcc agataagtgc                    40

<210> SEQ ID NO 83
<211> LENGTH: 40
<212> TYPE: DNA
<213> ORGANISM: Artificial Sequence
<220> FEATURE:
<223> OTHER INFORMATION: oligonucleotide

<400> SEQUENCE: 83
```

```
gcacttatct ggagtttgtt ctgcggttag tcgctggttg                              40
```

<210> SEQ ID NO 84
<211> LENGTH: 31
<212> TYPE: DNA
<213> ORGANISM: Artificial Sequence
<220> FEATURE:
<223> OTHER INFORMATION: oligonucleotide
<400> SEQUENCE: 84

```
attgcggccg cgctggcaac gcgtcattta a                                       31
```

<210> SEQ ID NO 85
<211> LENGTH: 20
<212> TYPE: DNA
<213> ORGANISM: Artificial Sequence
<220> FEATURE:
<223> OTHER INFORMATION: oligonucleotide
<400> SEQUENCE: 85

```
gtaacacaca cacttcatct                                                    20
```

<210> SEQ ID NO 86
<211> LENGTH: 20
<212> TYPE: DNA
<213> ORGANISM: Artificial Sequence
<220> FEATURE:
<223> OTHER INFORMATION: oligonucleotide
<400> SEQUENCE: 86

```
gatcccggat gctgatttag                                                    20
```

<210> SEQ ID NO 87
<211> LENGTH: 29
<212> TYPE: DNA
<213> ORGANISM: Artificial Sequence
<220> FEATURE:
<223> OTHER INFORMATION: oligonucleotide
<400> SEQUENCE: 87

```
cgcggatcca tactgcgatg tgatgggcc                                          29
```

<210> SEQ ID NO 88
<211> LENGTH: 40
<212> TYPE: DNA
<213> ORGANISM: Artificial Sequence
<220> FEATURE:
<223> OTHER INFORMATION: oligonucleotide
<400> SEQUENCE: 88

```
aataccagcc cttgttcgtg ctcacatcct caggcgataa                              40
```

<210> SEQ ID NO 89
<211> LENGTH: 40
<212> TYPE: DNA
<213> ORGANISM: Artificial Sequence
<220> FEATURE:
<223> OTHER INFORMATION: oligonucleotide
<400> SEQUENCE: 89

```
ttatcgcctg aggatgtgag cacgaacaag ggctggtatt                              40
```

<210> SEQ ID NO 90
<211> LENGTH: 31
<212> TYPE: DNA
<213> ORGANISM: Artificial Sequence

```
<220> FEATURE:
<223> OTHER INFORMATION: oligonucleotide

<400> SEQUENCE: 90
attgcggccg ccgttgccac ttcaatccca c                              31

<210> SEQ ID NO 91
<211> LENGTH: 20
<212> TYPE: DNA
<213> ORGANISM: Artificial Sequence
<220> FEATURE:
<223> OTHER INFORMATION: oligonucleotide

<400> SEQUENCE: 91
gctatgccaa caacgatatg                                           20

<210> SEQ ID NO 92
<211> LENGTH: 20
<212> TYPE: DNA
<213> ORGANISM: Artificial Sequence
<220> FEATURE:
<223> OTHER INFORMATION: oligonucleotide

<400> SEQUENCE: 92
ggttaatacg ccggttgagc                                           20

<210> SEQ ID NO 93
<211> LENGTH: 29
<212> TYPE: DNA
<213> ORGANISM: Artificial Sequence
<220> FEATURE:
<223> OTHER INFORMATION: oligonucleotide

<400> SEQUENCE: 93
cgcggatccg gaacgattgg tctggaaat                                 29

<210> SEQ ID NO 94
<211> LENGTH: 41
<212> TYPE: DNA
<213> ORGANISM: Artificial Sequence
<220> FEATURE:
<223> OTHER INFORMATION: oligonucleotide

<400> SEQUENCE: 94
ggcttcaatc aggtcaagga tatcctatcc tcaacgaatt a                   41

<210> SEQ ID NO 95
<211> LENGTH: 41
<212> TYPE: DNA
<213> ORGANISM: Artificial Sequence
<220> FEATURE:
<223> OTHER INFORMATION: oligonucleotide

<400> SEQUENCE: 95
taattcgttg aggataggat atccttgacc tgattgaagc c                   41

<210> SEQ ID NO 96
<211> LENGTH: 33
<212> TYPE: DNA
<213> ORGANISM: Artificial Sequence
<220> FEATURE:
<223> OTHER INFORMATION: oligonucleotide

<400> SEQUENCE: 96
attgcggccg ccgcgacgga tattatcaat gac                            33
```

<210> SEQ ID NO 97
<211> LENGTH: 20
<212> TYPE: DNA
<213> ORGANISM: Artificial Sequence
<220> FEATURE:
<223> OTHER INFORMATION: oligonucleotide

<400> SEQUENCE: 97
gcgccaaaat ccaaagtagc                                           20

<210> SEQ ID NO 98
<211> LENGTH: 20
<212> TYPE: DNA
<213> ORGANISM: Artificial Sequence
<220> FEATURE:
<223> OTHER INFORMATION: oligonucleotide

<400> SEQUENCE: 98
atgtgcgcgc tgggaaacat                                           20

<210> SEQ ID NO 99
<211> LENGTH: 30
<212> TYPE: DNA
<213> ORGANISM: Artificial Sequence
<220> FEATURE:
<223> OTHER INFORMATION: oligonucleotide

<400> SEQUENCE: 99
cgcggatcct atcttcgccg tgaccactga                                30

<210> SEQ ID NO 100
<211> LENGTH: 42
<212> TYPE: DNA
<213> ORGANISM: Artificial Sequence
<220> FEATURE:
<223> OTHER INFORMATION: oligonucleotide

<400> SEQUENCE: 100
accgaacata ttacaggcca gcgatccttt cattgtgttg tc                  42

<210> SEQ ID NO 101
<211> LENGTH: 42
<212> TYPE: DNA
<213> ORGANISM: Artificial Sequence
<220> FEATURE:
<223> OTHER INFORMATION: oligonucleotide

<400> SEQUENCE: 101
gacaacacaa tgaaaggatc gctggcctgt aatatgttcg gt                  42

<210> SEQ ID NO 102
<211> LENGTH: 32
<212> TYPE: DNA
<213> ORGANISM: Artificial Sequence
<220> FEATURE:
<223> OTHER INFORMATION: oligonucleotide

<400> SEQUENCE: 102
attgcggccg cctcgcgaag ttccatcatc ct                             32

<210> SEQ ID NO 103
<211> LENGTH: 21
<212> TYPE: DNA
<213> ORGANISM: Artificial Sequence
<220> FEATURE:
<223> OTHER INFORMATION: oligonucleotide

<400> SEQUENCE: 103
cctgtaacga gcgtaacgac t                                          21

<210> SEQ ID NO 104
<211> LENGTH: 21
<212> TYPE: DNA
<213> ORGANISM: Artificial Sequence
<220> FEATURE:
<223> OTHER INFORMATION: oligonucleotide

<400> SEQUENCE: 104
tatcttcgcc gtgaccactg a                                          21

<210> SEQ ID NO 105
<211> LENGTH: 30
<212> TYPE: DNA
<213> ORGANISM: Artificial Sequence
<220> FEATURE:
<223> OTHER INFORMATION: oligonucleotide

<400> SEQUENCE: 105
cccaagctta cagagtacac aacatccatg                                 30

<210> SEQ ID NO 106
<211> LENGTH: 29
<212> TYPE: DNA
<213> ORGANISM: Artificial Sequence
<220> FEATURE:
<223> OTHER INFORMATION: oligonucleotide

<400> SEQUENCE: 106
cccaagcttc attagcacca ccattacca                                  29

<210> SEQ ID NO 107
<211> LENGTH: 29
<212> TYPE: DNA
<213> ORGANISM: Artificial Sequence
<220> FEATURE:
<223> OTHER INFORMATION: oligonucleotide

<400> SEQUENCE: 107
cccaagcttc aggtaacggt gcgggctga                                  29

<210> SEQ ID NO 108
<211> LENGTH: 29
<212> TYPE: DNA
<213> ORGANISM: Artificial Sequence
<220> FEATURE:
<223> OTHER INFORMATION: oligonucleotide

<400> SEQUENCE: 108
cccaagcttc gcgtacagga aacacagaa                                  29

<210> SEQ ID NO 109
<211> LENGTH: 29
<212> TYPE: DNA
<213> ORGANISM: Artificial Sequence
<220> FEATURE:
<223> OTHER INFORMATION: oligonucleotide

<400> SEQUENCE: 109
cccaagcttg tgcgggcttt tttttttcga                                 29

<210> SEQ ID NO 110

```
<211> LENGTH: 29
<212> TYPE: DNA
<213> ORGANISM: Artificial Sequence
<220> FEATURE:
<223> OTHER INFORMATION: oligonucleotide

<400> SEQUENCE: 110
cccaagcttt cgaccaaagg taacgaggt                                    29

<210> SEQ ID NO 111
<211> LENGTH: 40
<212> TYPE: DNA
<213> ORGANISM: Artificial Sequence
<220> FEATURE:
<223> OTHER INFORMATION: oligonucleotide

<400> SEQUENCE: 111
catagaacca gaaccagaac ccaattgcgc cagcgggaac                        40

<210> SEQ ID NO 112
<211> LENGTH: 47
<212> TYPE: DNA
<213> ORGANISM: Artificial Sequence
<220> FEATURE:
<223> OTHER INFORMATION: oligonucleotide

<400> SEQUENCE: 112
caattgggtt ctggttctgg ttctatgacc atgattacgg attcact                47

<210> SEQ ID NO 113
<211> LENGTH: 29
<212> TYPE: DNA
<213> ORGANISM: Artificial Sequence
<220> FEATURE:
<223> OTHER INFORMATION: oligonucleotide

<400> SEQUENCE: 113
cgcggatcca cgcgaaatac gggcagaca                                    29

<210> SEQ ID NO 114
<211> LENGTH: 29
<212> TYPE: DNA
<213> ORGANISM: Artificial Sequence
<220> FEATURE:
<223> OTHER INFORMATION: oligonucleotide

<400> SEQUENCE: 114
tgctctagac aattccgacg tctaagaaa                                    29

<210> SEQ ID NO 115
<211> LENGTH: 29
<212> TYPE: DNA
<213> ORGANISM: Artificial Sequence
<220> FEATURE:
<223> OTHER INFORMATION: oligonucleotide

<400> SEQUENCE: 115
cccaagcttg gtcagtgcgt cctgctgat                                    29

<210> SEQ ID NO 116
<211> LENGTH: 48
<212> TYPE: DNA
<213> ORGANISM: Artificial Sequence
<220> FEATURE:
<223> OTHER INFORMATION: oligonucleotide

<400> SEQUENCE: 116
```
ttgggttctg gttctggttc tatgagtaaa ggagaagaac ttttcact          48

<210> SEQ ID NO 117
<211> LENGTH: 29
<212> TYPE: DNA
<213> ORGANISM: Artificial Sequence
<220> FEATURE:
<223> OTHER INFORMATION: oligonucleotide

<400> SEQUENCE: 117
cgcggatccc ttgcatgcct gcaggagat                               29

<210> SEQ ID NO 118
<211> LENGTH: 29
<212> TYPE: DNA
<213> ORGANISM: Artificial Sequence
<220> FEATURE:
<223> OTHER INFORMATION: oligonucleotide

<400> SEQUENCE: 118
tgctctagac aattccgacg tctaagaaa                               29

<210> SEQ ID NO 119
<211> LENGTH: 29
<212> TYPE: DNA
<213> ORGANISM: Artificial Sequence
<220> FEATURE:
<223> OTHER INFORMATION: oligonucleotide

<400> SEQUENCE: 119
cgcggatccg gtcagtgcgt cctgctgat                               29

<210> SEQ ID NO 120
<211> LENGTH: 31
<212> TYPE: DNA
<213> ORGANISM: Artificial Sequence
<220> FEATURE:
<223> OTHER INFORMATION: oligonucleotide

<400> SEQUENCE: 120
cgcggatccc acatatacag gaggagacag a                            31

<210> SEQ ID NO 121
<211> LENGTH: 75
<212> TYPE: DNA
<213> ORGANISM: Artificial Sequence
<220> FEATURE:
<223> OTHER INFORMATION: oligonucleotide

<400> SEQUENCE: 121
cgcggatccg tgcgggcttt tttttcgac caaaggtaac gaggtaacaa ccatgatcat    60
aggggttcct aaaga                                              75

<210> SEQ ID NO 122
<211> LENGTH: 34
<212> TYPE: DNA
<213> ORGANISM: Artificial Sequence
<220> FEATURE:
<223> OTHER INFORMATION: oligonucleotide

<400> SEQUENCE: 122
acatgcatgc gtcataattc gtgaaatggt ctct                         34

<210> SEQ ID NO 123

```
<210> SEQ ID NO 123
<211> LENGTH: 30
<212> TYPE: DNA
<213> ORGANISM: Artificial Sequence
<220> FEATURE:
<223> OTHER INFORMATION: oligonucleotide

<400> SEQUENCE: 123
cccaagctta cagagtacac aacatccatg                                30

<210> SEQ ID NO 124
<211> LENGTH: 40
<212> TYPE: DNA
<213> ORGANISM: Artificial Sequence
<220> FEATURE:
<223> OTHER INFORMATION: oligonucleotide

<400> SEQUENCE: 124
gaagtcgatg tcctaccagc atgcgatgga gctttcctac                     40

<210> SEQ ID NO 125
<211> LENGTH: 40
<212> TYPE: DNA
<213> ORGANISM: Artificial Sequence
<220> FEATURE:
<223> OTHER INFORMATION: oligonucleotide

<400> SEQUENCE: 125
gtaggaaagc tccatcgcat gctggtagga catcgacttc                     40

<210> SEQ ID NO 126
<211> LENGTH: 30
<212> TYPE: DNA
<213> ORGANISM: Artificial Sequence
<220> FEATURE:
<223> OTHER INFORMATION: oligonucleotide

<400> SEQUENCE: 126
cccgatatcg catttattga gaatttctcc                                30

<210> SEQ ID NO 127
<211> LENGTH: 30
<212> TYPE: DNA
<213> ORGANISM: Artificial Sequence
<220> FEATURE:
<223> OTHER INFORMATION: oligonucleotide

<400> SEQUENCE: 127
gcgtcgacat agaacccaac cgcctgctca                                30

<210> SEQ ID NO 128
<211> LENGTH: 44
<212> TYPE: DNA
<213> ORGANISM: Artificial Sequence
<220> FEATURE:
<223> OTHER INFORMATION: oligonucleotide

<400> SEQUENCE: 128
aacgatcgac tatcacagaa gaaacctgat tacctcacta cata                44

<210> SEQ ID NO 129
<211> LENGTH: 44
<212> TYPE: DNA
<213> ORGANISM: Artificial Sequence
<220> FEATURE:
<223> OTHER INFORMATION: oligonucleotide

<400> SEQUENCE: 129
```
tatgtagtga ggtaatcagg tttcttctgt gatagtcgat cgtt            44

<210> SEQ ID NO 130
<211> LENGTH: 33
<212> TYPE: DNA
<213> ORGANISM: Artificial Sequence
<220> FEATURE:
<223> OTHER INFORMATION: oligonucleotide

<400> SEQUENCE: 130
attgcggccg cccgaaataa aatcaggcaa cgt                         33

<210> SEQ ID NO 131
<211> LENGTH: 20
<212> TYPE: DNA
<213> ORGANISM: Artificial Sequence
<220> FEATURE:
<223> OTHER INFORMATION: oligonucleotide

<400> SEQUENCE: 131
cgttaatgaa atatcgccag                                        20

<210> SEQ ID NO 132
<211> LENGTH: 20
<212> TYPE: DNA
<213> ORGANISM: Artificial Sequence
<220> FEATURE:
<223> OTHER INFORMATION: oligonucleotide

<400> SEQUENCE: 132
tcgaaatcgg ccataaagac                                        20

<210> SEQ ID NO 133
<211> LENGTH: 29
<212> TYPE: DNA
<213> ORGANISM: Artificial Sequence
<220> FEATURE:
<223> OTHER INFORMATION: oligonucleotide

<400> SEQUENCE: 133
cgcggatccg gcacgatatt taagctgac                              29

<210> SEQ ID NO 134
<211> LENGTH: 40
<212> TYPE: DNA
<213> ORGANISM: Artificial Sequence
<220> FEATURE:
<223> OTHER INFORMATION: oligonucleotide

<400> SEQUENCE: 134
caaccagcga ctaaccgcag aacaaactcc agataagtgc                  40

<210> SEQ ID NO 135
<211> LENGTH: 40
<212> TYPE: DNA
<213> ORGANISM: Artificial Sequence
<220> FEATURE:
<223> OTHER INFORMATION: oligonucleotide

<400> SEQUENCE: 135
gcacttatct ggagtttgtt ctgcggttag tcgctggttg                  40

<210> SEQ ID NO 136
<211> LENGTH: 31
<212> TYPE: DNA

```
<213> ORGANISM: Artificial Sequence
<220> FEATURE:
<223> OTHER INFORMATION: oligonucleotide

<400> SEQUENCE: 136
attgcggccg cgctggcaac gcgtcattta a                              31

<210> SEQ ID NO 137
<211> LENGTH: 20
<212> TYPE: DNA
<213> ORGANISM: Artificial Sequence
<220> FEATURE:
<223> OTHER INFORMATION: oligonucleotide

<400> SEQUENCE: 137
gtaacacaca cacttcatct                                           20

<210> SEQ ID NO 138
<211> LENGTH: 20
<212> TYPE: DNA
<213> ORGANISM: Artificial Sequence
<220> FEATURE:
<223> OTHER INFORMATION: oligonucleotide

<400> SEQUENCE: 138
gatcccggat gctgatttag                                           20

<210> SEQ ID NO 139
<211> LENGTH: 29
<212> TYPE: DNA
<213> ORGANISM: Artificial Sequence
<220> FEATURE:
<223> OTHER INFORMATION: oligonucleotide

<400> SEQUENCE: 139
cgcggatcca tactgcgatg tgatgggcc                                 29

<210> SEQ ID NO 140
<211> LENGTH: 40
<212> TYPE: DNA
<213> ORGANISM: Artificial Sequence
<220> FEATURE:
<223> OTHER INFORMATION: oligonucleotide

<400> SEQUENCE: 140
aataccagcc cttgttcgtg ctcacatcct caggcgataa                     40

<210> SEQ ID NO 141
<211> LENGTH: 40
<212> TYPE: DNA
<213> ORGANISM: Artificial Sequence
<220> FEATURE:
<223> OTHER INFORMATION: oligonucleotide

<400> SEQUENCE: 141
ttatcgcctg aggatgtgag cacgaacaag ggctggtatt                     40

<210> SEQ ID NO 142
<211> LENGTH: 31
<212> TYPE: DNA
<213> ORGANISM: Artificial Sequence
<220> FEATURE:
<223> OTHER INFORMATION: oligonucleotide

<400> SEQUENCE: 142
attgcggccg ccgttgccac ttcaatccca c                              31
```

<210> SEQ ID NO 143
<211> LENGTH: 20
<212> TYPE: DNA
<213> ORGANISM: Artificial Sequence
<220> FEATURE:
<223> OTHER INFORMATION: oligonucleotide

<400> SEQUENCE: 143
gctatgccaa caacgatatg                                           20

<210> SEQ ID NO 144
<211> LENGTH: 20
<212> TYPE: DNA
<213> ORGANISM: Artificial Sequence
<220> FEATURE:
<223> OTHER INFORMATION: oligonucleotide

<400> SEQUENCE: 144
ggttaatacg ccggttgagc                                           20

<210> SEQ ID NO 145
<211> LENGTH: 29
<212> TYPE: DNA
<213> ORGANISM: Artificial Sequence
<220> FEATURE:
<223> OTHER INFORMATION: oligonucleotide

<400> SEQUENCE: 145
cgcggatccg gaacgattgg tctggaaat                                 29

<210> SEQ ID NO 146
<211> LENGTH: 41
<212> TYPE: DNA
<213> ORGANISM: Artificial Sequence
<220> FEATURE:
<223> OTHER INFORMATION: oligonucleotide

<400> SEQUENCE: 146
ggcttcaatc aggtcaagga tatcctatcc tcaacgaatt a                   41

<210> SEQ ID NO 147
<211> LENGTH: 41
<212> TYPE: DNA
<213> ORGANISM: Artificial Sequence
<220> FEATURE:
<223> OTHER INFORMATION: oligonucleotide

<400> SEQUENCE: 147
taattcgttg aggataggat atccttgacc tgattgaagc c                   41

<210> SEQ ID NO 148
<211> LENGTH: 33
<212> TYPE: DNA
<213> ORGANISM: Artificial Sequence
<220> FEATURE:
<223> OTHER INFORMATION: oligonucleotide

<400> SEQUENCE: 148
attgcggccg ccgcgacgga tattatcaat gac                            33

<210> SEQ ID NO 149
<211> LENGTH: 20
<212> TYPE: DNA
<213> ORGANISM: Artificial Sequence
<220> FEATURE:

```
<223> OTHER INFORMATION: oligonucleotide

<400> SEQUENCE: 149
gcgccaaaat ccaaagtagc                                               20

<210> SEQ ID NO 150
<211> LENGTH: 20
<212> TYPE: DNA
<213> ORGANISM: Artificial Sequence
<220> FEATURE:
<223> OTHER INFORMATION: oligonucleotide

<400> SEQUENCE: 150
atgtgcgcgc tgggaaacat                                               20

<210> SEQ ID NO 151
<211> LENGTH: 30
<212> TYPE: DNA
<213> ORGANISM: Artificial Sequence
<220> FEATURE:
<223> OTHER INFORMATION: oligonucleotide

<400> SEQUENCE: 151
cccaagctta cagagtacac aacatccatg                                    30

<210> SEQ ID NO 152
<211> LENGTH: 40
<212> TYPE: DNA
<213> ORGANISM: Artificial Sequence
<220> FEATURE:
<223> OTHER INFORMATION: oligonucleotide

<400> SEQUENCE: 152
gtaggaaagc tccatcgcat gctggtagga catcgacttc                         40

<210> SEQ ID NO 153
<211> LENGTH: 40
<212> TYPE: DNA
<213> ORGANISM: Artificial Sequence
<220> FEATURE:
<223> OTHER INFORMATION: oligonucleotide

<400> SEQUENCE: 153
gaagtcgatg tcctaccagc atgcgatgga gctttcctac                         40

<210> SEQ ID NO 154
<211> LENGTH: 30
<212> TYPE: DNA
<213> ORGANISM: Artificial Sequence
<220> FEATURE:
<223> OTHER INFORMATION: oligonucleotide

<400> SEQUENCE: 154
cccgatatcg catttattga gaatttctcc                                    30

<210> SEQ ID NO 155
<211> LENGTH: 29
<212> TYPE: DNA
<213> ORGANISM: Artificial Sequence
<220> FEATURE:
<223> OTHER INFORMATION: oligonucleotide

<400> SEQUENCE: 155
tgctctagac aattccgacg tctaagaaa                                     29
```

```
<210> SEQ ID NO 156
<211> LENGTH: 29
<212> TYPE: DNA
<213> ORGANISM: Artificial Sequence
<220> FEATURE:
<223> OTHER INFORMATION: oligonucleotide

<400> SEQUENCE: 156
cccaagcttg gtcagtgcgt cctgctgat                              29

<210> SEQ ID NO 157
<211> LENGTH: 28
<212> TYPE: DNA
<213> ORGANISM: Artificial Sequence
<220> FEATURE:
<223> OTHER INFORMATION: oligonucleotide

<400> SEQUENCE: 157
aactgcaggg cacgatattt aagctgac                               28

<210> SEQ ID NO 158
<211> LENGTH: 28
<212> TYPE: DNA
<213> ORGANISM: Artificial Sequence
<220> FEATURE:
<223> OTHER INFORMATION: oligonucleotide

<400> SEQUENCE: 158
gaagatctaa caaactccag ataagtgc                               28

<210> SEQ ID NO 159
<211> LENGTH: 29
<212> TYPE: DNA
<213> ORGANISM: Artificial Sequence
<220> FEATURE:
<223> OTHER INFORMATION: oligonucleotide

<400> SEQUENCE: 159
cgcggatccc tgcggttagt cgctggttg                              29

<210> SEQ ID NO 160
<211> LENGTH: 30
<212> TYPE: DNA
<213> ORGANISM: Artificial Sequence
<220> FEATURE:
<223> OTHER INFORMATION: oligonucleotide

<400> SEQUENCE: 160
ctagtctaga gctggcaacg cgtcatttaa                             30

<210> SEQ ID NO 161
<211> LENGTH: 28
<212> TYPE: DNA
<213> ORGANISM: Artificial Sequence
<220> FEATURE:
<223> OTHER INFORMATION: oligonucleotide

<400> SEQUENCE: 161
gaagatctca attccgacgt ctaagaaa                               28

<210> SEQ ID NO 162
<211> LENGTH: 30
<212> TYPE: DNA
<213> ORGANISM: Artificial Sequence
<220> FEATURE:
<223> OTHER INFORMATION: oligonucleotide
```

```
<400> SEQUENCE: 162
cgcggatccg catttattga gaatttctcc                                30

<210> SEQ ID NO 163
<211> LENGTH: 59
<212> TYPE: DNA
<213> ORGANISM: Artificial Sequence
<220> FEATURE:
<223> OTHER INFORMATION: oligonucleotide

<400> SEQUENCE: 163
taatcatccg gctcgtataa tgtaaccgag gagcagacaa tggctgactc gcaacccct  59

<210> SEQ ID NO 164
<211> LENGTH: 29
<212> TYPE: DNA
<213> ORGANISM: Artificial Sequence
<220> FEATURE:
<223> OTHER INFORMATION: oligonucleotide

<400> SEQUENCE: 164
cagcgtgttg gcgaagcgca gaaacgcgc                                 29

<210> SEQ ID NO 165
<211> LENGTH: 29
<212> TYPE: DNA
<213> ORGANISM: Artificial Sequence
<220> FEATURE:
<223> OTHER INFORMATION: oligonucleotide

<400> SEQUENCE: 165
gcgcgtttct gcgcttcgcc aacacgctg                                 29

<210> SEQ ID NO 166
<211> LENGTH: 44
<212> TYPE: DNA
<213> ORGANISM: Artificial Sequence
<220> FEATURE:
<223> OTHER INFORMATION: oligonucleotide

<400> SEQUENCE: 166
ctatatgaca ggaaatttat tgcgggcatt ctggaagatt ttgc                44

<210> SEQ ID NO 167
<211> LENGTH: 28
<212> TYPE: DNA
<213> ORGANISM: Artificial Sequence
<220> FEATURE:
<223> OTHER INFORMATION: oligonucleotide

<400> SEQUENCE: 167
cgcggatccg tgctgacctc aaacctgt                                  28

<210> SEQ ID NO 168
<211> LENGTH: 59
<212> TYPE: DNA
<213> ORGANISM: Artificial Sequence
<220> FEATURE:
<223> OTHER INFORMATION: oligonucleotide

<400> SEQUENCE: 168
ctcggttaca ttatacgagc cggatgatta attgtcaacg atcctttcat tgtgttgtc  59

<210> SEQ ID NO 169
<211> LENGTH: 45
```

```
<212> TYPE: DNA
<213> ORGANISM: Artificial Sequence
<220> FEATURE:
<223> OTHER INFORMATION: oligonucleotide

<400> SEQUENCE: 169
gcaaaatctt ccagaatgcc ccgcaataaa tttcctgtca tatag            45

<210> SEQ ID NO 170
<211> LENGTH: 41
<212> TYPE: DNA
<213> ORGANISM: Artificial Sequence
<220> FEATURE:
<223> OTHER INFORMATION: oligonucleotide

<400> SEQUENCE: 170
accgaacata ttacaggcca gcaaggcctt ctccaggaga a                41

<210> SEQ ID NO 171
<211> LENGTH: 41
<212> TYPE: DNA
<213> ORGANISM: Artificial Sequence
<220> FEATURE:
<223> OTHER INFORMATION: oligonucleotide

<400> SEQUENCE: 171
ttctcctgga gaaggccttg ctggcctgta atatgttcgg t                41

<210> SEQ ID NO 172
<211> LENGTH: 32
<212> TYPE: DNA
<213> ORGANISM: Artificial Sequence
<220> FEATURE:
<223> OTHER INFORMATION: oligonucleotide

<400> SEQUENCE: 172
attgcggccg cctcgcgaag ttccatcatc ct                          32

<210> SEQ ID NO 173
<211> LENGTH: 16
<212> TYPE: DNA
<213> ORGANISM: Artificial Sequence
<220> FEATURE:
<223> OTHER INFORMATION: oligonucleotide

<400> SEQUENCE: 173
aaccgaggag cagaca                                            16

<210> SEQ ID NO 174
<211> LENGTH: 31
<212> TYPE: DNA
<213> ORGANISM: Artificial Sequence
<220> FEATURE:
<223> OTHER INFORMATION: oligonucleotide

<400> SEQUENCE: 174
ttgacaatta atcatccggc tcgtataatg t                           31

<210> SEQ ID NO 175
<211> LENGTH: 28
<212> TYPE: DNA
<213> ORGANISM: Artificial Sequence
<220> FEATURE:
<223> OTHER INFORMATION: oligonucleotide

<400> SEQUENCE: 175
```

```
cgcggatccg gctgtaagct gttctgag                                      28
```

<210> SEQ ID NO 176
<211> LENGTH: 40
<212> TYPE: DNA
<213> ORGANISM: Artificial Sequence
<220> FEATURE:
<223> OTHER INFORMATION: oligonucleotide

<400> SEQUENCE: 176

```
caaaaaaaac ccccggacct gcatcttgtt cgaaggaatg                         40
```

<210> SEQ ID NO 177
<211> LENGTH: 40
<212> TYPE: DNA
<213> ORGANISM: Artificial Sequence
<220> FEATURE:
<223> OTHER INFORMATION: oligonucleotide

<400> SEQUENCE: 177

```
cattccttcg aacaagatgc aggtccgggg gttttttttg                         40
```

<210> SEQ ID NO 178
<211> LENGTH: 31
<212> TYPE: DNA
<213> ORGANISM: Artificial Sequence
<220> FEATURE:
<223> OTHER INFORMATION: oligonucleotide

<400> SEQUENCE: 178

```
attgcggccg cccagacgtt ctcaagttcg t                                  31
```

<210> SEQ ID NO 179
<211> LENGTH: 13
<212> TYPE: DNA
<213> ORGANISM: Artificial Sequence
<220> FEATURE:
<223> OTHER INFORMATION: oligonucleotide

<400> SEQUENCE: 179

```
aagaaaagac aaa                                                      13
```

<210> SEQ ID NO 180
<211> LENGTH: 31
<212> TYPE: DNA
<213> ORGANISM: Artificial Sequence
<220> FEATURE:
<223> OTHER INFORMATION: oligonucleotide

<400> SEQUENCE: 180

```
attgcggccg ccaactcttc cagcgactgc a                                  31
```

<210> SEQ ID NO 181
<211> LENGTH: 31
<212> TYPE: DNA
<213> ORGANISM: Artificial Sequence
<220> FEATURE:
<223> OTHER INFORMATION: oligonucleotide

<400> SEQUENCE: 181

```
ctagtctaga gcttttcatt ctgactgcaa c                                  31
```

<210> SEQ ID NO 182
<211> LENGTH: 59
<212> TYPE: DNA
<213> ORGANISM: Artificial Sequence

```
<220> FEATURE:
<223> OTHER INFORMATION: oligonucleotide

<400> SEQUENCE: 182
cccaagctta cattatacga gccggatgat taattgtcaa ctgtctgtgc gctatgcct      59

<210> SEQ ID NO 183
<211> LENGTH: 36
<212> TYPE: DNA
<213> ORGANISM: Artificial Sequence
<220> FEATURE:
<223> OTHER INFORMATION: oligonucleotide

<400> SEQUENCE: 183
cccaagctta agatgcaaga aaagacaaaa tgacag                               36

<210> SEQ ID NO 184
<211> LENGTH: 59
<212> TYPE: DNA
<213> ORGANISM: Artificial Sequence
<220> FEATURE:
<223> OTHER INFORMATION: oligonucleotide

<400> SEQUENCE: 184
agttcttctc ctttactcat agaaccagaa ccagaacctg agaaacagaa ttttgtgct      59

<210> SEQ ID NO 185
<211> LENGTH: 43
<212> TYPE: DNA
<213> ORGANISM: Artificial Sequence
<220> FEATURE:
<223> OTHER INFORMATION: oligonucleotide

<400> SEQUENCE: 185
ggttctggtt ctggttctat gagtaaagga gaagaacttt tca                      43

<210> SEQ ID NO 186
<211> LENGTH: 83
<212> TYPE: DNA
<213> ORGANISM: Artificial Sequence
<220> FEATURE:
<223> OTHER INFORMATION: oligonucleotide

<400> SEQUENCE: 186
acatgcatgc caaaaaaccc ctcaagaccc gtttagaggc cccaaggggt tatgctagtt     60
atttgtagag ctcatccatg cca                                            83

<210> SEQ ID NO 187
<211> LENGTH: 20
<212> TYPE: DNA
<213> ORGANISM: Artificial Sequence
<220> FEATURE:
<223> OTHER INFORMATION: oligonucleotide

<400> SEQUENCE: 187
aagatgcaag aaaagacaaa                                                20

<210> SEQ ID NO 188
<211> LENGTH: 31
<212> TYPE: DNA
<213> ORGANISM: Artificial Sequence
<220> FEATURE:
<223> OTHER INFORMATION: oligonucleotide

<400> SEQUENCE: 188
```

```
cccaagctta ggtccggggg ttttttttga c                              31
```

<210> SEQ ID NO 189
<211> LENGTH: 29
<212> TYPE: DNA
<213> ORGANISM: Artificial Sequence
<220> FEATURE:
<223> OTHER INFORMATION: oligonucleotide

<400> SEQUENCE: 189

```
cccaagctta cataaccgag gagcagaca                                 29
```

<210> SEQ ID NO 190
<211> LENGTH: 29
<212> TYPE: DNA
<213> ORGANISM: Artificial Sequence
<220> FEATURE:
<223> OTHER INFORMATION: oligonucleotide

<400> SEQUENCE: 190

```
cgcggatccg aaagtgtacg aaagccagg                                 29
```

<210> SEQ ID NO 191
<211> LENGTH: 40
<212> TYPE: DNA
<213> ORGANISM: Artificial Sequence
<220> FEATURE:
<223> OTHER INFORMATION: oligonucleotide

<400> SEQUENCE: 191

```
gcgctatcag gcattttcc tattaacccc ccagtttcga                      40
```

<210> SEQ ID NO 192
<211> LENGTH: 40
<212> TYPE: DNA
<213> ORGANISM: Artificial Sequence
<220> FEATURE:
<223> OTHER INFORMATION: oligonucleotide

<400> SEQUENCE: 192

```
tcgaaactgg ggggttaata ggaaaaatgc ctgatagcgc                     40
```

<210> SEQ ID NO 193
<211> LENGTH: 31
<212> TYPE: DNA
<213> ORGANISM: Artificial Sequence
<220> FEATURE:
<223> OTHER INFORMATION: oligonucleotide

<400> SEQUENCE: 193

```
attgcggccg cgtgaagcgg atctggcgat t                              31
```

<210> SEQ ID NO 194
<211> LENGTH: 20
<212> TYPE: DNA
<213> ORGANISM: Artificial Sequence
<220> FEATURE:
<223> OTHER INFORMATION: oligonucleotide

<400> SEQUENCE: 194

```
atggctgtat ccgctcgctg                                           20
```

<210> SEQ ID NO 195
<211> LENGTH: 21
<212> TYPE: DNA
<213> ORGANISM: Artificial Sequence

```
<220> FEATURE:
<223> OTHER INFORMATION: oligonucleotide

<400> SEQUENCE: 195
acaccatcga tcagcaaggg c                                              21

<210> SEQ ID NO 196
<211> LENGTH: 29
<212> TYPE: DNA
<213> ORGANISM: Artificial Sequence
<220> FEATURE:
<223> OTHER INFORMATION: oligonucleotide

<400> SEQUENCE: 196
tgctctagac aattccgacg tctaagaaa                                      29

<210> SEQ ID NO 197
<211> LENGTH: 29
<212> TYPE: DNA
<213> ORGANISM: Artificial Sequence
<220> FEATURE:
<223> OTHER INFORMATION: oligonucleotide

<400> SEQUENCE: 197
cgcggatccg gtcagtgcgt cctgctgat                                      29

<210> SEQ ID NO 198
<211> LENGTH: 36
<212> TYPE: DNA
<213> ORGANISM: Artificial Sequence
<220> FEATURE:
<223> OTHER INFORMATION: oligonucleotide

<400> SEQUENCE: 198
cgcggatcca agatgcaaga aaagacaaaa tgacag                              36

<210> SEQ ID NO 199
<211> LENGTH: 31
<212> TYPE: DNA
<213> ORGANISM: Artificial Sequence
<220> FEATURE:
<223> OTHER INFORMATION: oligonucleotide

<400> SEQUENCE: 199
cgcggatcca ggtccggggg tttttttga c                                    31

<210> SEQ ID NO 200
<211> LENGTH: 29
<212> TYPE: DNA
<213> ORGANISM: Artificial Sequence
<220> FEATURE:
<223> OTHER INFORMATION: oligonucleotide

<400> SEQUENCE: 200
cgcggatcca cataaccgag gagcagaca                                      29

<210> SEQ ID NO 201
<211> LENGTH: 32
<212> TYPE: DNA
<213> ORGANISM: Artificial Sequence
<220> FEATURE:
<223> OTHER INFORMATION: oligonucleotide

<400> SEQUENCE: 201
tgacctgatg ttgcatcatg ataatttctc ca                                  32
```

<210> SEQ ID NO 202
<211> LENGTH: 32
<212> TYPE: DNA
<213> ORGANISM: Artificial Sequence
<220> FEATURE:
<223> OTHER INFORMATION: oligonucleotide

<400> SEQUENCE: 202
tggagaaatt atcatgatgc aacatcaggt ca                                    32

<210> SEQ ID NO 203
<211> LENGTH: 82
<212> TYPE: DNA
<213> ORGANISM: Artificial Sequence
<220> FEATURE:
<223> OTHER INFORMATION: oligonucleotide

<400> SEQUENCE: 203
aaacggccgc aaaaaacccc tcaagacccg tttagaggcc caaggggtt atgctagtta       60 accccccagt ttcgatttat cg                                               82

<210> SEQ ID NO 204
<211> LENGTH: 20
<212> TYPE: DNA
<213> ORGANISM: Artificial Sequence
<220> FEATURE:
<223> OTHER INFORMATION: oligonucleotide

<400> SEQUENCE: 204
aagatgcaag aaaagacaaa                                                  20

<210> SEQ ID NO 205
<211> LENGTH: 29
<212> TYPE: DNA
<213> ORGANISM: Artificial Sequence
<220> FEATURE:
<223> OTHER INFORMATION: oligonucleotide

<400> SEQUENCE: 205
cccaagctta cgtaaaaagg gtatcgaca                                        29

<210> SEQ ID NO 206
<211> LENGTH: 59
<212> TYPE: DNA
<213> ORGANISM: Artificial Sequence
<220> FEATURE:
<223> OTHER INFORMATION: oligonucleotide

<400> SEQUENCE: 206
agttcttctc ctttactcat agaaccagaa ccagaaccca gttcgagagt cggttttg        59

<210> SEQ ID NO 207
<211> LENGTH: 43
<212> TYPE: DNA
<213> ORGANISM: Artificial Sequence
<220> FEATURE:
<223> OTHER INFORMATION: oligonucleotide

<400> SEQUENCE: 207
ggttctggtt ctggttctat gagtaaagga gaagaacttt tca                        43

<210> SEQ ID NO 208
<211> LENGTH: 83
<212> TYPE: DNA
<213> ORGANISM: Artificial Sequence
<220> FEATURE:
<223> OTHER INFORMATION: oligonucleotide

<400> SEQUENCE: 208
acatgcatgc caaaaaaccc ctcaagaccc gtttagaggc cccaaggggt tatgctagtt    60
atttgtagag ctcatccatg cca                                           83

<210> SEQ ID NO 209
<211> LENGTH: 35
<212> TYPE: DNA
<213> ORGANISM: Artificial Sequence
<220> FEATURE:
<223> OTHER INFORMATION: oligonucleotide

<400> SEQUENCE: 209
cccaagcttc taatgagcgg gcttttttt gaaca                               35

<210> SEQ ID NO 210
<211> LENGTH: 29
<212> TYPE: DNA
<213> ORGANISM: Artificial Sequence
<220> FEATURE:
<223> OTHER INFORMATION: oligonucleotide

<400> SEQUENCE: 210
cccaagcttg cgggcttttt tttgaacaa                                     29

<210> SEQ ID NO 211
<211> LENGTH: 37
<212> TYPE: DNA
<213> ORGANISM: Artificial Sequence
<220> FEATURE:
<223> OTHER INFORMATION: oligonucleotide

<400> SEQUENCE: 211
cccaagctta acaaaattag agaataacaa tgcaaac                            37

<210> SEQ ID NO 212
<211> LENGTH: 31
<212> TYPE: DNA
<213> ORGANISM: Artificial Sequence
<220> FEATURE:
<223> OTHER INFORMATION: oligonucleotide

<400> SEQUENCE: 212
ctagctagca tctcgttttt cgcgacaatc t                                  31

<210> SEQ ID NO 213
<211> LENGTH: 40
<212> TYPE: DNA
<213> ORGANISM: Artificial Sequence
<220> FEATURE:
<223> OTHER INFORMATION: oligonucleotide

<400> SEQUENCE: 213
caggtcagcg agatattgta gggtgatcat atcgagaaac                         40

<210> SEQ ID NO 214
<211> LENGTH: 40
<212> TYPE: DNA
<213> ORGANISM: Artificial Sequence
<220> FEATURE:
<223> OTHER INFORMATION: oligonucleotide

<400> SEQUENCE: 214

```
gtttctcgat atgatcaccc tacaatatct cgctgacctg                               40
```

<210> SEQ ID NO 215
<211> LENGTH: 28
<212> TYPE: DNA
<213> ORGANISM: Artificial Sequence
<220> FEATURE:
<223> OTHER INFORMATION: oligonucleotide

<400> SEQUENCE: 215

```
cgcggatcca gcgaaagcag cggcggtt                                            28
```

<210> SEQ ID NO 216
<211> LENGTH: 29
<212> TYPE: DNA
<213> ORGANISM: Artificial Sequence
<220> FEATURE:
<223> OTHER INFORMATION: oligonucleotide

<400> SEQUENCE: 216

```
cgcggatcca tccagagatt tctgaagcg                                           29
```

<210> SEQ ID NO 217
<211> LENGTH: 48
<212> TYPE: DNA
<213> ORGANISM: Artificial Sequence
<220> FEATURE:
<223> OTHER INFORMATION: oligonucleotide

<400> SEQUENCE: 217

```
aatcggccgt taatttctta tataacattg agttatagat ataacaac                      48
```

<210> SEQ ID NO 218
<211> LENGTH: 29
<212> TYPE: DNA
<213> ORGANISM: Artificial Sequence
<220> FEATURE:
<223> OTHER INFORMATION: oligonucleotide

<400> SEQUENCE: 218

```
tgctctagac aattccgacg tctaagaaa                                           29
```

<210> SEQ ID NO 219
<211> LENGTH: 29
<212> TYPE: DNA
<213> ORGANISM: Artificial Sequence
<220> FEATURE:
<223> OTHER INFORMATION: oligonucleotide

<400> SEQUENCE: 219

```
cccaagcttg gtcagtgcgt cctgctgat                                           29
```

<210> SEQ ID NO 220
<211> LENGTH: 29
<212> TYPE: DNA
<213> ORGANISM: Artificial Sequence
<220> FEATURE:
<223> OTHER INFORMATION: oligonucleotide

<400> SEQUENCE: 220

```
cgcggatcca cgtaaaaagg gtatcgaca                                           29
```

<210> SEQ ID NO 221
<211> LENGTH: 35
<212> TYPE: DNA
<213> ORGANISM: Artificial Sequence

```
<220> FEATURE:
<223> OTHER INFORMATION: oligonucleotide

<400> SEQUENCE: 221
cgcggatccc taatgagcgg ctttttttt gaaca                               35

<210> SEQ ID NO 222
<211> LENGTH: 37
<212> TYPE: DNA
<213> ORGANISM: Artificial Sequence
<220> FEATURE:
<223> OTHER INFORMATION: oligonucleotide

<400> SEQUENCE: 222
cgcggatcca acaaaattag agaataacaa tgcaaac                            37

<210> SEQ ID NO 223
<211> LENGTH: 37
<212> TYPE: DNA
<213> ORGANISM: Artificial Sequence
<220> FEATURE:
<223> OTHER INFORMATION: oligonucletide

<400> SEQUENCE: 223
atcctgcata aaaaacgtgt acgggctggg attactc                            37

<210> SEQ ID NO 224
<211> LENGTH: 37
<212> TYPE: DNA
<213> ORGANISM: Artificial Sequence
<220> FEATURE:
<223> OTHER INFORMATION: oligonucleotide

<400> SEQUENCE: 224
gagtaatccc agcccgtaca cgttttttat gcaggat                            37

<210> SEQ ID NO 225
<211> LENGTH: 33
<212> TYPE: DNA
<213> ORGANISM: Artificial Sequence
<220> FEATURE:
<223> OTHER INFORMATION: oligonucleotide

<400> SEQUENCE: 225
acatgcatgc gttatgttgc gggattaatt tgt                                33

<210> SEQ ID NO 226
<211> LENGTH: 29
<212> TYPE: DNA
<213> ORGANISM: Artificial Sequence
<220> FEATURE:
<223> OTHER INFORMATION: oligonucleotide

<400> SEQUENCE: 226
tgctctagac aattccgacg tctaagaga                                     29

<210> SEQ ID NO 227
<211> LENGTH: 29
<212> TYPE: DNA
<213> ORGANISM: Artificial Sequence
<220> FEATURE:
<223> OTHER INFORMATION: oligonucleotide

<400> SEQUENCE: 227
cccaagcttg gtcagtgcgt cctgctgat                                     29
```

<210> SEQ ID NO 228
<211> LENGTH: 36
<212> TYPE: DNA
<213> ORGANISM: Artificial Sequence
<220> FEATURE:
<223> OTHER INFORMATION: oligonucleotide

<400> SEQUENCE: 228
cccaagctta aacattcaca gagactttta tgacac                     36

<210> SEQ ID NO 229
<211> LENGTH: 58
<212> TYPE: DNA
<213> ORGANISM: Artificial Sequence
<220> FEATURE:
<223> OTHER INFORMATION: oligonucleotide

<400> SEQUENCE: 229
agttcttctc ctttactcat agaaccagaa ccagaaccaa tgccacagcg cgccagca   58

<210> SEQ ID NO 230
<211> LENGTH: 43
<212> TYPE: DNA
<213> ORGANISM: Artificial Sequence
<220> FEATURE:
<223> OTHER INFORMATION: oligonucleotide

<400> SEQUENCE: 230
ggttctggtt ctggttctat gagtaaagga gaagaacttt tca              43

<210> SEQ ID NO 231
<211> LENGTH: 83
<212> TYPE: DNA
<213> ORGANISM: Artificial Sequence
<220> FEATURE:
<223> OTHER INFORMATION: oligonucleotide

<400> SEQUENCE: 231
acatgcatgc caaaaaaccc ctcaagaccc gtttagaggc cccaaggggt tatgctagtt   60
atttgtagag ctcatccatg cca                                         83

<210> SEQ ID NO 232
<211> LENGTH: 20
<212> TYPE: DNA
<213> ORGANISM: Artificial Sequence
<220> FEATURE:
<223> OTHER INFORMATION: oligonucleotide

<400> SEQUENCE: 232
aaacattcac agagactttt                                        20

<210> SEQ ID NO 233
<211> LENGTH: 33
<212> TYPE: DNA
<213> ORGANISM: Artificial Sequence
<220> FEATURE:
<223> OTHER INFORMATION: oligonucleotide

<400> SEQUENCE: 233
cccaagctta ccttccgggg gcttttttat tgc                         33

<210> SEQ ID NO 234
<211> LENGTH: 35
<212> TYPE: DNA
<213> ORGANISM: Artificial Sequence
<220> FEATURE:
<223> OTHER INFORMATION: oligonucleotide

<400> SEQUENCE: 234
cccaagcttg tttaaagagg aataacaaaa tgaca    35

<210> SEQ ID NO 235
<211> LENGTH: 28
<212> TYPE: DNA
<213> ORGANISM: Artificial Sequence
<220> FEATURE:
<223> OTHER INFORMATION: oligonucleotide

<400> SEQUENCE: 235
cgcggatccc gtcccatgat tcctcaga    28

<210> SEQ ID NO 236
<211> LENGTH: 43
<212> TYPE: DNA
<213> ORGANISM: Artificial Sequence
<220> FEATURE:
<223> OTHER INFORMATION: oligonucleotide

<400> SEQUENCE: 236 aaagccccccg gaaggtgatg tgaatgttta ttcaactgat gtc    43

<210> SEQ ID NO 237
<211> LENGTH: 43
<212> TYPE: DNA
<213> ORGANISM: Artificial Sequence
<220> FEATURE:
<223> OTHER INFORMATION: oligonucleotide

<400> SEQUENCE: 237
gacatcagtt gaataaacat tcacatcacc ttccgggggc ttt    43

<210> SEQ ID NO 238
<211> LENGTH: 37
<212> TYPE: DNA
<213> ORGANISM: Artificial Sequence
<220> FEATURE:
<223> OTHER INFORMATION: oligonucleotide

<400> SEQUENCE: 238
attgcggccg ccccagaaca gggttttgct gctgacc    37

<210> SEQ ID NO 239
<211> LENGTH: 31
<212> TYPE: DNA
<213> ORGANISM: Artificial Sequence
<220> FEATURE:
<223> OTHER INFORMATION: oligonucleotide

<400> SEQUENCE: 239
attgcggccg ccagaaccgt tcagtaagca g    31

<210> SEQ ID NO 240
<211> LENGTH: 31
<212> TYPE: DNA
<213> ORGANISM: Artificial Sequence
<220> FEATURE:
<223> OTHER INFORMATION: oligonucleotide

<400> SEQUENCE: 240
ctagtctaga gcttttcatt ctgactgcaa c    31

<210> SEQ ID NO 241
<211> LENGTH: 59
<212> TYPE: DNA
<213> ORGANISM: Artificial Sequence
<220> FEATURE:
<223> OTHER INFORMATION: oligonucleotide

<400> SEQUENCE: 241
cccaagctta cattatacga gccggatgat taattgtcaa ctgtctgtgc gctatgcct         59

<210> SEQ ID NO 242
<211> LENGTH: 33
<212> TYPE: DNA
<213> ORGANISM: Artificial Sequence
<220> FEATURE:
<223> OTHER INFORMATION: oligonucleotide

<400> SEQUENCE: 242
cccaagctta gtcacttaag gaaacaaaca tga                                     33

<210> SEQ ID NO 243
<211> LENGTH: 59
<212> TYPE: DNA
<213> ORGANISM: Artificial Sequence
<220> FEATURE:
<223> OTHER INFORMATION: oligonucleotide

<400> SEQUENCE: 243
agttcttctc ctttactcat agaaccagaa ccagaaccca gcgccagtaa cgggttttc         59

<210> SEQ ID NO 244
<211> LENGTH: 43
<212> TYPE: DNA
<213> ORGANISM: Artificial Sequence
<220> FEATURE:
<223> OTHER INFORMATION: oligonucleotide

<400> SEQUENCE: 244
ggttctggtt ctggttctat gagtaaagga gaagaacttt tca                          43

<210> SEQ ID NO 245
<211> LENGTH: 83
<212> TYPE: DNA
<213> ORGANISM: Artificial Sequence
<220> FEATURE:
<223> OTHER INFORMATION: oligonucleotide

<400> SEQUENCE: 245
acatgcatgc caaaaaaccc ctcaagaccc gtttagaggc cccaaggggt tatgctagtt        60
atttgtagag ctcatccatg cca                                                83

<210> SEQ ID NO 246
<211> LENGTH: 39
<212> TYPE: DNA
<213> ORGANISM: Artificial Sequence
<220> FEATURE:
<223> OTHER INFORMATION: oligonucleotide

<400> SEQUENCE: 246
cccaagcttc ttttttattg ataacaaaaa ggcaacact                               39

<210> SEQ ID NO 247
<211> LENGTH: 33
<212> TYPE: DNA
<213> ORGANISM: Artificial Sequence

```
<220> FEATURE:
<223> OTHER INFORMATION: oligonucleotide

<400> SEQUENCE: 247
cccaagcttg ataacaaaaa ggcaacacta tga                              33

<210> SEQ ID NO 248
<211> LENGTH: 29
<212> TYPE: DNA
<213> ORGANISM: Artificial Sequence
<220> FEATURE:
<223> OTHER INFORMATION: oligonucleotide

<400> SEQUENCE: 248
tgctctagac aattccgacg tctaagaaa                                   29

<210> SEQ ID NO 249
<211> LENGTH: 29
<212> TYPE: DNA
<213> ORGANISM: Artificial Sequence
<220> FEATURE:
<223> OTHER INFORMATION: oligonucleotide

<400> SEQUENCE: 249
cccaagcttg gtcagtgcgt cctgctgat                                   29

<210> SEQ ID NO 250
<211> LENGTH: 33
<212> TYPE: DNA
<213> ORGANISM: Artificial Sequence
<220> FEATURE:
<223> OTHER INFORMATION: oligonucleotide

<400> SEQUENCE: 250
cccaagctta gtcacttaag gaaacaaaca tga                              33

<210> SEQ ID NO 251
<211> LENGTH: 39
<212> TYPE: DNA
<213> ORGANISM: Artificial Sequence
<220> FEATURE:
<223> OTHER INFORMATION: oligonucleotide

<400> SEQUENCE: 251
cccaagcttc tttttattg ataacaaaaa ggcaacact                         39

<210> SEQ ID NO 252
<211> LENGTH: 33
<212> TYPE: DNA
<213> ORGANISM: Artificial Sequence
<220> FEATURE:
<223> OTHER INFORMATION: oligonucleotide

<400> SEQUENCE: 252
cccaagcttg ataacaaaaa ggcaacacta tga                              33

<210> SEQ ID NO 253
<211> LENGTH: 28
<212> TYPE: DNA
<213> ORGANISM: Artificial Sequence
<220> FEATURE:
<223> OTHER INFORMATION: oligonucleotide

<400> SEQUENCE: 253
cttcaaccag cgcacaggct tgttgccc                                    28
```

<210> SEQ ID NO 254
<211> LENGTH: 28
<212> TYPE: DNA
<213> ORGANISM: Artificial Sequence
<220> FEATURE:
<223> OTHER INFORMATION: oligonucleotide

<400> SEQUENCE: 254
gggcaacaag cctgtgcgct ggttgaag                               28

<210> SEQ ID NO 255
<211> LENGTH: 28
<212> TYPE: DNA
<213> ORGANISM: Artificial Sequence
<220> FEATURE:
<223> OTHER INFORMATION: oligonucleotide

<400> SEQUENCE: 255
cgcggatccc gcacagcgtt ttcagagt                               28

<210> SEQ ID NO 256
<211> LENGTH: 20
<212> TYPE: DNA
<213> ORGANISM: Artificial Sequence
<220> FEATURE:
<223> OTHER INFORMATION: oligonucleotide

<400> SEQUENCE: 256
agtcacttaa ggaaacaaac                                        20

<210> SEQ ID NO 257
<211> LENGTH: 32
<212> TYPE: DNA
<213> ORGANISM: Artificial Sequence
<220> FEATURE:
<223> OTHER INFORMATION: oligonucleotide

<400> SEQUENCE: 257
acatgcatgc caaagcatag cggattgttt tc                          32

<210> SEQ ID NO 258
<211> LENGTH: 29
<212> TYPE: DNA
<213> ORGANISM: Artificial Sequence
<220> FEATURE:
<223> OTHER INFORMATION: oligonucleotide

<400> SEQUENCE: 258
cgcggatcct taagccacgc gagccgtca                              29

METHOD FOR MODIFYING AMINO ACID ATTENUATOR AND USE OF SAME IN PRODUCTION

FIELD OF THE INVENTION

The present invention belongs to the field of biotechnology, and specifically relates to a method for modifying an amino acid attenuator, a class of amino acid attenuator mutants, an engineered bacteria created on the basis of the amino acid attenuator mutants, and a use of the engineered bacteria.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 55569222_1, the date of creation of the ASCII text file is May 31, 2022, and the size of the ASCII text file is 256 KB.

BACKGROUND ART

Amino acids are basic substances for constituting proteins, and are widely used in industries such as foods, medical health care, agriculture and animal husbandry, daily chemicals, and the like.

For expressing a target protein in a bioreactor, it is usually performed by introducing a DNA molecule having a promoter and a gene coding for a target protein into a bioreactor, starting an expression of the coding gene by the promoter, and obtaining the target protein. Thus, it is of great applicable promise to enhance the ability for expressing a target protein.

L-alanine is a non-essential amino acid in human. It has a sweet taste and is easily dissolved in water and can be used in a variety of fields. In the food industry, L-alanine can be used for improving food taste and bioavailability of proteins. In the pharmaceutical field, L-alanine is often used as an amino acid-based nutrient medicine, and meanwhile, it is also an important material for producing organic compounds like amino-propanol, vitamin B6, and the like. In recent years, L-alanine has also been used for the synthesis of engineering plastics such as polyamides, polyesteramides, and so on. Especially, use of L-alanine as the precursor for synthesizing surfactants in the washing and cosmetics industry has greatly increased the demand for its amount in the market and expanded the fields of its application. The chemical name of L-threonine is α-amino-β-hydroxybutyric acid, which is one of eight essential amino acids in human. As a basic component for constituting biomacromolecules, threonine has a crutial physiological effect on the nutrition and health of human and animals, and is widely used in the industries of foods, feeds, and pharmaceuticals, belonging to one of three types of amino acids for bulk fermentation. In recent years, there has been an increasing demand for the amount of threonine in the market, in which feed industry is in the largest demand for the amount of threonine. As a safe feed additive, threonine is the second limiting amino acid for the growth of pigs following lysine, as well as the third limiting amino acid for the growth of poultry, only inferior to lysine and methionine. L-isoleucine is one of eight essential amino acids in human, collectively referred to as branched chain amino acid along with leucine and valine. Due to its special structure and function, L-isoleucine plays important roles in both human and animal metabolism, involving in the synthesis of hormones, enzymes, and the like. Currently, L-isoleucine is mainly used for additives in feeds and functional beverages. In addition, L-isoleucine is also widely used in the fields of biomedicine, food industry, cosmetics, and the like. Moreover, its new use has increasingly emerged, resulting in a great amount of its demand in the market. L-valine is one of eight essential amino acids in human, collectively referred to as branched chain amino acids along with leucine and isoleucine. Due to its special structure and function, L-valine essentially functions in the metabolism of human and animals. L-valine is commonly used as a flavor agent and a nutrient enhancer in the food industry. L-valine can be a supplemental product for animals' nutrition used in feed additives, having the capability for improving immune mechanism of livestock. Pharmaceutically, high purity L-valine is often used for producing complex amino acid infusion or amino acid injection, and is also used for synthesizing medicines against hypertension and tumors, and the like. In addition, L-valine can also be used in the fields of antibiotics, herbicides, cosmetics, and the like. L-tryptophan is an aromatic amino acid with an indolyl group and is one of essential amino acids in human and animals, which is widely used in the industries of foods, pharmaceuticals, feeds, and so on. In the pharmaceutical industry, tryptophan can be amino acid injections and drugs for treating tristimania, improving sleep quality, working against hypertension and analgesia, and etc. In the food industry, tryptophan can be used as an additive for enhancing the availability of proteins for organisms. In the feed industry, tryptophan is a safe feed additive and can adjust the amino acid balance of animals' feeds and promote the growth of poultry and livestock. Some important physiologically active substances such as hydroxytryptamine, niacin, coenzyme, indoleacetic acid, pigment and alkaloid, and etc. can also derive from L-tryptophan, and these tryptophan derivatives have found broad applications across markets. L-histidine is the ninth essential amino acid for human and animals, participating in important physiological processes such as growth and development, antioxidation, and immunoregulation of organisms, which functions as an important pharmaceutical amino acid and can be used in transfusion formulations for the treatment of heart disease, anemia, gastric and intestinal ulcers. L-phenylalanine is one of eight essential amino acids in human and animals, and is mainly used as a raw material for aspartame, a novel sweetener, which has a high sweetness and low calorie. It can also be widely used in the fields of foods, feed additives, and pharmaceuticals. Compounds having important application values, such as D-phenylalanine, phenylpyruvic acid, mandelic acid, phenyl acetate, phenyl ethanol, phenethylamine, styrene and cinnamic acid and so on, can further be derived from L-phenylalanine via microbial metabolic pathways.

Currently, microbial fermentation is mainly used in industrial production of amino acids at home and abroad. There exists an attenuation adjustment mechanism in the transcriptional expression of an amino acid (such as L-histidine, L-threonine, L-phenylalanine, L-leucine, L-isoleucine, L-valine, L-tryptophan, and etc.) operon gene synthesized by microorganisms. The transcription of an amino acid operon is terminated in advance when the concentration of a specific amino acid in cells is high. In contrast, when a specific amino acid in cells is deficient, RNA polymerase transcribes an amino acid operon. Synthetic pathways and regulation manners of amino acids in microorganisms are relatively complex, and are key limiting factors for producing amino acids and derivatives thereof by virtue of high-efficiency fermentation. In the process of producing L-isoleucine and derivatives thereof, L-isoleucine is increasingly accumulating in cells, with feedback repressing the expression of the ilvLXGMEDA operon via the above attenuation regulation mechanism, thereby feedback inhibiting the biosynthesis of L-isoleucine or derivatives thereof. In order to construct an engineered bacteria for efficiently producing isoleucine or derivatives thereof, the method for modifying the ilv attenuator is in dire need, so that the expression level of the ilvLXGMEDA operon and the yield of isoleucine can be improved. In the process of producing L-valine or derivatives thereof, L-valine is increasingly accumulating in cells, with feedback repressing the expression of the ilvLXGMED operon via the above attenuation regulation mechanism, not assisting in the biosynthesis of L-valine or derivatives thereof. Thus, it is crucial to efficiently relieve the attenuation regulation of valine on the ilvLXGMED operon for the biosynthesis of L-valine and derivatives thereof. In the process of producing L-tryptophan or derivatives thereof, L-tryptophan is increasingly accumulating in cells, with feedback repressing the expression of the tryptophan operon via the above attenuation regulation mechanism, not assisting in the biosynthesis of L-tryptophan or derivatives thereof. Thus, it is crucial to efficiently relieve the attenuation regulation of tryptophan on the tryptophan operon for the biosynthesis of L-tryptophan and derivatives thereof. In the process of producing L-histidine or derivatives thereof, L-histidine is increasingly accumulating in cells, with feedback repressing the expression of the histidine operon via the above attenuation regulation mechanism, not assisting in the biosynthesis of L-histidine or derivatives thereof. Thus, In order to construct an engineered bacteria for efficiently producing histidine or derivatives thereof, the method for modifying the histidine attenuator is in dire need, so that the expression level of the histidine operon and the yield of histidine can be improved. In the process of producing L-phenylalanine or derivatives thereof, L-phenylalanine is increasingly accumulating in cells, with feedback repressing the expression of the phenylalanine operon via the above attenuation regulation mechanism, not assisting in the biosynthesis of L-phenylalanine or derivatives thereof. Thus, in order to construct an engineered bacteria for efficiently producing phenylalanine or derivatives thereof, the method for modifying the phenylalanine attenuator is in dire need, so that the expression level of the phenylalanine operon and the yield of phenylalanine can be improved.

DISCLOSURE OF THE INVENTION

The present invention provides a method for modifying an amino acid attenuator, a class of amino acid attenuator mutants, an engineered bacteria created on the basis of the amino acid attenuator mutants, and a use of the engineered bacteria.

The present invention surprisingly obtains a method for modifying an amino acid attenuator to significantly improve the expression level of a gene through removing a functional sequence of the amino acid attenuator from a 5' end section by section.

The present invention protects a method for relieving the attenuation regulation of an amino acid operon gene, which is modification of the amino acid operon gene by: removing a gene coding for a leader peptide and an anterior reverse complementary palindromic sequence in the terminator stem-loop structure, and maintaining a posterior reverse complementary palindromic sequence in the terminator.

The present invention protects a method for modifying an amino acid operon gene, which is modification of the amino acid operon gene by: removing a gene coding for a leader peptide and an anterior reverse complementary palindromic sequence in the terminator stem-loop structure, and maintaining a posterior reverse complementary palindromic sequence in the terminator.

The present invention protects a method for modifying an attenuator mutant, which is modification of the amino acid attenuator by: removing a gene coding for a leader peptide and an anterior reverse complementary palindromic sequence in the terminator stem-loop structure, and maintaining a posterior reverse complementary palindromic sequence in the terminator.

The present invention protects a DNA molecule (an amino acid operon gene with relieved attenuation regulation, also referred to as an amino acid operon gene mutant), which is obtained by modifying an amino acid operon gene as follows: removing a gene coding for a leader peptide and an anterior reverse complementary palindromic sequence in the terminator stem-loop structure, and maintaining a posterior reverse complementary palindromic sequence in the terminator.

The present invention protects a DNA molecule (an attenuator mutant), which is obtained by modifying an amino acid attenuator as follows: removing a gene coding for a leader peptide and an anterior reverse complementary palindromic sequence in the terminator stem-loop structure, and maintaining a posterior reverse complementary palindromic sequence in the terminator.

It is obvious and easy for the skilled in the art, according to the experimental results of the present patent, to conclude that removing a portion of an anterior reverse complementary palindromic sequence in the terminator stem-loop structure of the attenuator as mentioned above, which destroys the secondary complementary structure of the terminator in a certain degree, may likewise obtain an amino acid attenuator mutant and an amino acid operon mutant having a similar performance. Thus, such similar method for modifying an amino acid attenuator falls into the protection scope of the present patent as well.

Said amino acid operon can be, in particular, an amino acid operon of *E. coli*. Obviously, the method for relieving an amino acid attenuator of *E. coli* in the present invention can also be applied to the amino acid attenuator of other bacteria having the same attenuator mechanism.

Said amino acid operon can be, in particular, a histidine operon, a tryptophan operon, a phenylalanine operon, an alanine operon, a threonine operon, and the like.

Obviously, the present invention can also be used for the biosynthesis of amino acid derivatives.

The present invention verifies the effect of modifying an amino acid attenuator with a method for translating a fusion reporter gene. The effect of an amino acid attenuator mutant on the expression of downstream genes is verified by fusing and expressing a reporter gene gfp, then determining the fluorescence value of a green fluorescent protein GFP, and calculating the amount of a gene expression under regulation by different amino acid attenuator mutants.

The beneficial effect of the present invention is obtaining an amino acid attenuator mutant with feedback repression efficiently relieved, and the mutant can significantly improve the expression level of subsequent genes. Engineered bacteria overexpressing an amino acid operon containing the mutant can significantly improve the yields of the amino acid and derivatives thereof. Mutants in the present invention can be practically used for producing amino acids and derivatives thereof in fermentation by bacteria. Amino acids produced by applying the present invention are specifically L-threonine, L-alanine, L-tryptophan, L-phenylalanine, L-histidine, L-isoleucine and L-valine.

The expression levels of an amino acid operon or other genes can be significantly improved by using the method provided by the present invention for modifying an amino acid attenuator, and thereby, the performance of engineered bacteria for fermenting amino acids and derivatives thereof is improved. The present invention obtains a nucleic acid sequence for efficiently relieving feedback repression and constructs a bacterial strain used for efficiently producing amino acids, providing a new method for improving the production of amino acids in fermentation.

The present invention firstly provides a DNA molecule A, as shown by the nucleotides at positions 294-n1 of SEQ ID No: 14 of the sequence listing, wherein n1 is a natural number greater than or equal to 310 but smaller than or equal to 606. n1 is a natural number greater than or equal to 310 but smaller than or equal to 336. n1 can be, in particular, 311 or 336 or 606.

The present invention also protects the use of said DNA molecule A as a regulation element in facilitating expression of a target gene. In said use, said DNA molecule A is located between the initiation codon of said target gene and the promoter of said target gene. Said target gene particularly can be a gene coding for alanine dehydrogenase, a lacZ gene or a gfp gene.

The present invention also protects a DNA molecule B sequentially comprising the following elements from upstream to downstream: a promoter, said DNA molecule A, and a target gene. Said DNA molecule B sequentially comprises the following elements from upstream to downstream: a promoter, said DNA molecule A, linker sequence "GGTTCTGGTTCTGGTTCT" (SEQ ID NO: 67), and a target gene. Said DNA molecule B sequentially consists of the following elements from upstream to downstream: a promoter, recognition sequence for enzymatic cleavage by restriction endonuclease Hind III, said DNA molecule A, a linker sequence "GGTTCTGGTTCTGGTTCT" (SEQ ID NO: 68), and a target gene. Said target gene can be, in particular, a lacZ gene or a gfp gene.

The recombinant plasmid B containing said DNA molecule B also falls into the protection scope of the present invention. Said recombinant plasmid B particularly can be a recombinant plasmid obtained by inserting said DNA molecule B at the multiple cloning site of the starting plasmid. Said starting plasmid is a plasmid having low-copy, medium-copy or high-copy numbers, for example, pSC101, pACYC184, pBR322 or pTrc99a. Said starting plasmid particularly can be plasmid pACYC184. Said recombinant plasmid B more particularly can be a recombinant plasmid obtained by inserting said DNA molecule B between the enzymatic cleavage sites of Xba I and BamH I of the plasmid pACYC184.

The present invention also protects recombinant bacteria B containing above any said DNA molecule B. Said recombinant bacteria B particularly can be recombinant bacteria obtained by introducing said recombinant plasmid B into the starting bacteria.

The present invention also protects a DNA molecule C, sequentially comprising the following elements from upstream to downstream: said DNA molecule A and a gene coding for alanine dehydrogenase. Said DNA molecule C sequentially consists of the following elements from upstream to downstream: said DNA molecule A and a gene coding for alanine dehydrogenase. Said DNA molecule C is particularly shown by SEQ ID No: 18 of the sequence listing.

The recombinant plasmid C containing said DNA molecule C also falls into the protection scope of the present invention. Said recombinant plasmid C particularly can be a recombinant plasmid obtained by inserting said DNA molecule C at the multiple cloning site of the starting plasmid. Said starting plasmid is a plasmid having low-copy, medium-copy or high-copy numbers, for example, pSC101, pACYC184, pBR322 or pTrc99a. Said starting plasmid particularly can be plasmid pACYC184. Said recombinant plasmid C more particularly can be a recombinant plasmid obtained by inserting said DNA molecule C between the enzymatic cleavage sites of Xba I and Sph I of plasmid pACYC184.

The present invention also protects recombinant bacteria C containing above any said DNA molecule C. Said recombinant bacteria C particularly can be recombinant bacteria obtained by introducing said recombinant plasmid C into the starting bacteria.

The present invention also protects a DNA molecule D sequentially comprising the following elements from upstream to downstream: a promoter, and DNA molecule C. Said DNA molecule D sequentially consists of the following elements from upstream to downstream: a promoter, recognition sequence for enzymatic cleavage by restriction endonuclease BamH I, and DNA molecule C.

The recombinant plasmid D containing said DNA molecule D also falls into the protection scope of the present invention. Said recombinant plasmid D particularly can be a recombinant plasmid obtained by inserting said DNA molecule D at the multiple cloning site of the starting plasmid. Said starting plasmid is a plasmid having low-copy, medium-copy or high-copy numbers, for example, pSC101, pACYC184, pBR322 or pTrc99a. Said starting plasmid particularly can be plasmid pACYC184. Said recombinant plasmid D more particularly can be a recombinant plasmid obtained by inserting said DNA molecule D between the enzymatic cleavage sites of Xba I and Sph I of plasmid pACYC184.

The present invention also protects the recombinant bacteria D containing above any said DNA molecule D. Said recombinant bacteria D particularly can be recombinant bacteria obtained by introducing said recombinant plasmid D into the starting bacteria.

Above any said alanine dehydrogenase particularly can be one from *Bacillus subtilis* W168.

Above any said alanine dehydrogenase particularly can be (a1) or (a2) as follows:

(a1) a protein consisting of the amino acid sequence shown by SEQ ID No: 19 of the sequence listing;

(a2) a protein derived from SEQ ID No: 19 having alanine dehydrogenase function after one or several amino acid residues of the amino acid sequence of SEQ ID No: 19 are subjected to substitution and/or deletion and/or addition.

Above any said gene coding for alanine dehydrogenase is (a3) or (a4) or (a5) or (a6) as follows:

(a3) a DNA molecule, having a coding region shown by the nucleotides at positions 44-1180 of SEQ ID No: 18 of the sequence listing;

(a4) a DNA molecule shown by the nucleotides at positions 44-1262 of SEQ ID No: 18 of the sequence listing;

(a5) a DNA molecule, which is hybridized with the DNA sequence defined by (a3) or (a4) under strict condition and codes for alanine dehydrogenase;

(a6) a DNA molecule, having more than or equal to 90% homology with the DNA sequence defined by (a3) or (a4) and coding for alanine dehydrogenase.

Above any said lacZ gene is (b1) or (b2) or (b3) or (b4) as follows:

(b1) a DNA molecule, having a coding region shown by the nucleotides at positions 1-3075 of SEQ ID No: 15 of the sequence listing;

(b2) a DNA molecule, shown by SEQ ID No: 15 of the sequence listing;

(b3) a DNA molecule, which is hybridized with the DNA sequence defined by (b1) or (b2) under strict condition and codes for β-galactosidase;

(b4) a DNA molecule, having more than or equal to 90% homology with the DNA sequence defined by (b1) or (b2) and coding for β-galactosidase.

Above any said gfp gene is (c1) or (c2) or (c3) as follows:

(c1) a DNA molecule, having a coding region shown by SEQ ID No: 16 of the sequence listing;

(c2) a DNA molecule, which is hybridized with the DNA sequence defined by (c1) under strict condition and codes for green fluorescent protein;

(c3) a DNA molecule, having more than or equal to 90% homology with the DNA sequence defined by (c1) or (c2) and coding for green fluorescent protein.

Above any said promoter particularly can be a strong promoter, for example, L promoter, trc promoter, T5 promoter, lac promoter, tac promoter or T7 promoter.

Above any said promoter particularly can be the promoter $P_{PL}$. The promoter $P_{PL}$ is (d1) or (d2) or (d3) as follows:

(d1) a DNA molecule shown by SEQ ID No: 13 of the sequence listing;

(d2) a DNA molecule, which is hybridized with the DNA sequence defined by (d1) under strict condition and has promoter function;

(d3) a DNA molecule, having more than or equal to 90% homology with the DNA sequence defined by (d1) and having promoter function.

Above any said strict condition can be hybridizing and washing membrane at the temperature of 65° C. in a DNA or RNA hybridization experiment with a solution of 0.1× SSPE (or 0.1×SSC) and 0.1% SDS.

Above any said starting bacteria can be a bacterium, further can be one belonging to the genus *Escherichia*, and more particularly can be *E. coli*.

Above any said starting bacteria more particularly can be *E. coli* K12 W3110.

Above any said starting bacteria more particularly can be a strain obtained by suppressing the expression of the metA gene, the ilvA gene, the lysA gene, the tdh gene, the tdcC gene and the sstT gene, with *E. coli* K12 W3110 as the starting bacteria strain.

Said metA gene is a gene coding for homoserine transsuccinylase (MetA protein). Said MetA protein is (g1) or (g2) as follows:

(g1) a protein consisting of the amino acid sequence shown by SEQ ID No: 2 of the sequence listing;

(g2) a protein derived from SEQ ID No: 2 having the same function after one or several amino acid residues of the amino acid sequence of SEQ ID No: 2 are subjected to substitution and/or deletion and/or addition.

Said metA gene is (g3) or (g4) or (g5) or (g6) as follows:

(g3) a DNA molecule, having a coding region shown by the nucleotides at positions 752-1681 of SEQ ID No: 1 of the sequence listing;

(g4) a DNA molecule shown by SEQ ID No: 1 of the sequence listing;

(g5) a DNA molecule, which is hybridized with the DNA sequence defined by (g3) or (g4) under strict condition and codes for a protein having the same function;

(g6) a DNA molecule, having more than or equal to 90% homology with the DNA sequence defined by (g3) or (g4) and coding for a protein having the same function.

Said ilvA gene is a gene coding for threonine deaminase (IlvA protein). Said IlvA protein is (h1) or (h2) as follows:

(h1) a protein consisting of the amino acid sequence shown by SEQ ID No: 4 of the sequence listing;

(h2) a protein derived from SEQ ID No: 4 having the same function after one or several amino acid residues of the amino acid sequence of SEQ ID No: 4 are subjected to substitution and/or deletion and/or addition.

Said ilvA gene is (h3) or (h4) or (h5) or (h6) as follows:

(h3) a DNA molecule, having a coding region shown by the nucleotides at positions 638-2182 of SEQ ID No: 3 of the sequence listing;

(h4) a DNA molecule shown by SEQ ID No: 3 of the sequence listing;

(h5) a DNA molecule, which is hybridized with the DNA sequence defined by (h3) or (h4) under strict condition and codes for a protein having the same function;

(h6) a DNA molecule, having more than or equal to 90% homology with the DNA sequence defined by (h3) or (h4) and coding for a protein having the same function.

Said lysA gene is a gene coding for diaminopimelic acid decarboxylase (LysA protein). Said LysA protein is (i1) or (i2) as follows:

(i1) a protein consisting of the amino acid sequence shown by SEQ ID No: 6 of the sequence listing;

(i2) a protein derived from SEQ ID No: 6 having the same function after one or several amino acid residues of the amino acid sequence of SEQ ID No: 6 are subjected to substitution and/or deletion and/or addition.

Said lysA gene is (i3) or (i4) or (i5) or (i6) as follows:

(i3) a DNA molecule, having a coding region shown by the nucleotides at positions 639-1901 of SEQ ID No: 5 of the sequence listing;

(i4) a DNA molecule shown by SEQ ID No: 5 of the sequence listing;

(i5) a DNA molecule, which is hybridized with the DNA sequence defined by (i3) or (i4) under strict condition and codes for a protein having the same function;

(i6) a DNA molecule, having more than or equal to 90% homology with the DNA sequence defined by (i3) or (i4) and coding for a protein having the same function.

Said tdh gene is a gene coding for threonine dehydratase (Tdh protein). Said Tdh protein is (j1) or (j2) as follows:

(j1) a protein consisting of the amino acid sequence shown by SEQ ID No: 8 of the sequence listing; (j2) a protein derived from SEQ ID No: 8 having the same function after one or several amino acid residues of the amino acid sequence of SEQ ID No: 8 are subjected to substitution and/or deletion and/or addition.

Said tdh gene is (j3) or (j4) or (j5) or (j6) as follows:

(j3) a DNA molecule, having a coding region shown by the nucleotides at positions 753-1778 of SEQ ID No: 7 of the sequence listing;

(j4) a DNA molecule shown by SEQ ID No: 7 of the sequence listing;

(j5) a DNA molecule, which is hybridized with the DNA sequence defined by (j3) or (j4) under strict condition and codes for a protein having the same function;

(j6) a DNA molecule, having more than or equal to 90% homology with the DNA sequence defined by (j3) or (j4) and coding for a protein having the same function.

Said tdcC gene is a gene coding for threonine absorption and transport protein (TdcC protein). Said TdcC protein is (k1) or (k2) as follows:

(k1) a protein consisting of the amino acid sequence shown by SEQ ID No: 10 of the sequence listing;

(k2) a protein derived from SEQ ID No: 10 having the same function after one or several amino acid residues of the amino acid sequence of SEQ ID No: 10 are subjected to substitution and/or deletion and/or addition.

Said tdcC gene is (k3) or (k4) or (k5) or (k6) as follows:

(k3) a DNA molecule, having a coding region shown by the nucleotides at positions 701-2032 of SEQ ID No: 9 of the sequence listing;

(k4) a DNA molecule shown by SEQ ID No: 9 of the sequence listing;

(k5) a DNA molecule, which is hybridized with the DNA sequence defined by (k3) or (k4) under strict condition and codes for a protein having the same function;

(k6) a DNA molecule, having more than or equal to 90% homology with the DNA sequence defined by (k3) or (k4) and coding for a protein having the same function.

Said sstT gene is a gene coding for threonine absortion and transport protein (SstT protein). Said SstT protein is (m1) or (m2) as follows:

(m1) a protein consisting of the amino acid sequence shown by SEQ ID No: 12 of the sequence listing;

(m2) a protein derived from SEQ ID No: 12 having the same function after one or several amino acid residues of the amino acid sequence of SEQ ID No: 12 are subjected to substitution and/or deletion and/or addition.

Said sstT gene is (m3) or (m4) or (m5) or (m6) as follows:

(m3) a DNA molecule, having a coding region shown by the nucleotides at positions 701-1945 of SEQ ID No: 11 of the sequence listing;

(m4) a DNA molecule shown by SEQ ID No: 11 of the sequence listing; (m5) a DNA molecule, which is hybridized with the DNA sequence defined by (m3) or (m4) under strict condition and codes for a protein having the same function;

(m6) a DNA molecule, having more than or equal to 90% homology with the DNA sequence defined by (m3) or (m4) and coding for a protein having the same function.

Above any said strict condition can be hybridizing and washing membranes at the temperature of 65° C. in a DNA or RNA hybridization experiment with a solution of 0.1× SSPE (or 0.1×SSC) and 0.1% SDS.

Above any said starting bacteria more particularly can be a strain obtained by knocking out the following six gene sections, with E. coli K12 W3110 as the starting bacteria strain:

the open reading frame of the metA gene (the nucleotides at positions 752-1681 of SEQ ID No: 1 of the sequence listing);

the open reading frame of the ilvA gene (the nucleotides at positions 638-2182 of SEQ ID No: 3 of the sequence listing);

the open reading frame of the lysA gene (the nucleotides at positions 639-1901 of SEQ ID No: 5 of the sequence listing);

the open reading frame of the tdh gene (the nucleotides at positions 753-1778 of SEQ ID No: 7 of the sequence listing);

the following section of the tdcC gene: the nucleotides at positions 701-1852 of SEQ ID No: 9;

the following section of the sstT gene: the nucleotides at positions 697-1759 of SEQ ID No: 11.

Knockout of the open reading frame of the metA gene is particularly achieved by introducing an interference fragment I or an interference plasmid I. The interference fragment I sequentially consists, from upstream to downstream, of an upstream section shown by the nucleotides at positions 245-751 of SEQ ID No: 1 of the sequence listing, and a downstream section shown by the nucleotides at positions 1682-2154 of SEQ ID No: 1 of the sequence listing. The interference plasmid I is a recombinant plasmid with the interference fragment I. The interference plasmid I particularly can be a recombinant plasmid obtained by inserting the interference fragment I at the multiple cloning site of plasmid pKOV (e.g., between the enzymatic cleavage sites of Sal I and Not I).

Knockout of the open reading frame of the ilvA gene is particularly achieved by introducing an interference fragment II or an interference plasmid II. The interference fragment II sequentially consists, from upstream to downstream, of an upstream section shown by the nucleotides at positions 140-637 of SEQ ID No: 3 of the sequence listing, and a downstream section shown by the nucleotides at positions 2183-2712 of SEQ ID No: 3 of the sequence listing. The interference plasmid II is a recombinant plasmid with the interference fragment II. The interference plasmid II particularly can be a recombinant plasmid obtained by inserting the interference fragment II at the multiple cloning site of plasmid pKOV (e.g., between the enzymatic cleavage sites of BamH I and Not I).

Knockout of the open reading frame of the lysA gene is particularly achieved by introducing an interference fragment III or an interference plasmid III. The interference fragment III sequentially consists, from upstream to downstream, of an upstream section shown by the nucleotides at positions 132-638 of SEQ ID No: 5 of the sequence listing, and a downstream section shown by the nucleotides at positions 1902-2445 of SEQ ID No: 5 of the sequence listing. The interference plasmid III is a recombinant plasmid with the interference fragment III. The interference plasmid III particularly can be a recombinant plasmid obtained by inserting the interference fragment III at the multiple cloning site of plasmid pKOV (e.g., between the enzymatic cleavage sites of BamH I and Not I).

Knockout of the open reading frame of the tdh gene is particularly achieved by introducing an interference fragment IV or an interference plasmid IV. The interference fragment IV sequentially consists, from upstream to downstream, of an upstream section shown by the nucleotides at positions 227-752 of SEQ ID No: 7 of the sequence listing, and a downstream section shown by the nucleotides at positions 1779-2271 of SEQ ID No: 7 of the sequence listing. The interference plasmid IV is a recombinant plasmid with the interference fragment IV. The interference plasmid IV particularly can be a recombinant plasmid obtained by inserting the interference fragment IV at the multiple cloning site of plasmid pKOV (e.g., between the enzymatic cleavage sites of BamH I and Not I).

Knockout of "the following section of the tdC gene: the nucleotides at positions 701-1852 of SEQ ID No: 9" is achieved by introducing an interference fragment V or an interference plasmid V. The interference fragment V sequentially consists, from upstream to downstream, of an upstream section shown by the nucleotides at positions 176-700 of SEQ ID No: 9 of the sequence listing, and a downstream section shown by the nucleotides at positions 1853-2388 of SEQ ID No: 9 of the sequence listing. The interference plasmid V is a recombinant plasmid with the interference fragment V. The interference plasmid V particularly can be a recombinant plasmid obtained by inserting the interference fragment V at the multiple cloning site of plasmid pKOV (e.g., between the enzymatic cleavage sites of BamH I and Not I).

Knockout of "the following section of the sstT gene: the nucleotides at positions 697-1759 of SEQ ID No: 11" is achieved by introducing an interference fragment VI or an interference plasmid VI. The interference fragment VI sequentially consists, from upstream to downstream, of an upstream section shown by the nucleotides at positions 14-696 of SEQ ID No: 11 of the sequence listing, and a downstream section shown by the nucleotides at positions 1760-2240 of SEQ ID No: 11 of the sequence listing. The interference plasmid VI is a recombinant plasmid with the interference fragment VI. The interference plasmid VI particularly can be a recombinant plasmid obtained by inserting the interference fragment VI at the multiple cloning site of plasmid pKOV (e.g., between the enzymatic cleavage sites of BamH I and Not I).

The present invention also protects the use of said recombinant bacteria C in producing L-alanine.

The present invention also protects the use of said recombinant bacteria D in producing L-alanine.

Glucose is used as a carbon source when applying said recombinant bacteria to produce L-alanine.

A fermentation medium is used to culture said recombinant bacteria when applying said recombinant bacteria to produce L-alanine.

Said fermentation medium can be either a rich medium, or an inorganic salt medium. A medium contains a carbon source, a nitrogen source, inorganic ions, antibiotics and other trophic factors. As a carbon source, saccharides such as glucose, lactose, galactose and etc. can be used; alcohols such as glycerin, mannitol and etc. can also be used; organic acids such as gluconic acid, citric acid, succinic acid and etc. can be used as well. As a nitrogen source, inorganic nitrogen sources such as ammoniacal liquor, ammonium sulfate, ammonium phosphate, ammonium chloride and etc. can be used; organic nitrogen sources such as corn steep liquor, soybean meal hydrolysates, hair powders, yeast extracts, peptone and etc. can be used as well. Inorganic ions comprise one or more ions selected from the group consisting of iron, calcium, magnesium, manganese, molybdenum, cobalt, cuprum, potassium and etc. ions. Other trophic factors also comprise vitamins such as biotin, vitamin B1, pyridoxal and etc.

The carbon source in said fermentation medium is glucose.

Said fermentation medium particularly can be: glucose 20.0 g/L, yeast powders 2.0 g/L, peptone 4 g/L, ammonium sulfate 6.0 g/L, potassium dihydrogen phosphate 2.0 g/L, magnesium sulfate heptahydrate 1.0 g/L, betaine 1.0 g/L, calcium carbonate 15.0 g/L, microelement mixture 1 mL/L, and water as the remainder.

The microelement mixture is: $FeSO_4 \cdot 7H_2O$ 10 g/L, $CaCl_2$ 1.35 g/L, $ZnSO_4 \cdot 7H_2O$ 2.25 g/L, $MnSO_4 \cdot 4H_2O$ 0.5 g/L, $CuSO_4 \cdot 5H_2O$ 1 g/L, $(NH_4)_6Mo_7O_{24} \cdot 4H_2O$ 0.106 g/L, $Na_2B_4O_7 \cdot 10H_2O$ 0.23 g/L, $CoCl_2 \cdot 6H_2O$ 0.48 g/L, 35% HCl 10 mL/L, and water as the remainder.

Said culture condition particularly can be that: shaking culture for 12-48 h at 37° C., 220 rpm.

Said culture conditions particularly can be that: the seed solution is seeded into the fermentation medium in a seeding amount of 3%, followed by shaking culture for 12-48 h at 37° C., 220 rpm. A method for preparing the seed solution is as follows: the recombinant bacteria is seeded into a liquid LB medium, followed by shaking culture for 12 h at 37° C., 220 rpm, and a seed solution is obtained.

Processes to be controlled during said culture are as follows: during the culture, the pH value of the reaction system is adjusted with ammoniacal liquor to make it maintain at 6.8-7.0; during the culture, sampling is made once every 3-4 h to detect the content of glucose, and when the content of glucose in the system is less than 5 g/L, glucose is supplemented to make the concentration of glucose in the system up to 10 g/L.

The present invention provides a threonine attenuator mutant with relieved feedback repression and use thereof, and obtains a 5'-UTR mutant significantly enhancing expression of gene; the mutant is applied to regulate the expression of alanine dehydrogenase, and a strain is constructed to efficiently produce L-alanine, which provides a new approach to improve the production of L-alanine in fermentation.

The present invention verifies the effect of modifying a threonine attenuator with a method for translating a fusion reporter gene. The effect of the threonine attenuator mutant on regulation of gene expression is verified by fusing the 5' end sequence of the thrA gene with the complete reading expressing frames of two reporter genes lacZ and gfp, followed by determining the enzyme activity of reporter protein LacZ and the fluorescence value of GFP and calculating the amount of gene expression under regulation of different threonine attenuator mutants.

The present invention aims to provide a threonine attenuator mutant and use thereof in the production of threonine in fermentation.

The present invention firstly provides a threonine operon gene with relieved repression, sequentially comprising, from upstream to downstream, element A and element B; said element A is shown by the nucleotides at positions 294-n1 of SEQ ID No: 20 of the sequence listing, wherein n1 is a natural number greater than or equal to 310 but smaller than or equal to 336; said element B is a gene coding for the threonine operon.

n1 particularly can be 311 or 336.

Said "threonine operon gene with relieved repression" is free of the nucleotides at positions 1-293 of SEQ ID No: 20 of the sequence listing.

Said "gene coding for the threonine operon" is a gene coding for aspartokinase I-homoserine dehydrogenase complex, a gene coding for homoserine dehydrogenase and a gene coding for threonine synthetase.

Said aspartokinase I-homoserine dehydrogenase complex is a ThrA protein (wild protein) or a ThrA*protein (mutant protein). Said homoserine dehydrogenase is a ThrB protein. Said threonine synthetase is a ThrC protein. The gene coding for the ThrA protein is a thrA gene. The gene coding for the ThrA*protein is a thrA*gene. The gene coding for the ThrB protein is a thrB gene. The gene coding for the ThrC protein is a thrC gene.

Said ThrA*protein is (a1) or (a2) as follows:

(a1) a protein consisting of the amino acid sequence shown by SEQ ID No: 21 of the sequence listing;

(a2) a protein derived from SEQ ID No: 21 having aspartokinase I-homoserine dehydrogenase complex function after one or several amino acid residues of the amino acid sequence of SEQ ID No: 21 are subjected to substitution and/or deletion and/or addition.

Said thrA*gene is (a3) or (a4) or (a5) as follows:

(a3) a DNA molecule, having a coding region shown by the nucleotides at positions 337-2799 of SEQ ID No: 20 of the sequence listing;

(a4) a DNA molecule, which is hybridized with the DNA sequence defined by (a3) under strict condition and codes for aspartokinase I-homoserine dehydrogenase complex;

(a5) a DNA molecule, having more than or equal to 90% homology with the DNA sequence defined by (a3) and coding for aspartokinase I-homoserine dehydrogenase complex.

In comparison with the ThrA protein, the ThrA*protein only differs in one amino acid residue, that is, the amino acid residue at position 253 is mutated from glutamic acid to histidine.

Said thrA gene is (a6) or (a7) or (a8) as follows:

(a6) a DNA molecule, having a coding region shown by the nucleotides at positions 337-2799 of SEQ ID No: 14 of the sequence listing;

(a7) a DNA molecule, which is hybridized with the DNA sequence defined by (a6) under strict condition and codes for aspartokinase I-homoserine dehydrogenase complex;

(a8) a DNA molecule, having more than or equal to 90% homology with the DNA sequence defined by (a6) and coding for aspartokinase I-homoserine dehydrogenase complex.

Said ThrB protein is (b1) or (b2) as follows:

(b1) a protein consisting of the amino acid sequence shown by SEQ ID No: 22 of the sequence listing;

(b2) a protein derived from SEQ ID No: 22 having homoserine dehydrogenase function after one or several amino acid residues of the amino acid sequence of SEQ ID No: 22 are subjected to substitution and/or deletion and/or addition.

Said thrB gene is (b3) or (b4) or (b5) as follows:

(b3) a DNA molecule, having a coding region shown by the nucleotides at positions 2801-3733 of SEQ ID No: 20 of the sequence listing;

(b4) a DNA molecule, which is hybridized with the DNA sequence defined by (b3) under strict condition and codes for homoserine dehydrogenase;

(b5) a DNA molecule, having more than or equal to 90% homology with the DNA sequence defined by (b3) and coding for homoserine dehydrogenase.

Said ThrCprotein is (c1) or (c2) as follows:

(c1) a protein consisting of the amino acid sequence shown by SEQ ID No: 23 of the sequence listing;

(c2) a protein derived from SEQ ID No: 23 having threonine synthetase function after one or several amino acid residues of the amino acid sequence of SEQ ID No: 23 are subjected to substitution and/or deletion and/or addition.

Said thrC gene is (c3) or (c4) or (c5) as follows:

(c3) a DNA molecule, having a coding region shown by the nucleotides at positions 3734-5020 of SEQ ID No: 20 of the sequence listing;

(c4) a DNA molecule, which is hybridized with the DNA sequence defined by (c3) under strict condition and codes for threonine synthetase;

(c5) a DNA molecule, having more than or equal to 90% homology with the DNA sequence defined by (c3) and coding for threonine synthetase.

Said "threonine operon gene with relieved repression" is (d1) or (d2) or (d3) or (d4) or (d5) as follows:

(d1) a DNA molecule sequentially comprising, from upstream to downstream, the following elements: the nucleotides at positions 294-336 of SEQ ID No: 20 of the sequence listing, the nucleotides at positions 337-2799 of SEQ ID No: 20 of the sequence listing, the nucleotides at positions 2801-3733 of SEQ ID No: 20 of the sequence listing, and the nucleotides at positions 3734-5020 of SEQ ID No: 20 of the sequence listing;

(d2) a DNA molecule shown by the nucleotides at positions 294-5020 of SEQ ID No: 20 of the sequence listing;

(d3) a DNA molecule shown by the nucleotides at positions 294-5132 of SEQ ID No: 20 of the sequence listing;

(d4) a DNA molecule sequentially comprising, from upstream to downstream, the following elements: the nucleotides at positions 294-336 of SEQ ID No: 14 of the sequence listing, the nucleotides at positions 337-2799 of SEQ ID No: 14 of the sequence listing, the nucleotides at positions 2801-3733 of SEQ ID No: 14 of the sequence listing, and the nucleotides at positions 3734-5020 of SEQ ID No: 14 of the sequence listing;

(d5) a DNA molecule shown by the nucleotides at positions 294-5020 of SEQ ID No: 14 of the sequence listing.

The present invention also protects a specific DNA molecule, sequentially comprising, from upstream to downstream, a promoter and above any said "threonine operon gene with relieved repression". Said promoter particularly can be a strong promoter, for example, L promoter, trc promoter, T5 promoter, lac promoter, tac promoter or T7 promoter.

Said promoter particularly can be the promoter $P_{PL}$. The promoter $P_{PL}$ is (e1) or (e2) or (e3) as follows:

(e1) a DNA molecule shown by SEQ ID No: 13 of the sequence listing;

(e2) a DNA molecule, which is hybridized with the DNA sequence defined by (e1) under strict condition and has promoter function;

(e3) a DNA molecule, having more than or equal to 90% homology with the DNA sequence defined by (e1) and having promoter function.

Said specific DNA molecule particularly can be (f1) or (f2) as follows:

(f1) sequentially comprising, from upstream to downstream, the following elements: a promoter and said "threonine operon gene with relieved repression";

(f2) sequentially consisting, from upstream to downstream, of the following elements: a promoter, recognition sequence for enzymatic cleavage by restriction endonuclease Hind III and said threonine operon gene with relieved repression.

The present invention also protects the recombinant plasmid A containing above any said "threonine operon gene with relieved repression". Said recombinant plasmid A particularly can be a recombinant plasmid obtained by inserting said "threonine operon gene with relieved repression" at the multiple cloning site of the starting plasmid. Said starting plasmid is a plasmid having a low-copy, medium-copy or high-copy number, for example, pSC101, pACYC184, pBR322 or pTrc99a. Said starting plasmid particularly can be plasmid pACYC184.

The present invention also protects the recombinant plasmid B containing above any said specific DNA molecule. Said recombinant plasmid B particularly can be a recombinant plasmid obtained by inserting said specific DNA molecule at the multiple cloning site of the starting plasmid. Said starting plasmid is a plasmid having a low-copy, medium-copy or high-copy number, for example, pSC101, pACYC184, pBR322 or pTrc99a. Said starting plasmid particularly can be plasmid pACYC184. Said starting plasmid particularly can be plasmid pACYC184. Said recombinant plasmid B more particularly can be a recombinant plasmid obtained by inserting said specific DNA molecule between the enzymatic cleavage sites of Xba I and EcoR V of plasmid pACYC184.

The present invention also protects the recombinant bacteria A containing above any said "threonine operon gene with relieved repression". Said recombinant bacteria A particularly can be recombinant bacteria obtained by introducing said recombinant plasmid A into the starting bacteria.

The present invention also protects the recombinant bacteria B containing above any said specific DNA molecule. Said recombinant bacteria B particularly can be recombinant bacteria obtained by introducing said recombinant plasmid B into the starting bacteria.

Above any said starting bacteria particularly can be *E. coli*, for example, *E. coli* K-12 or a strain derived therefrom.

Above any said starting bacteria more particularly can be a strain obtained by suppressing the expression of the metA gene, the ilvA gene, the lysA gene, the tdh gene, the tdcC gene and the sstT gene with *E. coli* K12 W3110 as the starting bacteria strain.

Said metA gene is a gene coding for homoserine trans-succinylase (MetAprotein). Said MetA protein is (g1) or (g2) as follows:
(g1) a protein consisting of the amino acid sequence shown by SEQ ID No: 2 of the sequence listing;
(g2) a protein derived from SEQ ID No: 2 having the same function after one or several amino acid residues of the amino acid sequence of SEQ ID No: 2 are subjected to substitution and/or deletion and/or addition.

Said metA gene is (g3) or (g4) or (g5) or (g6) as follows:
(g3) a DNA molecule, having a coding region shown by the nucleotides at positions 752-1681 of SEQ ID No: 1 of the sequence listing;
(g4) a DNA molecule shown by SEQ ID No: 1 of the sequence listing;
(g5) a DNA molecule, which is hybridized with the DNA sequence defined by (g3) or (g4) under strict condition and codes for a protein having the same function;
(g6) a DNA molecule, having more than or equal to 90% homology with the DNA sequence defined by (g3) or (g4) and coding for a protein having the same function.

Said ilvA gene is a gene coding for threonine deaminase (IlvA protein). Said IlvA protein is (h1) or (h2) as follows:
(h1) a protein consisting of the amino acid sequence shown by SEQ ID No: 4 of the sequence listing;
(h2) a protein derived from SEQ ID No: 4 having the same function after one or several amino acid residues of the amino acid sequence of SEQ ID No: 4 are subjected to substitution and/or deletion and/or addition.

Said ilvA gene is (h3) or (h4) or (h5) or (h6) as follows:
(h3) a DNA molecule, having a coding region shown by the nucleotides at positions 638-2182 of SEQ ID No: 3 of the sequence listing;
(h4) a DNA molecule shown by SEQ ID No: 3 of the sequence listing;
(h5) a DNA molecule, which is hybridized with the DNA sequence defined by (h3) or (h4) under strict condition and codes for a protein having the same function under strict condition;
(h6) a DNA molecule, having more than or equal to 90% homology with the DNA sequence defined by (h3) or (h4) and coding for a protein having the same function.

Said lysA gene is a gene coding for diaminopimelic acid decarboxylase (LysA protein). Said LysA protein is (i1) or (i2) as follows:
(i1) a protein consisting of the amino acid sequence shown by SEQ ID No: 6 of the sequence listing;
(i2) a protein derived from SEQ ID No: 6 having the same function after one or several amino acid residues of the amino acid sequence of SEQ ID No: 6 are subjected to substitution and/or deletion and/or addition.

Said lysA gene is (i3) or (i4) or (i5) or (i6) as follows:
(i3) a DNA molecule, having a coding region shown by the nucleotides at positions 639-1901 of SEQ ID No: 5 of the sequence listing;
(i4) a DNA molecule shown by SEQ ID No: 5 of the sequence listing;
(i5) a DNA molecule, which is hybridized with the DNA sequence defined by (i3) or (i4) under strict condition and codes for a protein having the same function;
(i6) a DNA molecule, having more than or equal to 90% homology with the DNA sequence defined by (i3) or (i4) and coding for a protein having the same function.

Said tdh gene is a gene coding for threonine dehydratase (Tdh protein). Said Tdh protein is (j1) or (j2) as follows:
(j1) a protein consisting of the amino acid sequence shown by SEQ ID No: 8 of the sequence listing;
(j2) a protein derived from SEQ ID No: 8 having the same function after one or several amino acid residues of the amino acid sequence of SEQ ID No: 8 are subjected to substitution and/or deletion and/or addition.

Said tdh gene is (j3) or (j4) or (j5) or (j6) as follows:
(j3) a DNA molecule, having a coding region shown by the nucleotides at positions 753-1778 of SEQ ID No: 7 of the sequence listing;
(j4) a DNA molecule shown by SEQ ID No: 7 of the sequence listing;
(j5) a DNA molecule, which is hybridized with the DNA sequence defined by (j3) or (j4) under strict condition and codes for a protein having the same function;
(j6) a DNA molecule, having more than or equal to 90% homology with the DNA sequence defined by (j3) or (j4) and coding for a protein having the same function.

Said tdcC gene is a gene coding for threonine absortion and transport protein (TdcC protein). Said TdcC protein is (k1) or (k2) as follows:
(k1) a protein consisting of the amino acid sequence shown by SEQ ID No: 10 of the sequence listing;
(k2) a protein derived from SEQ ID No: 10 having the same function after one or several amino acid residues of the amino acid sequence of SEQ ID No: 10 are subjected to substitution and/or deletion and/or addition.

Said tdcC gene is (k3) or (k4) or (k5) or (k6) as follows:
(k3) a DNA molecule, having a coding region shown by the nucleotides at positions 701-2032 of SEQ ID No: 9 of the sequence listing;
(k4) a DNA molecule shown by SEQ ID No: 9 of the sequence listing;
(k5) a DNA molecule, which is hybridized with the DNA sequence defined by (k3) or (k4) under strict condition and codes for a protein having the same function;
(k6) a DNA molecule, having more than or equal to 90% homology with the DNA sequence defined by (k3) or (k4) and coding for a protein having the same function.

Said sstT gene is a gene coding for threonine absortion and transport protein (SstTprotein). Said SstT protein is (m1) or (m2) as follows:
(m1) a protein consisting of the amino acid sequence shown by SEQ ID No: 12 of the sequence listing;
(m2) a protein derived from SEQ ID No: 12 having the same function after one or several amino acid residues of the amino acid sequence of SEQ ID No: 12 are subjected to substitution and/or deletion and/or addition.

Said sstT gene is (m3) or (m4) or (m5) or (m6) as follows:
(m3) a DNA molecule, having a coding region shown by the nucleotides at positions 701-1945 of SEQ ID No: 11 of the sequence listing;
(m4) a DNA molecule shown by SEQ ID No: 11 of the sequence listing;

(m5) a DNA molecule, which is hybridized with the DNA sequence defined by (m3) or (m4) under strict condition and codes for a protein having the same function;

(m6) a DNA molecule, having more than or equal to 90% homology with the DNA sequence defined by (m3) or (m4) and coding for a protein having the same function.

Above any said strict condition can be hybridizing and washing membranes at the temperature of 65° C. in a DNA or RNA hybridization experiment with a solution of 0.1× SSPE (or 0.1×SSC) and 0.1% SDS.

Above any said starting bacteria more particularly can be a strain obtained by knocking out the following six gene sections with *E. coli* K12 W3110 as the starting bacteria strain:

The open reading frame of the metA gene (the nucleotides at positions 752-1681 of SEQ ID No: 1 of the sequence listing);

The open reading frame of the ilvA gene (the nucleotides at positions 638-2182 of SEQ ID No: 3 of the sequence listing);

The open reading frame of the lysA gene (the nucleotides at positions 639-1901 of SEQ ID No: 5 of the sequence listing);

The open reading frame of the tdh gene (the nucleotides at positions 753-1778 of SEQ ID No: 7 of the sequence listing);

The following section of the tdcC gene: the nucleotides at positions 701-1852 of SEQ ID No: 9;

The following section of the sstT gene: the nucleotides at positions 697-1759 of SEQ ID No: 11.

Knockout of the open reading frame of the metA gene is particularly achieved by introducing an interference fragment I or an interference plasmid I. The interference fragment I sequentially consists, from upstream to downstream, of an upstream section shown by the nucleotides at positions 245-751 of SEQ ID No: 1 of the sequence listing, and a downstream section shown by the nucleotides at positions 1682-2154 of SEQ ID No: 1 of the sequence listing. The interference plasmid I is a recombinant plasmid with the interference fragment I. The interference plasmid I particularly can be a recombinant plasmid obtained by inserting the interference fragment I at the multiple cloning site of plasmid pKOV (e.g., between the enzymatic cleavage sites of Sal I and Not I).

Knockout of the open reading frame of the ilvA gene is particularly achieved by introducing an interference fragment II or an interference plasmid II. The interference fragment II sequentially consists, from upstream to downstream, of an upstream section shown by the nucleotides at positions 140-637 of SEQ ID No: 3 of the sequence listing, and a downstream section shown by the nucleotides at positions 2183-2712 of SEQ ID No: 3 of the sequence listing. The interference plasmid II is a recombinant plasmid with the interference fragment II. The interference plasmid II particularly can be a recombinant plasmid obtained by inserting the interference fragment II at the multiple cloning site of plasmid pKOV (e.g., between the enzymatic cleavage sites of BamH I and Not I).

Knockout of the open reading frame of the lysA gene is particularly achieved by introducing an interference fragment III or an interference plasmid III. The interference fragment III sequentially consists, from upstream to downstream, of an upstream section shown by the nucleotides at positions 132-638 of SEQ ID No: 5 of the sequence listing, and a downstream section shown by the nucleotides at positions 1902-2445 of SEQ ID No: 5 of the sequence listing. The interference plasmid III is a recombinant plasmid with the interference fragment III. The interference plasmid III particularly can be a recombinant plasmid obtained by inserting the interference fragment III at the multiple cloning site of plasmid pKOV (e.g., between the enzymatic cleavage sites of BamH I and Not I).

Knockout of the open reading frame of the tdh gene is particularly achieved by introducing an interference fragment IV or an interference plasmid IV. The interference fragment IV sequentially consists, from upstream to downstream, of an upstream section shown by the nucleotides at positions 227-752 of SEQ ID No: 7 of the sequence listing, and a downstream section shown by the nucleotides at positions 1779-2271 of SEQ ID No: 7 of the sequence listing. The interference plasmid IV is a recombinant plasmid with the interference fragment IV. The interference plasmid IV particularly can be a recombinant plasmid obtained by inserting the interference fragment IV at the multiple cloning site of plasmid pKOV (e.g., between the enzymatic cleavage sites of BamH I and Not I).

Knockout of "the section of the tdC gene as follows: the nucleotides at positions 701-1852 of SEQ ID No: 9" is achieved by introducing an interference fragment V or an interference plasmid V. The interference fragment V sequentially consists, from upstream to downstream, of an upstream section shown by the nucleotides at positions 176-700 of SEQ ID No: 9 of the sequence listing, and a downstream section shown by the nucleotides at positions 1853-2388 of SEQ ID No: 9 of the sequence listing. The interference plasmid V is a recombinant plasmid with the interference fragment V. The interference plasmid V particularly can be a recombinant plasmid obtained by inserting the interference fragment V at the multiple cloning site of plasmid pKOV (e.g., between the enzymatic cleavage sites of BamH I and Not I).

Knockout of "the following section of the sstT gene: the nucleotides at positions 697-1759 of SEQ ID No: 11" is achieved by introducing an interference fragment VI or an interference plasmid VI. The interference fragment VI sequentially consists, from upstream to downstream, of an upstream section shown by the nucleotides at positions 14-696 of SEQ ID No: 11 of the sequence listing, and a downstream section shown by the nucleotides at positions 1760-2240 of SEQ ID No: 11 of the sequence listing. The interference plasmid VI is a recombinant plasmid with the interference fragment VI. The interference plasmid VI particularly can be a recombinant plasmid obtained by inserting the interference fragment VI at the multiple cloning site of plasmid pKOV (e.g., between the enzymatic cleavage sites of BamH I and Not I).

The present invention also protects the use of said recombinant bacteria A in producing threonine (for example, L-threonine).

The present invention also protects the use of said recombinant bacteria B in producing threonine (for example, L-threonine).

Glucose is used as a carbon source when said recombinant bacteria are applied to produce threonine.

A fermentation medium is used to culture said recombinant bacteria when said recombinant bacteria are applied to produce threonine.

Said fermentation medium can be either a rich medium, or an inorganic salt medium. A medium comprises a carbon source, a nitrogen source, inorganic ions, antibiotics and other trophic factors. As a carbon source, saccharides such as glucose, lactose, galactose and etc. can be used; alcohols such as glycerin, mannitol and etc. can also be used; organic acids such as gluconic acid, citric acid, succinic acid and etc.

can be used as well. As a nitrogen source, inorganic nitrogen sources such as ammoniacal liquor, ammonium sulfate, ammonium phosphate, ammonium chloride and etc. can be used; organic nitrogen sources such as corn steep liquor, soybean meal hydrolysates, hair powders, yeast extracts, peptone and etc. can be used as well. Inorganic ions comprise one or more ions selected from the group consisting of iron, calcium, magnesium, manganese, molybdenum, cobalt, cuprum, potassium, and etc. ions. Other trophic factors also comprise vitamins such as biotin, vitamin B1, pyridoxal, and the like.

The carbon source in said fermentation medium is glucose.

Said fermentation medium particularly can be: glucose 20.0 g/L, ammonium sulfate 15.0 g/L, potassium dihydrogen phosphate 2.0 g/L, magnesium sulfate heptahydrate 2.0 g/L, yeast powders 2.0 g/L, isoleucine 0.6 g/L, methionine 0.6 g/L, lysine hydrochloride 1.2 g/L, calcium carbonate 15.0 g/L, microelement mixture 5 mL/L, and water as the remainder.

The microelement mixture is: $FeSO_4.7H_2O$ 10 g/L, $CaCl_2$ 1.35 g/L, $ZnSO_4.7H_2O$ 2.25 g/L, $MnSO_4.4H_2O$ 0.5 g/L, $CuSO_4.5H_2O$ 1 g/L, $(NH_4)_6Mo_7O_{24}.4H_2O$ 0.106 g/L, $Na_2B_4O_7.10H_2O$ 0.23 g/L, $CoCl_2.6H_2O$ 0.48 g/L, 35% HCl 10 mL/L, and water as the remainder.

Said culture condition particularly can be: shaking culture for 24 h at 37° C., 220 rpm.

Said culture condition particularly can be that: the seed solution is seeded into the fermentation medium in a seeding amount of 3%, followed by shaking culture for 24 h at 37° C., 220 rpm. A method for preparing the seed solution is as follows: the recombinant bacteria are seeded into a liquid LB medium, followed by shaking culture for 12 h at 37° C., 220 rpm, and a seed solution is obtained.

Processes to be controlled during said culture are as follows: during the culture, the pH value of the reaction system is adjusted with ammoniacal liquor to make it maintain at 6.8-7.0; during the culture, sampling is made once every 3-4 h to detect the content of glucose. When the content of glucose in the system is less than 5 g/L, glucose is supplemented to make the concentration of glucose in the system up to 10 g/L.

The present invention also protects a method for relieving feedback repression of a threonine operon, comprising the steps of: deleting the following DNA section in a threonine operon: the nucleotides at positions 1-293 of SEQ ID No: 20 of the sequence listing. In said method, the following step can also be comprised: deleting the following DNA section in a threonine operon: the nucleotides at positions n2-336 of SEQ ID No: 20 of the sequence listing; n2 is a natural number greater than or equal to 311 but smaller than or equal to 336.

The present invention verifies the effect of modifying a threonine attenuator with a method for translating a fusion reporter gene. The effect of relieving the repression of the threonine attenuator mutant is verified by fusing the 5' end sequence of the thrA gene with the complete reading expressing frames of two reporter genes lacZ and gfp, followed by determining the enzyme activity of reporter protein LacZ and the fluorescence value of GFP and calculating the amount of a gene expression under regulation of different threonine attenuator mutants.

The present invention firstly provides a DNA molecule A (an ilv attenuator mutant), which is (a1), (a2) or (a3) as follows:

(a1) a DNA molecule obtained by removing the nucleotides at positions 1-n4 of the ilv attenuator; n4 is a natural number greater than or equal to 128 but smaller than or equal to 147 (preferably, n4 is 136);

(a2) a DNA molecule obtained by linking a tag sequence to the end of (a1);

(a3) a DNA molecule obtained by linking a linker sequence to the end of (a1).

Said DNA molecule A particularly can be shown by the nucleotides at positions n1-n2 of SEQ ID No: 27 of the sequence listing. Said DNA molecule A particularly can be shown by the nucleotides at positions n1-155 of SEQ ID No: 27 of the sequence listing (a truncated ilv attenuator). Said DNA molecule A particularly can be shown by the nucleotides at positions n1-n3 of SEQ ID No: 27 of the sequence listing (an ilv attenuator variant). n1 is a natural number greater than or equal to 129 but smaller than or equal to 148 (preferably, n1 is 137). n2 is a natural number greater than or equal to 155 but smaller than or equal to 215 (particularly, n2 can be a natural number greater than or equal to 155 but smaller than or equal to 185, or a natural number greater than or equal to 186 but smaller than or equal to 215, and more particularly 155, 185 or 215). n3 is a natural number greater than or equal to 156 but smaller than or equal to 215 (particularly, n3 can be a natural number greater than or equal to 156 but smaller than or equal to 185, or a natural number greater than or equal to 186 but smaller than or equal to 215, and more particularly 185 or 215).

The present invention also protects the use of said DNA molecule A in promoting the expression of a downstream target gene. In said use, said DNA molecule A functions as a regulation element. In said use, said DNA molecule A is located between the promoter of said target gene and the initiation codon of said target gene. In said use, said promoter particularly can be the promoter $P_{thr-trc}$ shown by SEQ ID No: 29 of the sequence listing. In said use, said target gene particularly can be the gfp gene shown by SEQ ID No: 30 of the sequence listing.

The present invention also protects a DNA molecule B, sequentially comprising, from upstream to downstream: said DNA molecule A and a target gene. Said target gene particularly can be the gfp gene shown by SEQ ID No: 30 of the sequence listing.

The present invention also protects DNA molecule C, sequentially comprising, from upstream to downstream: a promoter, said DNA molecule A, a target gene and a terminator. Said promoter particularly can be the promoter $P_{thr-trc}$ shown by SEQ ID No: 29 of the sequence listing. Said target gene particularly can be the gfp gene shown by SEQ ID No: 30 of the sequence listing. Said terminator particularly can be

CTAGCATAACCCCTTGGGGCCTCTAAACGGGTCTTGAGGGGTTTTTTG.

Said DNA molecule B sequentially consists, from upstream to downstream, of the the following elements: the nucleotides at positions 137-215 of SEQ ID No: 27 of the sequence listing, linker sequence "GGTTCTGGTTCTGGTTCT" (SEQ ID NO: 67), and the gfp gene shown by SEQ ID No: 30 of the sequence listing.

Said DNA fragment C sequentially consists, from upstream to downstream, of the the following elements: the promoter $P_{thr-trc}$ shown by SEQ ID No: 29 of the sequence listing, the recognition sequence for enzymatic cleavage by restriction endonuclease Hind III, the nucleotides at positions 137-215 of SEQ ID No: 27 of the sequence listing, linker sequence "GGTTCTGGTTCTGGTTCT" (SEQ ID NO: 67), the gfp gene shown by SEQ ID No: 30 of the sequence listing, and the terminator sequence

CTAGCATAACCCCTTGGGGCCTCTAAACGGGTCTTGAGGGGTTTTTG.

The present invention also protects a DNA molecule D (an ilvLXGMEDA operon gene with relieved feedback repression, also referred to as the ilvLXGMEDA operon gene mutant), which is a DNA molecule obtained by removing the nucleotides at positions 1-n4 of the ilvLXGMEDA operon gene, counting from the first nucleotide of the ilv attenuator; n4 is a natural number greater than or equal to 128 but smaller than or equal to 147 (preferably, n4 is 136).

Said DNA molecule D particularly can be the double-stranded DNA molecule shown by the nucleotides at positions 137-6556 of SEQ ID No: 27 of the sequence listing.

The present invention also protects a DNA molecule E, comprising said DNA molecule D. In the DNA molecule E, the nucleotides at positions 1-n4 of SEQ ID No: 27 of the sequence listing are absent; n4 is a natural number greater than or equal to 128 but smaller than or equal to 147 (preferably, n4 is 136). The DNA molecule E sequentially consists, from upstream to downstream, of the following elements: a DNA molecule shown by the nucleotides at positions 1-987 of SEQ ID No: 28 of the sequence listing, and a DNA molecule shown by the nucleotides at positions 137-6556 of SEQ ID No: 27 of the sequence listing.

A recombinant vector containing said DNA molecule D or said DNA molecule E also falls into the protection scope of the present invention.

A recombinant bacteria containing said DNA molecule D or said DNA molecule E also falls into the protection scope of the present invention. In the genome of said recombinant bacteria, the nucleotides at positions 1-n4 of SEQ ID No: 27 of the sequence listing are absent; n4 is a natural number greater than or equal to 128 but smaller than or equal to 147 (preferably, n4 is 136). In said recombinant bacteria, a gene coding for a threonine operon is present. In said recombinant bacteria, a gene coding for the IlvA*protein is present. In said recombinant bacteria, a gene coding for the IlvC protein is present. In said recombinant bacteria, a gene coding for the IlvG protein is present. In said recombinant bacteria, a gene coding for MetA protein is absent. In said recombinant bacteria, a gene coding for the LysA protein is absent. In said recombinant bacteria, a gene coding for the Tdh protein is absent. In said recombinant bacteria, a gene coding for the TDCC protein is absent. In said recombinant bacteria, a gene coding for the SstT protein is absent.

The present invention also protects a method for constructing recombinant bacteria, comprising the following step: recombinant bacteria are obtained by having said DNA molecule D or said DNA molecule E in the genome of the starting bacteria in a manner of homologous recombination.

Said starting bacteria particularly can be recombinant bacteria EC711.

Recombinant bacteria EC711 is recombinant bacteria obtained by knocking out a gene coding for homoserine transsuccinylase (MetA protein), a gene coding for diaminopimelic acid decarboxylase (LysA protein), a gene coding for threonine dehydratase (Tdh protein), a gene coding for threonine absortion and transport protein (TDCC protein) and a gene coding for threonine absortion and transport protein (SstT protein), and introducing a gene coding for a threonine operon, with E. coli K12 W3110 as the initial bacteria.

Recombinant bacteria EC711 are recombinant bacteria obtained by knocking out a gene coding for homoserine transsuccinylase (MetA protein), a gene coding for diaminopimelic acid decarboxylase (LysA protein), a gene coding for threonine dehydratase (Tdh protein), a gene coding for threonine absortion and transport protein (TDCC protein) and threonine absortion and transport protein (SstT protein), and introducing a gene coding for a threonine operon and a gene coding for threonine deaminase (IlvA protein or IlvA*protein, preferably IlvA*protein; the IlvA protein is a wild-type protein, and the IlvA*protein is a protein with relieved feedback inhibition obtained by mutation on the basis of the IlvA protein), with E. coli K12 W3110 as the initial bacteria.

Recombinant bacteria EC711 are recombinant bacteria obtained by knocking out a gene coding for homoserine transsuccinylase (MetA protein), a gene coding for diaminopimelic acid decarboxylase (LysA protein), a gene coding for threonine dehydratase (Tdh protein), a gene coding for threonine absortion and transport protein (TDCC protein) and threonine absortion and transport protein (SstT protein), and introducing a gene coding for a threonine operon, a gene coding for threonine deaminase (IlvA protein or IlvA*protein, preferably IlvA*protein) and a gene coding for acetohydroxyacid isomeroreductase (IlvC protein), with E. coli K12 W3110 as the initial bacteria.

Since the IlvA protein subjects to the feedback inhibition of isoleucine, which is a rate-limiting step for synthesizing isoleucine, the present invention uses the IlvA*protein with relieved feedback inhibition. Both the MetA protein and the LysA protein are a protein competing for a metabolic pathway; the Tdh protein is a protein in the degradation pathway of threonine; and the TDCC protein and the SstT protein are a protein for the influx transport of threonine. In order to better realize the synthesis of isoleucine, there is still a need for efficient accumulation of its precursor's metabolite, namely threonine. As a modifying method for metabolic engineering with an efficient biosynthesis of threonine, overexpressing a threonine operon gene is needed. As an overexpressing method, expressing elements having an enhanced expressing intensity can be used, such as a promoter, RBS, and etc.; copy numbers of a gene required to be expressed can also be increased on the chromosomes; a plasmid carrying the gene required to be overexpressed can also be introduced into engineered bacteria species.

Said "gene coding for a threonine operon" is a gene coding for aspartokinase I-homoserine dehydrogenase complex, a gene coding for homoserine dehydrogenase and a gene coding for threonine synthetase.

Said aspartokinase I-homoserine dehydrogenase complex is a ThrA protein (a wild protein) or a ThrA*protein (a mutant protein). Said homoserine dehydrogenase is a ThrB protein. Said threonine synthetase is a ThrC protein. A gene coding for the ThrA protein is a thrA gene. A gene coding for the ThrA*protein is a thrA*gene. A gene coding for the ThrB protein is a thrB gene. A gene coding for the ThrC protein is a thrC gene.

Said ThrA*protein is (b1) or (b2) as follows:
(b1) a protein consisting of the amino acid sequence shown by SEQ ID No: 21 of the sequence listing;
(b2) a protein derived from SEQ ID No: 21 having aspartokinase I-homoserine dehydrogenase complex function after one or several amino acid residues of the amino acid sequence of SEQ ID No: 21 are subjected to substitution and/or deletion and/or addition.

Said thrA*gene is a DNA molecule having a coding region shown by the nucleotides at positions 337-2799 of SEQ ID No: 20 of the sequence listing.

Said ThrB protein is (c1) or (c2) as follows:

(c1) a protein consisting of the amino acid sequence shown by SEQ ID No: 22 of the sequence listing;

(c2) a protein derived from SEQ ID No: 22 having homoserine dehydrogenase function after one or several amino acid residues of the amino acid sequence of SEQ ID No: 22 are subjected to substitution and/or deletion and/or addition.

Said thrB gene is a DNA molecule having a coding region shown by the nucleotides at positions 2801-3733 of SEQ ID No: 20 of the sequence listing.

Said ThrC protein is (d1) or (d2) as follows: (d1) a protein consisting of the amino acid sequence shown by SEQ ID No: 23 of the sequence listing;

(d2) a protein derived from SEQ ID No: 23 having threonine synthetase function after one or several amino acid residues of the amino acid sequence of SEQ ID No: 23 are subjected to substitution and/or deletion and/or addition.

Said thrC gene is a DNA molecule having a coding region shown by the nucleotides at positions 3734-5020 of SEQ ID No: 20 of the sequence listing.

Said "gene coding for a threonine operon" is a DNA molecule shown by the nucleotides at positions 172-5132 of SEQ ID No: 20 of the sequence listing.

Said IlvA*protein is (e1) or (e2) as follows:

(e1) a protein consisting of the amino acid sequence shown by SEQ ID No: 25 of the sequence listing;

(e2) a protein derived from SEQ ID No: 25 having threonine deaminase function after one or several amino acid residues of the amino acid sequence of SEQ ID No: 25 are subjected to substitution and/or deletion and/or addition.

A gene coding for the IlvA*protein is a DNA molecule having an open reading frame shown by the nucleotides at positions 1-1545 of SEQ ID No: 24 of the sequence listing, or a DNA molecule shown by the nucleotides at positions 1-1630 of SEQ ID No: 24 of the sequence listing.

Said IlvC protein is (f1) or (f2) as follows:

(f1) a protein consisting of the amino acid sequence shown by SEQ ID No: 26 of the sequence listing;

(f2) a protein derived from SEQ ID No: 26 having acetohydroxyacid isomeroreductase function after one or several amino acid residues of the amino acid sequence of SEQ ID No: 26 are subjected to substitution and/or deletion and/or addition.

A gene coding for the IlvC protein is a DNA molecule having an open reading frame shown by the nucleotides at positions 1717-3192 of SEQ ID No: 24 of the sequence listing, or a DNA molecule shown by the nucleotides at positions 1631-3275 of SEQ ID No: 24 of the sequence listing.

In said recombinant bacteria EC711, a gene coding for the threonine operon is integrated into the lysA gene site of the genome (the lysA gene site is a site of the gene coding for LysA protein).

In said recombinant bacteria EC711, a gene coding for the threonine deaminase is integrated into the sstT gene site of the genome (the sstT gene site is a site of the gene coding for SstT protein).

In said recombinant bacteria EC711, a gene coding for the threonine deaminase and a gene coding for acetohydroxyacid isomeroreductase are integrated into the sstT gene site of the genome (the sstT gene site is a site of the gene coding for SstT protein).

Said MetA protein is (g1) or (g2) as follows:

(g1) a protein consisting of the amino acid sequence shown by SEQ ID No: 2 of the sequence listing;

(g2) a protein derived from SEQ ID No: 2 having the same function after one or several amino acid residues of the amino acid sequence of SEQ ID No: 2 are subjected to substitution and/or deletion and/or addition.

Said metA gene is a DNA molecule having a coding region shown by the nucleotides at positions 752-1681 of SEQ ID No: 1 of the sequence listing, or a DNA molecule shown by SEQ ID No: 1 of the sequence listing.

Said LysA protein is (i1) or (i2) as follows:

(i1) a protein consisting of the amino acid sequence shown by SEQ ID No: 6 of the sequence listing;

(i2) a protein derived from SEQ ID No: 6 having the same function after one or several amino acid residues of the amino acid sequence of SEQ ID No: 6 are subjected to substitution and/or deletion and/or addition.

Said lysA gene is a DNA molecule having a coding region shown by the nucleotides at positions 639-1901 of SEQ ID No: 5 of the sequence listing, or a DNA molecule shown by SEQ ID No: 5 of the sequence listing.

Said Tdh protein is (j1) or (j2) as follows:

(j1) a protein consisting of the amino acid sequence shown by SEQ ID No: 8 of the sequence listing;

(j2) a protein derived from SEQ ID No: 8 having the same function after one or several amino acid residues of the amino acid sequence of SEQ ID No: 8 are subjected to substitution and/or deletion and/or addition.

Said tdh gene is a DNA molecule having a coding region shown by the nucleotides at positions 753-1778 of SEQ ID No: 7 of the sequence listing, or a DNA molecule shown by SEQ ID No: 7 of the sequence listing.

Said TDCC protein is (k1) or (k2) as follows:

(k1) a protein consisting of the amino acid sequence shown by SEQ ID No: 10 of the sequence listing;

(k2) a protein derived from SEQ ID No: 10 having the same function after one or several amino acid residues of the amino acid sequence of SEQ ID No: 10 are subjected to substitution and/or deletion and/or addition.

Said tdcC gene is a DNA molecule having a coding region shown by the nucleotides at positions 701-2032 of SEQ ID No: 9 of the sequence listing, or a DNA molecule shown by SEQ ID No: 9 of the sequence listing.

Said SstT protein is (m1) or (m2) as follows:

(m1) a protein consisting of the amino acid sequence shown by SEQ ID No: 12 of the sequence listing;

(m2) a protein derived from SEQ ID No: 12 having the same function after one or several amino acid residues of the amino acid sequence of SEQ ID No: 12 are subjected to substitution and/or deletion and/or addition.

Said sstT gene is a DNA molecule having a coding region shown by the nucleotides at positions 701-1945 of SEQ ID No: 11 of the sequence listing, or a DNA molecule shown by SEQ ID No: 11 of the sequence listing.

Said starting bacteria can be bacteria of the genus *Escherichia* or bacteria of the genus *Corynebacteria*. Said bacteria of the genus *Escherichia* particularly can be *E. coli*. Said bacteria of the genus *Corynebacteria* particularly can be *Corynebacterium glutamicum*.

The present invention also protects the use of above any said recombinant bacteria in producing isoleucine.

Glucose is used as a carbon source when applying said recombinant bacteria to produce isoleucine.

A fermentation medium is used to culture said recombinant bacteria when applying said recombinant bacteria to produce isoleucine.

Said fermentation medium can either be a rich medium or an inorganic salt medium. A medium comprises a carbon source, a nitrogen source, inorganic ions, antibiotics and other trophic factors. As a carbon source, saccharides such as glucose, lactose, galactose and etc. can be used; alcohols such as glycerin, mannitol and etc. can also be used; organic acids such as gluconic acid, citric acid, succinic acid and etc. can be used as well. As a nitrogen source, inorganic nitrogen sources such as ammoniacal liquor, ammonium sulfate, ammonium phosphate, ammonium chloride and etc. can be used; organic nitrogen sources such as corn steep liquor, soybean meal hydrolysates, hair powders, yeast extracts, peptone and etc. can be used as well. Inorganic ions comprise one or more ions selected from the group consisting of iron, calcium, magnesium, manganese, molybdenum, cobalt, cuprum, potassium and etc. ions. Other trophic factors also comprise vitamins such as biotin, vitamin B1, pyridoxal and etc.

The carbon source in said fermentation medium is glucose.

Said fermentation medium particularly can be: glucose 20.0 g/L, ammonium sulfate 15.0 g/L, potassium dihydrogen phosphate 2.0 g/L, magnesium sulfate heptahydrate 2.0 g/L, yeast powders 2.0 g/L, methionine 0.6 g/L, L-lysine-hydrochloride 1.2 g/L, calcium carbonate 15.0 g/L, microelement mixture 5 mL/L, and water as the remainder.

The microelement mixture is: $FeSO_4 \cdot 7H_2O$ 10 g/L, $CaCl_2$ 1.35 g/L, $ZnSO_4 \cdot 7H_2O$ 2.25 g/L, $MnSO_4 \cdot 4H_2O$ 0.5 g/L, $CuSO_4 \cdot 5H_2O$ 1 g/L, $(NH_4)_6Mo_7O_{24} \cdot 4H_2O$ 0.106 g/L, $Na_2B_4O_7 \cdot 10H_2O$ 0.23 g/L, $CoCl_2 \cdot 6H_2O$ 0.48 g/L, 35% HCl 10 mL/L, and water as the remainder.

Said culture condition particularly can be: shaking culture for 36 h at 37° C., 220 rpm.

Said culture condition particularly can be that: the seed solution is seeded into the fermentation medium in a seeding amount of 3%, followed by shaking culture for 36 h at 37° C., 220 rpm. A method for preparing the seed solution is as follows: the recombinant bacteria are seeded into a liquid LB medium, followed by shaking culture for 12 h at 37° C., 220 rpm, and a seed solution is obtained. The OD600 nm value of said seed solution particularly can be 5.0.

Processes to be controlled during said culture are as follows: during the culture, the pH value of the reaction system is adjusted with ammoniacal liquor to make it maintain at 6.8-7.0; during the culture, sampling is made once every 3-4 h to detect the content of glucose. When the content of glucose in the system is less than 5 g/L, glucose is supplemented to make the concentration of glucose in the system up to 10 g/L.

The present invention also protects a method for improving the capability of producing isoleucine by microorganisms, comprising the following step: deleting the nucleotides at positions 1-n4 of the ilvLXGMEDA operon gene of the microorganisms, counting from the first nucleotide of the ilv attenuator; n4 is a natural number greater than or equal to 128 but smaller than or equal to 147 (preferably, n4 is 136). Said microorganisms are microorganisms having an ilvLXGMEDA operon. Said microorganisms particularly can be the microorganisms of the genus *Escherichia*. Said microorganisms of the genus *Escherichia* particularly can be *E. coli*, and more particularly *E. coli* K-12 or a strain derived therefrom.

The present invention also protects a method for relieving the feedback repression of the ilvLXGMEDA operon in microorganisms, comprising the following step: deleting the nucleotides at positions 1-n4 of the ilvLXGMEDA operon gene of the microorganisms, counting from the first nucleotide of the ilv attenuator; n4 is a natural number greater than or equal to 128 but smaller than or equal to 147 (preferably, n4 is 136). Said microorganisms are microorganisms having an ilvLXGMEDA operon. Said microorganisms particularly can be the microorganisms of the genus *Escherichia*. Said microorganisms of the genus *Escherichia* particularly can be *E. coli*, and more particularly *E. coli* K-12 or a strain derived therefrom.

Above any said ilvLXGMEDA operon can be an ilvLXGMEDA operon from the microorganisms of the genus *Escherichia*, particularly can be an ilvLXGMEDA operon from *E. coli*. Microorganisms of the genus *Escherichia* are not specifically limited to a specific one for use. If a wild-type strain is used as the strain of DNA donor containing the ilvLXGMEDA operon, a DNA containing a wild-type ilvLXGMEDA operon can be obtained. However, the strain of *E. coli* K-12 does not express an active isoenzyme II of acetohydroxyacid synthetase. Thus, the ilvG gene of the present invention is from the chromosome DNA donor of the strain of *E. coli* BL21.

Above any said ilvLXGMEDA operon gene comprises an ilv attenuator, a gene coding for the IlvX protein, a gene coding for the IlvG protein (acetolactate synthase), a gene coding for the IlvM protein (acetolactate synthase), a gene coding for the IlvE protein (branched amino acid transaminase), a gene coding for the IlvD protein (dihydroxyacid dehydratase) and a gene coding for the IlvA protein (threonine deaminase).

Said IlvX protein can be (p1) or (p2) as follows:
(p1) a protein consisting of the amino acid sequence shown by SEQ ID No: 32 of the sequence listing;
(p2) a protein derived from SEQ ID No: 32 having the same function after one or several amino acid residues of the amino acid sequence of SEQ ID No: 32 are subjected to substitution and/or deletion and/or addition.

Said IlvG protein can be (q1) or (q2) as follows: (q1) a protein consisting of the amino acid sequence shown by SEQ ID No: 33 of the sequence listing;
(q2) a protein derived from SEQ ID No: 33 having acetolactate synthase function after one or several amino acid residues of the amino acid sequence of SEQ ID No: 33 are subjected to substitution and/or deletion and/or addition.

Said IlvM protein can be (r1) or (r2) as follows:
(r1) a protein consisting of the amino acid sequence shown by SEQ ID No: 34 of the sequence listing;
(r2) a protein derived from SEQ ID No: 34 having acetolactate synthase function after one or several amino acid residues of the amino acid sequence of SEQ ID No: 34 are subjected to substitution and/or deletion and/or addition.

Said IlvE protein can be (s1) or (s2) as follows:
(s1) a protein consisting of the amino acid sequence shown by SEQ ID No: 35 of the sequence listing;
(s2) a protein derived from SEQ ID No: 35 having branched chain amino acid transaminase function after one or several amino acid residues of the amino acid sequence of SEQ ID No: 35 are subjected to substitution and/or deletion and/or addition.

Said IlvD protein can be (t1) or (t2) as follows:
(t1) a protein consisting of the amino acid sequence shown by SEQ ID No: 36 of the sequence listing;
(t2) a protein derived from SEQ ID No: 36 having dihydroxyacid dehydratase function after one or several amino acid residues of the amino acid sequence of SEQ ID No: 36 are subjected to substitution and/or deletion and/or addition.

Said IlvA protein can be (w1) or (w2) as follows: (w1) a protein consisting of the amino acid sequence shown by SEQ ID No: 37 of the sequence listing;

(w2) a protein derived from SEQ ID No: 37 having dihydroxyacid dehydratase function after one or several amino acid residues of the amino acid sequence of SEQ ID No: 37 are subjected to substitution and/or deletion and/or addition.

A gene coding for the IlvX protein particularly can be shown by the nucleotides at positions 186-236 of SEQ ID No: 27 of the sequence listing.

A gene coding for the IlvG protein particularly can be shown by the nucleotides at positions 239-1885 of SEQ ID No: 27 of the sequence listing.

A gene coding for the IlvM protein particularly can be shown by the nucleotides at positions 1882-2145 of SEQ ID No: 27 of the sequence listing.

A gene coding for the IlvE protein particularly can be shown by the nucleotides at positions 2165-3094 of SEQ ID No: 27 of the sequence listing.

A gene coding for the IlvD protein particularly can be shown by the nucleotides at positions 3159-5009 of SEQ ID No: 27 of the sequence listing.

A gene coding for the IlvA protein particularly can be shown by the nucleotides at positions 5012-6556 of SEQ ID No: 27 of the sequence listing.

The ilv attenuator is shown by the nucleotides at positions 1-155 of SEQ ID No: 27 of the sequence listing.

The ilvLXGMEDA operon particularly can be shown by SEQ ID No: 27 of the sequence listing.

Above any said isoleucines particularly can be L-isoleucine.

The present invention surprisingly obtains an ilv attenuator mutant which can significantly improve the expression level of a gene through removing the specific sequences of the ilv attenuator. In the present invention, the expression level of the subsequent genes can be significantly improved by deleting the ilvL gene coding for a leader peptide and an anterior reverse complementary palindromic sequence in the terminator stem-loop structure of the attenuator. Obviously, according to the test results of the present invention, the skilled in the art can readily conclude that an ilv attenuator mutant having a similar performance may likewise be obtained by simultaneously maintaining a portion of the above said anterior reverse complementary palindromic sequence in the terminator stem-loop structure of the attenuator on the ilv attenuator mutant protected by the present invention, but not yet forming a steady stem-loop structure. Thus, such similar method for modifying an ilv attenuator also falls into the protection scope of the present invention. Obviously, deleting several base pairs upstream of the open reading frame of the ilvL while modifying the ilv attenuator on the chromosomes of a strain also falls into the protection scope of the present invention. Obviously, the method for relieving the ilv attenuator of *E. coli* in the present invention can likewise be applied to the ilv attenuators of other strains. The ilvLXGMEDA operon gene codes for the enzymes for the reaction of synthesizing isoleucine from threonine in five steps. Thus, the attenuation regulation of the ilvLXGMEDA operon can be efficiently relieved by modifying the ilv attenuator, thereby improving the expression level of the ilvLXGMEDA operon.

The present invention firstly protects a DNA molecule A (an ilv attenuator mutant), which is (a1), (a2) or (a3) as follows:

(a1) a DNA molecule shown by the nucleotides at positions n1-n2 of SEQ ID No: 38 of the sequence listing; n1 is a natural number greater than or equal to 129 but smaller than or equal to 148 (preferably, n1 is 137), and n2 is a natural number greater than or equal to 155 but smaller than or equal to 215 (n2 particularly can be a natural number greater than or equal to 155 but smaller than or equal to 185, or a natural number greater than or equal to 186 but smaller than or equal to 215, and more particularly 155, 185 or 215);

(a2) a DNA molecule obtained by linking a tag sequence to the end of (a1);

(a3) a DNA molecule obtained by linking a linker sequence to the end of (a1).

The ilv attenuator mutant is a truncated ilv attenuator or an ilv attenuator variant. The truncated ilv attenuator truncation is shown by the nucleotides at positions n1-155 of SEQ ID No: 38 of the sequence listing. The ilv attenuator variant is shown by the nucleotides at positions n1-n3 of SEQ ID No: 38 of the sequence listing 38; n3 is a natural number greater than or equal to 156 but smaller than or equal to 215 (n3 particularly can be a natural number greater than or equal to 156 but smaller than or equal to 185, or a natural number greater than or equal to 186 but smaller than or equal to 215, and more particularly 185 or 215).

The present invention also protects the use of said DNA molecule A in promoting the expression of a downstream target gene. In said use, said DNA molecule A functions as a regulation element. In said use, said DNA molecule A is located between the promoter of said target gene and the initiation codon of said target gene. In said use, said promoter particularly can be the promoter $P_{thr-trc}$ shown by SEQ ID No: 29 of the sequence listing. In said use, said target gene particularly can be the gfp gene shown by SEQ ID No: 30 of the sequence listing.

The present invention also protects a DNA molecule B, sequentially comprising, from upstream to downstream: said DNA molecule A and a target gene. Said target gene particularly can be the gfp gene shown by SEQ ID No: 30 of the sequence listing.

The present invention also protects a DNA molecule C, sequentially comprising, from upstream to downstream: a promoter, said DNA molecule A, a target gene and a terminator. Said promoter particularly can be the promoter $P_{thr-trc}$ shown by SEQ ID No: 29 of the sequence listing. Said target gene particularly can be the gfp gene shown by SEQ ID No: 30 of the sequence listing. Said terminator particularly can be

CTAGCATAACCCCTTGGGGCCTCTAAACGGGTCTTGAGGGGTTTTTTG.

Said DNA molecule A or said DNA molecule B or said DNA molecule C is free of the nucleotides at positions 1-n4 of the ilv attenuator, and n4 is a natural number greater than or equal to 128 but smaller than or equal to 147 (preferably, n4 is 136).

Said DNA molecule B sequentially consists, from upstream to downstream, of the following elements: the nucleotides at positions 137-215 of SEQ ID No: 38 of the sequence listing, a linker sequence "GGTTCTGGTTCTGGTTCT" (SEQ ID NO: 67), and the gfp gene shown by SEQ ID No: 30 of the sequence listing.

Said DNA fragment C sequentially consists, from upstream to downstream, of the following elements: the promoter $P_{thr-trc}$ shown by SEQ ID No: 29 of the sequence listing, a recognition sequence for enzymatic cleavage by restriction endonuclease Hind III, the nucleotides at positions 137-215 of SEQ ID No: 38 of the sequence listing, a linker sequence "GGTTCTGGTTCTGGTTCT" (SEQ ID NO: 67), the gfp gene shown by SEQ ID No: 30 of the sequence listing, and the terminator sequence

```
CTAGCATAACCCCTTGGGGCCTCTAAACGGGTCTTGAGGGGTTTTTTG.
```

The present invention also protects a DNA molecule D (an ilvLXGMED operon gene with relieved feedback repression, also referred to as an ilvLXGMED operon gene mutant), which is a DNA molecule obtained by removing the nucleotides at positions 1-n4 of the ilvLXGMED operon gene, counting from the first nucleotide of the ilv attenuator; n4 is a natural number greater than or equal to 128 but smaller than or equal to 147 (preferably, n4 is 136).

Said DNA molecule D particularly can be the double-stranded DNA molecule shown by the nucleotides at positions 137-5009 of SEQ ID No: 38 of the sequence listing.

The present invention also protects a DNA molecule E, sequentially comprising, from upstream to downstream, the following elements: a promoter, said DNA molecule D and a terminator. Said promoter particularly can be the promoter $P_{JJ}$ shown by SEQ ID No: 39 of the sequence listing. Said terminator particularly can be

```
CTAGCATAACCCCTTGGGGCCTCTAAACGGGTCTTGAGGGGTTTTTTG.
```

Said DNA molecule E sequentially consists, from upstream to downstream, of the following elements: the promoter $P_{JJ}$ shown by SEQ ID No: 39 of the sequence listing, a recognition sequence for enzymatic cleavage by restriction endonuclease BamH I, and the double-stranded DNA molecule shown by the nucleotides at positions 137-5057 of SEQ ID No: 38 of the sequence listing 38.

A recombinant vector comprising said DNA molecule D or said DNA molecule E also falls into the protection scope of the present invention.

Recombinant bacteria comprising said DNA molecule D or said DNA molecule E also falls into the protection scope of the present invention.

Said recombinant bacteria are obtained by introducing said DNA molecule D or said DNA molecule E into starting bacteria. Said starting bacteria can be the bacteria of the genus *Escherichia* or *Corynebacteria*. Said bacteria of the genus *Escherichia* particularly can be *E. coli*, and more particularly *E. coli* K-12 or a strain derived therefrom, and even more particularly *E. coli* K12 MG1655 or *E. coli* K-12 MG1655ΔilvA. Said bacteria of the genus *Corynebacteria* particularly can be *Corynebacterium glutamicum*, for example, *Corynebacterium glutamicum* ATCC13032 and etc.

*E. coli* K-12 MG1655 ΔilvA is a strain obtained by knocking out the gene coding for the IlvA protein in the genome of *E. coli* K12 MG1655. *E. coli* K-12 MG1655ΔilvA is a strain obtained by knocking out the open reading frame of the gene coding for the IlvA protein in the genome of *E. coli* K12 MG1655. Said knock out particularly can be achieved by a method of introducing an interference fragment or an interference plasmid into the *E. coli* K12 MG1655. Said interference fragment particularly can be the following DNA molecule: a DNA molecule sequentially consisting, from upstream to downstream, of the upstream section shown by the nucleotides at positions 140-637 of SEQ ID No: 3 of the sequence listing and the downstream section shown by the nucleotides at positions 2183-2712 of SEQ ID No: 3 of the sequence listing. Said interference plasmid particularly can be a recombinant plasmid obtained by inserting said interference fragment into the plasmid pKOV.

Said IlvA protein is (b1) or (b2) as follows:
(b1) a protein consisting of the amino acid sequence shown by SEQ ID No: 4 of the sequence listing;
(b2) a protein derived from SEQ ID No: 4 having the same function after one or several amino acid residues of the amino acid sequence of SEQ ID No: 4 are subjected to substitution and/or deletion and/or addition.

A gene coding for the IlvA protein particularly can be shown by SEQ ID No: 3 of the sequence listing.

The open reading frame of the gene coding for the IlvA protein particularly can be the nucleotides at positions 638-2182 of SEQ ID No: 3 of the sequence listing.

The present invention also protects the use of said recombinant bacteria in producing valine.

Glucose is used as a carbon source when applying said recombinant bacteria to produce valine.

A fermentation medium is used to culture said recombinant bacteria when applying said recombinant bacteria to produce valine.

Said fermentation medium can be either a rich medium, or an inorganic salt medium. A medium comprises a carbon source, a nitrogen source, inorganic ions, antibiotics and other trophic factors. As a carbon source, saccharides such as glucose, lactose, galactose and etc. can be used; alcohols such as glycerin, mannitol and etc. can also be used; organic acids such as gluconic acid, citric acid, succinic acid and etc. can be used as well. As a nitrogen source, inorganic nitrogen sources such as ammoniacal liquor, ammonium sulfate, ammonium phosphate, ammonium chloride and etc. can also be used; organic nitrogen sources such as corn steep liquor, soybean meal hydrolysates, hair powders, yeast extracts, peptone and etc. can be used as well. Inorganic ions comprise one or more ions selected from the group consisting of iron, calcium, magnesium, manganese, molybdenum, cobalt, cuprum, potassium and etc. ions. Other trophic factors also comprise vitamins such as biotin, vitamin B1, pyridoxal and etc.

The carbon source in said fermentation medium is glucose.

Said fermentation medium particularly can be: a fermentation medium: glucose 20.0 g/L, ammonium sulfate 15.0 g/L, potassium dihydrogen phosphate 2.0 g/L, magnesium sulfate heptahydrate 2.0 g/L, yeast powders 2.0 g/L, isoleucine 0.6 g/L, calcium carbonate 15.0 g/L, microelement mixture 5 mL/L, and water as the remainder.

The microelement mixture is: $FeSO_4 \cdot 7H_2O$ 10 g/L, $CaCl_2$ 1.35 g/L, $ZnSO_4 \cdot 7H_2O$ 2.25 g/L, $MnSO_4 \cdot 4H_2O$ 0.5 g/L, $CuSO_4 \cdot 5H_2O$ 1 g/L, $(NH_4)_6Mo_7O_{24} \cdot 4H_2O$ 0.106 g/L, $Na_2B_4O_7 \cdot 10H_2O$ 0.23 g/L, $CoCl_2 \cdot 6H_2O$ 0.48 g/L, 35% HCl 10 mL/L, and water as the remainder.

Said culture condition particularly can be: shaking culture for 36 h at 37° C., 220 rpm.

Said culture condition particularly can be that: the seed solution is seeded into the fermentation medium in a seeding amount of 3%, followed by shaking culture for 36 h at 37° C., 220 rpm. A method for preparing the seed solution is as follows: the recombinant bacteria are seeded into a liquid LB medium, followed by shaking culture for 12 h at 37° C., 220 rpm, and a seed solution is obtained. The $OD_{600nm}$ value of said seed solution particularly can be 5.0.

Processes to be controlled during said culture are as follows: during the culture, the pH value of the reaction system is adjusted with ammoniacal liquor to make it maintain at 6.8-7.0; during the culture, sampling is made once every 3-4 h to detect the content of glucose. When the content of glucose in the system is less than 5 g/L, glucose is supplemented to make the concentration of glucose in the system up to 10 g/L.

The present invention also protects a method for improving the capability of producing valine by microorganisms, comprising the following step: deleting the nucleotides at positions 1-n4 of the ilvLXGMED operon gene of the microorganisms, counting from the first nucleotide of the ilv attenuator; n4 is a natural number greater than or equal to 128 but smaller than or equal to 147 (preferably, n4 is 136). Said microorganisms are microorganisms having an ilvLXGMED operon. Said microorganisms particularly can be the microorganisms of the genus *Escherichia*. Said microorganisms of the genus *Escherichia* particularly can be *E. coli*, and more particularly *E. coli* K-12 or a strain derived therefrom, and even more particularly *E. coli* K12 MG1655 or *E. coli* K-12 MG1655ΔilvA.

The present invention also protects a method for relieving the feedback repression of the ilvLXGMED operon in microorganisms, comprising the following step: deleting the nucleotides at positions 1-n4 of the ilvLXGMED operon gene of the microorganisms, counting from the first nucleotide of the ilv attenuator; n4 is a natural number greater than or equal to 128 but smaller than or equal to 147 (preferably, n4 is 136). Said microorganisms are microorganisms having an ilvLXGMED operon. Said microorganisms particularly can be the microorganisms of the genus *Escherichia*. Said microorganisms of the genus *Escherichia* particularly can be *E. coli*, and more particularly *E. coli* K-12 or a strain derived therefrom, and even more particularly *E. coli* K12 MG1655 or *E. coli* K-12 MG1655ΔilvA.

Above any said ilvLXGMED operon can be an ilvLXGMED operon from the microorganisms of the genus *Escherichia*, particularly can be an ilvLXGMED operon from *E. coli*. Microorganisms of the genus *Escherichia* are not specifically limited to a specific one for use. If a wild-type strain is used as the strain of DNA donor containing the ilvLXGMED operon, a DNA containing a wild-type ilvLXGMED operon can be obtained. However, the strain of *E. coli* K-12 does not express an active ilvG gene. Thus, the ilvG gene of the present invention is from the chromosomes of the strain of *E. coli* BL21.

Above any said ilvLXGMED operon gene comprises an ilv attenuator, a gene coding for the IlvX protein, a gene coding for the IlvG protein (acetolactate synthase), a gene coding for the IlvM protein (acetolactate synthase), a gene coding for the IlvE protein (branched chain amino acidtransaminase) and a gene coding for the IlvD protein (dihydroxyacid dehydratase).

Said IlvX protein can be (c1) or (c2) as follows:
(c1) a protein consisting of the amino acid sequence shown by SEQ ID No: 32 of the sequence listing;
(c2) a protein derived from SEQ ID No: 32 having the same function after one or several amino acid residues of the amino acid sequence of SEQ ID No: 32 are subjected to substitution and/or deletion and/or addition.

Said IlvG protein can be (d1) or (d2) as follows:
(d1) a protein consisting of the amino acid sequence shown by SEQ ID No: 33 of the sequence listing;
(d2) a protein derived from SEQ ID No: 33 having acetolactate synthase function after one or several amino acid residues of the amino acid sequence of SEQ ID No: 33 are subjected to substitution and/or deletion and/or addition.

Said IlvM protein can be (e1) or (e2) as follows:
(e1) a protein consisting of the amino acid sequence shown by SEQ ID No: 34 of the sequence listing;
(e2) a protein derived from SEQ ID No: 34 having acetolactate synthase function after one or several amino acid residues of the amino acid sequence of SEQ ID No: 34 are subjected to substitution and/or deletion and/or addition.

Said IlvE protein can be (f1) or (f2) as follows:
(f1) a protein consisting of the amino acid sequence shown by SEQ ID No: 35 of the sequence listing;
(f2) a protein derived from SEQ ID No: 35 having branched chain amino acidtransaminase function after one or several amino acid residues of the amino acid sequence of SEQ ID No: 35 are subjected to substitution and/or deletion and/or addition.

Said IlvD protein can be (g1) or (g2) as follows:
(g1) a protein consisting of the amino acid sequence shown by SEQ ID No: 36 of the sequence listing;
(g2) a protein derived from SEQ ID No: 36 having dihydroxyacid dehydratase function after one or several amino acid residues of the amino acid sequence of SEQ ID No: 36 are subjected to substitution and/or deletion and/or addition.

A gene coding for the IlvX protein particularly can be shown by the nucleotides at positions 186-236 of SEQ ID No: 38 of the sequence listing.

A gene coding for the IlvG protein particularly can be shown by the nucleotides at positions 239-1885 of SEQ ID No: 38 of the sequence listing.

A gene coding for the IlvM protein particularly can be shown by the nucleotides at positions 1882-2145 of SEQ ID No: 38 of the sequence listing.

A gene coding for the IlvE protein particularly can be shown by the nucleotides at positions 2165-3094 of SEQ ID No: 38 of the sequence listing.

A gene coding for the IlvD protein particularly can be shown by the nucleotides at positions 3159-5009 of SEQ ID No: 38 of the sequence listing.

The ilv attenuator is shown by the nucleotides at positions 1-155 of SEQ ID No: 38 of the sequence listing.

The ilvLXGMED operon gene particularly can be shown by SEQ ID No: 38 of the sequence listing.

The ilvLXGMED operon gene particularly can be shown by the nucleotides at positions 1-5009 of SEQ ID No: 38 of the sequence listing.

Above any said valine particularly can be L-valine.

The present invention surprisingly obtains an ilv attenuator mutant which can significantly improve the expression level of a gene through removing the specific sequences of the ilv attenuator. In the present invention, the expression level of the subsequent genes can be significantly improved by deleting the ilvL gene coding for a leader peptide and an anterior reverse complementary palindromic sequence in the terminator stem-loop structure of the attenuator. Obviously, according to the test results of the present invention, the skilled in the art can readily conclude that an ilv attenuator mutant and an ilvLXGMED operon gene mutant having a similar performance may likewise be obtained by simultaneously maintaining a portion of the above said anterior reverse complementary palindromic sequence in the terminator stem-loop structure of the attenuator on the ilv attenuator mutant protected by the present invention, but not yet forming a steady stem-loop structure. Thus, such similar method for modifying an ilv attenuator also falls into the protection scope of the present invention. Obviously, deleting several base pairs upstream of the open reading frame of the ilvL while modifying the ilv attenuator on the chromosomes of a strain also falls into the protection scope of the present invention. Obviously, the method for relieving the ilv attenuator of *E. coli* in the present invention can likewise be applied to the ilv attenuators of other strains.

The present invention firstly protects a DNA molecule A (a tryptophan attenuator mutant), which is (a1), (a2), (a3), (a4) or (a5) as follows:

(a1) a DNA molecule shown by the nucleotides at positions n1-n2 of SEQ ID No: 40 of the sequence listing; n1 is a natural number greater than or equal to 115 but smaller than or equal to 122 (preferably, n1 is 115), and n2 is a natural number greater than or equal to 135 but smaller than or equal to 186 (n2 particularly can be a natural number greater than or equal to 135 but smaller than or equal to 156, or a natural number greater than or equal to 157 but smaller than or equal to 186, and more particularly 135, 156 or 186);

(a2) a DNA molecule obtained by removing the nucleotides at positions 1-n3 of the tryptophan attenuator; n3 is a natural number greater than or equal to 114 but smaller than or equal to 121 (preferably, n3 is 114);

(a3) a DNA molecule obtained by removing the nucleotides at positions 1-n3 of the sequence associated with the tryptophan attenuator; n3 is a natural number greater than or equal to 114 but smaller than or equal to 121 (preferably, n3 is 114);

(a4) a DNA molecule obtained by linking a tag sequence to the end of (a1) or (a2) or (a3);

(a5) a DNA molecule obtained by linking a linker sequence to the end of (a1) or (a2) or (a3).

The tryptophan attenuator mutant is a truncated tryptophan attenuator or a tryptophan attenuator variant. The truncated tryptophan attenuator is shown by the nucleotides at positions n1-135 of SEQ ID No: 40 of the sequence listing. The tryptophan attenuator variant is shown by the nucleotides at positions n1-n4 of SEQ ID No: 40 of the sequence listing; n4 is a natural number greater than or equal to 136 but smaller than or equal to 186 (n4 particularly can be a natural number greater than or equal to 136 but smaller than or equal to 156, or a natural number greater than or equal to 157 but smaller than or equal to 186, and more particularly 156 or 186).

The present invention also protects the use of said DNA molecule A in promoting the expression of a downstream target gene. In said use, said DNA molecule A functions as a regulation element. In said use, said DNA molecule A is located between the promoter of said target gene and the initiation codon of said target gene. In said use, said promoter particularly can be the promoter $P_{thr-trc}$ shown by SEQ ID No: 29 of the sequence listing. In said use, said target gene particularly can be the gfp gene shown by SEQ ID No: 30 of the sequence listing.

The present invention also protects a DNA molecule B, sequentially comprising, from upstream to downstream: said DNA molecule A and a target gene. Said target gene particularly can be the gfp gene shown by SEQ ID No: 30 of the sequence listing.

The present invention also protects a DNA molecule C, sequentially comprising, from upstream to downstream: a promoter, said DNA molecule A, a target gene and a terminator. Said promoter particularly can be the promoter $P_{thr-trc}$ shown by SEQ ID No: 29 of the sequence listing. Said target gene particularly can be the gfp gene shown by SEQ ID No: 30 of the sequence listing. Said terminator particularly can be

```
CTAGCATAACCCCTTGGGGCCTCTAAACGGGTCTTGAGGGGTTTTTG.
```

Said DNA molecule A or said DNA molecule B or said DNA molecule C is free of the nucleotides at positions 1-n3 of the tryptophan attenuator; n3 is a natural number greater than or equal to 114 but smaller than or equal to 121 (preferably, n3 is 114).

Said DNA molecule B sequentially consists, from upstream to downstream, of the following elements: the nucleotides at positions 115-186 of SEQ ID No: 40 of the sequence listing, a linker sequence "GGTTCTGGTTCTGGTTCT" (SEQ ID NO: 67), and the gfp gene shown by SEQ ID No: 30 of the sequence listing.

Said DNA molecule B sequentially consists, from upstream to downstream, of the following elements: the nucleotides at positions 122-186 of SEQ ID No: 40 of the sequence listing, a linker sequence "GGTTCTGGTTCTGGTTCT" (SEQ ID NO: 67), and the gfp gene shown by SEQ ID No: 30 of the sequence listing.

Said DNA molecule C sequentially consists, from upstream to downstream, of the following elements: the promoter $P_{thr-trc}$ shown by SEQ ID No: 29 of the sequence listing, a recognition sequence for enzymatic cleavage by restriction endonuclease Hind III, the nucleotides at positions 115-186 of SEQ ID No: 40 of the sequence listing, a linker sequence "GGTTCTGGTTCTGGTTCT" (SEQ ID NO: 67), the gfp gene shown by SEQ ID No: 30 of the sequence listing, and a terminator sequence

```
"CTAGCATAACCCCTTGGGGCCTCTAAACGGGTCTTGAGGGGTTT
TTTG".
```

Said DNA molecule C sequentially consists, from upstream to downstream, of the following elements: the promoter $P_{thr-trc}$ shown by SEQ ID No: 29 of the sequence listing, a recognition sequence for enzymatic cleavage by restriction endonuclease Hind III, the nucleotides at positions 122-186 of SEQ ID No: 40 of the sequence listing, a linker sequence "GGTTCTGGTTCTGGTTCT" (SEQ ID NO: 67), the gfp gene shown by SEQ ID No: 30 of the sequence listing, and a terminator sequence

```
"CTAGCATAACCCCTTGGGGCCTCTAAACGGGTCTTGAGGGGTTTT
TTG".
```

The present invention also protects a DNA molecule D (a tryptophan operon gene with relieved attenuation regulation, also referred to as a tryptophan operon gene mutant), which is a DNA molecule obtained by removing the nucleotides at positions 1-n3 of the tryptophan attenuator of the tryptophan operon gene; n3 is a natural number greater than or equal to 114 but smaller than or equal to 121 (preferably, n3 is 114).

Said DNA molecule D particularly can be the DNA molecule shown by the nucleotides at positions 115-6687 of SEQ ID No: 40 of the sequence listing.

The present invention also protects a DNA molecule E, sequentially comprising, from upstream to downstream, the following elements: a promoter and said DNA molecule D. Said promoter can be the promoter $P_{JJ}$ shown by the SEQ ID No: 39 of the sequence listing.

Said DNA molecule E sequentially consists, from upstream to downstream, of the following elements: the promoter $P_{JJ}$ shown by SEQ ID No: 39 of the sequence listing, the small fragment between the enzymatic cleavage sites of Hind III and BamH I in the plasmid pACYC184, and the DNA molecule shown by the nucleotides at positions 115-6687 of SEQ ID No: 40 of the sequence listing.

Said DNA molecule E sequentially consists, from upstream to downstream, of the following elements: the promoter $P_{JJ}$ shown by SEQ ID No: 39 of the sequence listing, the small fragment between the enzymatic cleavage sites of Hind III and BamH I in the plasmid pACYC184, and the DNA molecule shown by the nucleotides at positions 115-6865 of SEQ ID No: 40 of the sequence listing.

A recombinant vector comprising said DNA molecule D or said DNA molecule E also falls into the protection scope of the present invention.

Recombinant bacteria comprising said DNA molecule D or said DNA molecule E also falls into the protection scope of the present invention.

Said recombinant vector can be a recombinant plasmid obtained by inserting said DNA molecule D or said DNA molecule E into the starting plasmid. Said starting plasmid is a plasmid having a low-copy, medium-copy or high-copy number, for example, pSC101, pACYC184, pBR322 or pTrc99a.

Said recombinant bacteria are obtained by introducing said DNA molecule D or said DNA molecule E into the starting bacteria. Said starting bacteria can be the bacteria of the genus *Escherichia* or *Corynebacteria*. Said bacteria of the genus *Escherichia* particularly can be *E. coli*, and more particularly *E. coli* K-12 or a strain derived therefrom, and even more particularly *E. coli* K12 MG1655 or *E. coli* AT. Said bacteria of the genus *Corynebacteria* particularly can be *Corynebacterium glutamicum*, for example, *Corynebacterium glutamicum* ATCC13032 and etc.

The *E. coli* AT are recombinant bacteria obtained by introducing a gene coding for 3-deoxy-D-arobino-heptulosonate-7-phosphate synthetase (AroG protein or AroG*protein; the AroG protein is a wild-type protein, and the AroG*protein is a protein with relieved feedback inhibition obtained by a mutation on the basis of the AroG protein) and a gene coding for transketolase A (TktA protein) in the *E. coli* K12 MG1655.

The AroG*protein is (b1) or (b2) as follows:
(b1) a protein consisting of the amino acid sequence shown by SEQ ID No: 42 of the sequence listing;
(b2) a protein derived from SEQ ID No: 42 having the same function after one or several amino acid residues of the amino acid sequence of SEQ ID No: 42 are subjected to substitution and/or deletion and/or addition.

The TktA protein is (c1) or (c2) as follows:
(c1) a protein consisting of the amino acid sequence shown by SEQ ID No: 44 of the sequence listing;
(c2) a protein derived from SEQ ID No: 44 having the same function after one or several amino acid residues of the amino acid sequence of SEQ ID No: 44 are subjected to substitution and/or deletion and/or addition.

A gene coding for the AroG*protein particularly can be shown by SEQ ID No: 41 of the sequence listing.

The open reading frame of the gene coding for the AroG*protein particularly can be the nucleotides at positions 151-1203 of SEQ ID No: 41 of the sequence listing.

A gene coding for the TktA protein particularly can be shown by SEQ ID No: 43 of the sequence listing.

The open reading frame of the gene coding for the TktA protein particularly can be the nucleotides at positions 151-2142 of SEQ ID No: 43 of the sequence listing.

The present invention also protects the use of said recombinant bacteria in producing tryptophan.

A fermentation medium is used to culture said recombinant bacteria when applying said recombinant bacteria to produce tryptophan.

Said fermentation medium can be either a rich medium, or an inorganic salt medium. A medium comprises a carbon source, a nitrogen source, inorganic ions, antibiotics and other trophic factors. As a carbon source, saccharides such as glucose, lactose, galactose and etc. can be used; alcohols such as glycerin, mannitol and etc. can also be used; organic acids such as gluconic acid, citric acid, succinic acid and etc. can be used as well. As a nitrogen source, inorganic nitrogen sources such as ammoniacal liquor, ammonium sulfate, ammonium phosphate, ammonium chloride and etc. can also be used; organic nitrogen sources such as corn steep liquor, soybean meal hydrolysates, hair powders, yeast extracts, peptone and etc. can be used as well. Inorganic ions comprise one or more ions selected from the group consisting of iron, calcium, magnesium, manganese, molybdenum, cobalt, cuprum, potassium and etc. ions. Other trophic factors also comprise vitamins such as biotin, vitamin B1, pyridoxal and etc.

The carbon source in said fermentation medium is glucose.

Said fermentation medium particularly can be: glucose 20.0 g/L, ammonium sulfate 15.0 g/L, potassium dihydrogen phosphate 2.0 g/L, magnesium sulfate heptahydrate 2.0 g/L, yeast powders 2.0 g/L, calcium carbonate 15.0 g/L, microelement mixture 5 mL/L, and water as the remainder.

The microelement mixture is: $FeSO_4.7H_2O$ 10 g/L, $CaCl_2$ 1.35 g/L, $ZnSO_4.7H_2O$ 2.25 g/L, $MnSO_4.4H_2O$ 0.5 g/L, $CuSO_4.5H_2O$ 1 g/L, $(NH_4)_6Mo_7O_{24}.4H_2O$ 0.106 g/L, $Na_2B_4O_7.10H_2O$ 0.23 g/L, $CoCl_2.6H_2O$ 0.48 g/L, 35% HCl 10 mL/L, and water as the remainder.

Said culture condition particularly can be: shaking culture for 36 h at 37° C., 220 rpm.

Said culture condition particularly can be that: the seed solution is seeded into the fermentation medium in a seeding amount of 3%, followed by shaking culture for 36 h at 37° C., 220 rpm. A method for preparing the seed solution is as follows: the recombinant bacteria are seeded into a liquid LB medium containing 100 mg/L ampicillin and 34 mg/L chloramphenicol, followed by shaking culture for 8 h at 37° C., 220 rpm, and a seed solution is obtained. The $OD_{600nm}$ value of said seed solution particularly can be 5.0.

Processes to be controlled during said culture are as follows: during the culture, the pH value of the reaction system is adjusted with ammoniacal liquor to make it maintain at 6.8-7.0; during the culture, sampling is made once every 3-4 h to detect the content of glucose. When the content of glucose in the system is less than 5 g/L, glucose is supplemented to make the concentration of glucose in the system up to 10 g/L.

The present invention also protects a method for improving the capability of producing tryptophan by microorganisms, comprising the following step: deleting the nucleotides at positions 1-n3 of the tryptophan operon gene of the microorganisms, counting from the first nucleotide of the tryptophan attenuator; n3 is a natural number greater than or equal to 114 but smaller than or equal to 121 (preferably, n3 is 114). Said microorganisms are microorganisms having a tryptophan operon. Said microorganisms particularly can be the microorganisms of the genus *Escherichia*. Said microorganisms of the genus *Escherichia* particularly can be *E. coli*, and more particularly *E. coli* K-12 or a strain derived therefrom, and even more particularly *E. coli* K12 MG1655 or *E. coli* AT.

The present invention also protects a method for relieving the feedback repression of the tryptophan operon in microorganisms, comprising the following step: deleting the nucleotides at positions 1-n3 of the tryptophan operon gene of the microorganisms, counting from the first nucleotide of the tryptophan attenuator; n3 is a natural number greater than or equal to 114 but smaller than or equal to 121 (preferably, n3 is 114). Said microorganisms are microorganisms having a tryptophan operon. Said microorganisms particularly can be the microorganisms of the genus *Escherichia*. Said microorganisms of the genus *Escherichia* particularly can be *E. coli*, and more particularly *E. coli* K-12 or a strain derived therefrom, and even more particularly *E. coli* K12 MG1655 or *E. coli* AT.

Above any said tryptophan operon comprises a tryptophan attenuator, a gene coding for o-aminobenzoic acid synthetase (TrpE protein or TrpE*protein; the TrpE protein is a wild-type protein, and the TrpE*protein is a protein obtained by a mutation on the basis of the TrpE protein with relieved feedback inhibition), a gene coding for phosphoribosyl-o-aminobenzoic acid pyrophosphorylase (TrpD protein), a gene coding for o-aminophosphoribosylbenzoic acid isomerase (TrpC protein), a gene coding for tryptophan synthase β subunit (TrpB protein) and a gene coding for tryptophan synthase a subunit (TrpA protein).

Said TrpE*protein is (d1) or (d2) as follows:

(d1) a protein consisting of the amino acid sequence shown by SEQ ID No: 45 of the sequence listing;

(d2) a protein derived from SEQ ID No: 45 having o-aminobenzoic acid synthetase function after one or several amino acid residues of the amino acid sequence of SEQ ID No: 45 are subjected to substitution and/or deletion and/or addition.

Said TrpD protein is (e1) or (e2) as follows:

(e1) a protein consisting of the amino acid sequence shown by SEQ ID No: 46 of the sequence listing;

(e2) a protein derived from SEQ ID No: 46 having phosphoribosylo-aminobenzoic acid pyrophosphorylase function after one or several amino acid residues of the amino acid sequence of SEQ ID No: 46 are subjected to substitution and/or deletion and/or addition.

Said TrpC protein is (f1) or (f2) as follows:

(f1) a protein consisting of the amino acid sequence shown by SEQ ID No: 47 of the sequence listing;

(f2) a protein derived from SEQ ID No: 47 having o-aminophosphoribosylbenzoic acid isomerase function after one or several amino acid residues of the amino acid sequence of SEQ ID No: 47 are subjected to substitution and/or deletion and/or addition.

Said TrpB protein is (g1) or (g2) as follows:

(g1) a protein consisting of the amino acid sequence shown by SEQ ID No: 48 of the sequence listing;

(g2) a protein derived from SEQ ID No: 48 having tryptophan synthase 13 subunit function after one or several amino acid residues of the amino acid sequence of SEQ ID No: 48 are subjected to substitution and/or deletion and/or addition.

Said TrpA protein is (h1) or (h2) as follows:

(h1) a protein consisting of the amino acid sequence shown by SEQ ID No: 39 of the sequence listing;

(h2) a protein derived from SEQ ID No: 39 having tryptophan synthase a subunit function after one or several amino acid residues of the amino acid sequence of SEQ ID No: 39 are subjected to substitution and/or deletion and/or addition.

A gene coding for the TrpE*protein particularly can be shown by the nucleotides at positions 157-1719 of SEQ ID No: 40 of the sequence listing.

A gene coding for the TrpD protein particularly can be shown by the nucleotides at positions 1719-3314 of SEQ ID No: 40 of the sequence listing.

A gene coding for the TrpC protein particularly can be shown by the nucleotides at positions 3315-4676 of SEQ ID No: 40 of the sequence listing.

A gene coding for the TrpB protein particularly can be shown by the nucleotides at positions 4688-5881 of SEQ ID No: 40 of the sequence listing.

A gene coding for the TrpA protein particularly can be shown by the nucleotides at positions 5881-6687 of SEQ ID No: 40 of the sequence listing.

Said tryptophan attenuator particularly can be shown by the nucleotides at positions 21-135 of SEQ ID No: 40 of the sequence listing.

The sequence associated with said tryptophan attenuator particularly can be shown by the nucleotides at positions 21-186 of SEQ ID No: 40 of the sequence listing.

Said tryptophan operon gene particularly can be shown by the nucleotides at positions 21-6687 of SEQ ID No: 40 of the sequence listing.

Said tryptophan operon gene particularly can be shown by the nucleotides at positions 21-6865 of SEQ ID No: 40 of the sequence listing.

Above any said tryptophan particularly can be L-tryptophan.

The present invention discloses a method for modifying a tryptophan attenuator and the use thereof in the production of tryptophan in fermentation. In the present invention, a tryptophan attenuator mutant capable of significantly improving the translation level of a gene is obtained by truncating the functional sequence of the tryptophan attenuator step by step. In the present invention, the expression level of the subsequent genes can be significantly improved by deleting the trpL gene coding for a leader peptide and an anterior reverse complementary palindromic sequence in the terminator stem-loop structure of the attenuator. Obviously, according to the test results of the present invention, the skilled in the art can readily conclude that a tryptophan attenuator mutant and a tryptophan operon gene mutant having a similar performance may likewise be obtained by simultaneously maintaining a portion of the above said anterior reverse complementary palindromic sequence in the terminator stem-loop structure of the attenuator on the tryptophan attenuator mutant protected by the present invention, but not ye forming a steady stem-loop structure. Thus, such similar method for modifying a tryptophan attenuator also falls into the protection scope of the present invention.

The present invention also protects the recombinant bacteria comprising the tryptophan operon gene having said tryptophan attenuator mutant and the use of said recombinant bacteria in producing tryptophan. The performance for fermentation of tryptophan by engineered bacteria has been significantly improved by applying the method provided by the present invention for modifying tryptophan. The present invention practically can be used for the production of tryptophan in fermentation by bacteria.

In the present invention, a tryptophan attenuator mutant which can significantly improve the expression level of a gene is surprisingly obtained by truncating the sequence of the tryptophan attenuator from the 5' end step by step. Correspondingly, a tryptophan operon gene mutant is obtained in the present invention, and the engineered bacteria overexpressing the tryptophan operon gene mutant can significantly improve the yields of tryptophan and derivatives thereof.

The present invention firstly protects a DNA molecule A (a histidine attenuator mutant), which is (a1), (a2), (a3), (a4) or (a5) as follows:

(a1) a DNA molecule shown by the nucleotides at positions n1-n2 of SEQ ID No: 51 of the sequence listing; n1 is a natural number greater than or equal to 126 but smaller than or equal to 143 (preferably, n1 is a natural number greater than or equal to 127 but smaller than or equal to 130), and n2 is a natural number greater than or equal to 148 but smaller than or equal to 286 (n2 particularly can be a natural number greater than or equal to 148 but smaller than or equal to 196, or a natural number greater than or equal to 197 but smaller than or equal to 286, and more particularly 148, 196 or 286);

(a2) a DNA molecule obtained by removing the nucleotides at positions 1-n3 of the histidine attenuator; n3 is a natural number greater than or equal to 125 but smaller than or equal to 142 (preferably, n3 is a natural number greater than or equal to 126 but smaller than or equal to 129);

(a3) a DNA molecule obtained by removing the nucleotides at positions 1-n3 of the sequence associated with the histidine attenuator; n3 is a natural number greater than or equal to 125 but smaller than or equal to 142 (preferably, n3 is a natural number greater than or equal to 126 but smaller than or equal to 129);

(a4) a DNA molecule obtained by linking a tag sequence to the end of (a1) or (a2) or (a3);

(a5) a DNA molecule obtained by linking a linker sequence to the end of (a1) or (a2) or (a3).

The histidine attenuator mutant is a truncated histidine attenuator or a histidine attenuator variant. The truncated histidine attenuator truncation is shown by the nucleotides at positions n1-148 of SEQ ID No: 51 of the sequence listing. The histidine attenuator variant is shown by the nucleotides at positions n1-n4 of SEQ ID No: 51 of the sequence listing; n4 is a natural number greater than or equal to 149 but smaller than or equal to 286 (n4 particularly can be a natural number greater than or equal to 149 but smaller than or equal to 196, or a natural number greater than or equal to 197 but smaller than or equal to 286, and more particularly 196 or 286).

The present invention also protects the use of said DNA molecule A in promoting the expression of a downstream target gene. In said use, said DNA molecule A functions as a regulation element. In said use, said DNA molecule A is located between the promoter of said target gene and the initiation codon of said target gene. In said use, said promoter particularly can be the promoter $P_{BB}$ shown as SEQ ID No: 50 of the sequence listing. In said use, said target gene particularly can be the gfp gene shown as SEQ ID No: 30 of the sequence listing.

The present invention also protects a DNA molecule B, sequentially comprising, from upstream to downstream: said DNA molecule A and a target gene. Said target gene particularly can be the gfp gene shown by SEQ ID No: 30 of the sequence listing.

The present invention also protects a DNA molecule C, sequentially comprising, from upstream to downstream: a promoter, said DNA molecule A, a target gene and a terminator. Said promoter particularly can be the promoter $P_{BB}$ shown by SEQ ID No: 50 of the sequence listing. Said target gene particularly can be the gfp gene shown by SEQ ID No: 30 of the sequence listing. Said terminator particularly can be

"CTAGCATAACCCCTTGGGGCCTCTAAACGGGTCTTGAGGGGTTTT

TTG".

Said DNA molecule A or said DNA molecule B or said DNA molecule C is free of the nucleotides at positions 1-n3 of the histidine attenuator; n3 is a natural number greater than or equal to 125 but smaller than or equal to 142 (preferably, n3 is a natural number greater than or equal to 126 but smaller than or equal to 129).

Said DNA molecule B sequentially consists, from upstream to downstream, of the following elements: the nucleotides at positions 130-286 of SEQ ID No: 51 of the sequence listing, a linker sequence "GGTTCTGGTTCTGGTTCT" (SEQ ID NO: 67), and the gfp gene shown by SEQ ID No: 30 of the sequence listing.

Said DNA molecule C sequentially consists, from upstream to downstream, of the following elements: the promoter $P_{BB}$ shown by SEQ ID No: 50 of the sequence listing, a recognition sequence for enzymatic cleavage by restriction endonuclease Hind III, the nucleotides at positions 130-286 of SEQ ID No: 51 of the sequence listing, a linker sequence "GGTTCTGGTTCTGGTTCT" (SEQ ID NO: 67), the gfp gene shown by SEQ ID No: 30 of the sequence listing, and a terminator sequence

"CTAGCATAACCCCTTGGGGCCTCTAAACGGGTCTTGAGGGGTTT

TTTG".

The present invention also protects a DNA molecule D (a histidine operon gene with relieved attenuation regulation, also referred to as a histidine operon gene mutant), which is a DNA molecule obtained by removing the nucleotides at positions 1-n3 of the histidine attenuator of the histidine operon gene; n3 is a natural number greater than or equal to 125 but smaller than or equal to 142 (preferably, n3 is a natural number greater than or equal to 126 but smaller than or equal to 129).

The present invention also protects a DNA molecule E, which is a DNA molecule obtained by performing two modifications on the histidine operon gene as follows: (1) removing the nucleotides at positions 1-n3 of the histidine attenuator; n3 is a natural number greater than or equal to 125 but smaller than or equal to 142 (preferably, n3 is a natural number greater than or equal to 126 but smaller than or equal to 129); (2) mutating the gene coding for ATP phosphoribosyltransferase to the gene coding for a mutant protein with relieved feedback repression from the gene coding for a wild-type protein.

Said mutant protein with relieved feedback repression particularly can be a HisG*protein.

Said wild-type protein particularly can be a HisG protein.

Said DNA molecule E particularly can be a DNA molecule shown by the nucleotides at positions 127-7230 of SEQ ID No: 51 of the sequence listing.

A recombinant vector comprising said DNA molecule D or said DNA molecule E also falls into the protection scope of the present invention.

Recombinant bacteria comprising said DNA molecule D or said DNA molecule E also falls into the protection scope of the present invention.

Said recombinant bacteria can be recombinant bacteria obtained by introducing said DNA molecule D or said DNA molecule E into the starting bacteria and performing an overexpression. Said starting bacteria are bacteria of the genus *Escherichia* or *Corynebacteria*. Said bacteria of the genus *Escherichia* particularly can be *E. coli*, for example, *E. coli* K-12 or a strain derived therefrom. Said bacteria of the genus *Corynebacteria* particularly can be *Corynebacterium glutamicum*, for example, *Corynebacterium glutamicum* ATCC13032.

Said recombinant bacteria can be recombinant bacteria obtained by modifying the histidine operon of the starting bacteria. Said starting bacteria are bacteria of the genus *Escherichia* or *Corynebacteria*. Said bacteria of the genus *Escherichia* particularly can be *E. coli*, for example, *E. coli* K-12 or a strain derived therefrom. Said bacteria of the genus *Corynebacteria* particularly can be *Corynebacterium glutamicum*, for example, *Corynebacterium glutamicum* ATCC13032. Said recombinant bacteria particularly can be recombinant bacteria obtained by performing the following modifications on *E. coli* K12 MG1655: (1) deleting the nucleotides at positions 586-721 of the DNA molecule shown by SEQ ID No: 52 in the genome; (2) mutating the nucleotide at position 1602 of the DNA molecule shown by SEQ ID No: 52 in the genome to A from G. Said modifications can be achieved by the following method: introducing the recombinant plasmid pKOV-ΔhisL-hisG* into the *E. coli* K12 MG1655 and obtaining recombinant bacteria, to which a homologous recombination has occurred. The recombinant plasmid pKOV-ΔhisL-hisG* can be a recombinant plasmid comprising a specific DNA molecule; the specific DNA molecule sequentially consists, from upstream to downstream, of the following elements: the upstream homology arm shown by the nucleotides at positions 32-585 of SEQ ID No: 52 of the sequence listing, and the downstream homology arm shown by the nucleotides at positions 722-1617 of SEQ ID No: 52 of the sequence listing. The recombinant plasmid pKOV-ΔhisL-hisG* particularly can be a recombinant plasmid obtained by inserting a specific DNA molecule between the enzymatic cleavage sites of BamH I and Not I of the plasmid pKOV; the specific DNA molecule sequentially consists, from upstream to downstream, of the following elements: the upstream homology arm shown by the nucleotides at positions 32-585 of SEQ ID No: 52 of the sequence listing, and the downstream homology arm shown by the nucleotides at positions 722-1617 of SEQ ID No: 52 of the sequence listing.

In addition to modifying the in situ histidine operon gene on the chromosomes, other methods as overexpressing a gene, such as integrating one or more copies of the above said histidine operon gene with relieved attenuation regulation on the chromosomes likewise falls into the protection scope of the present invention; in addition, overexpressing the above said histidine operon gene with relieved attenuation regulation in a plasmid likewise falls into the protection scope of the present invention.

The present invention also protects the use of above any said recombinant bacteria in preparing histidine.

A fermentation medium is used to culture said recombinant bacteria when applying said recombinant bacteria to produce histidine.

Said fermentation medium can be either a rich medium, or an inorganic salt medium. A medium comprises a carbon source, a nitrogen source, inorganic ions, antibiotics and other trophic factors. As a carbon source, saccharides such as glucose, lactose, galactose and etc. can be used; alcohols such as glycerin, mannitol and etc. can also be used; organic acids such as gluconic acid, citric acid, succinic acid and etc. can be used as well. As a nitrogen source, inorganic nitrogen sources such as ammoniacal liquor, ammonium sulfate, ammonium phosphate, ammonium chloride and etc. can also be used; organic nitrogen sources such as corn steep liquor, soybean meal hydrolysates, hair powders, yeast extracts, peptone and etc. can be used as well. Inorganic ions comprise one or more ions selected from the group consisting of iron, calcium, magnesium, manganese, molybdenum, cobalt, cuprum, potassium and etc. ions. Other trophic factors also comprise vitamins such as biotin, vitamin B1, pyridoxal and etc.

The carbon source in said fermentation medium is glucose.

Said fermentation medium particularly can be: glucose 20.0 g/L, ammonium sulfate 15.0 g/L, potassium dihydrogen phosphate 2.0 g/L, magnesium sulfate heptahydrate 2.0 g/L, yeast powders 2.0 g/L, calcium carbonate 15.0 g/L, microelement mixture 5 mL/L, and water as the remainder.

The microelement mixture is: $FeSO_4 \cdot 7H_2O$ 10 g/L, $CaCl_2$ 1.35 g/L, $ZnSO_4 \cdot 7H_2O$ 2.25 g/L, $MnSO_4 \cdot 4H_2O$ 0.5 g/L, $CuSO_4 \cdot 5H_2O$ 1 g/L, $(NH_4)_6Mo_7O_{24} \cdot 4H_2O$ 0.106 g/L, $Na_2B_4O_7 \cdot 10H_2O$ 0.23 g/L, $CoCl_2 \cdot 6H_2O$ 0.48 g/L, 35% HCl 10 mL/L, and water as the remainder.

Said culture condition particularly can be: shaking culture for 36 h at 37° C., 220 rpm.

Said culture condition particularly can be that: the seed solution is seeded into the fermentation medium in a seeding amount of 3%, followed by shaking culture for 36 h at 37° C., 220 rpm. A method for preparing the seed solution is as follows: the recombinant bacteria are seeded into a liquid LB medium, followed by shaking culture for 8 h at 37° C., 220 rpm, and a seed solution is obtained. The $OD_{600nm}$ value of said seed solution particularly can be 5.0.

Processes to be controlled during said culture are as follows: during the culture, the pH value of the reaction system is adjusted with ammoniacal liquor to make it maintain at 6.8-7.0; during the culture, sampling is made once every 3-4 h to detect the content of glucose. When the content of glucose in the system is less than 5 g/L, glucose is supplemented to make the concentration of glucose in the system up to 10 g/L.

The present invention also protects a method for improving the capability of producing histidine by microorganisms, comprising the following step: deleting the nucleotides at positions 1-n3 of the histidine operon gene of the microorganisms, counting from the first nucleotide of the histidine attenuator; n3 is a natural number greater than or equal to 125 but smaller than or equal to 142. Said microorganisms are microorganisms having a histidine operon. Said microorganisms particularly can be the microorganisms of the genus *Escherichia*. Said microorganisms of the genus *Escherichia* particularly can be *E. coli*, and more particularly *E. coli* K-12 or a strain derived therefrom, and even more particularly *E. coli* K12 MG1655 or a strain derived therefrom.

The present invention also protects a method for relieving the feedback repression of the histidine operon in microorganisms, comprising the following step: deleting the nucleotides at positions 1-n3 of the histidine operon gene of the microorganisms, counting from the first nucleotide of the histidine attenuator; n3 is a natural number greater than or equal to 125 but smaller than or equal to 142. Said microorganisms are microorganisms having a histidine operon. Said microorganisms particularly can be the microorganisms of the genus *Escherichia*. Said microorganisms of the genus *Escherichia* particularly can be *E. coli*, and more particularly *E. coli* K-12 or a strain derived therefrom, and even more particularly *E. coli* K12 MG1655 or a strain derived therefrom.

Above any said histidine operon comprises a histidine attenuator, a gene coding for ATP phosphoribosyltransferase (HisG*protein or HisG protein), a gene coding for histidinal/histidinol dehydrogenase complex (HisD protein), a gene coding for histidinol phosphate transaminase (HisC protein), a gene coding for imidazole glycerol phosphate dehydrase/histidinol phosphatase complex (HisB protein), a gene coding for imidazole glycerol phosphate synthetase subunit H (HisH protein), a gene coding for imidazole formamide isomerase (HisA protein), a gene coding for imidazole glycerol phosphate synthetase subunit F (HisF protein) and a gene coding for phosphoribosyl-AMP cyclohydrolase (HisI protein).

Said HisG*protein is (b1) or (b2) as follows:
(b1) a protein consisting of the amino acid sequence shown by SEQ ID No: 53 of the sequence listing;
(b2) a protein derived from SEQ ID No: 53 having ATP phosphoribosyltransferase function after one or several amino acid residues of the amino acid sequence of SEQ ID No: 53 are subjected to substitution and/or deletion and/or addition.

Said HisG protein is (c1) or (c2) as follows:
(c1) a protein consisting of the amino acid sequence shown by SEQ ID No: 54 of the sequence listing;
(c2) a protein derived from SEQ ID No: 54 having ATP phosphoribosyltransferase function after one or several amino acid residues of the amino acid sequence of SEQ ID No: 54 are subjected to substitution and/or deletion and/or addition.

Said HisD protein is (d1) or (d2) as follows:
(d1) a protein consisting of the amino acid sequence shown by SEQ ID No: 55 of the sequence listing;
(d2) a protein derived from SEQ ID No: 55 having histidinal/histidinol dehydrogenase complex function after one or several amino acid residues of the amino acid sequence of SEQ ID No: 55 are subjected to substitution and/or deletion and/or addition.

Said HisC protein is (e1) or (e2) as follows:
(e1) a protein consisting of the amino acid sequence shown by SEQ ID No: 56 of the sequence listing;
(e2) a protein derived from SEQ ID No: 56 having histidinol phosphate transaminase function after one or several amino acid residues of the amino acid sequence of SEQ ID No: 56 are subjected to substitution and/or deletion and/or addition.

Said HisB protein is (f1) or (f2) as follows:
(f1) a protein consisting of the amino acid sequence shown by SEQ ID No: 57 of the sequence listing;
(f2) a protein derived from SEQ ID No: 57 having imidazole glycerol phosphate dehydrase/histidinol phosphatase complex function after one or several amino acid residues of the amino acid sequence of SEQ ID No: 57 are subjected to substitution and/or deletion and/or addition.

Said HisH protein is (g1) or (g2) as follows:
(g1) a protein consisting of the amino acid sequence shown by SEQ ID No: 58 of the sequence listing;
(g2) a protein derived from SEQ ID No: 58 having imidazole glycerol phosphate synthetase subunit H function after one or several amino acid residues of the amino acid sequence of SEQ ID No: 58 are subjected to substitution and/or deletion and/or addition.

Said HisA protein is (h1) or (h2) as follows:
(h1) a protein consisting of the amino acid sequence shown by SEQ ID No: 59 of the sequence listing;
(h2) a protein derived from SEQ ID No: 59 having imidazole formamide isomerase function after one or several amino acid residues of the amino acid sequence of SEQ ID No: 59 are subjected to substitution and/or deletion and/or addition.

Said HisF protein is (i1) or (i2) as follows:
(i1) a protein consisting of the amino acid sequence shown by SEQ ID No: 60 of the sequence listing;
(i2) a protein derived from SEQ ID No: 60 having imidazole glycerol phosphate synthetase subunit F function after one or several amino acid residues of the amino acid sequence of SEQ ID No: 60 are subjected to substitution and/or deletion and/or addition.

Said HisI protein is (j1) or (j2) as follows:
(j1) a protein consisting of the amino acid sequence shown by SEQ ID No: 61 of the sequence listing;
(j2) a protein derived from SEQ ID No: 61 having phosphoribosyl-AMP cyclohydrolase function after one or several amino acid residues of the amino acid sequence of SEQ ID No: 61 are subjected to substitution and/or deletion and/or addition.

Gene coding for the HisG*protein particularly can be shown by the nucleotides at positions 197-1096 of SEQ ID No: 51 of the sequence listing.

Gene coding for the HisG protein particularly can be shown by the nucleotides at positions 792-1691 of SEQ ID No: 52 of the sequence listing.

Gene coding for the HisD protein particularly can be shown by the nucleotides at positions 1102-2406 of SEQ ID No: 51 of the sequence listing.

Gene coding for the HisC protein particularly can be shown by the nucleotides at positions 2403-3473 of SEQ ID No: 51 of the sequence listing.

Gene coding for the HisB protein particularly can be shown by the nucleotides at positions 3473-4540 of SEQ ID No: 51 of the sequence listing.

Gene coding for the HisH protein particularly can be shown by the nucleotides at positions 4540-5130 of SEQ ID No: 51 of the sequence listing.

Gene coding for the HisA protein particularly can be shown by the nucleotides at positions 5130-5867 of SEQ ID No: 51 of the sequence listing.

Gene coding for the HisF protein particularly can be shown by the nucleotides at positions 5849-6625 of SEQ ID No: 51 of the sequence listing.

Gene coding for the HisI protein particularly can be shown by the nucleotides at positions 6619-7230 of SEQ ID No: 51 of the sequence listing.

Said histidine attenuator particularly can be shown by the nucleotides at positions 1-148 of SEQ ID No: 51 of the sequence listing.

The sequence associated with said histidine attenuator particularly can be shown by the nucleotides at positions 1-286 of SEQ ID No: 51 of the sequence listing.

Said histidine operon gene particularly can be shown by the nucleotides at positions 1-7230 of SEQ ID No: 51 of the sequence listing.

Above any said histidine particularly can be L-histidine.

The present invention discloses a method for modifying a histidine attenuator by deleting the ilvL gene coding for a leader peptide and an anterior reverse complementary palindromic sequence in the terminator stem-loop structure of the attenuator, while maintaining a posterior reverse complementary palindromic sequence in the terminator. In the present invention, a histidine attenuator mutant which can significantly improve the expression level of a gene is surprisingly obtained by removing a specific sequence of the histidine attenuator. Obviously, according to the test results of the present invention, the skilled in the art can readily conclude that a histidine attenuator mutant and a histidine operon mutant having a similar performance may likewise be obtained by removing a portion of the above said anterior reverse complementary palindromic sequence in the terminator stem-loop structure of the attenuator, which destroys the secondary complementary structure of the terminator in a certain degree. Thus, such similar method for modifying a histidine attenuator also falls into the protection scope of the present invention. Obviously, the method for relieving the histidine attenuator of *E. coli* in the present invention can likewise be applied to the histidine attenuators of other strains. The present invention also discloses a histidine operon gene with relieved attenuation regulation, and particularly, the histidine operon is one obtained by removing the hisL gene coding for a leader peptide and an anterior reverse complementary palindromic sequence in the terminator stem-loop structure, while maintaining a posterior reverse complementary palindromic sequence in the terminator.

The present invention firstly protects a DNA molecule A (a phenylalanine attenuator mutant), which is (a1), (a2), (a3), (a4) or (a5) as follows:

(a1) a DNA molecule shown by the nucleotides at positions n1-n2 of SEQ ID No: 62 of the sequence listing; n1 is a natural number greater than or equal to 105 but smaller than or equal to 118 (preferably, n1 is 117), and n2 is a natural number greater than or equal to 123 but smaller than or equal to 176 (n2 particularly can be a natural number greater than or equal to 123 but smaller than or equal to 146, or a natural number greater than or equal to 147 but smaller than or equal to 176, and more particularly 123, 146 or 176);

(a2) a DNA molecule obtained by removing the nucleotides at positions 1-n3 of the phenylalanine attenuator; n3 is a natural number greater than or equal to 104 but smaller than or equal to 117 (preferably, n3 is 116);

(a3) a DNA molecule obtained by removing the nucleotides at positions 1-n3 of the sequence associated with the phenylalanine attenuator; n3 is a natural number greater than or equal to 104 but smaller than or equal to 117 (preferably, n3 is 116);

(a4) a DNA molecule obtained by linking a tag sequence to the end of (a1) or (a2) or (a3);

(a5) a DNA molecule obtained by linking a linker sequence to the end of (a1) or (a2) or (a3).

The phenylalanine attenuator mutant is a truncated phenylalanine attenuator or a phenylalanine attenuator variant. The truncated phenylalanine attenuator is shown by the nucleotides at positions n1-123 of SEQ ID No: 62 of the sequence listing. The phenylalanine attenuator variant is shown by the nucleotides at positions n1-n4 of SEQ ID No: 62 of the sequence listing; n4 is a natural number greater than or equal to 124 but smaller than or equal to 176 (n4 particularly can be a natural number greater than or equal to 124 but smaller than or equal to 146, or a natural number greater than or equal to 147 but smaller than or equal to 176, and more particularly 146 or 176).

The present invention also protects the use of said DNA molecule A in promoting the expression of a downstream target gene. In said use, said DNA molecule A functions as a regulation element. In said use, said DNA molecule A is located between the promoter of said target gene and the initiation codon of said target gene. In said use, said promoter particularly can be the promoter $P_{thr-trc}$ shown by SEQ ID No: 29 of the sequence listing. In said use, said target gene particularly can be the gfp gene shown by SEQ ID No: 30 of the sequence listing.

The present invention also protects a DNA molecule B, sequentially comprising, from upstream to downstream: said DNA molecule A and a target gene. Said target gene particularly can be the gfp gene shown by SEQ ID No: 30 of the sequence listing.

The present invention also protects a DNA molecule C, sequentially comprising, from upstream to downstream: a promoter, said DNA molecule A, a target gene and a terminator. Said promoter particularly can be the promoter $P_{thr-trc}$ shown by SEQ ID No: 29 of the sequence listing. Said target gene particularly can be the gfp gene shown by SEQ ID No: 30 of the sequence listing. Said terminator particularly can be

"CTAGCATAACCCCTTGGGGCCTCTAAACGGGTCTTGAGGGGTTTT

TTG".

Said DNA molecule A or said DNA molecule B or said DNA molecule C is free of the nucleotides at positions 1-n3 of the phenylalanine attenuator; n3 is a natural number greater than or equal to 104 but smaller than or equal to 117 (preferably, n3 is 116).

Said DNA molecule B sequentially consists, from upstream to downstream, of the following elements: the nucleotides at positions 117-176 of SEQ ID No: 62 of the sequence listing, a linker sequence "GGTTCTGGTTCTGGTTCT" (SEQ ID NO: 67), and the gfp gene shown by SEQ ID No: 30 of the sequence listing.

Said DNA molecule C sequentially consists, from upstream to downstream, of the following elements: the promoter $P_{thr-trc}$ shown by SEQ ID No: 29 of the sequence listing, a recognition sequence for enzymatic cleavage by restriction endonuclease Hind III, the nucleotides at positions 117-176 of SEQ ID No: 62 of the sequence listing, a linker sequence "GGTTCTGGTTCTGGTTCT" (SEQ ID NO: 67), the gfp gene shown by SEQ ID No: 30 of the sequence listing, and a terminator sequence

"CTAGCATAACCCCTTGGGGCCTCTAAACGGGTCTTGAGGGGTTTT

TTG".

The present invention also protects a DNA molecule D (a phenylalanine operon gene with relieved attenuation regulation, also referred to as a phenylalanine operon gene mutant), which is a DNA molecule obtained by removing the nucleotides at positions 1-n3 of the phenylalanine attenuator of the phenylalanine operon gene; n3 is a natural number greater than or equal to 104 but smaller than or equal to 117 (preferably, n3 is 116).

The present invention also protects a DNA molecule E, which is a DNA molecule obtained by performing the following two modifications on the phenylalanine operon gene: (1) removing the nucleotides at positions 1-n3 of the phenylalanine attenuator; n3 is a natural number greater than or equal to 104 but smaller than or equal to 117 (preferably, n3 is 116); (2) mutating the gene coding for a bifunctional enzyme of chorismate mutase-prephenate dehydratase, to the gene coding for a mutant protein with relieved feedback repression from the gene coding for a wild-type protein.

Said mutant protein with relieved feedback repression particularly can be a PheA*protein.

Said wild-type protein particularly can be a PheA protein.

Said DNA molecule E particularly can be a DNA molecule shown by the nucleotides at positions 117-1307 of SEQ ID No: 62 of the sequence listing.

Said DNA molecule E particularly can be a DNA molecule shown by the nucleotides at positions 117-1413 of SEQ ID No: 62 of the sequence listing.

A recombinant vector comprising said DNA molecule D or said DNA molecule E also falls into the protection scope of the present invention.

Recombinant bacteria comprising said DNA molecule D or said DNA molecule E also falls into the protection scope of the present invention.

Said recombinant bacteria can be recombinant bacteria obtained by introducing said DNA molecule D or said DNA molecule E into the starting bacteria and performing an overexpression. Said starting bacteria are bacteria of the genus *Escherichia* or *Corynebacteria*. Said bacteria of the genus *Escherichia* particularly can be *E. coli*, for example, *E. coli* K-12 or a strain derived therefrom. Said bacteria of the genus *Corynebacteria* particularly can be *Corynebacterium glutamicum*, for example, *Corynebacterium glutamicum* ATCC13032. Said starting bacteria can be the recombinant bacteria obtained by introducing a gene coding for 3-deoxy-D-arabino-heptulosonate-7-phosphate synthetase (AroF protein) into the initial bacteria. Said initial bacteria are bacteria of the genus *Escherichia* or *Corynebacteria*. Said bacteria of the genus *Escherichia* particularly can be *E. coli*, for example, *E. coli* K-12 or a strain derived therefrom. Said bacteria of the genus *Corynebacteria* particularly can be *Corynebacterium glutamicum*, for example, *Corynebacterium glutamicum* ATCC13032. A gene coding for the AroF protein also can be introduced into said starting bacteria with said DNA molecule D. A gene coding for the AroF protein also can be introduced into said starting bacteria with said DNA molecule E.

The AroF protein is (Ill) or (b2) as follows:

(b1) a protein consisting of the amino acid sequence shown by SEQ ID No: 66 of the sequence listing;

(b2) a protein derived from SEQ ID No: 66 having 3-deoxy-D-arabino-heptulosonate-7-phosphate synthetase function after one or several amino acid residues of the amino acid sequence of SEQ ID No: 66 are subjected to substitution and/or deletion and/or addition.

The open reading frame of a gene coding for the AroF protein can be shown by the nucleotides at positions 195-1265 of SEQ ID No: 65 of the sequence listing.

A gene coding for the AroF protein can be shown by SEQ ID No: 65 of the sequence listing.

The present invention also protects the use of above any said recombinant bacteria in preparing phenylalanine.

A fermentation medium is used to culture said recombinant bacteria when applying said recombinant bacteria to produce phenylalanine.

Said fermentation medium can be either a rich medium, or an inorganic salt medium. A medium comprises a carbon source, a nitrogen source, inorganic ions, antibiotics and other trophic factors. As a carbon source, saccharides such as glucose, lactose, galactose and etc. can be used; alcohols such as glycerin, mannitol and etc. can also be used; organic acids such as gluconic acid, citric acid, succinic acid and etc. can be used as well. As a nitrogen source, inorganic nitrogen sources such as ammoniacal liquor, ammonium sulfate, ammonium phosphate, ammonium chloride and etc. can also be used; organic nitrogen sources such as corn steep liquor, soybean meal hydrolysates, hair powders, yeast extracts, peptone and etc. can be used as well. Inorganic ions comprise one or more ions selected from the group consisting of iron, calcium, magnesium, manganese, molybdenum, cobalt, cuprum, potassium and etc. inons. Other trophic factors also comprise vitamins such as biotin, vitamin B1, pyridoxal and etc.

The carbon source in said fermentation medium is glucose.

Said fermentation medium particularly can be: glucose 20.0 g/L, ammonium sulfate 15.0 g/L, potassium dihydrogen phosphate 2.0 g/L, magnesium sulfate heptahydrate 2.0 g/L, yeast powders 2.0 g/L, calcium carbonate 15.0 g/L, microelement mixture 5 mL/L, and water as the remainder.

The microelement mixture is: $FeSO_4.7H_2O$ 10 g/L, $CaCl_2$ 1.35 g/L, $ZnSO_4.7H_2O$ 2.25 g/L, $MnSO_4.4H_2O$ 0.5 g/L, $CuSO_4.5H_2O$ 1 g/L, $(NH_4)_6Mo_7O_{24}.4H_2O$ 0.106 g/L, $Na_2B_4O_7.10H_2O$ 0.23 g/L, $CoCl_2.6H_2O$ 0.48 g/L, 35% HCl 10 mL/L, and water as the remainder.

Said culture condition particularly can be: shaking culture for 36 h at 37° C., 220 rpm.

Said culture condition particularly can be that: the seed solution is seeded into the fermentation medium in a seeding amount of 3%, followed by shaking culture for 36 h at 37° C., 220 rpm. A method for preparing the seed solution is as follows: the recombinant bacteria are seeded into a liquid LB medium, followed by shaking culture for 8 h at 37° C., 220 rpm, and a seed solution is obtained. The $OD_{600nm}$ value of said seed solution particularly can be 5.0.

Processes to be controlled during said culture are as follows: during the culture, the pH value of the reaction system is adjusted with ammoniacal liquor to make it maintain at 6.8-7.0; during the culture, sampling is made once every 3-4 h to detect the content of glucose. When the content of glucose in the system is less than 5 g/L, glucose is supplemented to make the concentration of glucose in the system up to 10 g/L.

The present invention also protects a method for improving the capability of producing phenylalanine by microorganisms, comprising the following step: deleting the nucleotides at positions 1-n3 of the phenylalanine operon gene of the microorganisms, counting from the first nucleotide of the phenylalanine attenuator; n3 is a natural number greater than or equal to 104 but smaller than or equal to 117 (preferably, n3 is 116). Said microorganisms are microorganisms having a phenylalanine operon. Said microorganisms particularly can be the microorganisms of the genus *Escherichia*. Said microorganisms of the genus *Escherichia* particularly can be *E. coli*, and more particularly *E. coli* K-12 or a strain derived therefrom.

The present invention also protects a method for relieving the feedback repression of the phenylalanine operon in microorganisms, comprising the following step: deleting the nucleotides at positions 1-n3 of the phenylalanine operon gene of the microorganisms, counting from the first nucleotide of the phenylalanine attenuator; n3 is a natural number greater than or equal to 104 but smaller than or equal to 117 (preferably, n3 is 116). Said microorganisms are microorganisms having a phenylalanine operon. Said microorganisms particularly can be the microorganisms of the genus *Escherichia*. Said microorganisms of the genus *Escherichia* particularly can be *E. coli*, and more particularly *E. coli* K-12 or a strain derived therefrom.

Above any said phenylalanine operon gene comprises a phenylalanine attenuator and a gene coding for a bifunctional enzyme of chorismate mutase-prephenate dehydratase (PheA*protein or PheA protein).

PheA*protein is (c1) or (c2) as follows:

(c1) a protein consisting of the amino acid sequence shown by SEQ ID No: 64 of the sequence listing;

(c2) a protein derived from SEQ ID No: 64 having a bifunctional enzyme function of chorismate mutase-prephenate dehydratase after one or several amino acid residues of the amino acid sequence of SEQ ID No: 64 are subjected to substitution and/or deletion and/or addition.

PheA protein is (d1) or (d2) as follows:

(d1) a protein consisting of the amino acid sequence shown by SEQ ID No: 63 of the sequence listing;

(d2) a protein derived from SEQ ID No: 63 having a bifunctional enzyme function of chorismate mutase-prephenate dehydratase after one or several amino acid residues of the amino acid sequence of SEQ ID No: 63 are subjected to substitution and/or deletion and/or addition.

Said phenylalanine attenuator particularly can be shown by the nucleotides at positions 1-123 of SEQ ID No: 62 of the sequence listing.

The sequence associated with said phenylalanine attenuator particularly can be shown by the nucleotides at positions 1-176 of the sequence listing.

Gene coding for the PheA*protein particularly can be shown by the nucleotides at positions 147-1307 of SEQ ID No: 62 of the sequence listing.

Said phenylalanine operon gene particularly can be shown by the nucleotides at positions 1-1307 of SEQ ID No: 62 of the sequence listing.

Said phenylalanine operon gene particularly can be shown by the nucleotides at positions 1-1413 of SEQ ID No: 62 of the sequence listing.

Above any said phenylalanine particularly can be L-phenylalanine.

The present invention discloses a method for modifying a phenylalanine attenuator by deleting the pheL gene coding for a leader peptide and an anterior reverse complementary palindromic sequence in the terminator stem-loop structure of the attenuator, while maintaining a posterior reverse complementary palindromic sequence in the terminator. The inventor of the present invention surprisingly obtains a phenylalanine attenuator mutant which can significantly improve the expression level of a gene by removing a specific sequence of the phenylalanine attenuator. Obviously, according to the test results of the present invention, the skilled in the art can readily conclude that a phenylalanine attenuator mutant and a phenylalanine operon mutant having a similar performance may likewise be obtained by simultaneously removing a portion of the above said anterior reverse complementary palindromic sequence in the terminator stem-loop structure of the attenuator, which destroys the secondary complementary structure of the terminator in a certain degree. Thus, such similar method for modifying a phenylalanine attenuator also falls into the protection scope of the present invention. Obviously, the method for relieving the phenylalanine attenuator of E. coli in the present invention can likewise be applied to the phenylalanine attenuators of other strains.

The present invention also discloses a phenylalanine operon gene with relieved attenuation regulation, and particularly, the phenylalanine operon gene is one obtained by removing the pheL gene coding for a leader peptide and an anterior reverse complementary palindromic sequence in the terminator stem-loop structure, while maintaining a posterior reverse complementary palindromic sequence in the terminator.

In addition to modifying the in situ phenylalanine operon gene in the chromosomes, other methods as overexpressing a gene, such as integrating one or more copies of the above said phenylalanine operon gene with relieved attenuation regulation on the chromosomes likewise falls into the protection scope of the present invention; in addition, overexpressing the above said phenylalanine operon gene with relieved attenuation regulation in a plasmid likewise falls into the protection scope of the present invention.

BEST EMBODIMENTS OF THE INVENTION

Figure 1:
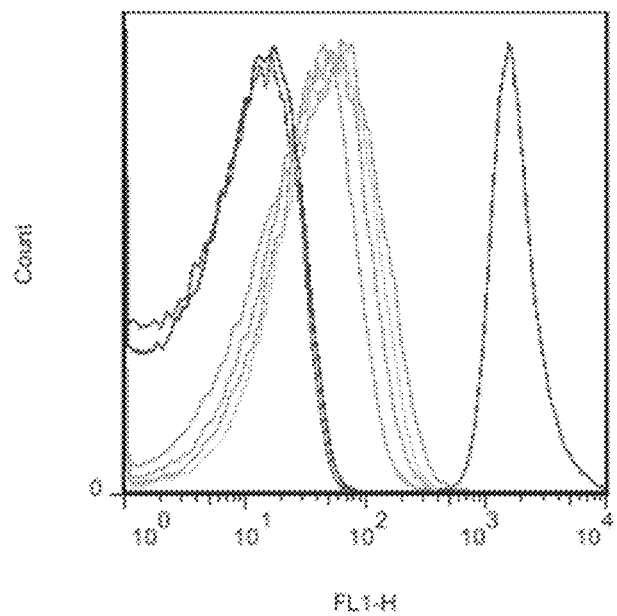
FIG. 1 shows the intensities of GFP expressed under regulations of different attenuator mutants analyzed by the flow cytometer in Example 3.

The following examples are intended to facilitate a better understanding of the present invention, but are not to limit the present invention. All the experimental methods in the following examples are conventional methods, unless otherwise specified. All the test materials used in the following examples are available from a conventional shop selling biochemical reagents, unless otherwise specified. All the quantitative tests in the following examples are done in triplicate, the results of which are averaged. The technical means used in the following examples, which are conventional means well known by the skilled in the art, and the conventional apparatuses and reagents commercially available in the market, can find reference in "Molecular Cloning: A Laboratory Manual, Third Edition" (Science Press), "Laboratory Experiments In Microbiology, Fourth Edition" (Higher Education Press) and the instructions from the manufacturers of the corresponding apparatuses and reagents etc., unless otherwise indicated in the examples.

The E. coli K12 W3110 (also referred to as E. coli K12 W3110) is available from the NITE Biological Resource Center, NBRC, in Japan. The plasmid pKOV designated as No. 25769 in a product catalog is available from the Addgene company. The plasmid pACYC184 designated as No. E4152S in a product catalog is available from the NEB company. The pAD123 plasmid can find reference in Gene, 1999. 226(2): 297-305. The full name of ONPG is o-nitrophenyl-β-D-galactopyranoside. Bacillus subtilis W168 designated as Item No. 1A308 is available from the Bacillus Genetic Stock Center in the United States. The E. coli K12 MG1655 designated as No. 700926 is available from the ATCC. The plasmid pKOV designated as No. 25769 in a product catalog is available from the Addgene company. The pGFPuv vector designated as Catalog No. 632312 is available from the Clontech Laboratories, Inc. The E. coli EC135 is recorded in the reference as follows: Zhang et al., Plos Genetics, 2012. 8(9): e1002987. The plasmid pBR322 designated as No. D3050 in a product catalog is available from the TaKaRa company.

ATCC: on the internet at: www.atcc.org.

Each of the primer sequences used in Examples 1-5 is set forth as follows (5'→3'):

WY569: GCGTCGACATAGAACCCAACCGCCTGCTCA;

WY570: AACGATCGACTATCACAGAAGAAACCTGATTACCTCACTACATA;

WY571: TATGTAGTGAGGTAATCAGGTTTCTTCTGTGATAGTCGATCGTT;

WY572: ATTGCGGCCGCCCGAAATAAAATCAGGCAACGT;

-continued

WY583: CGTTAATGAAATATCGCCAG;

WY584: TCGAAATCGGCCATAAAGAC.

WY577: CGC<u>GGATCC</u>GAAAGTGTACGAAAGCCAGG;

WY578: GCGCTATCAGGCATTTTTCCTATTAACCCCCCAGTTTCGA;

WY579: TCGAAACTGGGGGGTTAATAGGAAAAATGCCTGATAGCGC;

WY580: ATT<u>GCGGCCGC</u>GTGAAGCGGATCTGGCGATT;

WY587: ATGGCTGTATCCGCTCGCTG;

WY588: ACACCATCGATCAGCAAGGGC.

WY573: CGC<u>GGATCC</u>GGCACGATATTTAAGCTGAC;

WY574: CAACCAGCGACTAACCGCAGAACAAACTCCAGATAAGTGC;

WY575: GCACTTATCTGGAGTTTGTTCTGCGGTTAGTCGCTGGTTG;

WY576: ATT<u>GCGGCCGC</u>GCTGGCAACGCGTCATTTAA;

WY585: GTAACACACACACTTCATCT;

WY586: GATCCCGGATGCTGATTTAG.

WY598: CGC<u>GGATCC</u>ATACTGCGATGTGATGGGCC;

WY599: AATACCAGCCCTTGTTCGTGCTCACATCCTCAGGCGATAA;

WY600: TTATCGCCTGAGGATGTGAGCACGAACAAGGGCTGGTATT;

WY601: ATT<u>GCGGCCGC</u>CGTTGCCACTTCAATCCCAC;

WY602: GCTATGCCAACAACGATATG;

WY603: GGTTAATACGCCGGTTGAGC.

WY476: CGC<u>GGATCC</u>GGAACGATTGGTCTGGAAAT;

WY477: GGCTTCAATCAGGTCAAGGATATCCTATCCTCAACGAATTA;

WY478: TAATTCGTTGAGGATAGGATATCCTTGACCTGATTGAAGCC;

WY479: ATT<u>GCGGCCGC</u>CGCGACGGATATTATCAATGAC;

WY497: GCGCCAAAATCCAAAGTAGC;

WY498: ATGTGCGCGCTGGGAAACAT.

WY945: CGC<u>GGATCC</u>TATCTTCGCCGTGACCACTGA;

WY946: ACCGAACATATTACAGGCCAGCGATCCTTTCATTGTGTTGTC;

WY947: GACAACACAATGAAAGGATCGCTGGCCTGTAATATGTTCGGT;

WY948: ATT<u>GCGGCCGC</u>CTCGCGAAGTTCCATCATCCT;

WY949: CCTGTAACGAGCGTAACGACT;

WY950: TATCTTCGCCGTGACCACTGA.

WY914: CCC<u>AAGCTT</u>ACAGAGTACACAACATCCATG;

WY1630: CCC<u>AAGCTT</u>CATTAGCACCACCATTACCA;

WY1629: CCC<u>AAGCTT</u>CAGGTAACGGTGCGGGCTGA;

WY1628: CCC<u>AAGCTT</u>CGCGTACAGGAAACACAGAA;

WY1627: CCC<u>AAGCTT</u>GTGCGGGCTTTTTTTTCGA;

WY913: CCC<u>AAGCTTT</u>CGACCAAAGGTAACGAGGT;

WY1746: CATAGAACCAGAACCAGAACCCAATTGCGCCAGCGGGAAC.

-continued

WY1752: CAATTGGGTTCTGGTTCTGGTTCTATGACCATGATTACGGATTCACT;

WY1750: CGC<u>GGATCC</u>ACGCGAAATACGGGCAGACA.

Example 1. Construction of the *E. coli* K-12 W3110ΔmetAΔilvAΔlysAΔtdhΔtdcCΔsstT Chassis engineered bacteria are obtained by sequentially knocking out the metA gene (a gene coding for homoserine transsuccinylase), the ilvA gene (a gene coding for threonine deaminase), the lysA gene (a gene coding for diaminopimelic acid decarboxylase), the tdh gene (a gene coding for threonine dehydratase), the tdcC gene (a gene coding for threonine absortion and transport protein) and the sstT gene (a gene coding for threonine absortion and transport protein) with the *E. coli* K12 W3110 as the starting bacteria strain, and named as *E. coli* K-12 W3110ΔmetAΔilvAΔlysAΔtdhΔtdcCΔsstT.

1. Knockout of the metA Gene (1) A DNA fragment I-A (a region upstream of the metA gene) is obtained by performing a PCR amplification using the genome DNA of the *E. coli* K12 W3110 as a template and using a primer pair comprised of WY569 and WY570.

(2) A DNA fragment I-B (a region downstream of the metA gene) is obtained by performing a PCR amplification using the genome DNA of the *E. coli* K12 W3110 as a template and using a primer pair comprised of WY571 and WY572.

(3) A DNA fragment I-C is obtained by performing a PCR amplification using a mixture of the DNA fragment I-A and the DNA fragment I-B as a template and using a primer pair comprised of WY569 and WY572.

(4) The vector backbone (about 5.6 kb) of the plasmid pKOV, after being subjected to a double enzymatic cleavage using the restriction endonucleases Sal I and Not I, is recovered.

(5) The enzymatically cleaved product of the DNA fragment I-C, after being subjected to a double enzymatic cleavage using the restriction endonucleases Sal I and Not I, is recovered.

(6) A recombinant plasmid I is obtained by linking the vector backbone obtained in step (4) and the enzymatically cleaved product obtained in step (5). According to the sequencing result, a structural description for the recombinant plasmid I is set forth as follows: the following specific DNA molecule is inserted between the enzymatic cleavage sites of Sal I and Not I of the plasmid pKOV: sequentially consisting, from upstream to downstream, of the upstream section shown by the nucleotides at positions 245-751 of SEQ ID No: 1 of the sequence listing and the downstream section shown by the nucleotides at positions 1682-2154 of SEQ ID No: 1 of the sequence listing. The metA gene is shown by SEQ ID No: 1 of the sequence listing, wherein the open reading frame is shown by the nucleotides at positions 752-1681 (coding for the metA protein shown by SEQ ID No: 2 of the sequence listing).

(7) Recombinant bacteria with metA gene knocked out is obtained by introducing the recombinant plasmid I into the *E. coli* K12 W3110 and named as *E. coli* K12 W3110ΔmetA.

A method for identyfing the recombinant bacteria with metA gene knocked out is that: a PCR amplification is performed using a primer pair comprised of WY583 and WY584; if an amplification product with 1375 bp is obtained, the recombinant bacteria preliminarily can be determined as a candidate for the target bacteria; and sequencing will be further performed to verify that the open reading frame of the metA gene on the chromosomes of the bacteria has been knocked out.

2. Knockout of the ilvA Gene (1) A DNA fragment II-A (a region upstream of the ilvA gene) is obtained by performing a PCR amplification using the genome DNA of the *E. coli* K12 W3110 as a template and using a primer pair comprised of WY577 and WY578.

(2) A DNA fragment II-B (a region downstream of the ilvA gene) is obtained by performing a PCR amplification using the genome DNA of the *E. coli* K12 W3110 as a template and using a primer pair comprised of WY579 and WY580.

(3) A DNA fragment II-C is obtained by performing a PCR amplification using a mixture of the DNA fragment II-A and the DNA fragment II-B as a template and using a primer pair comprised of WY577 and WY580.

(4) The vector backbone (about 5.6 kb) of the plasmid pKOV, after being subjected to a double enzymatic cleavage using the restriction endonucleases BamH I and Not I, is recovered.

(5) The enzymatically cleaved product of the DNA fragment II-C, after being subjected to a double enzymatic cleavage using the restriction endonucleases BamH I and Not I, is recovered.

(6) A recombinant plasmid II is obtained by linking the vector backbone obtained in step (4) and the enzymatically cleaved product obtained in step (5). According to the sequencing result, a structural description for the recombinant plasmid II is set forth as follows: the following specific DNA molecule is inserted between the enzymatic cleavage sites of BamH I and Not I of the plasmid pKOV: sequentially consisting, from upstream to downstream, of the upstream section shown by the nucleotides at positions 140-637 of SEQ ID No: 3 of the sequence listing and the downstream section shown by the nucleotides at positions 2183-2712 of SEQ ID No: 3 of the sequence listing. The ilvA gene is shown by SEQ ID No: 3 of the sequence listing, wherein the open reading frame is shown by the nucleotides at positions 638-2182 (coding for the ilvA protein shown by SEQ ID No: 4 of the sequence listing).

(7) Recombinant bacteria with ilvA gene knocked out are obtained by introducing the recombinant plasmid II into the *E. coli* K12 W3110ΔmetA, and named as *E. coli* K12 W3110ΔmetAΔilvA.

A method for identifying the recombinant bacteria with ilvA gene knocked out is that: a PCR amplification is performed using a primer pair comprised of WY587 and WY588; if an amplification product with 1344 bp is obtained, the recombinant bacteria preliminarily can be determined as a candidate for the target bacteria; and sequencing will be further performed to verify that the open reading frame of the ilvA gene on the chromosomes of the bacteria has been knocked out.

3. Knockout of the lysA Gene (1) A DNA fragment III-A (a region upstream of the lysA gene) is obtained by performing a PCR amplification using the genome DNA of the *E. coli* K12 W3110 as a template and using a primer pair comprised of WY573 and WY574.

(2) A DNA fragment III-B (a region downstream of the lysA gene) is obtained by performing a PCR amplification using the genome DNA of the *E. coli* K12 W3110 as a template and using a primer pair comprised of WY575 and WY576.

(3) A DNA fragment III-C is obtained by performing a PCR amplification using a mixture of the DNA fragment III-A and the DNA fragment III-B as a template and using a primer pair comprised of WY573 and WY576.

(4) The vector backbone (about 5.6 kb) of the plasmid pKOV, after being subjected to a double enzymatic cleavage using the restriction endonucleases BamH I and Not I, is recovered.

(5) The enzymatically cleaved product of the DNA fragment III-C, after being subjected to a double enzymatic cleavage using the restriction endonucleases BamH I and Not I, is recovered.

(6) A recombinant plasmid III is obtained by linking the vector backbone obtained in step (4) and the enzymatically cleaved product obtained in step (5). According to the sequencing result, a structural description for the recombinant plasmid III is set forth as follows: the following specific DNA molecule is inserted between the enzymatic cleavage sites of BamH I and Not I of the plasmid pKOV: sequentially consisting, from upstream to downstream, of the upstream section shown by the nucleotides at positions 132-638 of SEQ ID No: 5 of the sequence listing and the downstream section shown by the nucleotides at positions 1902-2445 of SEQ ID No: 5 of the sequence listing. The lysA gene is shown by SEQ ID No: 5 of the sequence listing, wherein the open reading frame is shown by the nucleotides at positions 639-1901 (coding for the lysA protein shown by SEQ ID No: 6 of the sequence listing).

(7) Recombinant bacteria with lysA gene knocked out are obtained by introducing the recombinant plasmid III into the *E. coli* K-12 W3110ΔmetAΔilvA, and named as *E. coli* K-12 W3110ΔmetAΔilvAΔlysA.

A method for identyfing the recombinant bacteria with lysA gene knocked out is that: a PCR amplification is performed using a primer pair comprised of WY585 and WY586; if an amplification product with 1302 bp is obtained, the recombinant bacteria preliminarily can be determined as a candidate for the target bacteria; and sequencing will be further performed to verify that the open reading frame of the lysA gene on the chromosomes of the bacteria has been knocked out.

4. Knockout of the tdh Gene (1) A DNA fragment IV-A (a region upstream of the tdh gene) is obtained by performing a PCR amplification using the genome DNA of the *E. coli* K12 W3110 as a template and using a primer pair comprised of WY598 and WY599.

(2) A DNA fragment IV-B (a region downstream of the tdh gene) is obtained by performing a PCR amplification using the genome DNA of the *E. coli* K12 W3110 as a template and using a primer pair comprised of WY600 and WY601.

(3) A DNA fragment IV-C is obtained by performing a PCR amplification using a mixture of the DNA fragment IV-A and the DNA fragment IV-B as a template and using a primer pair comprised of WY598 and WY601.

(4) The vector backbone (about 5.6 kb) of the plasmid pKOV, after being subjected to a double enzymatic cleavage using the restriction endonucleases BamH I and Not I, is recovered.

(5) The enzymatically cleaved product of the DNA fragment IV-C, after being subjected to a double enzymatic cleavage using the restriction endonucleases BamH I and Not I, is recovered.

(6) A recombinant plasmid IV is obtained by linking the vector backbone obtained in step (4) and the enzymatically cleaved product obtained in step (5). According to the sequencing result, a structural description for the recombinant plasmid IV is set forth as follows: the following specific DNA molecule is inserted between the enzymatic cleavage sites of BamH I and Not I of the plasmid pKOV: sequentially consisting, from upstream to downstream, of the upstream section shown by the nucleotides at positions 227-752 of SEQ ID No: 7 of the sequence listing and the downstream section shown by the nucleotides at positions 1779-2271 of SEQ ID No: 7 of the sequence listing. The tdh gene is shown by SEQ ID No: 7 of the sequence listing, wherein the open reading frame is shown by the nucleotides at positions 753-1778 (coding for the tdh protein shown by SEQ ID No: 8 of the sequence listing).

(7) Recombinant bacteria with tdh gene knocked out are obtained by introducing the recombinant plasmid IV into the E. coli K-12 W3110ΔmetAΔilvAΔlysA, and named as E. coli K-12 W3110ΔmetAΔilvAΔlysAΔtdh.

A method for identyfing the recombinant bacteria with tdh gene knocked out is that: a PCR amplification is performed using a primer pair comprised of WY602 and WY603; if an amplification product with 1434 bp is obtained, the recombinant bacteria preliminarily can be determined as a candidate for the target bacteria; and sequencing will be further performed to verify that the open reading frame of the tdh gene on the chromosomes of the bacteria has been knocked out.

5. Knockout of the tdcC Gene (1) A DNA fragment V-A (a region upstream of the tdcC gene) is obtained by performing a PCR amplification using the genome DNA of the E. coli K12 W3110 as a template and using a primer pair comprised of WY476 and WY477.

(2) A DNA fragment V-B (a region downstream of the tdcC gene) is obtained by performing a PCR amplification using the genome DNA of the E. coli K12 W3110 as a template and using a primer pair comprised of WY478 and WY479.

(3) A DNA fragment V-C is obtained by performing a PCR amplification using a mixture of the DNA fragment V-A and the DNA fragment V-B as a template and using a primer pair comprised of WY476 and WY479.

(4) The vector backbone (about 5.6 kb) of the plasmid pKOV, after being subjected to a double enzymatic cleavage using the restriction endonucleases BamH I and Not I, is recovered.

(5) The enzymatically cleaved product of the DNA fragment V-C, after being subjected to a double enzymatic cleavage using the restriction endonucleases BamH I and Not I, is recovered.

(6) A recombinant plasmid V is obtained by linking the vector backbone obtained in step (4) and the enzymatically cleaved product obtained in step (5). According to the sequencing result, a structural description for the recombinant plasmid V is set forth as follows: the following specific DNA molecule is inserted between the enzymatic cleavage sites of BamH I and Not I of the plasmid pKOV: sequentially consisting, from upstream to downstream, of the upstream section shown by the nucleotides at positions 176-700 of SEQ ID No: 9 of the sequence listing and the downstream section shown by the nucleotides at positions 1853-2388 of SEQ ID No: 9 of the sequence listing. The tdcC gene is shown by SEQ ID No: 9 of the sequence listing, wherein the open reading frame is shown by the nucleotides at positions 701-2032 (coding for the tdcC protein shown by SEQ ID No: 10 of the sequence listing).

(7) Recombinant bacteria with tdcC gene knocked out are obtained by introducing the recombinant plasmid V into the E. coli K-12 W3110ΔmetAΔilvAΔlysAΔtdh, and named as E. coli K-12 W3110ΔmetAΔilvAΔlysAΔtdhΔtdcC.

A method for identyfing the recombinant bacteria with tdcC gene knocked out is that: a PCR amplification is performed using a primer pair comprised of WY497 and WY498; if an amplification product with 1453 bp is obtained, the recombinant bacteria preliminarily can be determined as a candidate for the target bacteria; and sequencing will be further performed to verify that the following section of the tdcC gene on the chromosomes of the bacteria has been knocked out: the nucleotides at positions 701-1852 of SEQ ID No: 9.

6. Knockout of the sstT Gene (1) A DNA fragment VI-A (a region upstream of the sstT gene) is obtained by performing a PCR amplification using the genome DNA of the E. coli K12 W3110 as a template and using a primer pair comprised of WY945 and WY946.

(2) A DNA fragment VI-B (a region downstream of the sstT gene) is obtained by performing a PCR amplification using the genome DNA of the E. coli K12 W3110 as a template and using a primer pair comprised of WY947 and WY948.

(3) A DNA fragment VI-C is obtained by performing a PCR amplification using a mixture of the DNA fragment VI-A and the DNA fragment VI-B as a template and using a primer pair comprised of WY945 and WY948.

(4) The vector backbone (about 5.6 kb) of the plasmid pKOV, after being subjected to a double enzymatic cleavage using the restriction endonucleases BamH I and Not I, is recovered.

(5) The enzymatically cleaved product of the DNA fragment VI-C, after being subjected to a double enzymatic cleavage using the restriction endonucleases BamH I and Not I, is recovered.

(6) A recombinant plasmid VI is obtained by linking the vector backbone obtained in step (4) and the enzymatically cleaved product obtained in step (5). According to the sequencing result, a structural description for the recombinant plasmid VI is set forth as follows: the following specific DNA molecule is inserted between the enzymatic cleavage sites of BamH I and Not I of the plasmid pKOV: sequentially consisting, from upstream to downstream, of the upstream section shown by the nucleotides at positions 14-696 of SEQ ID No: 11 of the sequence listing and the downstream section shown by the nucleotides at positions 1760-2240 of SEQ ID No: 11 of the sequence listing. The sstT gene is shown by SEQ ID No: 11 of the sequence listing, wherein the open reading frame is shown by the nucleotides at positions 701-1945 (coding for the sstT protein shown by SEQ ID No: 12 of the sequence listing).

(7) Recombinant bacteria with sstT gene knocked out are obtained by introducing the recombinant plasmid VI into the E. coli K-12 W3110ΔmetAΔilvAΔlysAΔtdhΔtdcC, and named as E. coli K-12 W3110ΔmetAΔilvAΔlysAΔtdhΔtdcCΔsstT.

A method for identyfing the recombinant bacteria with sstT gene knocked out is that: a PCR amplification is performed using a primer pair comprised of WY949 and WY950; if an amplification product with 1569 bp is obtained, the recombinant bacteria preliminarily can be determined as a candidate for the target bacteria; and sequencing will be further performed to verify that the following section of the sstT gene on the chromosomes of the bacteria has been knocked out: the nucleotides at positions 697-1759 of SEQ ID No: 11.

Example 2. The Expression of the lacZ Gene Under Regulation of an Attenuator Mutant I. Construction of the Recombinant Plasmid pACYC184-$P_{PL}$ 1. The double-stranded DNA molecule (the promoter $P_{PL}$) shown by SEQ ID No: 13 of the sequence listing 13 is synthesized.

2. A PCR amplification product is obtained by performing a PCR amplification using the double-stranded DNA molecule prepared in step 1 as a template and using a primer pair comprised of WY843 and WY842.

```
WY843: TGCTCTAGACAATTCCGACGTCTAAGAAA;

WY842: CCCAAGCTTGGTCAGTGCGTCCTGCTGAT.
```

3. The enzymatically cleaved product of the PCR amplification product obtained in step 2, after being subjected to a double enzymatic cleavage using the restriction endonucleases Xba I and Hind III, is recovered.

4. The vector backbone (about 4.1 kb) of the plasmid pACYC184, after being subjected to a double enzymatic cleavage using the restriction endonucleases Xba I and Hind III, is recovered.

5. A recombinant plasmid pACYC184-$P_{PL}$ is obtained by linking the enzymatically cleaved product in step 3 and the vector backbone in step 4.

II. Construction of Each of the Recombinant Plasmids

1. Construction of the Recombinant Plasmid A (1) A PCR amplification product A1 is obtained by performing a PCR amplification using the genome DNA of the E. coli K12 W3110 as a template and using a primer pair comprised of WY914 and WY1746; a PCR amplification product A2 is obtained by performing a PCR amplification using the double-stranded DNA molecule as a template, which is artificially synthesized and shown by SEQ ID No: 15 of the sequence listing, and using a primer pair comprised of WY1752 and WY1750; a PCR amplification product A3 is obtained by performing a PCR amplification using a mixture of the PCR amplification product A1 and the PCR amplification product A2 as a template and using a primer pair comprised of WY914 and WY1750.

(2) The enzymatically cleaved product of the PCR amplification product A3, after being subjected to a double enzymatic cleavage using the restriction endonucleases Hind III and BamH I, is recovered.

(3) The vector backbone (about 4.0 kb) of the recombinant plasmid pACYC184-$P_{PL}$, after being subjected to a double enzymatic cleavage using the restriction endonucleases Hind III and BamH I, is recovered.

(4) A recombinant plasmid A is obtained by linking the enzymatically cleaved product in step (2) and the vector backbone in step (3). According to the sequencing result, a structural description for the recombinant plasmid A is set forth as follows: a specific DNA molecule A is inserted between the enzymatic cleavage sites of Xba I and BamH I of the plasmid pACYC184; and the specific DNA molecule A sequentially consists, from upstream to downstream, of the following elements: the promoter $P_{PL}$ shown by SEQ ID No: 13 of the sequence listing, a recognition sequence for enzymatic cleavage by restriction endonuclease Hind III, the nucleotides at positions 172-606 of SEQ ID No: 14 of the sequence listing, a linker sequence "GGTTCTGGTTCTGGTTCT" (SEQ ID NO: 67), and the lacZ gene shown by SEQ ID No: 15 of the sequence listing (wherein the open reading frame is at positions 1-3075 of SEQ ID No: 15). The recombinant plasmid A is named as pACYC184-$P_{PL}$-thrLA-lacZ914.

2. Construction of the Recombinant Plasmid B (1) A PCR amplification product B1 is obtained by performing a PCR amplification using the genome DNA of the E. coli K12 W3110 as a template and using a primer pair comprised of WY1630 and WY1746; a PCR amplification product B2 is obtained by performing a PCR amplification using the double-stranded DNA molecule as a template, which is artificially synthesized and shown by SEQ ID No: 15 of the sequence listing, and using a primer pair comprised of WY1752 and WY1750; a PCR amplification product B3 is obtained by performing a PCR amplification using a mixture of the PCR amplification product B1 and the PCR amplification product B2 as a template and using a primer pair comprised of WY1630 and WY1750.

(2) The enzymatically cleaved product of the PCR amplification product B3, after being subjected to a double enzymatic cleavage using the restriction endonucleases Hind III and BamH I, is recovered.

(3) The vector backbone (about 4.0 kb) of the recombinant plasmid pACYC184-$P_{PL}$, after being subjected to a double enzymatic cleavage using the restriction endonucleases Hind III and BamH I, is recovered.

(4) A recombinant plasmid B is obtained by linking the enzymatically cleaved product in step (2) and the vector backbone in step (3). According to the sequencing result, a structural description for the recombinant plasmid B is set forth as follows: a specific DNA molecule B is inserted between the enzymatic cleavage sites of Xba I and BamH I of the plasmid pACYC184; and the specific DNA molecule B sequentially consists, from upstream to downstream, of the following elements: the promoter $P_{PL}$ shown by SEQ ID No: 13 of the sequence listing, a recognition sequence for enzymatic cleavage by restriction endonuclease Hind III, the nucleotides at positions 198-606 of SEQ ID No: 14 of the sequence listing, a linker sequence "GGTTCTGGTTCTGGTTCT" (SEQ ID NO: 67), and the lacZ gene shown by SEQ ID No: 15 of the sequence listing. The recombinant plasmid B is named as pACYC184-$P_{PL}$-thrLA-lacZ1630.

3. Construction of the Recombinant Plasmid C (1) A PCR amplification product C1 is obtained by performing a PCR amplification using the genome DNA of the E. coli K12 W3110 as a template and using a primer pair comprised of WY1629 and WY1746; a PCR amplification product C2 is obtained by performing a PCR amplification using the double-stranded DNA molecule as a template, which is artificially synthesized and shown by SEQ ID No: 15 of the sequence listing, and using a primer pair comprised of WY1752 and WY1750; a PCR amplification product C3 is obtained by performing a PCR amplification using a mixture of the PCR amplification product C1 and the PCR amplification product C2 as a template and using a primer pair comprised of WY1629 and WY1750.

(2) The enzymatically cleaved product of the PCR amplification product C3, after being subjected to a double enzymatic cleavage using the restriction endonucleases Hind III and BamH I, is recovered.

(3) The vector backbone (about 4.0 kb) of the recombinant plasmid pACYC184-$P_{PL}$, after being subjected to a double enzymatic cleavage using the restriction endonucleases Hind III and BamH I, is recovered.

(4) A recombinant plasmid C is obtained by linking the enzymatically cleaved product in step (2) and the vector backbone in step (3). According to the sequencing result, a structural description for the recombinant plasmid C is set forth as follows: a specific DNA molecule C is inserted between the enzymatic cleavage sites of Xba I and BamH I of the plasmid pACYC184; and the specific DNA molecule C sequentially consists, from upstream to downstream, of the following elements: the promoter $P_{PL}$ shown by SEQ ID No: 13 of the sequence listing, a recognition sequence for enzymatic cleavage by restriction endonuclease Hind III, the nucleotides at positions 236-606 of SEQ ID No: 14 of the sequence listing, a linker sequence "GGTTCTGGTTCTGGTTCT" (SEQ ID NO: 67), and the lacZ gene shown by SEQ ID No: 15 of the sequence listing. The recombinant plasmid C is named as pACYC184-$P_{PL}$-thrLA-lacZ1629.

4. Construction of the Recombinant Plasmid D (1) A PCR amplification product D1 is obtained by performing a PCR amplification using the genome DNA of the *E. coli* K12 W3110 as a template and using a primer pair comprised of WY1628 and WY1746; a PCR amplification product D2 is obtained by performing a PCR amplification using the double-stranded DNA molecule as a template, which is artificially synthesized and shown by SEQ ID No: 15 of the sequence listing, and using a primer pair comprised of WY1752 and WY1750; a PCR amplification product D3 is obtained by performing a PCR amplification using a mixture of the PCR amplification product D1 and the PCR amplification product D2 as a template and using a primer pair comprised of WY1628 and WY1750.

(2) The enzymatically cleaved product of the PCR amplification product D3, after being subjected to a double enzymatic cleavage using the restriction endonucleases Hind III and BamH I, is recovered.

(3) The vector backbone (about 4.0 kb) of the recombinant plasmid pACYC184-$P_{PL}$, after being subjected to a double enzymatic cleavage using the restriction endonucleases Hind III and BamH I, is recovered.

(4) A recombinant plasmid D is obtained by linking the enzymatically cleaved product in step (2) and the vector backbone in step (3). According to the sequencing result, a structural description for the recombinant plasmid D is set forth as follows: a specific DNA molecule D is inserted between the enzymatic cleavage sites of Xba I and BamH I of the plasmid pACYC184; and the specific DNA molecule D sequentially consists, from upstream to downstream, of the following elements: the promoter $P_{PL}$ shown by SEQ ID No: 13 of the sequence listing, a recognition sequence for enzymatic cleavage by restriction endonuclease Hind III, the nucleotides at positions 256-606 of SEQ ID No: 14 of the sequence listing, a linker sequence "GGTTCTGGTTCTGGTTCT" (SEQ ID NO: 67), and the lacZ gene shown by SEQ ID No: 15 of the sequence listing. The recombinant plasmid D is named as pACYC184-$P_{PL}$-thrLA-lacZ1628.

5. Construction of the Recombinant Plasmid E (1) A PCR amplification product E1 is obtained by performing a PCR amplification using the genome DNA of the *E. coli* K12 W3110 as a template and using a primer pair comprised of WY1627 and WY1746; a PCR amplification product E2 is obtained by performing a PCR amplification using the double-stranded DNA molecule as a template, which is artificially synthesized and shown by SEQ ID No: 15 of the sequence listing, and using a primer pair comprised of WY1752 and WY1750; a PCR amplification product E3 is obtained by performing a PCR amplification using a mixture of the PCR amplification product E1 and the PCR amplification product E2 as a template and using a primer pair comprised of WY1627 and WY1750.

(2) The enzymatically cleaved product of the PCR amplification product E3, after being subjected to a double enzymatic cleavage using the restriction endonucleases Hind III and BamH I, is recovered.

(3) The vector backbone (about 4.0 kb) of the recombinant plasmid pACYC184-$P_{PL}$, after being subjected to a double enzymatic cleavage using the restriction endonucleases Hind III and BamH I, is recovered.

(4) A recombinant plasmid E is obtained by linking the enzymatically cleaved product in step (2) and the vector backbone in step (3). According to the sequencing result, a structural description for the recombinant plasmid E is set forth as follows: a specific DNA molecule E is inserted between the enzymatic cleavage sites of Xba I and BamH I of the plasmid pACYC184; and the specific DNA molecule E sequentially consists, from upstream to downstream, of the following elements: the promoter $P_{PL}$ shown by SEQ ID No: 13 of the sequence listing, a recognition sequence for enzymatic cleavage by restriction endonuclease Hind III, the nucleotides at positions 294-606 of SEQ ID No: 14 of the sequence listing, a linker sequence "GGTTCTGGTTCTGGTTCT" (SEQ ID NO: 67), and the lacZ gene shown by SEQ ID No: 15 of the sequence listing. The recombinant plasmid E is named as pACYC184-$P_{PL}$-thrLA-lacZ1627.

6. Construction of the Recombinant Plasmid F (1) A PCR amplification product F1 is obtained by performing a PCR amplification using the genome DNA of the *E. coli* K12 W3110 as a template and using a primer pair comprised of WY913 and WY1746; a PCR amplification product F2 is obtained by performing a PCR amplification using the double-stranded DNA molecule as a template, which is artificially synthesized and shown by SEQ ID No: 15 of the sequence listing, and using a primer pair comprised of WY1752 and WY1750; a PCR amplification product F3 is obtained by performing a PCR amplification using a mixture of the PCR amplification product F1 and the PCR amplification product F2 as a template and using a primer pair comprised of WY913 and WY1750.

(2) The enzymatically cleaved product of the PCR amplification product F3, after being subjected to a double enzymatic cleavage using the restriction endonucleases Hind III and BamH I, is recovered.

(3) The vector backbone (about 4.0 kb) of the recombinant plasmid pACYC184-$P_{PL}$, after being subjected to a double enzymatic cleavage using the restriction endonucleases Hind III and BamH I, is recovered.

(4) A recombinant plasmid F is obtained by linking the enzymatically cleaved product in step (2) and the vector backbone in step (3). According to the sequencing result, a structural description for the recombinant plasmid F is set forth as follows: a specific DNA molecule F is inserted between the enzymatic cleavage sites of Xba I and BamH I of the plasmid pACYC184; and the specific DNA molecule F sequentially consists, from upstream to downstream, of the following elements: the promoter $P_{PL}$ shown by SEQ ID No: 13 of the sequence listing, a recognition sequence for enzymatic cleavage by restriction endonuclease Hind III, the nucleotides at positions 310-606 of SEQ ID No: 14 of the sequence listing, a linker sequence "GGTTCTGGTTCTGGTTCT" (SEQ ID NO: 67), and the lacZ gene shown by SEQ ID No: 15 of the sequence listing. The recombinant plasmid F is named as pACYC184-$P_{PL}$-thrLA-lacZ913.

III. Construction of Recombinant Bacteria

Recombinant bacteria is obtained by introducing pACYC184-P$_{PL}$-thrLA-lacZ914 into E. coli K-12 W3110ΔmetAΔilvAΔlysAΔtdhΔtdcCΔsstT, and named as LAC914.

Recombinant bacteria is obtained by introducing pACYC184-P$_{PL}$-thrLA-lacZ1630 into E. coli K-12 W3110ΔmetAΔilvAΔlysAΔtdhΔtdcCΔsstT, and named as LAC1630.

Recombinant bacteria is obtained by introducing pACYC184-P$_{PL}$-thrLA-lacZ1629 into E. coli K-12 W3110ΔmetAΔilvAΔlysAΔtdhΔtdcCΔsstT, and named as LAC1629.

Recombinant bacteria is obtained by introducing pACYC184-P$_{PL}$-thrLA-lacZ1628 into E. coli K-12 W3110ΔmetAΔilvAΔlysAΔtdhΔtdcCΔsstT, and named as LAC1628.

Recombinant bacteria is obtained by introducing pACYC184-P$_{PL}$-thrLA-lacZ1627 into E. coli K-12 W3110ΔmetAΔilvAΔlysAΔtdhΔtdcCΔsstT, and named as LAC1627.

Recombinant bacteria is obtained by introducing pACYC184-P$_{PL}$-thrLA-lacZ913 into E. coli K-12 W3110ΔmetAΔilvAΔlysAΔtdhΔtdcCΔsstT, and named as LAC913.

Recombinant bacteria is obtained by introducing the plasmid pACYC184 into E. coli K-12 W3110ΔmetAΔilvAΔlysAΔtdhΔtdcCΔsstT, and named as LAC control.

IV. Determination of the Activity of β-Galactosidase

The test strain is: LAC914, LAC1630, LAC1629, LAC1628, LAC1627 or LAC913.

1. The test strain is seeded into a liquid LB medium containing 34 mg/L chloramphenicol, followed by shaking culture for 12 h at 37° C., 220 rpm, and a seed solution is obtained.

2. The seed solution obtained in step 1 is seeded into a liquid 2YT medium containing 34 mg/L chloramphenicol in a seeding amount of 2%, followed by culture for 6 h at 37° C., 220 rpm.

3. After completion of step 2, 1.5 ml and 1 ml are sampled from the culture system for the determination of the optical density value at OD$_{600nm}$ and for the detection of the activity of β-galactosidase of a sample to be tested, respectively.

A method for detecting the activity of β-galactosidase:

(1) 1 ml of a sample to be tested is centrifuged at 10000×g for 5 min, and then bacteria precipitates are collected and washed twice with a PBS buffer solution at pH7.2, followed by making a constant volume to 1 ml with a Z-buffer and making the bacteria be fully suspended and placed on ice for use. The Z-buffer is: 40 mM NaH$_2$PO$_4$, 60 mM Na$_2$HPO$_4$, 10 mM KCl, 1 mM MgSO$_4$, and 50 mM β-mercaptoethanol, at pH 7.0.

(2) After completion of step (1), 0.05 mL is sampled, into which 0.2 mL of an aqueous solution containing 4 mg/ml ONPG and 0.8 mL of the Z-buffer are added and uniformly mixed, followed by being static at 37° C., and recording the starting time of the reaction. When the system appears light yellow, 1 mL of 1M Na$_2$CO$_3$ aqueous solution is added to terminate the reaction, and the termination time of the reaction is recorded. An OD$_{420nm}$ value is determined by an ultraviolet spectrophotometer.

Above steps are performed in the LAC control, which functions as a blank control for the OD$_{420nm}$ value determined by an ultraviolet spectrophotometer.

The activity of β-galactosidase (Miller Unit) is calculated as follows:

$$=1000 \times OD_{420nm}/(OD_{600nm} \times t \times V);$$

t, referred to a reaction time (the difference between the termination time and starting time of the reaction, min); V, referred to a loading volume, 0.05 mL.

The activity of β-galactosidase is defined as the amount of the enzyme that is required for decomposing 1 μmol of ONPG by one cell per minute.

Each of the strains is measured for three times, and a mean and a standard deviation are taken.

The results are shown in Table 1. Above steps are performed in different test strains, and the activities of the corresponding β-galactosidases appear significant differences, wherein the enzyme activity of LAC1627 is significantly higher than that of each of the other strains.

TABLE 1

| Test strains | Enzyme Activity (Miller Unit) |
| --- | --- |
| LAC914 | 47.72 ± 3.33 |
| LAC1630 | 26.17 ± 2.71 |
| LAC1629 | 31.20 ± 1.17 |
| LAC1628 | 16.11 ± 1.67 |
| LAC1627 | 132.09 ± 4.61 |
| LAC913 | 22.59 ± 4.23 |

Example 3. The Expression of the Gfp Gene Under Regulation of an Attenuator Mutant I. Construction of Recombinant Plasmids The following six recombinant plasmids are constructed: pACYC184-P$_{PL}$-thrLA-gfp914, pACYC184-P$_{PL}$-thrLA-gfp1630, pACYC184-P$_{PL}$-thrLA-gfp1629, pACYC184-P$_{PL}$-thrLA-gfp1628, pACYC184-P$_{PL}$-thrLA-gfp1627 and pACYC184-P$_{PL}$-thrLA-gfp913.

The pACYC184-P$_{PL}$-thrLA-gfp914 only differs from the pACYC184-P$_{PL}$-thrLA-lacZ914 in a substitution of a specific DNA molecule X for the lacZ gene shown by SEQ ID No: 15 of the sequence listing.

The pACYC184-P$_{PL}$-thrLA-gfp1630 only differs from the pACYC184-P$_{PL}$-thrLA-lacZ1630 in a substitution of a specific DNA molecule X for the lacZ gene shown by SEQ ID No: 15 of the sequence listing.

The pACYC184-P$_{PL}$-thrLA-gfp1629 only differs from the pACYC184-P$_{PL}$-thrLA-lacZ1629 in a substitution of a specific DNA molecule X for the lacZ gene shown by SEQ ID No: 15 of the sequence listing.

The pACYC184-P$_{PL}$-thrLA-gfp1628 only differs from the pACYC184-P$_{PL}$-thrLA-lacZ1628 in a substitution of a specific DNA molecule X for the lacZ gene shown by SEQ ID No: 15 of the sequence listing.

The pACYC184-P$_{PL}$-thrLA-gfp1627 only differs from the pACYC184-P$_{PL}$-thrLA-lacZ1627 in a substitution of a specific DNA molecule X for the lacZ gene shown by SEQ ID No: 15 of the sequence listing.

The pACYC184-P$_{PL}$-thrLA-gfp913 only differs from the pACYC184-P$_{PL}$-thrLA-lacZ913 in a substitution of a specific DNA molecule X for the lacZ gene shown by SEQ ID No: 15 of the sequence listing.

The specific DNA molecule X is: the nucleotide at position 22 from the beginning to the nucleotide at position 10 from the end of the PCR amplification product obtained by performing a PCR amplification using the pAD123 plasmid as a template and using a primer pair comprised of WY1751 and WY1748 (which having the gfp gene shown by SEQ ID No: 16 of the sequence listing).

WY1751: TTG GGTTCTGGTTCTGGTTCT ATGAGTAAAGGAGAAGAAC TTTTCACT;

WY1748: CGCGGATCCCTTGCATGCCTGCAGGAGAT.

II. Construction of Recombinant Bacteria

Recombinant bacteria is obtained by introducing pACYC184-P$_{PL}$-thrLA-gfp914 into E. coli K-12 W3110ΔmetAΔilvAΔlysAΔtdhΔtdcCΔsstT, and named as GFP914.

Recombinant bacteria is obtained by introducing pACYC184-P$_{PL}$-thrLA-gfp1630 into E. coli K-12 W3110ΔmetAΔilvAΔlysAΔtdhΔtdcCΔsstT, and named as GFP1630.

Recombinant bacteria is obtained by introducing pACYC184-P$_{PL}$-thrLA-gfp1629 into E. coli K-12 W3110ΔmetAΔilvAΔlysAΔtdhΔtdcCΔsstT, and named as GFP1629.

Recombinant bacteria is obtained by introducing pACYC184-P$_{PL}$-thrLA-gfp1628 into E. coli K-12 W3110ΔmetAΔilvAΔlysAΔtdhΔtdcCΔsstT, and named as GFP1628.

Recombinant bacteria is obtained by introducing pACYC184-P$_{PL}$-thrLA-gfp1627 into E. coli K-12 W3110ΔmetAΔilvAΔlysAΔtdhΔtdcCΔsstT, and named as GFP1627.

Recombinant bacteria is obtained by introducing pACYC184-P$_{PL}$-thrLA-gfp913 into E. coli K-12 W3110ΔmetAΔilvAΔlysAΔtdhΔtdcCΔsstT, and named as GFP913.

Recombinant bacteria is obtained by introducing the plasmid pACYC184 into E. coli K-12 W3110ΔmetAΔilvAΔlysAΔtdhΔtdcCΔsstT, and named as GFP control.

III. Analysis of the Expression of GFP in Cell Populations by a Flow Cytometer

The test strain is: GFP914, GFP1630, GFP1629, GFP1628, GFP1627, GFP913 or the GFP control (a blank control).

1. The test strain is seeded into a liquid LB medium containing 34 mg/L chloramphenicol, followed by shaking culture for 2 h at 37° C., 220 rpm, and then centrifugation and collection of the bacteria.

2. The bacteria obtained in step 1 is suspended with a PBS buffer solution at pH7.2, and a bacterial suspension having an OD$_{600nm}$ value of 0.5 is obtained.

3. The bacterial suspension obtained in step 2 is counted by a flow cytometer (FACSCalibur type, BD company of the United States) for 50,000 cells, and the experimental results are analyzed by using the FlowJ software.

The corresponding result of each of the test strains is shown in FIG. 1 and Table 2 (a mean of 50,000 cells). In FIG. 1, GFP1627, GFP913, GFP914, GFP1630, GFP1629, GFP1628 and the GFP control are respectively exhibited, from right to left, in fluorescence distribution curves of flora. The fluorescence level of the GFP1627 is improved by 30-1280 folds over other strains.

TABLE 2

| | Mean Fluorescence Intensity |
|---|---|
| GFP914 | 50.55 |
| GFP1630 | 39.15 |
| GFP1629 | 28.45 |
| GFP1628 | 1.40 |

TABLE 2-continued

| | Mean Fluorescence Intensity |
|---|---|
| GFP1627 | 1798.40 |
| GFP913 | 57.95 |

Example 4. Preparation of Alanine

I. Construction of Recombinant Plasmids

1. The double-stranded DNA molecule shown by SEQ ID No: 13 of the sequence listing is synthesized.

2. A PCR amplification product is obtained by performing a PCR amplification using the double-stranded DNA molecule synthesized in step 1 as a template and using a primer pair comprised of WY843 and WY1760.

3. The enzymatically cleaved product of the PCR amplification product obtained in step 2, after being subjected to a double enzymatic cleavage using restriction endonucleases Xba I and BamH I, is recovered.

4. The vector backbone (about 3.8 kb) of the plasmid pACYC184, after being subjected to a double enzymatic cleavage using restriction endonucleases Xba I and BamH I, is recovered.

5. A recombinant plasmid pACYC184-P$_{PL2}$ is obtained by linking the enzymatically cleaved product in step 3 and the vector backbone in step 4.

6. A PCR amplification product is obtained by performing a PCR amplification using the genome DNA of Bacillus subtilis W168 as a template and using a primer pair comprised of WY1785 and WY1778.

7. A PCR amplification product is obtained by performing a PCR amplification using the genome DNA of Bacillus subtilis W168 as a template and using a primer pair comprised of WY1786 and WY1778.

8. The vector backbone (about 4.2 kb) of the recombinant plasmid pACYC184-P$_{PL2}$, after being subjected to a double enzymatic cleavage using restriction endonucleases BamH I and Sph I, is recovered.

9. The enzymatically cleaved product of the PCR amplification product obtained in step 6, after being subjected to a double enzymatic cleavage using restriction endonucleases BamH I and Sph I, is recovered.

10. A recombinant plasmid is obtained by linking the enzymatically cleaved product in step 9 and the vector backbone in step 8, and named as pACYC184-P$_{PL}$-ald$_{WT}$. According to the sequencing result, a structural description for the pACYC184-P$_{PL}$-ald$_{WT}$ is set forth as follows: a specific DNA molecule I is inserted between the enzymatic cleavage sites of Xba I and Sph I of the plasmid pACYC184; and the DNA molecule I sequentially consists, from upstream to downstream, of the following elements: the promoter P$_{PL}$ shown by SEQ ID No: 13 of the sequence listing, a recognition sequence for enzymatic cleavage by restriction endonuclease BamH I, and the double-stranded DNA molecule shown by SEQ ID No: 17 of the sequence listing.

11. The enzymatically cleaved product of the PCR amplification product obtained in step 7, after being subjected to a double enzymatic cleavage using restriction endonucleases BamH I and Sph I, is recovered.

12. A recombinant plasmid is obtained by linking the enzymatically cleaved product in step 11 and the vector backbone in step 8, and named as pACYC184-P$_{PL}$-ald$_{5UTRthrA}$. According to the sequencing result, a structural description for the pACYC184-P$_{PL}$-ald$_{5UTRthrA}$ is set forth as follows: a specific DNA molecule II is inserted between the enzymatic cleavage sites of Xba I and Sph I of the plasmid pACYC184; and the DNA molecule II sequentially consists, from upstream to downstream, of the following elements: the promoter $P_{PL}$ shown by SEQ ID No: 13 of the sequence listing, a recognition sequence for enzymatic cleavage by restriction endonuclease BamH I, and the double-stranded DNA molecule shown by SEQ ID No: 18 of the sequence listing.

WY843:   TGCTCTAGACAATTCCGACGTCTAAGAAA;

WY1760:  CGCGGATCCGGTCAGTGCGTCCTGCTGAT;

WY1785:  CGCGGATCCCACATATACAGGAGGAGACAGA;

WY1786:  CGCGGATCCGTGCGGGCTTTTTTTTTCGACCAAAGGTAACGA
GGTAACAACCATGATCATAGGGGTTCCTAAAGA;

WY1778:  ACATGCATGCGTCATAATTCGTGAAATGGTCTCT.

II. Construction of Engineered Bacteria for Alanine

Recombinant bacteria is obtained by introducing pACYC184-$P_{PL}$-ald$_{WT}$ into E. coli K12 W3110, and named as E. coli K-12 W3110/pACYC184-$P_{PL}$-ald$_{WT}$.

Recombinant bacteria is obtained by introducing pACYC184-$P_{PL}$-ald$_{5UTRthrA}$ into E. coli K12 W3110, and named as E. coli K-12 W3110/pACYC184-$P_{PL}$-ald$_{5UTRthrA}$.

Recombinant bacteria is obtained by introducing pACYC184 plasmid into E. coli K12 W3110, and named as E. coli K-12 W3110/pACYC184.

III. Fermentation of Engineered Bacteria for Alanine in a Shake Flask

The test strain is: E. coli K-12 W3110/pACYC184-$P_{PL}$-ald$_{WT}$, E. coli K-12 W3110/pACYC184-$P_{PL}$-ald$_{5UTRthrA}$ or E. coli K-12 W3110/pACYC184.

1. The test strain is streaked onto a solid LB medium plate containing 34 mg/L chloramphenicol, followed by static culture for 12 h at 37° C.

2. After completion of step 1, a bacterial lawn on the plate is picked and seeded into 3 mL of a liquid LB medium, followed by shaking culture for 12 h at 37° C., 220 rpm, and a seed solution is obtained.

3. After completion of step 2, the seed solution is seeded into 30 mL of a fermentation medium in a seeding amount of 3%, followed by shaking culture at 37° C., 220 rpm.

The fermentation medium is: glucose 20.0 g/L, yeast powders 2.0 g/L, peptone 4 g/L, ammonium sulfate 6.0 g/L, potassium dihydrogen phosphate 2.0 g/L, magnesium sulfate heptahydrate 1.0 g/L, betaine 1.0 g/L, calcium carbonate 15.0 g/L, microelement mixture 1 mL/L, and water as the remainder.

The microelement mixture is: $FeSO_4 \cdot 7H_2O$ 10 g/L, $CaCl_2$ 1.35 g/L, $ZnSO_4 \cdot 7H_2O$ 2.25 g/L, $MnSO_4 \cdot 4H_2O$ 0.5 g/L, $CuSO_4 \cdot 5H_2O$ 1 g/L, $(NH_4)_6Mo_7O_{24} \cdot 4H_2O$ 0.106 g/L, $Na_2B_4O_7 \cdot 10H_2O$ 0.23 g/L, $CoCl_2 \cdot 6H_2O$ 0.48 g/L, 35% HCl 10 mL/L, and water as the remainder.

During the culture, ammoniacal liquor is used to adjust the pH value of the reaction system to make it maintain at 6.8-7.0.

During the culture, sampling is made once every 3-4 h to detect the content of glucose by using a biosensor analyzer SBA-40D. When the content of glucose in the system is less than 5 g/L, glucose is supplemented to make the concentration of glucose in the system up to 10 g/L.

Sampling is made after culture for 12 h and 48 h respectively, followed by centrifugation at 12,000 g for 2 min. The supernatant is taken for detection of the concentration of L-alanine.

Figure 2:
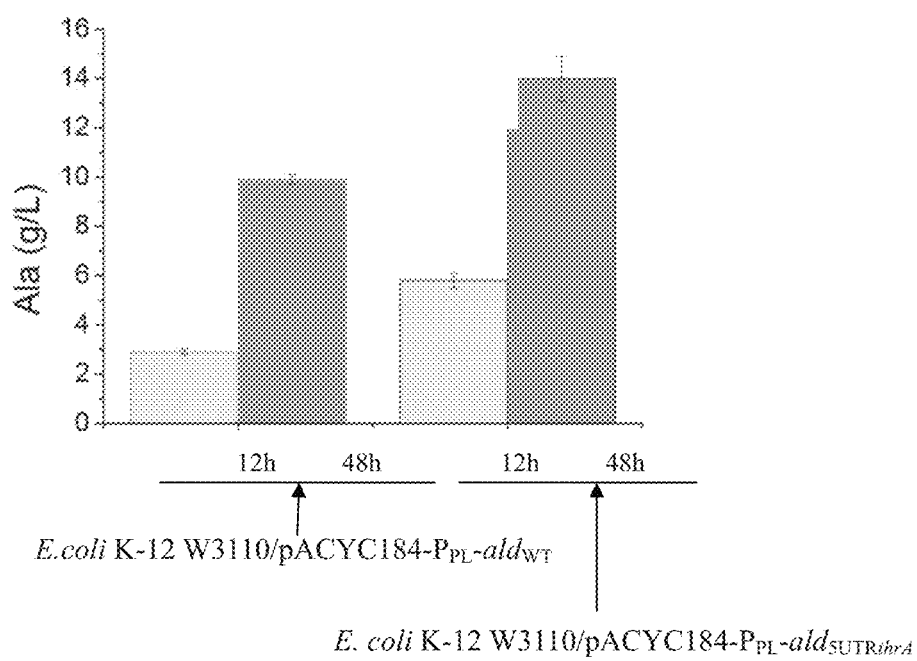
FIG. 2 shows the yield of L-alanine fermented by the engineered bacteria in a shake flask in Example 4.

After culture for 12 h and 48 h, the concentrations of L-alanine in the fermented supernatants are shown in FIG. 2 and Table 3 (by a mean±standard deviation from repeated tests in triplicate).

TABLE 3

| | Concentritions of L-alanine in fermented supernatant (g/L) | |
|---|---|---|
| | culture for 12 h | culture for 48 h |
| E. coli K-12 W3110/pACYC184-$P_{PL}$-ald$_{WT}$ | 2.9 ± 0.1 | 9.9 ± 0.2 |
| E. coli K-12 W3110/pACYC184-$P_{PL}$-ald$_{5UTRthrA}$ | 5.8 ± 0.3 | 14.0 ± 0.9 |
| E. coli K-12 W3110/pACYC184 | 0.4 ± 0.1 | 0.5 ± 0.1 |

After culture for 12 h, the concentration of L-alanine prepared by using the engineered bacteria E. coli K-12 W3110/pACYC184-$P_{PL}$-ald$_{5UTRthrA}$ with regulation of the expression of the ald gene by the 5'-untranslated region expressing element as screened by the present invention is improved by 98.6%, compared with that of the control strain E. coli K-12 W3110/pACYC184-$P_{PL}$-ald$_{WT}$. After culture for 48 h, the concentration of L-alanine prepared by using the engineered bacteria E. coli K-12 W3110/pACYC184-$P_{PL}$-ald$_{5UTRthrA}$ with regulation of the expression of the ald gene by the 5'-untranslated region expressing element as screened by the present invention is improved by 40.8%, compared with that of the control strain E. coli K-12 W3110/pACYC184-$P_{PL}$-ald$_{WT}$. These demonstrate that using the 5'-untranslated region expressing element provided by the present invention can significantly improve the fermentation yield of alanine.

A method for detecting the content of L-alanine in fermented broth is: HPLC, which is optimized based on the method for detecting amino acids in a reference (Amino Acids & Biotic Resources, 2000, 22, 59-60), and the method is particularly presented as follows (HPLC coupled to pre-column derivatization with 2, 4-dinitrofluorobenzene (FDBN)):

First, 10 μL of the supernatant is taken into a 2 mL centrifuge tube, into which 200 μL of 0.5M $NaHCO_3$ aqueous solution and 100 μL of 1% (v/v) FDBN-acetonitrile solution are added. Next, the centrifuge tube is placed in a water bath to be heated at a constant temperature of 60° C. for 60 min in the dark, then cooled to the room temperature, into which 700 μL of 0.04 mol/L $KH_2PO_4$ aqueous solution (pH=7.2±0.05; the pH is adjusted with 40 g/L KOH aqueous solution) is added, and shaken well. After being static for 15 min, filtration is performed and filtrates are collected. The filtrates are for injection, and injection volume is 15 μL.

C18 column (ZORBAX Eclipse XDB-C18, 4.6*150 mm, Agilent, USA) is used as the chromatographic column; column temperature: 40° C.; UV detection wavelength: 360 nm; mobile phase A: 0.04 mol/L $KH_2PO_4$ aqueous solution (pH=7.2±0.05; the pH is adjusted with 40 g/100 mL KOH aqueous solution), mobile phase B: 55% (v/v) acetonitrile aqueous solution, and total flux of the mobile phases: 1 mL/min.

The process of elution is presented as follows: at the starting time of elution (0 min), the mobile phase A accounts for 86% by volume of the total flux of the mobile phases, and mobile phase B for 14%; the process of elution is divided into 4 stages, and in each stage, parts by volume of the mobile phase A and the mobile phase B accounting for the total flux of the mobile phases appear a linear variation; when the first stage (a total duration of 2 min from the starting time) ends, the mobile phase A accounts for 88% by volume of the total flux of the mobile phases, and mobile phase B for 12%; when the second stage (a total duration of 2 min from the ending time for the first stage) ends, the mobile phase A accounts for 86% by volume of the total flux of the mobile phases, and mobile phase B for 14%; when the third stage (a total duration of 6 min from the ending time for the second stage) ends, the mobile phase A accounts for 70% by volume of the total flux of the mobile phases, and the mobile phase B for 30%; when the fourth stage (a total duration of 10 min from the ending time for the third stage) ends, the mobile phase A accounts for 30% by volume of the total flux of the mobile phases, and mobile phase B for 70%.

A standard curve is depicted by using the commercially available L-alanine as the standard, and the concentration of L-alanine in a sample is calculated.

Example 5. Preparation of Threonine

I. Preparation of thrA Mutant Gene

1. A PCR amplification product is obtained by performing a PCR amplification using the genome of the *E. coli* K12 W3110 as a template and using a primer pair comprised of WY914 and WY926.

2. A PCR amplification product is obtained by performing a PCR amplification using the genome of the *E. coli* K12 W3110 as a template and using a primer pair comprised of WY925 and WY832.

3. A PCR amplification product is obtained by performing a PCR amplification using a mixture of the PCR amplification product obtained in step 1 and the PCR amplification product obtained in step 2 as a template and using a primer pair comprised of WY914 and WY832.

After sequencing, the nucleotides between the recognition sites for enzymatic cleavage by restriction endonucleases Hind III and EcoR V of the PCR amplification product obtained in step 3 are shown by positions 172-5132 of SEQ ID No: 20 of the sequence listing. In SEQ ID No: 20 of the sequence listing, the nucleotides at positions 337-2799 code for the ThrA*protein; the nucleotides at positions 2801-3733 code for the ThrB protein; and the nucleotides at positions 3734-5020 code for the ThrC protein. The ThrA*protein (a mutant protein) is shown by SEQ ID No: 21 of the sequence listing. As compared with the ThrA protein (a wild-type protein), the mutant protein only differs in one amino acid residue, that is, the amino acid residue at position 253 is mutated to histidine from glutamic acid. The ThrB protein is shown by SEQ ID No: 22 of the sequence listing. The ThrC protein is shown by SEQ ID No: 23 of the sequence listing.

```
WY914: CCCAAGCTTACAGAGTACACAACATCCATG;
WY925:

GAAGTCGATGTCCTACCAGCATGCGATGGAGCTTTCCTAC;

WY926:

GTAGGAAAGCTCCATCGCATGCTGGTAGGACATCGACTTC;

WY832: CCCGATATCGCATTTATTGAGAATTTCTCC.
```

II. Construction of Recombinant Plasmid Having the thrA Mutant Gene

1. The vector backbone (about 4.2 kb) of the recombinant plasmid pACYC184-P$_{PL}$, after being subjected to a double enzymatic cleavage using the restriction endonucleases Hind III and EcoR V, is recovered.

2. The enzymatically cleaved product of the PCR amplification product obtained in 3 of step I, after being subjected to a double enzymatic cleavage using the restriction endonucleases Hind III and EcoR V, is recovered.

3. A recombinant plasmid pACYC184-P$_{PL}$-thrLA*BC914 is obtained by linking the vector backbone in step 1 and the enzymatically cleaved product in step 2. According to the sequencing result, a structural description for the recombinant plasmid pACYC184-P$_{PL}$-thrLA*BC914 is set forth as follows: a specific DNA molecule I is inserted between the enzymatic cleavage sites of Xba I and EcoR V of the plasmid pACYC184; and the specific DNA molecule I sequentially consists, from upstream to downstream, of the following elements: the promoter P$_{PL}$ shown by SEQ ID No: 13 of the sequence listing, a recognition sequence for enzymatic cleavage by restriction endonuclease Hind III, and a DNA molecule shown by the nucleotides at positions 172-5132 of SEQ ID No: 20 of the sequence listing.

4. Preparation of recombinant plasmid pACYC184-P$_{PL}$-thrLA*BC1630. According to the sequencing result, a structural description for the recombinant plasmid pACYC184-P$_{PL}$-thrLA*BC1630 is set forth as follows: a specific DNA molecule II is inserted between the enzymatic cleavage sites of Xba I and EcoR V of the plasmid pACYC184; and the specific DNA molecule II sequentially consists, from upstream to downstream, of the following elements: the promoter P$_{PL}$ shown by SEQ ID No: 13 of the sequence listing, a recognition sequence for enzymatic cleavage by restriction endonuclease Hind III, and a DNA molecule shown by the nucleotides at positions 198-5132 of SEQ ID No: 20 of the sequence listing.

5. Preparation of recombinant plasmid pACYC184-P$_{PL}$-thrLA*BC1629. According to the sequencing result, a structural description for the recombinant plasmid pACYC184-P$_{PL}$-thrLA*BC1629 is set forth as follows: a specific DNA molecule III is inserted between the enzymatic cleavage sites of Xba I and EcoR V of the plasmid pACYC184; and the specific DNA molecule III sequentially consists, from upstream to downstream, of the following elements: the promoter P$_{PL}$ shown by SEQ ID No: 13 of the sequence listing, a recognition sequence for enzymatic cleavage by restriction endonuclease Hind III, and a DNA molecule shown by the nucleotides at positions 236-5132 of SEQ ID No: 20 of the sequence listing.

6. Preparation of recombinant plasmid pACYC184-P$_{PL}$-thrLA*BC1628. According to the sequencing result, a structural description for the recombinant plasmid pACYC184-P$_{PL}$-thrLA*BC1628 is set forth as follows: a specific DNA molecule IV is inserted between the enzymatic cleavage sites of Xba I and EcoR V of the plasmid pACYC184; and the specific DNA molecule IV sequentially consists, from upstream to downstream, of the following elements: the promoter P$_{PL}$ shown by SEQ ID No: 13 of the sequence listing, a recognition sequence for enzymatic cleavage by restriction endonuclease Hind III, and a DNA molecule shown by the nucleotides at positions 256-5132 of SEQ ID No: 20 of the sequence listing.

7. Preparation of recombinant plasmid pACYC184-P$_{PL}$-thrLA*BC1627. According to the sequencing result, a structural description for the recombinant plasmid pACYC184-

P$_{PL}$-thrLA*BC1627 is set forth as follows: a specific DNA molecule V is inserted between the enzymatic cleavage sites of Xba I and EcoR V of the plasmid pACYC184; and the specific DNA molecule V sequentially consists, from upstream to downstream, of the following elements: the promoter P$_{PL}$ shown by SEQ ID No: 13 of the sequence listing, a recognition sequence for enzymatic cleavage by restriction endonuclease Hind III, and a DNA molecule shown by the nucleotides at positions 294-5132 of SEQ ID No: 20 of the sequence listing.

8. Preparation of recombinant plasmid pACYC184-P$_{PL}$-thrLA*BC913. According to the sequencing result, a structural description for the recombinant plasmid pACYC184-P$_{PL}$-thrLA*BC913 is set forth as follows: a specific DNA molecule VI is inserted between the enzymatic cleavage sites of Xba I and EcoR V of the plasmid pACYC184; and the specific DNA molecule VI sequentially consists, from upstream to downstream, of the following elements: the promoter P$_{PL}$ shown by SEQ ID No: 13 of the sequence listing, a recognition sequence for enzymatic cleavage by restriction endonuclease Hind III, and a DNA molecule shown by the nucleotides at positions 310-5132 of SEQ ID No: 20 of the sequence listing.

III. Construction of Recombinant Bacteria

Recombinant bacteria is obtained by introducing pACYC184-P$_{PL}$-thrLA*BC914 into E. coli K-12 W3110ΔmetAΔilvAΔlysAΔtdhΔtdcCΔsstT, and named as TA914.

Recombinant bacteria is obtained by introducing pACYC184-P$_{PL}$-thrLA*BC1630 into E. coli K-12 W3110ΔmetAΔilvAΔlysAΔtdhΔtdcCΔsstT, and named as TA1630.

Recombinant bacteria is obtained by introducing pACYC184-P$_{PL}$-thrLA*BC1629 into E. coli K-12 W3110ΔmetA ΔilvAΔlysAΔtdhΔtdcCΔsstT, and named as TA1629.

Recombinant bacteria is obtained by introducing pACYC184-P$_{PL}$-thrLA*BC1628 into E. coli K-12 W3110ΔmetAΔilvAΔlysAΔtdhΔtdcCΔsstT, and named as TA1628.

Recombinant bacteria is obtained by introducing pACYC184-P$_{PL}$-thrLA*BC1627 into E. coli K-12 W3110ΔmetA ΔilvAΔlysAΔtdhΔtdcCΔsstT, and named as TA1627.

Recombinant bacteria is obtained by introducing pACYC184-P$_{PL}$-thrLA*BC913 into E. coli K-12 W3110ΔmetAΔilvAΔlysAΔtdhΔtdcCΔsstT, and named as TA913.

Recombinant bacteria is obtained by introducing pACYC184 plasmid into E. coli K-12 W3110ΔmetAΔilvAΔlysAΔtdhΔtdcCΔsstT, and named as TA control.

IV. Fermentation Test of Engineered Bacteria for Threonine in a Shake Flask

The test strain is: TA914, TA1630, TA1629, TA1628, TA1627, TA913 or the TA control.

1. The test strain is streaked onto a solid LB medium plate containing 34 mg/L chloramphenicol, followed by static culture for 12 h at 37° C.

2. After completion of step 1, a bacterial lawn on the plate is picked and seeded onto a LB medium slant, followed by static culture for 10-12 h at 37° C.

3. After completion of step 2, a bacterial lawn on the plate is picked and seeded into a liquid LB medium, followed by shaking culture for 12 h at 37° C., 220 rpm.

4. After completion of step 3, the seed solution is seeded into a fermentation medium in a seeding amount of 3%, followed by shaking culture at 37° C., 220 rpm.

The fermentation medium is: glucose 20.0 g/L, ammonium sulfate 15.0 g/L, potassium dihydrogen phosphate 2.0 g/L, magnesium sulfate heptahydrate 2.0 g/L, yeast powders 2.0 g/L, isoleucine 0.6 g/L, methionine 0.6 g/L, lysinehydrochloride 1.2 g/L, calcium carbonate 15.0 g/L, microelement mixture 5 mL/L, and water as the remainder.

The microelement mixture is: FeSO$_4$.7H$_2$O 10 g/L, CaCl$_2$1.35 g/L, ZnSO$_4$.7H$_2$O 2.25 g/L, MnSO$_4$.4H$_2$O 0.5 g/L, CuSO$_4$.5H$_2$O 1 g/L, (NH$_4$)$_6$Mo$_7$O$_{24}$.4H$_2$O 0.106 g/L, Na$_2$B$_4$O$_7$-10H$_2$O 0.23 g/L, CoCl$_2$.6H$_2$O 0.48 g/L, 35% HCl 10 mL/L, and water as the remainder.

During the culture, ammoniacal liquor is used to adjust the pH value of the reaction system to make it maintain at 6.8-7.0.

During the culture, sampling is made once every 3-4 h to detect the content of glucose by using a biosensor analyzer SBA-40D. When the content of glucose in the system is less than 5 g/L, glucose is supplemented to make the concentration of glucose in the system up to 10 g/L.

Sampling is made after culture for 24 h, followed by centrifugation at 12,000 g for 2 min. The supernatant is taken for detection of the concentration of threonine.

The results are shown in Table 4 (by a mean±standard deviation from repeated tests in triplicate). TA1627 has the highest capability for producing threonine, and the concentration of threonine in the fermented supernatant is up to 9.52±1.35.

TABLE 4

| | Concentritions of threonine in fermented supernatant (g/L) |
|---|---|
| TA913 | 5.46 ± 0.53 |
| TA914 | 6.11 ± 0.41 |
| TA1627 | 9.52 ± 1.35 |
| TA1628 | 0.57 ± 0.11 |
| TA1629 | 2.22 ± 0.03 |
| TA1630 | 3.15 ± 0.35 |
| TA control | 0.21 ± 0.07 |

A method for detecting the concentration of threonine is: HPLC, which is optimized based on the method for detecting amino acids in a reference (Amino Acids & Biotic Resources, 2000, 22, 59-60), and the method is particularly presented as follows (HPLC coupled to pre-column derivatization with 2, 4-dinitrofluorobenzene (FDBN)):

First, 10 μL of the supernatant is taken into a 2 mL centrifuge tube, into which 200 μL of 0.5M NaHCO$_3$ aqueous solution and 100 μL of 1% (v/v) FDBN-acetonitrile solution are added. Next, the centrifuge tube is placed in a water bath to be heated at a constant temperature of 60° C. for 60 min in the dark, then cooled to the room temperature, into which 700 μL of 0.04 mol/L KH$_2$PO$_4$ aqueous solution (pH=7.2±0.05; the pH is adjusted with 40 g/L KOH aqueous solution) is added, and shaken well. After being static for 15 min, filtration is performed and filtrates are collected. The filtrates are for injection, and injection volume is 15 μL.

C18 column (ZORBAX Eclipse XDB-C18, 4.6*150 mm, Agilent, USA) is used as the chromatographic column; column temperature: 40° C.; UV detection wavelength: 360 nm; mobile phase A: 0.04 mol/L KH$_2$PO$_4$ aqueous solution (pH=7.2±0.05; the pH is adjusted with 40 g/100 mL KOH aqueous solution), mobile phase B: 55% (v/v) acetonitrile aqueous solution, and total flux of the mobile phases: 1 mL/min.

The process of elution is presented as follows: at the starting time of elution (0 min), the mobile phase A accounts for 86% by volume of the total flux of the mobile phases, and mobile phase B for 14%; the process of elution is divided into 4 stages, and in each stage, parts by volume of the mobile phase A and the mobile phase B accounting for the total flux of the mobile phases appear a linear variation; when the first stage (a total duration of 2 min from the starting time) ends, the mobile phase A accounts for 88% by volume of the total flux of the mobile phases, and mobile phase B for 12%; when the second stage (a total duration of 2 min from the ending time for the first stage) ends, the mobile phase A accounts for 86% by volume of the total flux of the mobile phases, and mobile phase B for 14%; when the third stage (a total duration of 6 min from the ending time for the second stage) ends, the mobile phase A accounts for 70% by volume of the total flux of the mobile phases, and the mobile phase B for 30%; when the fourth stage (a total duration of 10 min from the ending time for the third stage) ends, the mobile phase A accounts for 30% by volume of the total flux of the mobile phases, and mobile phase B for 70%.

A standard curve is depicted by using the commercially available L-threonine as the standard (available from Sigma, designated as Item No. 8917), and the concentration of threonine in a sample is calculated.

Example 6. Construction of E. coli K-12 W3110ΔmetAΔlysAΔtdhΔtdcC

Chassis engineered bacteria is obtained by sequentially knocking out the metA gene (a gene coding for homoserine transsuccinylase), the lysA gene (a gene coding for diaminopimelic acid decarboxylase), the tdh gene (a gene coding for threonine dehydratase) and the tdcC gene (a gene coding for threonine absortion and transport protein), with the E. coli K12 W3110 as the starting bacteria strain, and named as E. coli K-12 W3110ΔmetAΔlysAΔtdhΔtdcC.

1. Knockout of the metA Gene (1) A DNA fragment I-A (a region upstream of the metA gene) is obtained by performing a PCR amplification using the genome DNA of the E. coli K12 W3110 as a template and using a primer pair comprised of WY569 and WY570.

(2) A DNA fragment I-B (a region downstream of the metA gene) is obtained by performing a PCR amplification using the genome DNA of the E. coli K12 W3110 as a template and using a primer pair comprised of WY571 and WY572.

(3) A DNA fragment I-C is obtained by performing a PCR amplification using a mixture of the DNA fragment I-A and the DNA fragment I-B as a template and using a primer pair comprised of WY569 and WY572.

(4) The vector backbone (about 5.6 kb) of the plasmid pKOV, after being subjected to a double enzymatic cleavage using the restriction endonucleases Sal I and Not I, is recovered.

(5) The enzymatically cleaved product of the DNA fragment I-C, after being subjected to a double enzymatic cleavage using the restriction endonucleases Sal I and Not I, is recovered.

(6) A recombinant plasmid I is obtained by linking the vector backbone obtained in step (4) and the enzymatically cleaved product obtained in step (5). According to the sequencing result, a structural description for the recombinant plasmid I is set forth as follows: the following specific DNA molecule is inserted between the enzymatic cleavage sites of Sal I and Not I of the plasmid pKOV: sequentially consisting, from upstream to downstream, of the upstream section shown by the nucleotides at positions 245-751 of SEQ ID No: 1 of the sequence listing and the downstream section shown by the nucleotides at positions 1682-2154 of SEQ ID No: 1 of the sequence listing. The metA gene is shown by SEQ ID No: 1 of the sequence listing, wherein the open reading frame is shown by the nucleotides at positions 752-1681 (coding for the metA protein shown by SEQ ID No: 2 of the sequence listing).

(7) Recombinant bacteria with metA gene knocked out are obtained by introducing the recombinant plasmid I into the E. coli K12 W3110 and named as E. coli K12 W3110ΔmetA.

A method for identyfing the recombinant bacteria with metA gene knocked out is that: a PCR amplification is performed using a primer pair comprised of WY583 and WY584; if an amplification product with 1375 bp is obtained, the recombinant bacteria preliminarily can be determined as a candidate for the target bacteria; and sequencing will be further performed to verify that the open reading frame of the metA gene on the chromosomes of the bacteria has been knocked out.

2. Knockout of the lysA Gene (1) A DNA fragment III-A (a region upstream of the lysA gene) is obtained by performing a PCR amplification using the genome DNA of the E. coli K12 W3110 as a template and using a primer pair comprised of WY573 and WY574.

(2) A DNA fragment III-B (a region downstream of the lysA gene) is obtained by performing a PCR amplification using the genome DNA of the E. coli K12 W3110 as a template and using a primer pair comprised of WY575 and WY576.

(3) A DNA fragment III-C is obtained by performing a PCR amplification using a mixture of the DNA fragment III-A and the DNA fragment III-B as a template and using a primer pair comprised of WY573 and WY576.

(4) The vector backbone (about 5.6 kb) of the plasmid pKOV, after being subjected to a double enzymatic cleavage using the restriction endonucleases BamH I and Not I, is recovered.

(5) The enzymatically cleaved product of the DNA fragment III-C, after being subjected to a double enzymatic cleavage using the restriction endonucleases BamH I and Not I, is recovered.

(6) A recombinant plasmid III is obtained by linking the vector backbone obtained in step (4) and the enzymatically cleaved product obtained in step (5). According to the sequencing result, a structural description for the recombinant plasmid III is set forth as follows: the following specific DNA molecule is inserted between the enzymatic cleavage sites of BamH I and Not I of the plasmid pKOV: sequentially consisting, from upstream to downstream, of the upstream section shown by the nucleotides at positions 132-638 of SEQ ID No: 5 of the sequence listing and the downstream section shown by the nucleotides at positions 1902-2445 of SEQ ID No: 5 of the sequence listing. The lysA gene is shown by SEQ ID No: 5 of the sequence listing, wherein the open reading frame is shown by the nucleotides at positions 639-1901 (coding for the lysA protein shown by SEQ ID No: 6 of the sequence listing).

(7) Recombinant bacteria with lysA gene knocked out are obtained by introducing the recombinant plasmid III into the E. coli K-12 W3110ΔmetA, and named as E. coli K-12 W3110ΔmetAΔlysA.

A method for identyfing the recombinant bacteria with lysA gene knocked out is that: a PCR amplification is performed using a primer pair comprised of WY585 and WY586; if an amplification product with 1302 bp is obtained, the recombinant bacteria preliminarily can be determined as a candidate for the target bacteria; and sequencing will be further performed to verify that the open reading frame of the lysA gene on the chromosomes of the bacteria has been knocked out.

3. Knockout of the Tdh Gene (1) A DNA fragment IV-A (a region upstream of the tdh gene) is obtained by performing a PCR amplification using the genome DNA of the *E. coli* K12 W3110 as a template and using a primer pair comprised of WY598 and WY599.

(2) A DNA fragment IV-B (a region downstream of the tdh gene) is obtained by performing a PCR amplification using the genome DNA of the *E. coli* K12 W3110 as a template and using a primer pair comprised of WY600 and WY601.

(3) A DNA fragment IV-C is obtained by performing a PCR amplification using a mixture of the DNA fragment IV-A and the DNA fragment IV-B as a template and using a primer pair comprised of WY598 and WY601.

(4) The vector backbone (about 5.6 kb) of the plasmid pKOV, after being subjected to a double enzymatic cleavage using the restriction endonucleases BamH I and Not I, is recovered.

(5) The enzymatically cleaved product of the DNA fragment IV-C, after being subjected to a double enzymatic cleavage using the restriction endonucleases BamH I and Not I, is recovered.

(6) A recombinant plasmid IV is obtained by linking the vector backbone obtained in step (4) and the enzymatically cleaved product obtained in step (5). According to the sequencing result, a structural description for the recombinant plasmid IV is set forth as follows: the following specific DNA molecule is inserted between the enzymatic cleavage sites of BamH I and Not I of the plasmid pKOV: sequentially consisting, from upstream to downstream, of the upstream section shown by the nucleotides at positions 227-752 of SEQ ID No: 7 of the sequence listing and the downstream section shown by the nucleotides at positions 1779-2271 of SEQ ID No: 7 of the sequence listing. The tdh gene is shown by SEQ ID No: 7 of the sequence listing, wherein the open reading frame is shown by the nucleotides at positions 753-1778 (coding for the tdh protein shown by SEQ ID No: 8 of the sequence listing).

(7) Recombinant bacteria with tdh gene knocked out are obtained by introducing the recombinant plasmid IV into the *E. coli* K-12 W3110ΔmetAΔlysA, and named as *E. coli* K-12 W3110ΔmetAΔlysAΔtdh.

A method for identyfing the recombinant bacteria with tdh gene knocked out is that: a PCR amplification is performed using a primer pair comprised of WY602 and WY603; if an amplification product with 1434 bp is obtained, the recombinant bacteria preliminarily can be determined as a candidate for the target bacteria; and sequencing will be further performed to verify that the open reading frame of the tdh gene on the chromosomes of the bacteria has been knocked out.

4. Knockout of the tdcC Gene (1) A DNA fragment V-A (a region upstream of the tdcC gene) is obtained by performing a PCR amplification using the genome DNA of the *E. coli* K12 W3110 as a template and using a primer pair comprised of WY476 and WY477.

(2) A DNA fragment V-B (a region downstream of the tdcC gene) is obtained by performing a PCR amplification using the genome DNA of the *E. coli* K12 W3110 as a template and using a primer pair comprised of WY478 and WY479.

(3) A DNA fragment V-C is obtained by performing a PCR amplification using a mixture of the DNA fragment V-A and the DNA fragment V-B as a template and using a primer pair comprised of WY476 and WY479.

(4) The vector backbone (about 5.6 kb) of the plasmid pKOV, after being subjected to a double enzymatic cleavage using the restriction endonucleases BamH I and Not I, is recovered.

(5) The enzymatically cleaved product of the DNA fragment V-C, after being subjected to a double enzymatic cleavage using the restriction endonucleases BamH I and Not I, is recovered.

(6) A recombinant plasmid V is obtained by linking the vector backbone obtained in step (4) and the enzymatically cleaved product obtained in step (5). According to the sequencing result, a structural description for the recombinant plasmid V is set forth as follows: the following specific DNA molecule is inserted between the enzymatic cleavage sites of BamH I and Not I of the plasmid pKOV: sequentially consisting, from upstream to downstream, of the upstream section shown by the nucleotides at positions 176-700 of SEQ ID No: 9 of the sequence listing and the downstream section shown by the nucleotides at positions 1853-2388 of SEQ ID No: 9 of the sequence listing. The tdcC gene is shown by SEQ ID No: 9 of the sequence listing, wherein the open reading frame is shown by the nucleotides at positions 701-2032 (coding for the tdcC protein shown by SEQ ID No: 10 of the sequence listing).

(7) Recombinant bacteria with tdcC gene knocked out are obtained by introducing the recombinant plasmid V into the *E. coli* K-12 W3110ΔmetAΔlysAΔtdh, and named as *E. coli* K-12 W3110ΔmetAΔlysAΔtdhΔtdcC.

A method for identyfing the recombinant bacteria with tdcC gene knocked out is that: a PCR amplification is performed using a primer pair comprised of WY497 and WY498; if an amplification product with 1453 bp is obtained, the recombinant bacteria preliminarily can be determined as a candidate for the target bacteria; and sequencing will be further performed to verify that the following section of the tdcC gene on the chromosomes of the bacteria has been knocked out: the nucleotides at positions 701-1852 of SEQ ID No: 9.

Each of the primer sequences used in the examples is set forth as follows (5'→3'):

WY569: GCGTCGACATAGAACCCAACCGCCTGCTCA;

WY570: AACGATCGACTATCACAGAAGAAACCTGATTACCTCACTACATA;

WY571: TATGTAGTGAGGTAATCAGGTTTCTTCTGTGATAGTCGATCGTT;

WY572: ATTGCGGCCGCCCGAAATAAAATCAGGCAACGT;

WY583: CGTTAATGAAATATCGCCAG;

WY584: TCGAAATCGGCCATAAAGAC.

WY573: CGCGGATCCGGCACGATATTTAAGCTGAC;

WY574: CAACCAGCGACTAACCGCAGAACAAACTCCAGATAAGTGC;

WY575: GCACTTATCTGGAGTTTGTTCTGCGGTTAGTCGCTGGTTG;

WY576: ATTGCGGCCGCGCTGGCAACGCGTCATTTAA;

WY585: GTAACACACACACTTCATCT;

WY586: GATCCCGGATGCTGATTTAG.

-continued

```
WY598: CGCGGATCCATACTGCGATGTGATGGGCC;

WY599: AATACCAGCCCTTGTTCGTGCTCACATCCTCAGGCGATAA;

WY600: TTATCGCCTGAGGATGTGAGCACGAACAAGGGCTGGTATT;

WY601: ATTGCGGCCGCCGTTGCCACTTCAATCCCAC;

WY602: GCTATGCCAACAACGATATG;

WY603: GGTTAATACGCCGGTTGAGC.

WY476: CGCGGATCCGGAACGATTGGTCTGGAAAT;

WY477: GGCTTCAATCAGGTCAAGGATATCCTATCCTCAACGAATTA;

WY478: TAATTCGTTGAGGATAGGATATCCTTGACCTGATTGAAGCC;

WY479: ATTGCGGCCGCCGCGACGGATATTATCAATGAC;

WY497: GCGCCAAAATCCAAAGTAGC;

WY498: ATGTGCGCGCTGGGAAACAT.
```

Example 7. Preparation of Isoleucine

I. Preparation of a Threonine Operon Having the thrA Mutant Gene

1. A PCR amplification product is obtained by performing a PCR amplification using the genome of the E. coli K12 W3110 as a template and using a primer pair comprised of WY914 and WY926.

```
WY914: CCCAAGCTTACAGAGTACACAACATCCATG;

WY926:

GTAGGAAAGCTCCATCGCATGCTGGTAGGACATCGACTTC.
```

2. A PCR amplification product is obtained by performing a PCR amplification using the genome of the E. coli K12 W3110 as a template and using a primer pair comprised of WY925 and WY832.

```
WY925:

GAAGTCGATGTCCTACCAGCATGCGATGGAGCTTTCCTAC;

WY832: CCCGATATCGCATTTATTGAGAATTTCTCC.
```

3. A PCR amplification product is obtained by performing a PCR amplification using a mixture of the PCR amplification product obtained in step 1 and the PCR amplification product obtained in step 2 as a template and using a primer pair comprised of WY914 and WY832.

After sequencing, the nucleotides between the recognition sites for enzymatic cleavage by Hind III and EcoR V of the PCR amplification product obtained in step 3 are shown by SEQ ID NOs: 172-5132 of SEQ ID No: 20 of the sequence listing. In SEQ ID No: 20 of the sequence listing, the nucleotides at positions 337-2799 code for the ThrA*protein; the nucleotides at positions 2801-3733 code for the ThrB protein; and the nucleotides at positions 3734-5020 code for the ThrC protein. The ThrA*protein (a mutant protein) is shown by SEQ ID No: 21 of the sequence listing. As compared with the ThrA protein (a wild-type protein), the mutant protein only differs in one amino acid residue, that is, the amino acid residue at position 253 is mutated to histidine from glutamic acid. The ThrB protein is shown by SEQ ID No: 22 of the sequence listing. The ThrC protein is shown by SEQ ID No: 23 of the sequence listing.

II. Construction of the Recombinant Plasmid pACYC184-$P_{PL}$

1. The double-stranded DNA molecule (the promoter $P_{PL}$) shown by SEQ ID No: 13 of the sequence listing is synthesized.

2. A PCR amplification product is obtained by performing a PCR amplification using the double-stranded DNA molecule prepared in step 1 as a template and using a primer pair comprised of WY843 and WY842.

```
WY843: TGCTCTAGACAATTCCGACGTCTAAGAAA;

WY842: CCCAAGCTTGGTCAGTGCGTCCTGCTGAT.
```

3. The enzymatically cleaved product of the PCR amplification product obtained in step 2, after being subjected to a double enzymatic cleavage using the restriction endonucleases Xba I and Hind III, is recovered.

4. The vector backbone (about 4.1 kb) of the plasmid pACYC184, after being subjected to a double enzymatic cleavage using the restriction endonucleases Xba I and Hind III, is recovered.

5. A recombinant plasmid pACYC184-$P_{PL}$ is obtained by linking the enzymatically cleaved product in step 3 and the vector backbone in step 4.

III. Construction of a Recombinant Plasmid Having a Threonine Operon Comprising the thrA Mutant Gene 1. The vector backbone (about 4.2 kb) of the recombinant plasmid pACYC184-$P_{PL}$, after being subjected to a double enzymatic cleavage using the restriction endonucleases Hind III and EcoR V, is recovered.

2. The enzymatically cleaved product of the PCR amplification product obtained in 3 of step I, after being subjected to a double enzymatic cleavage using the restriction endonucleases Hind III and EcoR V, is recovered.

3. A recombinant plasmid pACYC184-$P_{PL}$-thrLA*BC914 is obtained by linking the vector backbone in step 1 and the enzymatically cleaved product in step 2. According to the sequencing result, a structural description for the recombinant plasmid pACYC184-$P_{PL}$-thrLA*BC914 is set forth as follows: a specific DNA molecule is inserted between the enzymatic cleavage sites of Xba I and EcoR V of the plasmid pACYC184; and the specific DNA molecule sequentially consists, from upstream to downstream, of the following elements: the promoter $P_{PL}$ shown by SEQ ID No: 13 of the sequence listing, a recognition sequence for enzymatic cleavage by restriction endonuclease Hind III, and the DNA molecule shown by the nucleotides at positions 172-5132 of SEQ ID No: 20 of the sequence listing.

IV. Construction of an Integrated Plasmid of Threonine Operon at the lysA Site

1. A PCR amplification product (the upstream homology arm integrated at the lysA site) is obtained by performing a PCR amplification using the genome of the E. coli K12 W3110 as a template and using a primer pair comprised of WY970 and WY971.

```
WY970: AACTGCAGGGCACGATATTTAAGCTGAC;

WY971: GAAGATCTAACAAACTCCAGATAAGTGC.
```

2. The enzymatically cleaved product of the PCR amplification product obtained in step 1, after being subjected to a double enzymatic cleavage using the restriction endonucleases Pst I and Bgl II, is recovered.

3. The vector backbone of the plasmid pKOV, after being subjected to a double enzymatic cleavage using the restriction endonucleases Pst I and Bgl II, is recovered.

4. A recombinant plasmid pKOV-Up$_{lysA}$ is obtained by linking the enzymatically cleaved product in step 2 and the vector backbone in step 3.

5. A PCR amplification product (the downstream homology arm integrated at the lysA gene site) is obtained by performing a PCR amplification using the genome of the E. coli K12 W3110 as a template, and using a primer pair comprised of WY974 and WY975.

```
WY974: CGCGGATCCCTGCGGTTAGTCGCTGGTTG;

WY975: CTAGTCTAGAGCTGGCAACGCGTCATTTAA.
```

6. The enzymatically cleaved product of the PCR amplification product obtained in step 5, after being subjected to a double enzymatic cleavage using the restriction endonucleases BamH I and Xba I, is recovered.

7. The vector backbone of the recombinant plasmid pKOV-Up$_{lysA}$, after being subjected to a double enzymatic cleavage using the restriction endonucleases BamH I and Xba I, is recovered.

8. A recombinant plasmid pKOV-UP$_{lysA}$-Down$_{lysA}$ is obtained by linking the enzymatically cleaved product in step 6 and the vector backbone in step 7.

9. A PCR amplification product (a P$_{PL}$-thrA*BC fragment) is obtained by performing a PCR amplification using the recombinant plasmid pACYC184-P$_{PL}$-thrLA*BC914 as a template and using a primer pair comprised of WY978 and WY979.

```
WY978: GAAGATCTCAATTCCGACGTCTAAGAAA;

WY979: CGCGGATCCGCATTTATTGAGAATTTCTCC.
```

10. The enzymatically cleaved product of the PCR amplification product obtained in step 9, after being subjected to a double enzymatic cleavage using the restriction endonucleases Bgl II and BamH I, is recovered.

11. The vector backbone of the recombinant plasmid pKOV-UP$_{lysA}$-Down$_{lysA}$, after being subjected to a double enzymatic cleavage using the restriction endonucleases Bgl II and BamH I, is recovered.

12. A recombinant plasmid pKOV-UP$_{lysA}$-P$_{PL}$-thrA*BC-Down$_{lysA}$ is obtained by linking the enzymatically cleaved product in step 10 and the vector backbone in step 11.

According to the sequencing result, a structural description for the recombinant plasmid pKOV-UP$_{lysA}$-P$_{PL}$-thrA*BC-Down$_{lysA}$ is set forth as follows: a specific DNA molecule is inserted between the enzymatic cleavage sites of Pst I and Xba I of the plasmid pKOV; and the specific DNA molecule sequentially consists, from upstream to downstream, of the following elements: the upstream homology arm integrated at the lysA gene site shown by the nucleotides at positions 132-638 of SEQ ID No: 5 of the sequence listing, a recognition sequence for enzymatic cleavage by restriction endonuclease Bgl II, the promoter P$_{PL}$ shown by SEQ ID No: 13 of the sequence listing, a recognition sequence for enzymatic cleavage by restriction endonuclease Hind III, the DNA molecule shown by the nucleotides at positions 172-5132 of SEQ ID No: 20 of the sequence listing, a recognition sequence for enzymatic cleavage by restriction endonuclease BamH I, and the downstream homology arm integrated at the lysA gene site shown by the nucleotides at positions 1902-2445 of SEQ ID No: 5 of the sequence listing.

V. Construction of Engineered Bacteria Integrated with a Threonine Operon

Recombinant bacteria integrated with said specific DNA molecule in 3 of step III at the lysA gene site are obtained by introducing the recombinant plasmid pKOV-UP$_{lysA}$-P$_{PL}$-thrA*BC-Down$_{lysA}$ into the E. coli K-12 W3110ΔmetAΔlysAΔtdhΔtdcC, and named as recombinant bacteria E. coli W3110ΔmetAΔtdhΔtdcCΔlysA::P$_{PL}$-thrA*BC, referred to as recombinant bacteria EC272 for short.

A method for identifying the recombinant bacteria integrated with said specific DNA molecule in 3 of step III at the lysA gene site is that: a PCR identification is performed by using the primers WY585 and WY586; if an amplification product with 6443 bp is obtained, the recombinant bacteria preliminarily can be determined as a candidate for the target bacteria; and sequencing will be further performed for verification.

VI. Construction of EC272sstT::ilvA*-ilvC

1. Site-Directed Mutagenesis of the ilvA Gene

A PCR amplification product A1 is obtained by performing a PCR amplification using the genome DNA of the E. coli K12 MG1655 as a template and using a primer pair comprised of WY4027 and WY4028; a PCR amplification product A2 is obtained by performing a PCR amplification using the genome DNA of the E. coli K12 MG1655 as a template and using a primer pair comprised of WY4029 and WY4030; a PCR amplification product A3 is obtained by performing a PCR amplification using a mixture of the PCR amplification product A1 and the PCR amplification product A2 as a template and using a primer pair comprised of WY4027 and WY4030.

```
WY4027:

taatcatccggctcgtataatgtAACCGAGGAGCAGACAatg

GCTGACTCGCAACCCCT;

WY4028: CAGCGTGTTGGCGAAGCGCAGAAACGCGC;
WY4029: GCGCGTTTCTGCGCTTCGCCAACACGCTG;
WY4030: CTATATGACAGGAAATTTATTGCGGGCATTCTGGAAGATT
TTGC.
```

In the primers, the box denotes the RBS, and the undulating underline denotes a portion of sections of the promoter P$_{trc}$. The primers WY4028 and WY4029 introduce 4 point mutations: the nucleotide at position 1339 in the open reading frame of the ilvA gene is mutated to T from C, and the nucleotide at position 1341 is mutated to T from G, and the base at position 1351 is mutated to G from C, and the base at position 1352 is mutated to C from T. The ilvA gene after being introduced with the above 4 point mutations is named as ilvA*gene.

2. A PCR amplification product B1 is obtained by performing a PCR amplification using the genome DNA of the E. coli K12 MG1655 as a template and using a primer pair comprised of WY4025 and WY4026;

WY4025: CGCGGATCCgtgctgacctcaaacctgt;

WY4026: CTCGGTTACATTATACGAGCCGGATGATTAATTGTCAACGAT
CCTTTCATTGTGTTGTC.

3. A PCR amplification product C1 is obtained by performing a PCR amplification using a mixture of the PCR amplification product A3 obtained in step 1 and the PCR amplification product B1 obtained in step 2 as a template and using a primer pair comprised of WY4025 and WY4030.

4. A PCR amplification product B2 is obtained by performing a PCR amplification using the genome DNA of the E. coli K12 MG1655 as a template and using a primer pair comprised of WY4031 and WY4032.

WY4031:
GCAAAATCTTCCAGAATGCCCCGCAATAAATTTCCTGTCATATAG;

WY4032:
ACCGAACATATTACAGGCCAGCAAGGCCTTCTCCAGGAGAA.

5. A PCR amplification product B3 is obtained by performing a PCR amplification using the genome DNA of the E. coli K12 MG1655 as a template and using a primer pair comprised of WY4033 and WY4034.

WY4033:
TTCTCCTGGAGAAGGCCTTGctggcctgtaatatgttcggt;

WY4034:
ATTGCGGCCGCCTCGCGAAGTTCCATCATCCT.

6. A PCR amplification product C2 is obtained by performing a PCR amplification using a mixture of the PCR amplification product B2 obtained in step 4 and the PCR amplification product B3 obtained in step 5 as a template and using a primer pair comprised of WY4031 and WY4034.

7. A PCR amplification product D is obtained by performing an overlapping PCR using a mixture of the PCR amplification product C1 obtained in step 3 and the PCR amplification product C2 obtained in step 6 as a template and using a primer pair comprised of WY4025 and WY4034.

8. The enzymatically cleaved product of the PCR amplification product D obtained in step 7, after being subjected to a double enzymatic cleavage using the restriction endonucleases BamH I and Not I, is recovered.

9. The vector backbone of the plasmid pKOV, after being subjected to a double enzymatic cleavage using the restriction endonucleases BamH I and Not I, is recovered.

10. A recombinant plasmid pKOV-ilvA*-ilvC is obtained by linking the enzymatically cleaved product obtained in step 8 and the vector backbone obtained in step 9. According to the sequencing result, a structural description for the recombinant plasmid pKOV-ilvA*-ilvC is set forth as follows: a specific DNA molecule is inserted between the enzymatic cleavage sites of BamH I and Not I of the plasmid pKOV; and the specific DNA molecule sequentially consists, from upstream to downstream, of the following elements: the upstream arm shown by the nucleotides at positions 45-696 of SEQ ID No: 11 of the sequence listing, the promoter $P_{trc}$ "ttgacaattaatcatccggctcgtataatgt", the RBS sequence "AACCGAGGAGCAGACA" (SEQ ID NO: 173), the DNA molecule shown by SEQ ID No: 24 of the sequence listing (in SEQ ID No: 24, the ilvA*gene is shown by positions 1-1630, and the ilvC gene is shown by positions 1631-3275), and the downstream arm shown by the nucleotides at positions 1760-2240 of SEQ ID No: 11 of the sequence listing. The open reading frame of the ilvA*gene is shown by the nucleotides at positions 1-1545 of SEQ ID No: 24 of the sequence listing, coding for the IlvA*protein (a mutant protein) shown by SEQ ID No: 25 of the sequence listing. The open reading frame of the ilvC gene is shown by the nucleotides at positions 1717-3192 of SEQ ID No: 24 of the sequence listing, coding for the IlvC protein shown by SEQ ID No: 26 of the sequence listing. The sstT gene is shown by SEQ ID No: 11 of the sequence listing, and has an open reading frame shown by the nucleotides at positions 701-1945, coding for the SstT protein shown by SEQ ID No: 12 of the sequence listing.

11. Recombinant bacteria is obtained by introducing the recombinant plasmid pKOV-ilvA*-ilvC into the recombinant bacteria EC272, and has a sstT gene which has been partially knocked out (the following section of the sstT gene is knocked out: the nucleotides at positions 697-1759 of SEQ ID No: 11) with a DNA molecule consisting of the promoter $P_{trc}$ "ttgacaattaatcatccggctcgtataatgt" (SEQ ID NO: 174), the RBS sequence "AACCGAGGAGCAGACA" (SEQ ID NO: 173) and the DNA molecule shown by SEQ ID No: 24 of the sequence listing integrated at the sstT gene site. The recombinant bacteria after being verified by sequencing is named as recombinant bacteria E. coli W3110 ΔmetAΔtdhΔtdcCΔlysA::$P_{PL}$-thrA*BC ΔsstT::ilvA*-ilvC, referred to as recombinant bacteria EC711 for short.

VII. Construction of Engineered Bacteria EC711ilvG$^+$ ΔhisL

1. A PCR amplification is performed using the genome DNA of the E. coli K12 MG1655 as a template and using a primer pair comprised of WY4037 and WY4038.

WY4037:
CGCGGATCC GGCTGTAAGCTGTTCTGAG;

WY4038:
CAAAAAAAACCCCCGGACCT GCATCTTGTTCGAAGGAATG.

2. A PCR amplification is performed using the genome DNA of the E. coli BL21 (DE3) as a template and using a primer pair comprised of WY4039 and WY4040.

WY4039:
CATTCCTTCGAACAAGATGC AGGTCCGGGGGTTTTTTTG;

WY4040:
ATTGCGGCCGCCCAGACGTTC TCAAGTTCGT.

3. A PCR amplification product is obtained by performing a PCR amplification using a mixture of the PCR amplification product obtained in step 1 and the PCR amplification product obtained in step 2 as a template and using a primer pair comprised of WY4037 and WY4040.

4. The enzymatically cleaved product of the PCR amplification product obtained in step 3, after being subjected to a double enzymatic cleavage using the restriction endonucleases BamH I and Not I, is recovered.

5. The vector backbone of the plasmid pKOV, after being subjected to a double enzymatic cleavage using the restriction endonucleases BamH I and Not I, is recovered.

6. A recombinant plasmid pKOV-ilvL*-ilvG is obtained by linking the enzymatically cleaved product obtained in step 4 and the vector backbone obtained in step 5. According to the sequencing result, a structural description for the recombinant plasmid is set forth as follows: a specific DNA molecule is inserted between the enzymatic cleavage sites of BamH I and Not I of the plasmid pKOV; and the specific DNA molecule sequentially consists, from upstream to downstream, of the following elements: the upstream arm shown by the nucleotides at positions 355-987 of SEQ ID No: 28 of the sequence listing, and the DNA molecule shown by the nucleotides at positions 137-1831 of SEQ ID No: 27 of the sequence listing.

7. Recombinant bacteria with homologous recombination are obtained by introducing the recombinant plasmid pKOV-ilvL*-ilvG into the recombinant bacteria EC711, and named as engineered bacteria EC711ilvG⁺ΔhisL. After being verified by sequencing, the genome of the engineered bacteria EC711ilvG⁺ΔhisL has a specific DNA molecule therein; and the specific DNA molecule sequentially consists, from upstream to downstream, of the following elements: the DNA molecule shown by the nucleotides at positions 1-987 of SEQ ID No: 28 of the sequence listing, and the DNA molecule shown by the nucleotides at positions 137-6556 of SEQ ID No: 27 of the sequence listing. As compared with the recombinant bacteria EC711, the engineered bacteria EC711ilvG⁺ΔhisL differs in the knockout of a DNA molecule formed by linking the sequence AAGAAAA-GACAAA (SEQ ID NO: 179) (upstream) in the genome of the recombinant bacteria EC711 and the nucleotides (downstream) at positions 1-136 of SEQ ID No: 27 of the sequence listing, as well as a substitution of a gene coding for an active IlvG protein for the one coding for the inactive IlvG protein in the recombinant bacteria EC711. The ilvLXGMEDA operon of the *E. coli* BL21 (DE3) has a gene (shown by the nucleotides at positions 239-1885 of SEQ ID No: 27 of the sequence listing) coding for the IlvG protein, while the corresponding gene in the ilvLXGMEDA operon of the *E. coli* K12 W3110 is subjected to a mutation (the corresponding gene after a mutation is shown by SEQ ID No: 31 of the sequence listing). Thus, the ilvLXGMEDA operon of the *E. coli* BL21 (DE3) cannot form an active IlvG protein.

VIII. Construction of engineered bacteria EC711ilvG⁺

1. A PCR amplification product is obtained by performing a PCR amplification using the genome DNA of the *E. coli* K12 MG1655 as a template and using a primer pair comprised of WY4037 and WY404.

```
WY4043:
ATTGCGGCCGCCAACTCTTCCAGCGACTGCA.
```

2. The enzymatically cleaved product of the PCR amplification product obtained in step 1, after being subjected to a double enzymatic cleavage using the restriction endonucleases BamH I and Not I, is recovered.

3. The vector backbone of the plasmid pKOV, after being subjected to a double enzymatic cleavage using the restriction endonucleases BamH I and Not I, is recovered.

4. A recombinant plasmid pKOV-ilvL is obtained by linking the enzymatically cleaved product in step 2 and the vector backbone in step 3.

5. Recombinant bacteria with homologous recombination are obtained by introducing the recombinant plasmid pKOV-ilvL into the engineered bacteria EC711ilvG⁺ΔhisL, and named as engineered bacteria EC711ilvG⁺. After being verified by sequencing, the genome of the engineered bacteria EC711ilvG⁺ΔhisL has a specific DNA molecule therein; and the specific DNA molecule sequentially consists, from upstream to downstream, of the following elements: the DNA molecule shown by SEQ ID No: 28 of the sequence listing, and the DNA molecule shown by SEQ ID No: 27 of the sequence listing.

IX. Fermentation Test of Engineered Bacteria for Isoleucine in a Shake Flask

The test strain is: the engineered bacteria EC711ilvG⁺ΔhisL or the engineered bacteria EC711ilvG⁺.

1. The test strain is streaked onto a solid LB medium plate, followed by static culture for 12 h at 37° C.

2. A bacterial lawn on the plate is picked and seeded onto a liquid LB medium, followed by shaking culture for 12 h at 37° C., 220 rpm, and a seed solution is obtained ($OD_{600nm}$ value=5.0).

3. After completion of step 2, the seed solution is seeded into a fermentation medium in a seeding amount of 3%, followed by shaking culture at 37° C., 220 rpm.

The fermentation medium is: glucose 20.0 g/L, ammonium sulfate 15.0 g/L, potassium dihydrogen phosphate 2.0 g/L, magnesium sulfate heptahydrate 2.0 g/L, yeast powders 2.0 g/L, methionine 0.6 g/L, L-lysinehydrochloride 1.2 g/L, calcium carbonate 15.0 g/L, microelement mixture 5 mL/L, and water as the remainder.

The microelement mixture is: $FeSO_4.7H_2O$ 10 g/L, $CaCl_2$ 1.35 g/L, $ZnSO_4.7H_2O$ 2.25 g/L, $MnSO_4.4H_2O$ 0.5 g/L, $CuSO_4.5H_2O$ 1 g/L, $(NH_4)_6Mo_7O_{24}.4H_2O$ 0.106 g/L, $Na_2B_4O_7.10H_2O$ 0.23 g/L, $CoCl_2.6H_2O$ 0.48 g/L, 35% HCl 10 mL/L, and water as the remainder.

During the culture, ammoniacal liquor is used to adjust the pH value of the reaction system to make it maintain at 6.8-7.0.

During the culture, sampling is made once every 3-4 h to detect the content of glucose by using a biosensor analyzer SBA-40D. When the content of glucose in the system is less than 5 g/L, glucose is supplemented to make the concentration of glucose in the system up to 10 g/L.

Sampling is made after culture for 36 h, followed by centrifugation at 12,000 g for 2 min. The supernatant is taken for detection of the concentration of L-isoleucine.

The results are shown in Table 5 (by a mean±standard deviation from repeated tests in triplicate). As compared with the engineered bacteria EC711ilvG⁺, the concentration of L-isoleucine in the fermented supernatant of the engineered bacteria EC711ilvG⁺ΔhisL gains a significant improvement.

TABLE 5

|   | Content of L-isoleucine in fermented supernatant (g/L) |
| --- | --- |
| The engineered bacteria EC711ilvG⁺ | 1.02 ± 0.17 |
| The engineered bacteria EC711ilvG⁺Δ/hisL | 2.55 ± 0.35 |

A method for detecting the concentration of L-isoleucine is: HPLC, which is optimized based on the method for detecting amino acids in a reference (Amino Acids & Biotic Resources, 2000, 22, 59-60), and the method is particularly presented as follows (HPLC coupled to pre-column derivatization with 2, 4-dinitrofluorobenzene (FDBN)):

First, 10 μL of the supernatant is taken into a 2 mL centrifuge tube, into which 200 μL of 0.5M $NaHCO_3$ aqueous solution and 100 μL of 1% (v/v) FDBN-acetonitrile solution are added. Next, the centrifuge tube is placed in a water bath to be heated at a constant temperature of 60° C. for 60 min in the dark, then cooled to the room temperature, into which 700 μL of 0.04 mol/L $KH_2PO_4$ aqueous solution (pH=7.2±0.05; the pH is adjusted with 40 g/L KOH aqueous solution) is added, and shaken well. After being static for 15 min, filtration is performed and filtrates are collected. The filtrates are for injection, and injection volume is 15 μL.

C18 column (ZORBAX Eclipse XDB-C18, 4.6*150 mm, Agilent, USA) is used as the chromatographic column; column temperature: 40° C.; UV detection wavelength: 360 nm; mobile phase A: 0.04 mol/L $KH_2PO_4$ aqueous solution (pH=7.2±0.05; the pH is adjusted with 40 g/100 mL KOH aqueous solution), mobile phase B: 55% (v/v) acetonitrile aqueous solution, and total flux of the mobile phases: 1 mL/min.

The process of elution is presented as follows: at the starting time of elution (0 min), the mobile phase A accounts for 86% by volume of the total flux of the mobile phases, and mobile phase B for 14%; the process of elution is divided into 4 stages, and in each stage, parts by volume of the mobile phase A and the mobile phase B accounting for the total flux of the mobile phases appear a linear variation; when the first stage (a total duration of 2 min from the starting time) ends, the mobile phase A accounts for 88% by volume of the total flux of the mobile phases, and mobile phase B for 12%; when the second stage (a total duration of 2 min from the ending time for the first stage) ends, the mobile phase A accounts for 86% by volume of the total flux of the mobile phases, and mobile phase B for 14%; when the third stage (a total duration of 6 min from the ending time for the second stage) ends, the mobile phase A accounts for 70% by volume of the total flux of the mobile phases, and the mobile phase B for 30%; when the fourth stage (a total duration of 10 min from the ending time for the third stage) ends, the mobile phase A accounts for 30% by volume of the total flux of the mobile phases, and mobile phase B for 70%.

A standard curve is depicted by using the commercially available L-isoleucine as the standard, and the concentration of the isoleucine in a sample is calculated.

Example 8. The Expression of the Gfp Gene Under Regulation of an Attenuator Mutant I. Construction of the Recombinant Plasmid pACYC184-$P_{thr-trc}$ 1. The double-stranded DNA molecule (the promoter $P_{thr-trc}$) shown by SEQ ID No: 29 of the sequence listing is synthesized.

2. A PCR amplification product is obtained by performing a PCR amplification using the genome DNA of the *E. coli* K12 MG1655 as a template and using a primer pair comprised of WY1947 and WY1948.

```
WY1947:
CTAGTCTAGAGCTTTTCATTCTGACTGCAAC;

WY1948:
CCCAAGCTTACATTATACGAGCCGGATGATTAATTGTCAACTGTCTGTG

CGCTATGCCT.
```

3. The enzymatically cleaved product of the PCR amplification product obtained in step 2, after being subjected to a double enzymatic cleavage using the restriction endonucleases Xba I and Hind III, is recovered.

4. The vector backbone (about 4.1 kb) of the plasmid pACYC184, after being subjected to a double enzymatic cleavage using the restriction endonucleases Xba I and Hind III, is recovered.

5. A recombinant plasmid pACYC184-$P_{thr-trc}$ is obtained by linking the enzymatically cleaved product in step 3 and the vector backbone in step 4.

II. Construction of Each Recombinant Plasmid and Corresponding Recombinant Bacteria 1. Construction of the Recombinant Bacteria GFP3227

(1) A PCR amplification product A1 is obtained by performing a PCR amplification using the genome DNA of the *E. coli* K12 MG1655 as a template and using a primer pair comprised of WY3227 and WY3254; a PCR amplification product A2 is obtained by performing a PCR amplification using the pGFPuv vector as a template and using a primer pair comprised of WY3105 and WY1859; a PCR amplification product A3 is obtained by performing a PCR amplification using a mixture of the PCR amplification product A1 and the PCR amplification product A2 as a template and using a primer pair comprised of WY3227 and WY1859.

```
WY3227: CCCAAGCTTAAGATGCAAGAAAAGACAAAatgACAG;
WY3254: AGTTCTTCTCCTTTACTCATAGAACCAGAACCAGAACCTG
AGAAACAGAATTTTGTGCT;
WY3105: GGTTCTGGTTCTGGTTCTATGAGTAAAGGAGAAGAAC
TTTTCA;
WY1859:

ACATGCATGCCAAAAAACCCCTCAAGACCCGTTTAGAGGCCCCAAGGGG

TTATGCTAGTTATTTGTAGAGCTCATCCATGCCA.
```

In the primers, the underline denotes a recognition sequence for enzymatic cleavage, and the box denotes a terminator sequence.

(2) The enzymatically cleaved product of the PCR amplification product A3 obtained in step (1), after being subjected to a double enzymatic cleavage using the restriction endonucleases Hind III and Sph I, is recovered.

(3) The vector backbone of the recombinant plasmid pACYC184-$P_{thr-trc}$, after being subjected to a double enzymatic cleavage using the restriction endonucleases Hind III and Sph I, is recovered.

(4) The recombinant plasmid pACYC184-$P_{thr-trc}$-ilvLX-gfp3227 is obtained by linking the enzymatically cleaved product in step (2) and the vector backbone in step (3), then transforming into the *E. coli* EC135, and extracting a plasmid from a transformant. According to the sequencing result, a structural description for the recombinant plasmid pACYC184-$P_{thr-trc}$-ilvLX-gfp3227 is set forth as follows: a specific DNA molecule is inserted between the enzymatic cleavage sites of Xba I and Sph I of the plasmid pACYC184; and the specific DNA molecule sequentially consists, from upstream to downstream, of the following elements: the promoter $P_{thr-trc}$ shown by SEQ ID No: 29 of the sequence listing, a recognition sequence for enzymatic cleavage by restriction endonuclease Hind III, the RBS sequence "AAGATGCAAGAAAAGACAAA" (SEQ ID NO: _187) of the ilvL gene, the nucleotides at positions 1-215 of SEQ ID No: 27 of the sequence listing (inclusive of a complete ilv attenuator sequence and the nucleotide sequence coding for the first 10 amino acid residues in the open reading frame of the ilvX gene), a linker sequence "GGTTCTGGTTCTGGTTCT" (SEQ ID NO: 67), the gfp gene shown by SEQ ID No: 30 of the sequence listing, and the terminator sequence

```
CTAGCATAACCCCTTGGGGCCTCTAAACGGGTCTTGAGGGGTTTTTG.
```

The E. coli EC135 comprising the recombinant plasmid pACYC184-P$_{thr-trc}$-ilvLX-gfp3227 is named as recombinant bacteria GFP3227.

2. Construction of the Recombinant Bacteria GFP3228

(1) A PCR amplification product A1 is obtained by performing a PCR amplification using the genome DNA of the E. coli K12 MG1655 as a template and using a primer pair comprised of WY3228 and WY3254; a PCR amplification product A2 is obtained by performing a PCR amplification using the pGFPuv vector as a template and using a primer pair comprised of WY3105 and WY1859; a PCR amplification product A3 is obtained by performing a PCR amplification using a mixture of the PCR amplification product A1 and the PCR amplification product A2 as a template and using a primer pair comprised of WY3228 and WY1859.

```
WY3228:
    CCCAAGCTTAGGTCCGGGGGTTTTTTTTGAC.
```

(2) The enzymatically cleaved product of the PCR amplification product A3 obtained in step (1), after being subjected to a double enzymatic cleavage using the restriction endonucleases Hind III and Sph I, is recovered.

(3) The vector backbone of the recombinant plasmid pACYC184-P$_{thr-trc}$, after being subjected to a double enzymatic cleavage using the restriction endonucleases Hind III and Sph I, is recovered.

(4) The recombinant plasmid pACYC184-P$_{thr-trc}$-ilvLX-gfp3228 is obtained by linking the enzymatically cleaved product in step (2) and the vector backbone in step (3), then transforming into the E. coli EC135, and extracting a plasmid from a transformant. According to the sequencing result, a structural description for the recombinant plasmid pACYC184-P$_{thr-trc}$-ilvLX-gfp3228 is set forth as follows: a specific DNA molecule is inserted between the enzymatic cleavage sites of Xba I and Sph I of the plasmid pACYC184; and the specific DNA molecule sequentially consists, from upstream to downstream, of the following elements: the promoter P$_{thr-trc}$ shown by SEQ ID No: 29 of the sequence listing, a recognition sequence for enzymatic cleavage by restriction endonuclease Hind III, the nucleotides at positions 137-215 of SEQ ID No: 27 of the sequence listing (inclusive of an ilv attenuator sequence after a truncation modification and the nucleotide sequence coding for the first 10 amino acid residues in the open reading frame of the ilvX gene), a linker sequence "GGTTCTGGTTCTGGTTCT" (SEQ ID NO: 67), the gfp gene shown by SEQ ID No: 30 of the sequence listing, and the terminator sequence

```
CTAGCATAACCCCTTGGGGCCTCTAAACGGGTCTTGAGGGGTTTTTG.
```

The E. coli EC135 comprising the recombinant plasmid pACYC184-P$_{thr-trc}$-ilvLX-gfp3228 is named as recombinant bacteria GFP3228.

3. Construction of the Recombinant Bacteria GFP3229

(1) A PCR amplification product A1 is obtained by performing a PCR amplification using the genome DNA of the E. coli K12 MG1655 as a template and using a primer pair comprised of WY3229 and WY3254; a PCR amplification product A2 is obtained by performing a PCR amplification using the pGFPuv vector as a template and using a primer pair comprised of WY3105 and WY1859; a PCR amplification product A3 is obtained by performing a PCR amplification using a mixture of the PCR amplification product A1 and the PCR amplification product A2 as a template and using a primer pair comprised of WY3229 and WY1859.

```
WY3229:
    CCCAAGCTTACATAACCGAGGAGCAGACA.
```

(2) The enzymatically cleaved product of the PCR amplification product A3 obtained in step (1), after being subjected to a double enzymatic cleavage using the restriction endonucleases Hind III and Sph I, is recovered.

(3) The vector backbone of the recombinant plasmid pACYC184-P$_{thr-trc}$, after being subjected to a double enzymatic cleavage using the restriction endonucleases Hind III and Sph I, is recovered.

(4) The recombinant plasmid pACYC184-P$_{thr-trc}$-ilvLX-gfp3229 is obtained by linking the enzymatically cleaved product in step (2) and the vector backbone in step (3), and then transforming into the E. coli EC135, and extracting a plasmid from a transformant. According to the sequencing result, a structural description for the recombinant plasmid pACYC184-P$_{thr-trc}$-ilvLX-gfp3229 is set forth as follows: a specific DNA molecule is inserted between the enzymatic cleavage sites of Xba I and Sph I of the plasmid pACYC184; and the specific DNA molecule sequentially consists, from upstream to downstream, of the following elements: the promoter P$_{thr-trc}$ shown by SEQ ID No: 29 of the sequence listing, a recognition sequence for enzymatic cleavage by restriction endonuclease Hind III, the nucleotides at positions 166-215 of SEQ ID No: 27 of the sequence listing (with the ilv attenuator completely removed and inclusive of the nucleotide sequence coding for the first 10 amino acid residues in the open reading frame of the ilvX gene), a linker sequence "GGTTCTGGTTCTGGTTCT" (SEQ ID NO: 67), the gfp gene shown by SEQ ID No: 30 of the sequence listing, and the terminator sequence

```
CTAGCATAACCCCTTGGGGCCTCTAAACGGGTCTTGAGGGGTTTTTG.
```

The E. coli EC135 comprising the recombinant plasmid pACYC184-P$_{thr-trc}$-ilvLX-gfp3229 is named as recombinant bacteria GFP3229.

4. Construction of the GFP control Recombinant bacteria is obtained by introducing the recombinant plasmid pACYC184-P$_{thr-trc}$ into the E. coli EC135, and named as GFP control.

III. Analysis for the Fluorescence Intensity of GFP

The test strain is: the recombinant bacteria GFP3227, the recombinant bacteria GFP3228 or the recombinant bacteria GFP3229.

The GFP control is set to the control strain.

1. The test strain or the control strain is seeded into a liquid LB medium containing 34 mg/L chloramphenicol, followed by shaking culture overnight at 37° C., 220 rpm.

2. The bacteria liquid obtained in step 1 is seeded into a liquid LB medium containing 34 mg/L chloramphenicol with a seeding amount of 1%, followed by shaking culture for 12 h at 37° C., 220 rpm.

3. 150 μL of the bacteria liquid obtained in step 2 is added into a 96-well plate having black edges and a transparent bottom, and the density of cells and the fluorescence signal of GFP are simultaneously detected by using a high throughput multifunctional microplate reader (the INFINITE 200 PRO type, TECAN, Switzerland). Parameters associated with detection of the density of cells are set as presented in Table 6. Parameters associated with detection of the fluorescence signal of GFP are set as presented in Table 7.

TABLE 6

| | Absorbance |
|---|---|
| Wavelength | 600 nm |
| Bandwidth | 9 nm |
| Number of Flashes | 25 |
| Settle Time | 0 ms |

TABLE 7

| | Fluorescence Top Reading |
|---|---|
| Excitation Wavelength | 400 nm |
| Emission Wavelength | 510 nm |
| Excitation Bandwidth | 9 nm |
| Emission Bandwidth | 20 nm |
| Gain | 100 (Manual) |
| Number of Flashes | 15 |
| Integration Time | 20 μs |
| LagTime | 0 μs |
| Settle Time | 0 ms |
| Z-Position | 20000 μm (Manual) |

The fluorescence intensity value of each test strain=the fluorescence value actually measured÷the density of cells−the fluorescence value actually measured from the control strain÷the density of cells of the control strain. Repeated tests are set in triplicate, and the results of the corresponding means and standard deviations are shown in Table 8.

As compared with the recombinant bacteria GFP3227 (carrying a complete ilv attenuator), the fluorescence intensity value of the recombinant bacteria GFP3228 (carrying a truncated ilv attenuator) is improved by 149.0%. As compared with the recombinant bacteria GFP3229 (carrying no ilv attenuator), the fluorescence intensity value of the recombinant bacteria GFP3228 is improved by 34.1%. The results indicate that the truncated ilv attenuator located between the promoter and the target gene can function as a regulation element to promote the expression of the target gene.

The ilv attenuator mutant is shown by the nucleotides at positions n1-n2 of SEQ ID No: 27 of the sequence listing; n1 is a natural number greater than or equal to 129 but smaller than or equal to 148 (preferably, n1 is 137), and n2 is a natural number greater than or equal to 155 but smaller than or equal to 215 (n2 particularly can be a natural number greater than or equal to 155 but smaller than or equal to 185, or a natural number greater than or equal to 186 but smaller than or equal to 215, and even more particularly 155, 185 or 215). The ilv attenuator mutant comprises a truncated ilv attenuator and an ilv attenuator variant (its full name is: a variant linking other nucleotides downstream of a truncated ilv attenuator). The truncated ilv attenuator is shown by the nucleotides at positions n1-155 of SEQ ID No: 27 of the sequence listing. The ilv attenuator variant is shown by the nucleotides at positions n1-n3 of SEQ ID No: 27 of the sequence listing; n3 is a natural number greater than or equal to 156 but smaller than or equal to 215 (n3 particularly can be a natural number greater than or equal to 156 but smaller than or equal to 185, or a natural number greater than or equal to 185 but smaller than or equal to 215, and even more particularly 185 or 215).

TABLE 8

| | Fluorescence intensity |
|---|---|
| Recombinant bacteria GFP3227 | 1465.4 ± 165.5 |
| Recombinant bacteria GFP3228 | 3649.3 ± 413.2 |
| Recombinant bacteria GFP3229 | 2721.1 ± 138.4 |

Example 9. Preparation of Valine

I. Construction of the E. coli K-12 MG1655ΔilvA

1. A DNA fragment-A (a region upstream of the ilvA gene) is obtained by performing a PCR amplification using the genome DNA of the E. coli K12 MG1655 as a template and using a primer pair comprised of WY577 and WY578.

WY577:
CGCGGATCCGAAAGTGTACGAAAGCCAGG;

WY578:
GCGCTATCAGGCATTTTTCCTATTAACCCCCCAGTTTCGA.

2. A DNA fragment-B (a region downstream of the ilvA gene) is obtained by performing a PCR amplification using the genome DNA of the E. coli K12 MG1655 as a template and using a primer pair comprised of WY579 and WY580.

WY579:
TCGAAACTGGGGGGTTAATAGGAAAAATGCCTGATAGCGC;

WY580:
ATTGCGGCCGCGTGAAGCGGATCTGGCGATT.

3. A DNA fragment-C is obtained by performing a PCR amplification using a mixture of the DNA fragment-A and the DNA fragment-B as a template and using a primer pair comprised of WY577 and WY580.

4. The vector backbone (about 5.6 kb) of the plasmid pKOV, after being subjected to a double enzymatic cleavage using the restriction endonucleases BamH I and Not I, is recovered.

5. The enzymatically cleaved product of the DNA fragment-C, after being subjected to a double enzymatic cleavage using the restriction endonucleases BamH I and Not I, is recovered.

6. A recombinant plasmid ΔilvA is obtained by linking the vector backbone obtained in step 4 and the enzymatically cleaved product obtained in step 5. According to the sequencing result, a structural description for the recombinant plasmid ΔilvA is set forth as follows: the following specific DNA molecule is inserted between the enzymatic cleavage sites of BamH I and Not I of the plasmid pKOV: sequentially consisting, from upstream to downstream, of the upstream section shown by the nucleotides at positions 140-637 of SEQ ID No: 3 of the sequence listing and the downstream section shown by the nucleotides at positions 2183-2712 of SEQ ID No: 3 of the sequence listing. The ilvA gene is shown by SEQ ID No: 3 of the sequence listing, wherein the open reading frame is shown by the nucleotides at positions 638-2182 (coding for the IlvA protein shown by SEQ ID No: 4 of the sequence listing).

7. Recombinant bacteria with ilvA gene knocked out are obtained by introducing the recombinant plasmid ΔilvA into the E. coli K12 MG1655, and named as E. coli K-12 MG1655ΔilvA.

A method for identifying the recombinant bacteria with ilvA gene knocked out is that: a PCR amplification is performed using a primer pair comprised of WY587 and WY588; if an amplification product with 1344 bp is obtained, the recombinant bacteria preliminarily can be determined as a candidate for the target bacteria; and sequencing will be further performed to verify that the open reading frame of the ilvA gene on the chromosomes of the bacteria has been knocked out.

```
WY587:
ATGGCTGTATCCGCTCGCTG;

WY588:
ACACCATCGATCAGCAAGGGC.
```

II. Construction of the Recombinant Plasmid pACYC184-$P_{JJ}$

1. The double-stranded DNA molecule (the promoter $P_{JJ}$) shown by SEQ ID No: 39 of the sequence listing is synthesized.

2. A PCR amplification product is obtained by performing a PCR amplification using the double-stranded DNA molecule prepared in step 1 as a template and using a primer pair comprised of WY843 and WY842.

```
WY843:
TGCTCTAGACAATTCCGACGTCTAAGAAA;

WY842:
CGCGGATCCGGTCAGTGCGTCCTGCTGAT.
```

3. The enzymatically cleaved product of the PCR amplification product obtained in step 2, after being subjected to a double enzymatic cleavage using the restriction endonucleases Xba I and BamHI, is recovered.

4. The vector backbone (about 4.1 kb) of the plasmid pACYC184, after being subjected to a double enzymatic cleavage using the restriction endonucleases Xba I and BamH I, is recovered.

5. A recombinant plasmid pACYC184-$P_{JJ}$ is obtained by linking the enzymatically cleaved product in step 3 and the vector backbone in step 4.

III. Construction of the Recombinant Plasmid pACYC184-$P_{JJ}$-ilvLXGMED

```
WY4047: CGCGGATCC AAGATGCAAGAAAAGACAAA atgACAG;
WY4048: CGCGGATCC AGGTCCGGGGGTTTTTTTTGAC;
WY4049: CGCGGATCC ACATAACCGAGGAGCAGACA;
WY4044: TGACCTGATGTTGCATCATGATAATTTCTCCA;
WY4045: TGGAGAAATTATCATGATGCAACATCAGGTCA;
WY4046: AAACGGCCG

CAAAAAACCCCTCAAGACCCGTTTAGAGGCCCCAAGGGGTTATGCTAG

TTAACCCCCCAGTTTCGATTTATCG.
```

1. A PCR amplification product B1 is obtained by performing a PCR amplification using the genome DNA of the E. coli BL21 (DE3) as a template and using a primer pair comprised of WY4047 and WY4044.

2. A PCR amplification product B2 is obtained by performing a PCR amplification using the genome DNA of the E. coli BL21 (DE3) as a template and using a primer pair comprised of WY4048 and WY4044.

3. A PCR amplification product B3 is obtained by performing a PCR amplification using the genome DNA of the E. coli BL21 (DE3) as a template and using a primer pair comprised of WY4049 and WY4044.

4. A PCR amplification product B4 is obtained by performing a PCR amplification using the genome DNA of the E. coli K12 MG1655 as a template and using a primer pair comprised of WY4045 and WY4046.

5. A PCR amplification product C1 is obtained by performing a PCR amplification using a mixture of the PCR amplification product B1 and the PCR amplification product B4 as a template and using a primer pair comprised of WY4047 and WY4046.

6. A PCR amplification product C2 is obtained by performing a PCR amplification using a mixture of the PCR amplification product B2 and the PCR amplification product B4 as a template and using a primer pair comprised of WY4048 and WY4046.

7. A PCR amplification product C3 is obtained by performing a PCR amplification using a mixture of the PCR amplification product B3 and the PCR amplification product B4 as a template and using a primer pair comprised of WY4049 and WY4046.

8. The vector backbone of the plasmid pACYC184-$P_{JJ}$, after being subjected to a double enzymatic cleavage using the restriction endonucleases BamH I and Eag I, is recovered.

9. The enzymatically cleaved product of the PCR amplification product C1, after being subjected to a double enzymatic cleavage using the restriction endonucleases BamH I and Eag I, is recovered.

10. A recombinant plasmid pACYC184-$P_{JJ}$-ilvL$^{4047}$XGMED is obtained by linking the vector backbone in step 8 and the enzymatically cleaved product in step 9. According to the sequencing result, a structural description for the recombinant plasmid pACYC184-$P_{JJ}$-ilvL$^{4047}$XGMED is set forth as follows: a specific DNA molecule is inserted between the enzymatic cleavage sites of Xba I and Eag I of the plasmid pACYC184; and the specific DNA molecule sequentially consists, from upstream to downstream, of the following elements: the promoter $P_{JJ}$ shown by SEQ ID No: 39 of the sequence listing, a recognition sequence for enzymatic cleavage by restriction endonuclease BamH I, the RBS sequence "AAGATGCAAGAAAAGACAAA" (SEQ ID NO: 204) of the ilvL gene, and the double-stranded DNA molecule shown by SEQ ID No: 38 of the sequence listing.

11. The enzymatically cleaved product of the PCR amplification product C2, after being subjected to a double enzymatic cleavage using the restriction endonucleases BamH I and Eag I, is recovered.

12. A recombinant plasmid pACYC184-$P_{JJ}$-ilvL$^{4048}$XGMED is obtained by linking the vector backbone in step 8 and the enzymatically cleaved product in step 11. According to the sequencing result, a structural description for the recombinant plasmid pACYC184-$P_{JJ}$-ilvL$^{4048}$XGMED is set forth as follows: a specific DNA molecule is inserted between the enzymatic cleavage sites of Xba I and Eag I of the plasmid pACYC184; and the specific DNA molecule sequentially consists, from upstream to downstream, of the following elements: the promoter $P_{JJ}$ shown by SEQ ID No: 39 of the sequence listing, a recognition sequence for enzymatic cleavage by restriction endonuclease BamH I, and the double-stranded DNA molecule shown by the nucleotides at positions 137-5057 of SEQ ID No: 38 of the sequence listing.

13. The enzymatically cleaved product of the PCR amplification product C3, after being subjected to a double enzymatic cleavage using the restriction endonucleases BamH I and Eag I, is recovered.

14. A recombinant plasmid pACYC184-$P_{JJ}$-ilvL$^{4049}$XGMED is obtained by linking the vector backbone in step 8 and the enzymatically cleaved product in step 13. According to the sequencing result, a structural description for the recombinant plasmid pACYC184-$P_{JJ}$-ilvL$^{4049}$XGMED is set forth as follows: a specific DNA molecule is inserted between the enzymatic cleavage sites of Xba I and Eag I of the plasmid pACYC184; and the specific DNA molecule sequentially consists, from upstream to downstream, of the following elements: the promoter $P_{JJ}$ shown by SEQ ID No: 39 of the sequence listing, a recognition sequence for enzymatic cleavage by restriction endonuclease BamH I, and the double-stranded DNA molecule shown by the nucleotides at positions 166-5057 of SEQ ID No: 38 of the sequence listing.

IV. Construction of Engineered Bacteria

Recombinant bacteria is obtained by introducing the recombinant plasmid pACYC184-$P_{JJ}$-ilvL$^{4047}$XGMED into the *E. coli* K-12 MG1655ΔilvA, and named as engineered bacteria IlvL4047.

Recombinant bacteria is obtained by introducing the recombinant plasmid pACYC184-$P_{JJ}$-ilvL$^{4048}$XGMED into the *E. coli* K-12 MG1655ΔilvA, and named as engineered bacteria IlvL4048.

Recombinant bacteria is obtained by introducing the recombinant plasmid pACYC184-$P_{JJ}$-ilvL$^{4049}$XGMED into the *E. coli* K-12 MG1655ΔilvA, and named as engineered bacteria IlvL4049.

V. Fermentation Test of Engineered Bacteria for Valine in a Shake Flask

The test strain is: the engineered bacteria IlvL4047, the engineered bacteria IlvL4048 or the engineered bacteria IlvL4049.

1. The test strain is streaked onto a solid LB medium plate containing 34 mg/L chloramphenicol, followed by static culture for 12 h at 37° C.

2. After completion of step 1, a bacterial lawn on the plate is picked and seeded into a liquid LB medium, followed by shaking culture for 12 h at 37° C., 220 rpm (OD$_{600nm}$ value=5.0), and a seed solution is obtained.

3. After completion of step 2, the seed solution is seeded into a fermentation medium in a seeding amount of 3%, followed by shaking culture at 37° C., 220 rpm.

The fermentation medium is: glucose 20.0 g/L, ammonium sulfate 15.0 g/L, potassium dihydrogen phosphate 2.0 g/L, magnesium sulfate heptahydrate 2.0 g/L, yeast powders 2.0 g/L, isoleucine 0.6 g/L, calcium carbonate 15.0 g/L, microelement mixture 5 mL/L, and water as the remainder.

The microelement mixture is: $FeSO_4.7H_2O$ 10 g/L, $CaCl_2$ 1.35 g/L, $ZnSO_4.7H_2O$ 2.25 g/L, $MnSO_4.4H_2O$ 0.5 g/L, $CuSO_4.5H_2O$ 1 g/L, $(NH_4)_6Mo_7O_{24}.4H_2O$ 0.106 g/L, $Na_2B_4O_7.10H_2O$ 0.23 g/L, $CoCl_2.6H_2O$ 0.48 g/L, 35% HCl 10 mL/L, and water as the remainder.

During the culture, ammoniacal liquor is used to adjust the pH value of the reaction system to make it maintain at 6.8-7.0.

During the culture, sampling is made once every 3-4 h to detect the content of glucose by using a biosensor analyzer SBA-40D. When the content of glucose in the system is less than 5 g/L, glucose is supplemented to make the concentration of glucose in the system up to 10 g/L.

Sampling is made after culture for 36 h, followed by centrifugation at 12,000 g for 2 min. The supernatant (the fermented supernatant) is taken for detection of the concentration of L-valine.

The results are shown in Table 9 (by a mean±standard deviation from repeated tests in triplicate). The engineered bacteria IlvL4048 have the highest capability for producing L-valine, and the concentration of L-valine in the fermented supernatant is up to 2.58±0.55.

TABLE 9

|  | Content of L-valine in fermented supernatant (g/L) |
| --- | --- |
| Engineered bacteria IlvL4047 | 1.02 ± 0.15 |
| Engineered bacteria IlvL4048 | 2.58 ± 0.55 |
| Engineered bacteria IlvL4049 | 1.82 ± 0.22 |

A method for detecting the concentration of L-valine in fermented supernatant is: HPLC, which is optimized based on the method for detecting amino acids in a reference (Amino Acids & Biotic Resources, 2000, 22, 59-60), and the method is particularly presented as follows (HPLC coupled to pre-column derivatization with 2, 4-dinitrofluorobenzene (FDBN)):

First, 10 μL of the supernatant is taken into a 2 mL centrifuge tube, into which 200 μL of 0.5M $NaHCO_3$ aqueous solution and 100 μL of 1% (v/v) FDBN-acetonitrile solution are added. Next, the centrifuge tube is placed in a water bath to be heated at a constant temperature of 60° C. for 60 min in the dark, then cooled to the room temperature, into which 700 μL of 0.04 mol/L $KH_2PO_4$ aqueous solution (pH=7.2±0.05; the pH is adjusted with 40 g/L KOH aqueous solution) is added, and shaken well. After being static for 15 min, filtration is performed and filtrates are collected. The filtrates are for injection, and injection volume is 15 μL.

C18 column (ZORBAX Eclipse XDB-C18, 4.6*150 mm, Agilent, USA) is used as the chromatographic column; column temperature: 40° C.; UV detection wavelength: 360 nm; mobile phase A: 0.04 mol/L $KH_2PO_4$ aqueous solution (pH=7.2±0.05; the pH is adjusted with 40 g/100 mL KOH aqueous solution), mobile phase B: 55% (v/v) acetonitrile aqueous solution, and total flux of the mobile phases: 1 mL/min.

The process of elution is presented as follows: at the starting time of elution (0 min), the mobile phase A accounts for 86% by volume of the total flux of the mobile phases, and mobile phase B for 14%; the process of elution is divided into 4 stages, and in each stage, parts by volume of the mobile phase A and the mobile phase B accounting for the total flux of the mobile phases appear a linear variation; when the first stage (a total duration of 2 min from the starting time) ends, the mobile phase A accounts for 88% by volume of the total flux of the mobile phases, and mobile phase B for 12%; when the second stage (a total duration of 2 min from the ending time for the first stage) ends, the mobile phase A accounts for 86% by volume of the total flux of the mobile phases, and mobile phase B for 14%; when the third stage (a total duration of 6 min from the ending time for the second stage) ends, the mobile phase A accounts for 70% by volume of the total flux of the mobile phases, and the mobile phase B for 30%; when the fourth stage (a total duration of 10 min from the ending time for the third stage) ends, the mobile phase A accounts for 30% by volume of the total flux of the mobile phases, and mobile phase B for 70%.

A standard curve is depicted by using the commercially available L-valine as the standard, and the concentration of valine in a sample is calculated.

Example 10. The Expression of the Gfp Gene Under Regulation of an Attenuator Mutant I. Construction of Each Recombinant Plasmid and Corresponding Recombinant Bacteria 1. Construction of the Recombinant Bacteria GFP3223

(1) A PCR amplification product A1 is obtained by performing a PCR amplification using the genome DNA of the E. coli K12 MG1655 as a template and using a primer pair comprised of WY3223 and WY3253; a PCR amplification product A2 is obtained by performing a PCR amplification using the pGFPuv vector as a template and using a primer pair comprised of WY3105 and WY1859; a PCR amplification product A3 is obtained by performing a PCR amplification using a mixture of the PCR amplification product A1 and the PCR amplification product A2 as a template and using a primer pair comprised of WY3223 and WY1859.

WY3223:
CCC<u>AAGCTT</u>ACGTAAAAAGGGTATCGACA;

WY3253:
AGTTCTTCTCCTTTACTCATAGAACCAGAACCAGAACCCAGTTCGAGAG
TCGGTTTTTG;

WY3105:
GGTTCTGGTTCTGGTTCTATGAGTAAAGGAGAAGAACTTTTCA;

WY1859:
ACAT<u>GCATGC</u>CAAAAAACCCCTCAAGACCCGTTTAGAGGCCCCAAGGGG

TTATGCTAGTTATTTGTAGAGCTCATCCATGCCA.

(2) The enzymatically cleaved product of the PCR amplification product A3 obtained in step (1), after being subjected to a double enzymatic cleavage using the restriction endonucleases Hind III and Sph I, is recovered.

(3) The vector backbone (about 4.0 kb) of the recombinant plasmid pACYC184-P$_{thr-trc}$, after being subjected to a double enzymatic cleavage using the restriction endonucleases Hind III and Sph I, is recovered.

(4) The recombinant plasmid pACYC184-P$_{thr-trc}$-trpLE-gfp3223 is obtained by linking the enzymatically cleaved product in step (2) and the vector backbone in step (3), then transforming into the E. coli EC135, and extracting a plasmid from a transformant. According to the sequencing result, a structural description for the recombinant plasmid pACYC184-P$_{thr-trc}$-trpLE-gfp3223 is set forth as follows: a specific DNA molecule is inserted between the enzymatic cleavage sites of Xba I and Sph I of the plasmid pACYC184; and the specific DNA molecule sequentially consists, from upstream to downstream, of the following elements: the promoter P$_{thr-trc}$ shown by SEQ ID No: 29 of the sequence listing, a recognition sequence for enzymatic cleavage by restriction endonuclease Hind III, the nucleotides at positions 1-186 of SEQ ID No: 40 of the sequence listing, a linker sequence "GGTTCTGGTTCTGGTTCT" (SEQ ID NO: 67), the gfp gene shown by SEQ ID No: 30 of the sequence listing, and the terminator sequence

"CTAGCATAACCCCTTGGGGCCTCTAAACGGGTCTTGAGGGG

TTTTTTG".

The E. coli EC135 comprising the recombinant plasmid pACYC184-P$_{thr-trc}$-trpLE-gfp3223 is named as recombinant bacteria GFP3223.

2. Construction of the recombinant bacteria GFP3224

(1) A PCR amplification product A1 is obtained by performing a PCR amplification using the genome DNA of the E. coli K12 MG1655 as a template and using a primer pair comprised of WY3224 and WY3253; a PCR amplification product A2 is obtained by performing a PCR amplification using the pGFPuv vector as a template and using a primer pair comprised of WY3105 and WY1859; a PCR amplification product A3 is obtained by performing a PCR amplification using a mixture of the PCR amplification product A1 and the PCR amplification product A2 as a template and using a primer pair comprised of WY3224 and WY1859.

WY3224: CCC<u>AAGCTT</u>CTAATGAGCGGGCTTTTTTTGAACA.

(2) The enzymatically cleaved product of the PCR amplification product A3 obtained in step (1), after being subjected to a double enzymatic cleavage using the restriction endonucleases Hind III and Sph I, is recovered.

(3) The vector backbone (about 4.0 kb) of the recombinant plasmid pACYC184-P$_{thr-trc}$, after being subjected to a double enzymatic cleavage using the restriction endonucleases Hind III and Sph I, is recovered.

(4) The recombinant plasmid pACYC184-P$_{thr-trc}$-trpLE-gfp3224 is obtained by linking the enzymatically cleaved product in step (2) and the vector backbone in step (3), then transforming into the E. coli EC135, and extracting a plasmid from a transformant. According to the sequencing result, a structural description for the recombinant plasmid pACYC184-P$_{thr-trc}$-trpLE-gfp3224 is set forth as follows: a specific DNA molecule is inserted between the enzymatic cleavage sites of Xba I and Sph I of the plasmid pACYC184; and the specific DNA molecule sequentially consists, from upstream to downstream, of the following elements: the promoter P$_{thr-trc}$ shown by SEQ ID No: 29 of the sequence listing, a recognition sequence for enzymatic cleavage by restriction endonuclease Hind III, the nucleotides at positions 115-186 of SEQ ID No: 40 of the sequence listing, a linker sequence "GGTTCTGGTTCTGGTTCT" (SEQ ID NO: 67), the gfp gene shown by SEQ ID No: 30 of the sequence listing, and the terminator sequence

"CTAGCATAACCCCTTGGGGCCTCTAAACGGGTCTTGAGGGG

TTTTTTG".

The E. coli EC135 comprising the recombinant plasmid pACYC184-P$_{thr-trc}$-trpLE-gfp3224 is named as recombinant bacteria GFP3224.

3. Construction of the Recombinant Bacteria GFP3225

(1) A PCR amplification product A1 is obtained by performing a PCR amplification using the genome DNA of the E. coli K12 MG1655 as a template and using a primer pair comprised of WY3225 and WY3253; a PCR amplification product A2 is obtained by performing a PCR amplification using the pGFPuv vector as a template and using a primer pair comprised of WY3105 and WY1859; a PCR amplification product A3 is obtained by performing a PCR amplification using a mixture of the PCR amplification product A1 and the PCR amplification product A2 as a template and using a primer pair comprised of WY3225 and WY1859.

WY3225: CCC<u>AAGCTT</u> GCGGGCTTTTTTTGAACAA.

(2) The enzymatically cleaved product of the PCR amplification product A3 obtained in step (1), after being subjected to a double enzymatic cleavage using the restriction endonucleases Hind III and Sph I, is recovered.

(3) The vector backbone (about 4.0 kb) of the recombinant plasmid pACYC184-P$_{thr-trc}$, after being subjected to a double enzymatic cleavage using the restriction endonucleases Hind III and Sph I, is recovered.

(4) The recombinant plasmid pACYC184-P$_{thr-trc}$-trpLE-gfp3225 is obtained by linking the enzymatically cleaved product in step (2) and the vector backbone in step (3), and then transforming into the E. coli EC135, and extracting a plasmid from a transformant. According to the sequencing result, a structural description for the recombinant plasmid pACYC184-P$_{thr-trc}$-trpLE-gfp3225 is set forth as follows: a specific DNA molecule is inserted between the enzymatic cleavage sites of Xba I and Sph I of the plasmid pACYC184; and the specific DNA molecule sequentially consists, from upstream to downstream, of the following elements: the promoter P$_{thr-trc}$ shown by SEQ ID No: 29 of the sequence listing, a recognition sequence for enzymatic cleavage by restriction endonuclease Hind III, the nucleotides at positions 122-186 of SEQ ID No: 40 of the sequence listing, a linker sequence "GGTTCTGGTTCTGGTTCT" (SEQ ID NO: 67), the gfp gene shown by SEQ ID No: 30 of the sequence listing, and the terminator sequence

"CTAGCATAACCCCTTGGGGCCTCTAAACGGGTCTTGAGGGG

TTTTTTG".

The E. coli EC135 comprising the recombinant plasmid pACYC184-P$_{thr-trc}$-trpLE-gfp3225 is named as recombinant bacteria GFP3225.

4. Construction of the recombinant bacteria GFP3226

(1) A PCR amplification product A1 is obtained by performing a PCR amplification using the genome DNA of the E. coli K12 MG1655 as a template and using a primer pair comprised of WY3226 and WY3253; a PCR amplification product A2 is obtained by performing a PCR amplification using the pGFPuv vector as a template and using a primer pair comprised of WY3105 and WY1859; a PCR amplification product A3 is obtained by performing a PCR amplification using a mixture of the PCR amplification product A1 and the PCR amplification product A2 as a template and using a primer pair comprised of WY3226 and WY1859.

WY3226: CCC<u>AAGCTT</u> AACAAAATTAGAGAATAACAATGCAAAC.

(2) The enzymatically cleaved product of the PCR amplification product A3 obtained in step (1), after being subjected to a double enzymatic cleavage using the restriction endonucleases Hind III and Sph I, is recovered.

(3) The vector backbone (about 4.0 kb) of the recombinant plasmid pACYC184-P$_{thr-trc}$, after being subjected to a double enzymatic cleavage using the restriction endonucleases Hind III and Sph I, is recovered.

(4) The recombinant plasmid pACYC184-P$_{thr-trc}$-trpLE-gfp3226 is obtained by linking the enzymatically cleaved product in step (2) and the vector backbone in step (3), then transforming into the E. coli EC135, and extracting a plasmid from a transformant. According to the sequencing result, a structural description for the recombinant plasmid pACYC184-P$_{thr-trc}$-trpLE-gfp3226 is set forth as follows: a specific DNA molecule is inserted between the enzymatic cleavage sites of Xba I and Sph I of the plasmid pACYC184; and the specific DNA molecule sequentially consists, from upstream to downstream, of the following elements: the promoter P$_{thr-trc}$ shown by SEQ ID No: 29 of the sequence listing, a recognition sequence for enzymatic cleavage by restriction endonuclease Hind III, the nucleotides at positions 137-186 of SEQ ID No: 40 of the sequence listing, a linker sequence "GGTTCTGGTTCTGGTTCT" (SEQ ID NO: 67), the gfp gene shown by SEQ ID No: 30 of the sequence listing, and the terminator sequence

"CTAGCATAACCCCTTGGGGCCTCTAAACGGGTCTTGAGGGG

TTTTTTG".

The E. coli EC135 comprising the recombinant plasmid pACYC184-P$_{thr-trc}$-trpLE-gfp3226 is named as recombinant bacteria GFP3226.

5. Construction of the GFP Control

Recombinant bacteria is obtained by introducing the recombinant plasmid pACYC184-P$_{thr-trc}$ into the E. coli EC135, and named as GFP control.

II. Analysis for the Fluorescence Intensity of GFP

The test strain is: the recombinant bacteria GFP3223, the recombinant bacteria GFP3224, the recombinant bacteria GFP3225 or the recombinant bacteria GFP3226.

The GFP control is set to the control strain.

1. The test strain or the control strain is seeded into a liquid LB medium containing 34 mg/L chloramphenicol, followed by shaking culture for overnight at 37° C., 220 rpm.

2. The bacteria liquid obtained in step 1 is seeded into a liquid LB medium containing 34 mg/L chloramphenicol with a seeding amount of 1%, followed by shaking culture for 12 h at 37° C., 220 rpm.

3. 150 μL of the bacteria liquid obtained in step 2 is added into a 96-well plate having black edges and a transparent bottom, and the density of cells and the fluorescence signal of GFP are simultaneously detected by using a high throughput multifunctional microplate reader (the INFINITE 200 PRO type, TECAN, Switzerland). Parameters associated with detection of the density of cells are set as presented in Table 10. Parameters associated with detection of the fluorescence signal of GFP are set as presented in Table 11.

TABLE 10

| | Absorbance |
|---|---|
| Wavelength | 600 nm |
| Bandwidth | 9 nm |
| Number of Flashes | 25 |
| Settle Time | 0 ms |

TABLE 11

| | Fluorescence Top Reading |
|---|---|
| Excitation Wavelength | 400 nm |
| Emission Wavelength | 510 nm |
| Excitation Bandwidth | 9 nm |
| Emission Bandwidth | 20 nm |
| Gain | 100 (Manual) |
| Number of Flashes | 15 |
| Integration Time | 20 μs |
| LagTime | 0 μs |

TABLE 11-continued

| | Fluorescence Top Reading |
|---|---|
| Settle Time | 0 ms |
| Z-Position | 20000 μm (Manual) |

The fluorescence intensity value of each test strain=the fluorescence value actually measured÷the density of cells−the fluorescence value actually measured from the control strain÷the density of cells of the control strain. Repeated tests are set in triplicate, and the results of the corresponding means and standard deviations are shown in Table 12.

As compared with the recombinant bacteria GFP3223 (remaining a complete tryptophan attenuator), the fluorescence intensity of the recombinant bacteria GFP3224 is improved by 10.7 folds. As compared with the recombinant bacteria GFP3226 (having completely removed the tryptophan attenuator), the fluorescence intensity of the recombinant bacteria GFP3224 is improved by 10.6 folds. As compared with the recombinant bacteria GFP3223, the fluorescence intensity of the recombinant bacteria GFP3225 is improved by 3.6 folds. As compared with the recombinant bacteria GFP3226, the fluorescence intensity of the recombinant bacteria GFP3225 is improved by 3.6 folds. The results indicate that the truncated tryptophan attenuator located between the promoter and the target gene can function as a regulation element to promote the expression of the target gene.

The tryptophan attenuator mutant is shown by the nucleotides at positions n1-n2 of SEQ ID No: 40 of the sequence listing; n1 is a natural number greater than or equal to 115 but smaller than or equal to 122 (preferably, n1 is 115), and n2 is a natural number greater than or equal to 135 but smaller than or equal to 186 (n2 particularly can be a natural number greater than or equal to 135 but smaller than or equal to 156, or a natural number greater than or equal to 157 but smaller than or equal to 186, even more particularly 135, 156 or 186). The tryptophan attenuator mutant comprises a truncated tryptophan attenuator and a tryptophan attenuator variant (its full name is: a variant linking other nucleotides downstream of a truncated tryptophan attenuator). The truncated tryptophan attenuator is shown by the nucleotides at positions n1-135 of SEQ ID No: 40 of the sequence listing. The tryptophan attenuator variant is shown by the nucleotides at positions n1-n4 of SEQ ID No: 40 of the sequence listing; n4 is a natural number greater than or equal to 136 but smaller than or equal to 186 (n4 particularly can be a natural number greater than or equal to 136 but smaller than or equal to 156, or a natural number greater than or equal to 157 but smaller than or equal to 186, even more particularly 156 or 186).

TABLE 12

| | Fluorescence intensity |
|---|---|
| Recombinant bacteria GFP3223 | 2841.4 ± 15.2 |
| Recombinant bacteria GFP3224 | 33141.9 ± 283.2 |
| Recombinant bacteria GFP3225 | 13084.2 ± 188.3 |
| Recombinant bacteria GFP3226 | 2865.1 ± 76.5 |

Example 11. Preparation of Tryptophan

I. Construction of the Recombinant Plasmid pBR322-aroG*

1. A PCR amplification product is obtained by performing a PCR amplification using the genome of the *E. coli* K12 MG1655 as a template and using a primer pair comprised of WY4001 and WY4002.

2. A PCR amplification product is obtained by performing a PCR amplification using the genome of the *E. coli* K12 MG1655 as a template and using a primer pair comprised of WY4003 and WY4004.

3. A PCR amplification product is obtained by performing a PCR amplification using a mixture of the PCR amplification product obtained in step 1 and the PCR amplification product obtained in step 2 as a template and using a primer pair comprised of WY4001 and WY4004.

After sequencing, the nucleotides between the recognition sites for enzymatic cleavage by Nhe I and BamH I of the PCR amplification product obtained in step 3 are shown by SEQ ID No: 41 of the sequence listing. In SEQ ID No: 41 of the sequence listing, the open reading frame is shown by the nucleotides at positions 151-1203, coding for the AroG*protein shown by SEQ ID No: 42 of the sequence listing. As compared with the AroG protein (a wild-type protein), the AroG*protein only differs in one amino acid residue, that is, the amino acid residue at position 150 of the AroG protein is mutated to leucine from proline.

WY4001: CTAGCTAGCATCTCGTTTTTCGCGACAATCT;

WY4002: CAGGTCAGCGAGATATTGTAGGGTGATCATATCGAGAAAC;

WY4003: GTTTCTCGATATGATCACCCTACAATATCTCGCTGACCTG;

WY4004: CGCGGATCC AGCGAAAGCAGCGGCGGTT.

4. The vector backbone (about 4.3 kb) of the plasmid pBR322, after being subjected to a double enzymatic cleavage using the restriction endonucleases Nhe I and BamH I, is recovered.

5. The enzymatically cleaved product of the PCR amplification product obtained in step 3, after being subjected to a double enzymatic cleavage using the restriction endonucleases Nhe I and BamH I, is recovered.

6. A recombinant plasmid pBR322-aroG* is obtained by linking the vector backbone in step 4 and the enzymatically cleaved product in step 5.

II. Construction of the Recombinant Plasmid pBR322-aroG*-tktA

1. A PCR amplification product is obtained by performing a PCR amplification using the genome of the *E. coli* K12 MG1655 as a template and using a primer pair comprised of WY4005 and WY4006. After sequencing, the nucleotides between the recognition sites for enzymatic cleavage by BamH I and Eco 52I of the PCR amplification product are shown by SEQ ID No: 43 of the sequence listing. In SEQ ID No: 43 of the sequence listing, the open reading frame is shown by the nucleotides at positions 151-2142, coding for the TktA protein shown by SEQ ID No: 44 of the sequence listing.

WY4005: CGC GGATCC ATCCAGAGATTTCTGAAGCG;

WY4006: AAT CGGCCG TTAATTTCTTATATAACATTGAGTTATAGATATAACAAC.

2. The vector backbone (about 5.2 kb) of the recombinant plasmid pBR322-aroG*, after being subjected to a double enzymatic cleavage using the restriction endonucleases BamH I and Eco 52I, is recovered.

3. The enzymatically cleaved product of the PCR amplification product obtained in step 1, after being subjected to a double enzymatic cleavage using the restriction endonucleases BamH I and Eco 52I, is recovered.

4. A recombinant plasmid pBR322-aroG*-tktA is obtained by linking the vector backbone in step 2 and the enzymatically cleaved product in step 3. According to the sequencing result, a structural description for the recombinant plasmid pBR322-aroG*-tktA is set forth as follows: a DNA molecule is inserted between the enzymatic cleavage sites of Nhe I and Eco 52I of the plasmid pBR322; and the DNA molecule sequentially consists, from upstream to downstream, of the following elements: the DNA molecule shown by SEQ ID No: 41 of the sequence listing, a recognition sequence for enzymatic cleavage by restriction endonuclease BamH I, and the DNA molecule shown by SEQ ID No: 43 of the sequence listing.

III. Construction of the Recombinant Plasmid pACYC184-P$_{JJ}$

1. The double-stranded DNA molecule (the promoter P$_{JJ}$) shown by SEQ ID No: 39 of the sequence listing is synthesized.

2. A PCR amplification product is obtained by performing a PCR amplification using the double-stranded DNA molecule prepared in step 1 as a template and using a primer pair comprised of WY843 and WY842.

WY843: TGCTCTAGACAATTCCGACGTCTAAGAAA;

WY842: CCCAAGCTTGGTCAGTGCGTCCTGCTGAT.

3. The enzymatically cleaved product of the PCR amplification product obtained in step 2, after being subjected to a double enzymatic cleavage using the restriction endonucleases XbaI and Hind III, is recovered.

4. The vector backbone (about 4.1 kb) of the plasmid pACYC184, after being subjected to a double enzymatic cleavage using the restriction endonucleases XbaI and Hind III, is recovered.

5. A recombinant plasmid pACYC184-P$_{JJ}$ is obtained by linking the enzymatically cleaved product in step 3 and the vector backbone in step 4.

IV. Construction of the Recombinant Plasmid pACYC184-P$_{JJ}$-trpL*E*DCBA

1. A PCR amplification product A1 is obtained by performing a PCR amplification using the genome DNA of the E. coli K12 MG1655 as a template and using a primer pair comprised of WY4007 and WY4010; a PCR amplification product A2 is obtained by performing a PCR amplification using the genome DNA of the E. coli K12 MG1655 as a template and using a primer pair comprised of WY4008 and WY4010; a PCR amplification product A3 is obtained by performing a PCR amplification using the genome DNA of the E. coli K12 MG1655 as a template and using a primer pair comprised of WY4009 and WY4010; a PCR amplification product A4 is obtained by performing a PCR amplification using the genome DNA of the E. coli K12 MG1655 as a template and using a primer pair comprised of WY4011 and WY4012.

WY4007: CGCggatccACGTAAAAAGGGTATCGACA;

WY4008: CGCggatccCTAATGAGCGGGCTTTTTTTTGAACA;

WY4009: CGCggatc AACAAAATTAGAGAATAACAATGCAAAC;

WY4010: ATCCTGCATAAAAAACGTGTACGGGCTGGGATTACTC;

WY4011: GAGTAATCCCAGCCCGTACACGTTTTTTATGCAGGAT;

WY4012: ACATGCATGC GTTATGTTGCGGGATTAATTTGT.

One point mutation is introduced into the trpE gene by using the primers WY4010 and WY4011, and the mutated gene codes for the TrpE*protein shown by SEQ ID No: 45 of the sequence listing. As compared with the TrpE protein (a wild-type protein), the TrpE*protein only differs in one amino acid residue, that is, the amino acid residue at position 293 of the TrpE protein is mutated to threonine from methionine.

2. A PCR amplification product B1 is obtained by performing a PCR amplification using a mixture of the PCR amplification product A1 and the PCR amplification product A4 as a template and using a primer pair comprised of WY4007 and WY4012; a PCR amplification product B2 is obtained by performing a PCR amplification using a mixture of the PCR amplification product A2 and the PCR amplification product A4 as a template and using a primer pair comprised of WY4008 and WY4012; a PCR amplification product B3 is obtained by performing a PCR amplification using a mixture of the PCR amplification product A3 and the PCR amplification product A4 as a template, and using a primer pair comprised of WY4009 and WY4012.

3. The vector backbone of the recombinant plasmid pACYC184-P$_{JJ}$, after being subjected to a double enzymatic cleavage using the restriction endonucleases BamH I and Sph I, is recovered.

4. The enzymatically cleaved product of the PCR amplification product B1 obtained in step 2, after being subjected to a double enzymatic cleavage using the restriction endonucleases BamH I and Sph I, is recovered.

5. A recombinant plasmid pACYC184-P$_{JJ}$-trpL$^{4007}$E*DCBA is obtained by linking the vector backbone in step 3 and the enzymatically cleaved product in step 4. According to the sequencing result, a structural description for the recombinant plasmid pACYC184-P$_{JJ}$-trpL$^{4007}$E*DCBA is set forth as follows: the plasmid pACYC184 is used as a starting vector, wherein the promoter P$_{JJ}$ shown by SEQ ID No: 39 of the sequence listing is inserted between the enzymatic cleavage sites of XbaI and Hind III, and the DNA molecule shown by SEQ ID No: 40 of the sequence listing is inserted between the enzymatic cleavage sites of BamH I and Sph I.

6. The enzymatically cleaved product of the PCR amplification product B2 obtained in step 2, after being subjected to a double enzymatic cleavage using the restriction endonucleases BamH I and Sph I, is recovered.

7. A recombinant plasmid pACYC184-P$_{JJ}$-trpL$^{4008}$E*DCBA is obtained by linking the vector backbone in step 3 and the enzymatically cleaved product in step 6. According to the sequencing result, a structural description for the recombinant plasmid pACYC184-P$_{JJ}$-trpL$^{4008}$E*DCBA is set forth as follows: the plasmid pACYC184 is used as a starting vector, wherein the promoter $P_{JJ}$ shown by SEQ ID No: 39 of the sequence listing is inserted between the enzymatic cleavage sites of XbaI and Hind III, and the DNA molecule shown by the nucleotides at positions 115-6865 of SEQ ID No: 40 of the sequence listing is inserted between the enzymatic cleavage sites of BamH I and Sph I.

8. The enzymatically cleaved product of the PCR amplification product B3 obtained in step 2, after being subjected to a double enzymatic cleavage using the restriction endonucleases BamH I and Sph I, is recovered.

9. A recombinant plasmid pACYC184-$P_{JJ}$-trpL$^{4009}$E*DCBA is obtained by linking the vector backbone in step 3 and the enzymatically cleaved product in step 8. According to the sequencing result, a structural description for the recombinant plasmid pACYC184-$P_{JJ}$-trpL$^{4009}$E*DCBA is set forth as follows: the plasmid pACYC184 is used as a starting vector, wherein the promoter $P_{JJ}$ shown by SEQ ID No: 39 of the sequence listing is inserted between the enzymatic cleavage sites of XbaI and Hind III, and the DNA molecule shown by the nucleotides at positions 137-6865 of SEQ ID No: 40 of the sequence listing is inserted between the enzymatic cleavage sites of BamH I and Sph I.

V. Construction of Recombinant Bacteria

Recombinant bacteria is obtained by introducing the recombinant plasmid pBR322-aroG*-tktA into the *E. coli* K12 MG1655, and named as recombinant bacteria AT.

Recombinant bacteria is obtained by introducing the recombinant plasmid pACYC184-$P_{JJ}$-trpL$^{4007}$E*DCBA into the recombinant bacteria AT, and named as engineered bacteria Trp4007.

Recombinant bacteria is obtained by introducing the recombinant plasmid pACYC184-$P_{JJ}$-trpL$^{4008}$E*DCBA into the recombinant bacteria AT, and named as engineered bacteria Trp4008.

Recombinant bacteria is obtained by introducing the recombinant plasmid pACYC184-$P_{JJ}$-trpL$^{4009}$E*DCBA into the recombinant bacteria AT, and named as engineered bacteria Trp4009.

VI. Fermentation Test of Engineered Bacteria for Tryptophan in a Shake Flask

The test strain is: the engineered bacteria Trp4007, the engineered bacteria Trp4008 or the engineered bacteria Trp4009.

1. The test strain is streaked onto a solid LB medium plate containing 100 mg/L ampicillin and 34 mg/L chloramphenicol, followed by static culture for 12 h at 37° C.

2. After completion of step 2, a bacterial lawn on the plate is picked and seeded into a liquid LB medium containing 100 mg/L ampicillin and 34 mg/L chloramphenicol, followed by shaking culture for 8 h at 37° C., 220 rpm, and a seed solution is obtained ($OD_{600\,nm}$ value=5.0).

3. After completion of step 3, the seed solution is seeded into a fermentation medium in a seeding amount of 3%, followed by shaking culture at 37° C., 220 rpm.

The fermentation medium is: glucose 20.0 g/L, ammonium sulfate 15.0 g/L, potassium dihydrogen phosphate 2.0 g/L, magnesium sulfate heptahydrate 2.0 g/L, yeast powders 2.0 g/L, calcium carbonate 15.0 g/L, microelement mixture 5 mL/L, and water as the remainder.

The microelement mixture is: $FeSO_4 \cdot 7H_2O$ 10 g/L, $CaCl_2$ 1.35 g/L, $ZnSO_4 \cdot 7H_2O$ 2.25 g/L, $MnSO_4 \cdot 4H_2O$ 0.5 g/L, $CuSO_4 \cdot 5H_2O$ 1 g/L, $(NH_4)_6Mo_7O_{24} \cdot 4H_2O$ 0.106 g/L, $Na_2B_4O_7 \cdot 10H_2O$ 0.23 g/L, $CoCl_2 \cdot 6H_2O$ 0.48 g/L, 35% HCl 10 mL/L, and water as the remainder.

During the culture, ammoniacal liquor is used to adjust the pH value of the reaction system to make it maintain at 6.8-7.0.

During the culture, sampling is made once every 3-4 h to detect the content of glucose by using a biosensor analyzer SBA-40D. When the content of glucose in the system is less than 5 g/L, glucose is supplemented to make the concentration of glucose in the system up to 10 g/L.

Sampling is made after culture for 36 h, followed by centrifugation at 12,000 g for 2 min. The supernatant (i.e., the fermented supernatant) is taken for detection of the concentration of L-tryptophan.

The results are shown in Table 13 (by a mean±standard deviation from repeated tests in triplicate). The engineered bacteria Trp4008 have the highest capability for producing L-tryptophan, and the concentration of L-tryptophan in the fermented supernatant is 1.20±0.15 g/L.

TABLE 13

|  | Content of L-tryptophan in fermented supernatant (g/L) |
|---|---|
| Engineered bacteria Trp4007 | 0.43 ± 0.08 |
| Engineered bacteria Trp4008 | 1.20 ± 0.15 |
| Engineered bacteria Trp4009 | 0.51 ± 0.10 |

A method for detecting the concentration of L-tryptophan in fermented supernatant is: HPLC, which is optimized based on the method for detecting amino acids in a reference (Amino Acids & Biotic Resources, 2000, 22, 59-60), and the method is particularly presented as follows (HPLC coupled to pre-column derivatization with 2, 4-dinitrofluorobenzene (FDBN)):

First, 10 μL of the supernatant is taken into a 2 mL centrifuge tube, into which 200 μL of 0.5M $NaHCO_3$ aqueous solution and 100 μL of 1% (v/v) FDBN-acetonitrile solution are added. Next, the centrifuge tube is placed in a water bath to be heated at a constant temperature of 60° C. for 60 min in the dark, then cooled to the room temperature, into which 700 μL of 0.04 mol/L $KH_2PO_4$ aqueous solution (pH=7.2±0.05; the pH is adjusted with 40 g/L KOH aqueous solution) is added, and shaken well. After being static for 15 min, filtration is performed and filtrates are collected. The filtrates are for injection, and injection volume is 15 μL.

C18 column (ZORBAX Eclipse XDB-C18, 4.6*150 mm, Agilent, USA) is used as the chromatographic column; column temperature: 40° C.; UV detection wavelength: 360 nm; mobile phase A: 0.04 mol/L $KH_2PO_4$ aqueous solution (pH=7.2±0.05; the pH is adjusted with 40 g/100 mL KOH aqueous solution), mobile phase B: 55% (v/v) acetonitrile aqueous solution, and total flux of the mobile phases: 1 mL/min.

The process of elution is presented as follows: at the starting time of elution (0 min), the mobile phase A accounts for 86% by volume of the total flux of the mobile phases, and mobile phase B for 14%; the process of elution is divided into 4 stages, and in each stage, parts by volume of the mobile phase A and the mobile phase B accounting for the total flux of the mobile phases appear a linear variation; when the first stage (a total duration of 2 min from the starting time) ends, the mobile phase A accounts for 88% by volume of the total flux of the mobile phases, and mobile phase B for 12%; when the second stage (a total duration of 2 min from the ending time for the first stage) ends, the mobile phase A accounts for 86% by volume of the total flux of the mobile phases, and mobile phase B for 14%; when the third stage (a total duration of 6 min from the ending time for the second stage) ends, the mobile phase A accounts for 70% by volume of the total flux of the mobile phases, and the mobile phase B for 30%; when the fourth stage (a total duration of 10 min from the ending time for the third stage) ends, the mobile phase A accounts for 30% by volume of the total flux of the mobile phases, and mobile phase B for 70%.

A standard curve is depicted by using the commercially available L-tryptophan as the standard, and the concentration of tryptophan in a sample is calculated.

Example 12. The Expression of the Gfp Gene Under Regulation of an Attenuator Mutant I. Construction of the Recombinant Plasmid pACYC184-P$_{BB}$ 1. The double-stranded DNA molecule (the promoter P$_{BB}$) shown by SEQ ID No: 50 of the sequence listing is synthesized.

2. A PCR amplification product is obtained by performing a PCR amplification using the double-stranded DNA molecule prepared in step 1 as a template and using a primer pair comprised of WY841 and WY842.

```
WY841: TGCTCTAGACAATTCCGACGTCTAAGAGA;

WY842: CCCAAGCTTGGTCAGTGCGTCCTGCTGAT.
```

3. The enzymatically cleaved product of the PCR amplification product obtained in step 2, after being subjected to a double enzymatic cleavage using the restriction endonucleases XbaI and Hind III, is recovered.

4. The vector backbone (about 4.1 kb) of the plasmid pACYC184, after being subjected to a double enzymatic cleavage using the restriction endonucleases XbaI and Hind III, is recovered.

5. A recombinant plasmid pACYC184-P$_{BB}$ is obtained by linking the enzymatically cleaved product in step 3 and the vector backbone in step 4.

II. Construction of Each Recombinant Plasmid and Corresponding Recombinant Bacteria 1. Construction of the recombinant bacteria GFP3230

(1) A PCR amplification product A1 is obtained by performing a PCR amplification using the genome DNA of the *E. coli* K12 MG1655 as a template and using a primer pair comprised of WY3230 and WY3236; a PCR amplification product A2 is obtained by performing a PCR amplification using the pGFPuv vector as a template and using a primer pair comprised of WY3105 and WY1859; a PCR amplification product A3 is obtained by performing a PCR amplification using a mixture of the PCR amplification product A1 and the PCR amplification product A2 as a template and using a primer pair comprised of WY3223 and WY1859.

```
WY3230: CCCAAGCTT AAACATTCACAGAGACTTTT atgACAC;
WY3236: AGTTCTTCTCCTTTACTCATAGAACCAGAACCAGAACCAA
TGCCACAGCGCGCCAGCA;
WY3105: GGTTCTGGTTCTGGTTCTATGAGTAAAGGAGAAGAACTTT
TCA;
WY1859:

ACATGCATGCCAAAAAACCCCTCAAGACCCGTTTAGAGGCCCCAAGGGG

TTATGCTAGTTATTTGTAGAGCTCATCCATGCCA.
```

(2) The enzymatically cleaved product of the PCR amplification product A3 obtained in step (1), after being subjected to a double enzymatic cleavage using the restriction endonucleases Hind III and Sph I, is recovered.

(3) The vector backbone (about 4.0 kb) of the recombinant plasmid pACYC184-P$_{BB}$, after being subjected to a double enzymatic cleavage using the restriction endonucleases Hind III and Sph I, is recovered.

(4) The recombinant plasmid pACYC184-P$_{BB}$-hisLG-gfp3230 is obtained by linking the enzymatically cleaved product in step (2) and the vector backbone in step (3), then transforming into the *E. coli* EC135, and extracting a plasmid from a transformant. According to the sequencing result, a structural description for the recombinant plasmid pACYC184-P$_{BB}$-hisLG-gfp3230 is set forth as follows: a specific DNA molecule is inserted between the enzymatic cleavage sites of Xba I and Sph I of the plasmid pACYC184; and the specific DNA molecule sequentially consists, from upstream to downstream, of the following elements: the promoter P$_{BB}$ shown by SEQ ID No: 50 of the sequence listing, a recognition sequence for enzymatic cleavage by restriction endonuclease Hind III, the RBS sequence "AAA-CATTCAC AGAGACTTTT" (SEQ ID NO: 232), the nucleotides at positions 1-286 of SEQ ID No: 51 of the sequence listing (inclusive of a complete histidine attenuator and the sequence coding for the first 30 amino acid residues in the open reading frame of the hisG gene), a linker sequence "GGTTCTGGTTCTGGTTCT" (SEQ ID NO: 67), the gfp gene shown by SEQ ID No: of the sequence listing, and the terminator sequence

```
"CTAGCATAACCCCTTGGGGCCTCTAAACGGGTCTTGAGGGG

TTTTTTG".
```

The *E. coli* EC135 comprising the recombinant plasmid pACYC184-P$_{BB}$-hisLG-gfp3230 is named as recombinant bacteria GFP3230.

2. Construction of the Recombinant Bacteria GFP3231

(1) A PCR amplification product A1 is obtained by performing a PCR amplification using the genome DNA of the *E. coli* K12 MG1655 as a template and using a primer pair comprised of WY3231 and WY3236; a PCR amplification product A2 is obtained by performing a PCR amplification using the pGFPuv vector as a template and using a primer pair comprised of WY3105 and WY1859; a PCR amplification product A3 is obtained by performing a PCR amplification using a mixture of the PCR amplification product A1 and the PCR amplification product A2 as a template and using a primer pair comprised of WY3231 and WY1859.

```
WY3231: CCCAAGCTT ACCTTCCGGGGGCTTTTTTATTGC.
```

(2) The enzymatically cleaved product of the PCR amplification product A3 obtained in step (1), after being subjected to a double enzymatic cleavage using the restriction endonucleases Hind III and Sph I, is recovered.

(3) The vector backbone of the recombinant plasmid pACYC184-P$_{BB}$, after being subjected to a double enzymatic cleavage using the restriction endonucleases Hind III and Sph I, is recovered.

(4) The recombinant plasmid pACYC184-P$_{BB}$-hisLG-gfp323/is obtained by linking the enzymatically cleaved product in step (2) and the vector backbone in step (3), then transforming into the *E. coli* EC135, and extracting a plasmid from a transformant. According to the sequencing result, a structural description for the recombinant plasmid pACYC184-P$_{BB}$-hisLG-gfp3231 is set forth as follows: a specific DNA molecule is inserted between the enzymatic cleavage sites of Xba I and Sph I of the plasmid pACYC184; and the specific DNA molecule sequentially consists, from upstream to downstream, of the following elements: the promoter P$_{BB}$ shown by SEQ ID No: 50 of the sequence listing, a recognition sequence for enzymatic cleavage by restriction endonuclease Hind III, the nucleotides at positions 130-286 of SEQ ID No: 51 of the sequence listing (inclusive of a truncated histidine attenuator and the sequence coding for the first 30 amino acid residues in the open reading frame of the hisG gene), a linker sequence "GGTTCTGGTTCTGGTTCT" (SEQ ID NO: 67), the gfp gene shown by SEQ ID No: 30 of the sequence listing, and the terminator sequence

"CTAGCATAACCCCTTGGGGCCTCTAAACGGGTCTTGAGGGGTTTTT

TG".

The *E. coli* EC135 comprising the recombinant plasmid pACYC184-P$_{BB}$-hisLG-gfp3231 is named as recombinant bacteria GFP3231.

3. Construction of the Recombinant Bacteria GFP3232

(1) A PCR amplification product A1 is obtained by performing a PCR amplification using the genome DNA of the *E. coli* K12 MG1655 as a template and using a primer pair comprised of WY3232 and WY3236; a PCR amplification product A2 is obtained by performing a PCR amplification using the pGFPuv vector as a template and using a primer pair comprised of WY3105 and WY1859; a PCR amplification product A3 is obtained by performing a PCR amplification using a mixture of the PCR amplification product A1 and the PCR amplification product A2 as a template and using a primer pair comprised of WY3232 and WY1859.

WY3232: CCC<u>AAGCTT</u> GTTTAAAGAGGAATAACAAAATGACA.

(2) The enzymatically cleaved product of the PCR amplification product A3 obtained in step (1), after being subjected to a double enzymatic cleavage using the restriction endonucleases Hind III and Sph I, is recovered.

(3) The vector backbone of the recombinant plasmid pACYC184-P$_{BB}$, after being subjected to a double enzymatic cleavage using the restriction endonucleases Hind III and Sph I, is recovered.

(4) The recombinant plasmid pACYC184-P$_{BB}$-hisLG-gfp3232 is obtained by linking the enzymatically cleaved product in step (2) and the vector backbone in step (3), then transforming into the *E. coli* EC135, and extracting a plasmid from a transformant. According to the sequencing result, a structural description for the recombinant plasmid pACYC184-P$_{BB}$-hisLG-gfp3232 is set forth as follows: a specific DNA molecule is inserted between the enzymatic cleavage sites of Xba I and Sph I of the plasmid pACYC184; and the specific DNA molecule sequentially consists, from upstream to downstream, of the following elements: the promoter P$_{BB}$ shown by SEQ ID No: 50 of the sequence listing, a recognition sequence for enzymatic cleavage by restriction endonuclease Hind III, the nucleotides at positions 177-286 of SEQ ID No: 51 of the sequence listing (inclusive of the sequence coding for the first 30 amino acid residues in the open reading frame of the hisG gene and having completely removed the histidine attenuator), a linker sequence "GGTTCTGGTTCTGGTTCT" (SEQ ID NO: 67), the gfp gene shown by SEQ ID No: 30 of the sequence listing, and the terminator sequence

"CTAGCATAACCCCTTGGGGCCTCTAAACGGGTCTTGAGGGGTTTTT

TG".

The *E. coli* EC135 comprising the recombinant plasmid pACYC184-P$_{BB}$-hisLG-gfp3232 is named as recombinant bacteria GFP3232.

4. Construction of the GFP Control

Recombinant bacteria is obtained by introducing the recombinant plasmid pACYC184-P$_{BB}$ into the *E. coli* EC135, and named as GFP control.

III. Analysis for the fluorescence intensity of GFP The test strain: the recombinant bacteria GFP3230, the recombinant bacteria GFP3231 or the recombinant bacteria GFP3232.

The GFP control is set to the control strain.

1. The test strain or the control strain is seeded into a liquid LB medium containing 34 mg/L chloramphenicol, followed by shaking culture overnight at 37° C., 220 rpm.

2. The bacteria liquid obtained in step 1 is seeded into a liquid 2×YT medium containing 34 mg/L chloramphenicol with a seeding amount of 1%, followed by shaking culture for 10 h at 37° C., 220 rpm.

3. 150 μL of the bacteria liquid obtained in step 2 is added into a 96-well plate having black edges and a transparent bottom, and the density of cells and the fluorescence signal of GFP are simultaneously detected by using a high throughput multifunctional microplate reader (the INFINITE 200 PRO type, TECAN, Switzerland). Parameters associated with detection of the density of cells are set as presented in Table 14. Parameters associated with detection of the fluorescence signal of GFP are set as presented in Table 15.

TABLE 14

| | Absorbance |
|---|---|
| Wavelength | 600 nm |
| Bandwidth | 9 nm |
| Number of Flashes | 25 |
| Settle Time | 0 ms |

TABLE 15

| | Fluorescence Top Reading |
|---|---|
| Excitation Wavelength | 400 nm |
| Emission Wavelength | 510 nm |
| Excitation Bandwidth | 9 nm |
| Emission Bandwidth | 20 nm |
| Gain | 100 (Manual) |

TABLE 15-continued

| | Fluorescence Top Reading |
|---|---|
| Number of Flashes | 15 |
| Integration Time | 20 μs |
| LagTime | 0 μs |
| Settle Time | 0 ms |
| Z-Position | 20000 μm (Manual) |

The fluorescence intensity value of each test strain=the fluorescence value actually measured÷the density of cells−the fluorescence value actually measured from the control strain÷the density of cells of the control strain. Repeated tests are set in triplicate, and the results of the corresponding means and standard deviations are shown in Table 16.

As compared with the recombinant bacteria GFP3230 (remaining a complete histidine attenuator), the fluorescence intensity of the recombinant bacteria GFP3231 is improved by 36.8 folds. As compared with the recombinant bacteria GFP3232 (having completely deleted the histidine attenuator), the fluorescence intensity of the recombinant bacteria GFP3231 is improved by 43.5 folds. The results indicate that the truncated histidine attenuator located between the promoter and the target gene can function as a regulation element to promote the expression of the target gene.

The histidine attenuator mutant is shown by the nucleotides at positions n1-n2 of SEQ ID No: 51 of the sequence listing; n1 is a natural number greater than or equal to 126 but smaller than or equal to 143 (preferably, n1 is 130), and n2 is a natural number greater than or equal to 148 but smaller than or equal to 286 (n2 particularly can be a natural number greater than or equal to 148 but smaller than or equal to 196, or a natural number greater than or equal to 197 but smaller than or equal to 286, even more particularly 148, 196 or 286). The histidine attenuator mutant comprises a truncated histidine attenuator and a histidine attenuator variant (its full name is: a variant linking other nucleotides downstream of a truncated histidine attenuator). The truncated histidine attenuator is shown by the nucleotides at positions n1-148 of SEQ ID No: 51 of the sequence listing. The histidine attenuator variant is shown by the nucleotides at positions n1-n4 of SEQ ID No: 51 of the sequence listing; n4 is a natural number greater than or equal to 149 but smaller than or equal to (n4 particularly can be a natural number greater than or equal to 149 but smaller than or equal to 196, or a natural number greater than or equal to 197 but smaller than or equal to 286, even more particularly 196 or 286).

TABLE 16

| | Fluorescence Intensity |
|---|---|
| Recombinant bacteria GFP3230 | 574.4 ± 35.2 |
| Recombinant bacteria GFP3231 | 21727.8 ± 583.2 |
| Recombinant bacteria GFP3232 | 488.5 ± 28.3 |

Example 13. Preparation of Histidine

I. Construction of the Engineered Bacteria E.coliMG1655 hisG*ΔhisL

1. A PCR amplification product A1 is obtained by performing a PCR amplification using the genome DNA of the E. coli K12 MG1655 as a template and using a primer pair comprised of WY4013 and WY4014. A PCR amplification product A2 is obtained by performing a PCR amplification using the genome DNA of the E. coli K12 MG1655 as a template and using a primer pair comprised of WY4015 and WY4016.

```
WY4013:
CGCGGATCCCGTCCCATGATTCCTCAGA;

WY4014:
AAAGCCCCCGGAAGGTGATGTGAATGTTTATTCAACTGATGTC.

WY4015:
GACATCAGTTGAATAAACATTCACATCACCTTCCGGGGGCTTT;

WY4016:
ATTGCGGCCGCCCCAGAACAG GGTTTTGCTGCTGACC.
```

The associated sequences in the genome of the E. coli K12 MG1655 are shown by SEQ ID No: 52 of the sequence listing, wherein the histidine attenuator is shown by the nucleotides at positions 596-743, and the nucleotides at positions 792-1691 are the gene coding for ATP phosphoribosyltransferase. The WY4013 and WY4014 are used for the amplification of the upstream homology arm; the WY4015 and WY4016 are used for the amplification of the downstream homology arm and introduction of one point mutation in the gene coding for ATP phosphoribosyltransferase. The upstream homology arm is located upstream of the histidine attenuator; the starting end of the downstream homology arm corresponds to the nucleotide at position 127 of the histidine attenuator, and the termination end of the downstream homology arm is located in the gene coding for ATP phosphoribosyltransferase. The ATP phosphoribosyltransferase coded by a corresponding gene before being introduced with the above point mutation in the genome of the E. coli K12 MG1655 is named as the HisG protein (shown by SEQ ID No: 54 of the sequence listing). The ATP phosphoribosyltransferase coded by a corresponding gene after being introduced with the above point mutation is named as the HisG*protein (shown by SEQ ID No: 53 of the sequence listing). As compared with the HisG protein, the HisG*protein only differs in that the amino acid residue at position 271 of the HisG protein is mutated to lysine from glutamic acid, thereby relieving the feedback repression.

2. A PCR amplification product is obtained by performing a PCR amplification using a mixture of the PCR amplification product A1 and the PCR amplification product A2 obtained in step 1 as a template and using a primer pair comprised of WY4013 and WY4016.

3. The enzymatically cleaved product of the PCR amplification product obtained in step 2, after being subjected to a double enzymatic cleavage using the restriction endonucleases BamH I and Not I, is recovered.

4. The vector backbone (about 5.6 kb) of the plasmid pKOV, after being subjected to a double enzymatic cleavage using the restriction endonucleases BamH I and Not I, is recovered.

5. A recombinant plasmid pKOV-ΔhisL-hisG* is obtained by linking the enzymatically cleaved product in step 3 and the vector backbone in step 4. According to the sequencing result, a structural description for the recombinant plasmid pKOV-ΔhisL-hisG* is set forth as follows: a specific DNA molecule is inserted between the enzymatic cleavage sites of BamH I and Not I of the plasmid pKOV; and the specific DNA molecule sequentially consists, from upstream to downstream, of the following elements: the upstream homology arm shown by the nucleotides at positions 32-585 of SEQ ID No: 52 of the sequence listing, and the downstream homology arm shown by the nucleotides at positions 722-1617 of SEQ ID No: 52 of the sequence listing.

6. Recombinant bacteria with homologous recombination are obtained by introducing the recombinant plasmid pKOV-ΔhisL-hisG* into the *E. coli* K12 MG1655, and named as engineered bacteria *E.coli*MG1655 hisG*ΔhisL. After being verified by sequencing, as compared with the genome DNA of the *E. coli* K12 MG1655, the engineered bacteria *E.coli*MG1655 hisG*ΔhisL differ in the two aspects as follows: (1) the nucleotides at positions 586-721 of the DNA molecule shown by SEQ ID No: 52 in the genome are deleted (in the deleted nucleotides: the first 10 nucleotides are the ones upstream of the histidine attenuator, and the remaining nucleotides are the ones at positions 1-126 of the histidine attenuator); (2) the nucleotide at position 1602 of the DNA molecule shown by SEQ ID No: 52 in the genome is mutated to A from G. The histidine operon of the engineered bacteria *E.coli*MG1655 hisG*ΔhisL is shown by the nucleotides at positions 127-7230 of SEQ ID No: 51 of the sequence listing.

II. Construction of the Engineered Bacteria *E.coli*MG1655 hisG*

1. A PCR amplification product is obtained by performing a PCR amplification using the genome DNA of the *E. coli* K12 MG1655 as a template and using a primer pair comprised of WY4013 and WY4019.

```
WY4019:
ATTGCGGCCGCCAGAACCGTTCAGTAAGCAG.
```

2. The enzymatically cleaved product of the PCR amplification product obtained in step 1, after being subjected to a double enzymatic cleavage using the restriction endonucleases BamH I and Not I, is recovered.

3. The vector backbone (about 5.6 kb) of the plasmid pKOV, after being subjected to a double enzymatic cleavage using the restriction endonucleases BamH I and Not I, is recovered.

4. A recombinant plasmid pKOV-hisL is obtained by linking the enzymatically cleaved product in step 2 and the vector backbone in step 3.

5. Recombinant bacteria with homologous recombination are obtained by introducing the recombinant plasmid pKOV-hisL into the engineered bacteria *E.coli*MG1655 hisG*ΔhisL, and named as engineered bacteria *E.coli*MG1655 hisG*.

After being verified by sequencing, as compared with the genome DNA of the *E. coli* K12 MG1655, the engineered bacteria *E.coli*MG1655 hisG* differ in one aspect as follows: the nucleotide at position 1602 of the DNA molecule shown by SEQ ID No: 52 in the genome is mutated to A from G.

III. Fermentation Test of Engineered Bacteria for Histidine in a Shake Flask

The test strain is: the engineered bacteria *E.coli*MG1655 hisG*ΔhisL or the engineered bacteria *E.coli*MG1655 hisG*.

1. The test strain is streaked onto a solid LB medium plate, followed by static culture for 12 h at 37° C.

2. After completion of step 1, a bacterial lawn on the plate is picked and seeded into a liquid LB medium, followed by shaking culture for 8 h at 37° C., 220 rpm, and a seed solution is obtained ($OD_{600nm}$ value=5.0).

3. After completion of step 2, the seed solution is seeded into a fermentation medium in a seeding amount of 3%, followed by shaking culture at 37° C., 220 rpm.

The fermentation medium is: glucose 20.0 g/L, ammonium sulfate 15.0 g/L, potassium dihydrogen phosphate 2.0 g/L, magnesium sulfate heptahydrate 2.0 g/L, yeast powders 2.0 g/L, calcium carbonate 15.0 g/L, microelement mixture 5 mL/L, and water as the remainder.

The microelement mixture is: $FeSO_4 \cdot 7H_2O$ 10 g/L, $CaCl_2$ 1.35 g/L, $ZnSO_4 \cdot 7H_2O$ 2.25 g/L, $MnSO_4 \cdot 4H_2O$ 0.5 g/L, $CuSO_4 \cdot 5H_2O$ 1 g/L, $(NH_4)_6Mo_7O_{24} \cdot 4H_2O$ 0.106 g/L, $Na_2B_4O_7 \cdot 10H_2O$ 0.23 g/L, $CoCl_2 \cdot 6H_2O$ 0.48 g/L, 35% HCl 10 mL/L, and water as the remainder.

During the culture, ammoniacal liquor is used to adjust the pH value of the reaction system to make it maintain at 6.8-7.0.

During the culture, sampling is made once every 3-4 h to detect the content of glucose by using a biosensor analyzer SBA-40D. When the content of glucose in the system is less than 5 g/L, glucose is supplemented to make the concentration of glucose in the system up to 10 g/L.

Sampling is made after culture for 36 h, followed by centrifugation at 12,000 g for 2 min. The supernatant (the fermented supernatant) is taken for detection of the concentration of L-histidine.

The results are shown in Table 17 (by a mean±standard deviation from repeated tests in triplicate). As compared with the engineered bacteria *E.coli*MG1655 hisG*, the yield of L-histidine produced in fermentation by the engineered bacteria *E.coli*MG1655 hisG*ΔhisL is significantly improved.

TABLE 17

| | Content of L-histidine in fermented supernatant (g/L) |
|---|---|
| Engineered bacteria *E. coli*MG1655 hisG* | 0.22 ± 0.05 |
| Engineered bacteria *E. coli*MG1655 hisG*ΔhisL | 1.35 ± 0.25 |

A method for detecting the concentration of L-histidine is: HPLC, which is optimized based on the method for detecting amino acids in a reference (Amino Acids & Biotic Resources, 2000, 22, 59-60), and the method is particularly presented as follows (HPLC coupled to pre-column derivatization with 2, 4-dinitrofluorobenzene (FDBN)):

First, 10 μL of the supernatant is taken into a 2 mL centrifuge tube, into which 200 μL of 0.5M $NaHCO_3$ aqueous solution and 100 μL of 1% (v/v) FDBN-acetonitrile solution are added. Next, the centrifuge tube is placed in a water bath to be heated at a constant temperature of 60° C. for 60 min in the dark, then cooled to the room temperature, into which 700 μL of 0.04 mol/L $KH_2PO_4$ aqueous solution (pH=7.2±0.05; the pH is adjusted with 40 g/L KOH aqueous solution) is added, and shaken well. After being static for 15 min, filtration is performed and filtrates are collected. The filtrates are for injection, and injection volume is 15 μL.

C18 column (ZORBAX Eclipse XDB-C18, 4.6*150 mm, Agilent, USA) is used as the chromatographic column; column temperature: 40° C.; UV detection wavelength: 360 nm; mobile phase A: 0.04 mol/L $KH_2PO_4$ aqueous solution (pH=7.2±0.05; the pH is adjusted with 40 g/100 mL KOH aqueous solution), mobile phase B: 55% (v/v) acetonitrile aqueous solution, and total flux of the mobile phases: 1 mL/min.

The process of elution is presented as follows: at the starting time of elution (0 min), the mobile phase A accounts for 86% by volume of the total flux of the mobile phases, and mobile phase B for 14%; the process of elution is divided into 4 stages, and in each stage, parts by volume of the mobile phase A and the mobile phase B accounting for the total flux of the mobile phases appear a linear variation; when the first stage (a total duration of 2 min from the starting time) ends, the mobile phase A accounts for 88% by volume of the total flux of the mobile phases, and mobile phase B for 12%; when the second stage (a total duration of 2 min from the ending time for the first stage) ends, the mobile phase A accounts for 86% by volume of the total flux of the mobile phases, and mobile phase B for 14%; when the third stage (a total duration of 6 min from the ending time for the second stage) ends, the mobile phase A accounts for 70% by volume of the total flux of the mobile phases, and the mobile phase B for 30%; when the fourth stage (a total duration of 10 min from the ending time for the third stage) ends, the mobile phase A accounts for 30% by volume of the total flux of the mobile phases, and mobile phase B for 70%.

A standard curve is depicted by using the commercially available L-histidine as the standard, and the concentration of histidine in a sample is calculated.

Example 14. The Expression of the Gfp Gene Under Regulation of an Attenuator Mutant I. Construction of Recombinant Plasmid pACYC184-P$_{thr-trc}$ 1. The double-stranded DNA molecule (the promoter P$_{thr-trc}$) shown by SEQ ID No: 29 of the sequence listing is synthesiezed.

2. A PCR amplification product is obtained by performing a PCR amplification using the genome DNA of the *E. coli* K12 MG1655 as a template and using a primer pair comprised of WY1947 and WY1948.

WY1947:
CTAG<u>TCTAGA</u> GCTTTTCATTCTGACTGCAAC;

WY1948:
CCC<u>AAGCTT</u>ACATTATACGAGCCGGATGATTAATTGTCAACTGTCTGTGC

GCTATGCCT.

3. The enzymatically cleaved product of the PCR amplification product obtained in step 2, after being subjected to a double enzymatic cleavage using the restriction endonucleases Xba I and Hind III, is recovered.

4. The vector backbone (about 4.1 kb) of the plasmid pACYC184, after being subjected to a double enzymatic cleavage using the restriction endonucleases Xba I and Hind III, is recovered.

5. A recombinant plasmid pACYC184-P$_{thr-trc}$ is obtained by linking the enzymatically cleaved product in step 3 and the vector backbone in step 4.

II. Construction of each recombinant plasmid 1. Construction of the recombinant bacteria GFP3248

(1) A PCR amplification product A1 is obtained by performing a PCR amplification using the genome DNA of the *E. coli* K12 MG1655 as a template and using a primer pair comprised of WY3248 and WY3258; a PCR amplification product A2 is obtained by performing a PCR amplification using the pGFPuv vector as a template and using a primer pair comprised of WY3105 and WY1859; a PCR amplification product A3 is obtained by performing a PCR amplification using a mixture of the PCR amplification product A1 and the PCR amplification product A2 as a template and using a primer pair comprised of WY3248 and WY1859.

WY3248:
CCC<u>AAGCTT</u> AGTCACTTAAGGAAACAAAC atgA;

WY3258:
AGTTCTTCTCCTTTACTCAT AGAACCAGAACCAGAACC

CAGCGCCAGTAACGGGTTTTC;

WY3105:
GGTTCTGGTTCTGGTTCTATGAGTAAAGGAGAAGAACTTTTCA;

WY1859:
ACAT<u>GCATGC</u>CAAAAAACCCCTCAAGACCCGTTTAGAGGCCCCAAGGGGT

TATGCTAGTTATTTGTAGAGCTCATCCATGCCA.

(2) The enzymatically cleaved product of the PCR amplification product A3 obtained in step (1), after being subjected to a double enzymatic cleavage using the restriction endonucleases Hind III and Sph I, is recovered.

(3) The vector backbone of the recombinant plasmid pACYC184-P$_{thr-trc}$, after being subjected to a double enzymatic cleavage using the restriction endonucleases Hind III and Sph I, is recovered.

(4) The recombinant plasmid pACYC184-P$_{thr-trc}$-pheLA-gfp3248 is obtained by linking the enzymatically cleaved product in step (2) and the vector backbone in step (3), then transforming into the *E. coli* EC135, and extracting a plasmid from a transformant. According to the sequencing result, a structural description for the recombinant plasmid pACYC184-P$_{thr-trc}$-pheLA-gfp3248 is set forth as follows: a specific DNA molecule is inserted between the enzymatic cleavage sites of Xba I and Sph I of the plasmid pACYC184; and the specific DNA molecule sequentially consists, from upstream to downstream, of the following elements: the promoter P$_{thr-trc}$ shown by SEQ ID No: 29 of the sequence listing, a recognition sequence for enzymatic cleavage by restriction endonuclease Hind III, the RBS sequence "AGTCACTTAAGGAAACAAAC", the nucleotides at positions 1-176 of SEQ ID No: 62 of the sequence listing (inclusive of a complete phenylalanine attenuator and the sequence coding for the first 10 amino acid residues in the open reading frame of the pheA gene), a linker sequence "GGTTCTGGTTCTGGTTCT" (SEQ ID NO: 67), the gfp gene shown by SEQ ID No: of the sequence listing, and the terminator sequence

"CTAGCATAACCCCTTGGGGCCTCTAAACGGGTCTTGAGGGGTTTTT

TG".

The *E. coli* EC135 comprising the recombinant plasmid pACYC184-P$_{thr-trc}$-pheLA-gfp3248 is named as recombinant bacteria GFP3248.

2. Construction of the recombinant bacteria GFP3250

(1) A PCR amplification product A1 is obtained by performing a PCR amplification using the genome DNA of the *E. coli* K12 MG1655 as a template and using a primer pair comprised of WY3250 and WY3258; a PCR amplification product A2 is obtained by performing a PCR amplification using the pGFPuv vector as a template and using a primer pair comprised of WY3105 and WY1859; a PCR amplification product A3 is obtained by performing a PCR amplification using a mixture of the PCR amplification product A1 and the PCR amplification product A2 as a template and using a primer pair comprised of WY3250 and WY1859.

```
WY3250:
CCCAAGCTT CTTTTTTATTGATAACAAAAAGGCAACACT.
```

(2) The enzymatically cleaved product of the PCR amplification product A3 obtained in step (1), after being subjected to a double enzymatic cleavage using the restriction endonucleases Hind III and Sph I, is recovered.

(3) The vector backbone of the recombinant plasmid pACYC184-P$_{thr-trc}$, after being subjected to a double enzymatic cleavage using the restriction endonucleases Hind III and Sph I, is recovered.

(4) The recombinant plasmid pACYC184-P$_{thr-trc}$-pheLA-gfp3250 is obtained by linking the enzymatically cleaved product in step (2) and the vector backbone in step (3), then transforming into the E. coli EC135, and extracting a plasmid from a transformant. According to the sequencing result, a structural description for the recombinant plasmid pACYC184-P$_{thr-trc}$-pheLA-gfp3250 is set forth as follows: a specific DNA molecule is inserted between the enzymatic cleavage sites of Xba I and Sph I of the plasmid pACYC184; and the specific DNA molecule sequentially consists, from upstream to downstream, of the following elements: the promoter P$_{thr-trc}$ shown by SEQ ID No: 29 of the sequence listing, a recognition sequence for enzymatic cleavage by restriction endonuclease Hind III, the nucleotides at positions 117-176 of SEQ ID No: 62 of the sequence listing (inclusive of a truncated phenylalanine attenuator and the sequence coding for the first 10 amino acid residues in the open reading frame of the pheA gene), a linker sequence "GGTTCTGGTTCTGGTTCT" (SEQ ID NO: 67), the gfp gene shown by SEQ ID No: 30 of the sequence listing, and the terminator sequence

```
"CTAGCATAACCCCTTGGGGCCTCTAAACGGGTCTTGAGGGGTTTTT
TG".
```

The E. coli EC135 comprising the recombinant plasmid pACYC184-P$_{thr-trc}$-pheLA-gfp3250 is named as recombinant bacteria GFP3250.

3. Construction of the recombinant bacteria GFP3251

(1) A PCR amplification product A1 is obtained by performing a PCR amplification using the genome DNA of the E. coli K12 MG1655 as a template and using a primer pair comprised of WY3251 and WY3258; a PCR amplification product A2 is obtained by performing a PCR amplification using the pGFPuv vector as a template and using a primer pair comprised of WY3105 and WY1859; a PCR amplification product A3 is obtained by performing a PCR amplification using a mixture of the PCR amplification product A1 and the PCR amplification product A2 as a template and using a primer pair comprised of WY3251 and WY1859.

```
WY3251:
CCCAAGCTT GATAACAAAAAGGCAACACTATGA.
```

(2) The enzymatically cleaved product of the PCR amplification product A3 obtained in step (1), after being subjected to a double enzymatic cleavage using the restriction endonucleases Hind III and Sph I, is recovered.

(3) The vector backbone of the recombinant plasmid pACYC184-P$_{thr-trc}$, after being subjected to a double enzymatic cleavage using the restriction endonucleases Hind III and Sph I, is recovered.

(4) The recombinant plasmid pACYC184-P$_{thr-trc}$-pheLA-gfp3251 is obtained by linking the enzymatically cleaved product in step (2) and the vector backbone in step (3), then transforming into the E. coli EC135, and extracting a plasmid from a transformant. According to the sequencing result, a structural description for the recombinant plasmid pACYC184-P$_{thr-trc}$-pheLA-gfp3251 is set forth as follows: a specific DNA molecule is inserted between the enzymatic cleavage sites of Xba I and Sph I of the plasmid pACYC184; and the specific DNA molecule sequentially consists, from upstream to downstream, of the following elements: the promoter P$_{thr-trc}$ shown by SEQ ID No: 29 of the sequence listing, a recognition sequence for enzymatic cleavage by restriction endonuclease Hind III, the nucleotides at positions 127-176 of SEQ ID No: 62 of the sequence listing (inclusive of the sequence coding for the first 10 amino acid residues in the open reading frame of the pheA gene and having completely removed the phenylalanine attenuator), a linker sequence "GGTTCTGGTTCTGGTTCT" (SEQ ID NO: 67), the gfp gene shown by SEQ ID No: 30 of the sequence listing, and the terminator sequence

```
"CTAGCATAACCCCTTGGGGCCTCTAAACGGGTCTTGAGGGGTTTTT
TG".
```

The E. coli EC135 comprising the recombinant plasmid pACYC184-P$_{thr-trc}$-pheLA-gfp3251 is named as recombinant bacteria GFP3251.

4. Construction of the GFP Control

Recombinant bacteria is obtained by introducing the recombinant plasmid pACYC184-P$_{thr-trc}$ into the E. coli EC135, and named as GFP control.

III. Analysis for the Fluorescence Intensity of GFP

The test strain is: the recombinant bacteria GFP3248, the recombinant bacteria GFP3250 or the recombinant bacteria GFP3251.

The GFP control is set to the control strain. 1. The test strain or the control strain is seeded into a liquid LB medium containing 34 mg/L chloramphenicol, followed by shaking culture for overnight at 37° C., 220 rpm.

2. The bacteria liquid obtained in step 1 is seeded into a liquid LB medium containing 34 mg/L chloramphenicol with a seeding amount of 1%, followed by shaking culture for 12 h at 37° C., 220 rpm.

3. 150 μL of the bacteria liquid obtained in step 2 is added into a 96-well plate having black edges and a transparent bottom, and the density of cells and the fluorescence signal of GFP are simultaneously detected by using a high throughput multifunctional microplate reader (the INFINITE 200 PRO type, TECAN, Switzerland). Parameters associated with detection of the density of cells are set as presented in Table 18. Parameters associated with detection of the fluorescence signal of GFP are set as presented in Table 19.

TABLE 18

| | Absorbance |
|---|---|
| Wavelength | 600 nm |
| Bandwidth | 9 nm |
| Number of Flashes | 25 |
| Settle Time | 0 ms |

TABLE 19

| | Fluorescence Top Reading | |
|---|---|---|
| Excitation Wavelength | 400 | nm |
| Emission Wavelength | 510 | nm |
| Excitation Bandwidth | 9 | nm |
| Emission Bandwidth | 20 | nm |
| Gain | 100 | (Manual) |
| Number of Flashes | 15 | |
| Integration Time | 20 | μs |
| LagTime | 0 | μs |
| Settle Time | 0 | ms |
| Z-Position | 20000 | μm (Manual) |

The fluorescence intensity value of each test strain=the fluorescence value actually measured÷the density of cells−the fluorescence value actually measured from the control strain÷the density of cells of the control strain. Repeated tests are set in triplicate, and the results of the corresponding means and standard deviations are shown in Table 20.

As compared with the recombinant bacteria GFP3248 (remaining a complete phenylalanine attenuator), the fluorescence intensity of the recombinant bacteria GFP3250 is improved by 5.2 folds. As compared with the recombinant bacteria GFP3251 (having completely deleted the phenylalanine attenuator), the fluorescence intensity of the recombinant bacteria GFP3250 is improved by 3.7 folds. The results indicate that the truncated phenylalanine attenuator located between the promoter and the target gene can function as a regulation element to promote the expression of the target gene.

The phenylalanine attenuator mutant is shown by the nucleotides at positions n1-n2 of SEQ ID No: 62 of the sequence listing; n1 is a natural number greater than or equal to 105 but smaller than or equal to 118 (preferably, n1 is 117), and n2 is a natural number greater than or equal to 123 but smaller than or equal to 176 (n2 particularly can be a natural number greater than or equal to 123 but smaller than or equal to 146, or a natural number greater than or equal to 147 but smaller than or equal to 176, even more particularly 123, 146 or 176). The phenylalanine attenuator mutant comprises a truncated phenylalanine attenuator and a phenylalanine attenuator variant (its full name is: a variant linking other nucleotides downstream of the phenylalanine attenuator truncation). The truncated phenylalanine attenuator is shown by the nucleotides at positions n1-123 of SEQ ID No: 62 of the sequence listing. The phenylalanine attenuator variant is shown by the nucleotides at positions n1-n4 of SEQ ID No: 62 of the sequence listing; n4 is a natural number greater than or equal to 124 but smaller than or equal to 176 (n4 particularly can be a natural number greater than or equal to 124 but smaller than or equal to 146, or a natural number greater than or equal to 147 but smaller than or equal to 176, even more particularly 146 or 176).

TABLE 20

| | Fluorescence Intensity |
|---|---|
| Recombinant bacteria GFP3248 | 770.4 ± 65.2 |
| Recombinant bacteria GFP3250 | 4778.4 ± 463.2 |
| Recombinant bacteria GFP3251 | 1010.9 ± 128.6 |

Example 15. Preparation of Phenylalanine

I. Construction of the recombinant plasmid pACYC184-$P_{JJ}$

1. The double-stranded DNA molecule (the promoter $P_{JJ}$) shown by SEQ ID No: 39 of the sequence listing is synthesized.
2. A PCR amplification product is obtained by performing a PCR amplification using the double-stranded DNA molecule prepared in step 1 as a template and using a primer pair comprised of WY843 and WY842.

```
WY843:
    TGCTCTAGA CAATTCCGACGTCTAAGAAA;

WY842:
    CCCAAGCTT GGTCAGTGCGTCCTGCTGAT.
```

3. The enzymatically cleaved product of the PCR amplification product obtained in step 2, after being subjected to a double enzymatic cleavage using the restriction endonucleases Xba I and Hind III, is recovered.
4. The vector backbone (about 4.1 kb) of the plasmid pACYC184, after being subjected to a double enzymatic cleavage using the restriction endonucleases Xba I and Hind III, is recovered.
5. A recombinant plasmid pACYC184-$P_{JJ}$ is obtained by linking the enzymatically cleaved product in step 3 and the vector backbone in step 4.

II. Construction of Three Recombinant Plasmids

1. A PCR amplification product A1 is obtained by performing a PCR amplification using the genome DNA of the *E. coli* K12 MG1655 as a template and using a primer pair comprised of WY3248 and WY4020; a PCR amplification product A2 is obtained by performing a PCR amplification using the genome DNA of the *E. coli* K12 MG1655 as a template and using a primer pair comprised of WY3250 and WY4020; a PCR amplification product A3 is obtained by performing a PCR amplification using the genome DNA of the *E. coli* K12 MG1655 as a template and using a primer pair comprised of WY3251 and WY4020; a PCR amplification product A4 is obtained by performing a PCR amplification using the genome DNA of the *E. coli* K12 MG1655 as a template and using a primer pair comprised of WY4021 and WY4022.

```
WY3248:
    CCCAAGCTT AGTCACTTAAGGAAACAAAC atgA;

WY3250:
    CCCAAGCTT CTTTTTTATTGATAACAAAAAGGCAACACT;

WY3251:
    CCCAAGCTT GATAACAAAAGGCAACACTATGA;

WY4020:
    CTTCAACCAGCGCACAGGCTTGTTGCCC;

WY4021:
    GGGCAACAAGCCTGTGCGCTGGTTGAAG

WY4022:
    CGCGGATCC CGCACAGCGTTTTCAGAGT
```

The WY4020 and WY4021 are used for introducing one point mutation into the gene coding for a bifunctional enzyme of chorismate mutase-prephenate dehydratase (said point mutation is a mutation of G→T corresponding to the nucleotide at position 1071 of SEQ ID No: 62 of the sequence listing). The bifunctional enzyme of chorismate mutase-prephenate dehydratase coded by a corresponding gene before being introduced with the above point mutation in the genome of the E. coli K12 MG1655 is named as the PheA protein (shown by SEQ ID No: 63 of the sequence listing). The bifunctional enzyme of chorismate mutase-prephenate dehydratase coded by a corresponding gene after being introduced with the above point mutation is named as the PheA*protein (shown by SEQ ID No: 64 of the sequence listing). As compared with the PheA protein, the PheA*protein only differs in that the amino acid residue at position 309 of the PheA protein is mutated to cysteine from glycine, thereby relieving the feedback repression.

2. A PCR amplification product B1 is obtained by performing a PCR amplification using a mixture of the PCR amplification product A1 and the PCR amplification product A4 obtained in step 1 as a template and using a primer pair comprised of WY3248 and WY4022; a PCR amplification product B2 is obtained by performing a PCR amplification using a mixture of the PCR amplification product A2 and the PCR amplification product A4 obtained in step 1 as a template and using a primer pair comprised of WY3250 and WY4022; a PCR amplification product B3 is obtained by performing a PCR amplification using a mixture of the PCR amplification product A3 and the PCR amplification product A4 obtained in step 1 as a template and using a primer pair comprised of WY3251 and WY4022.

3. The vector backbone of the recombinant plasmid pACYC184-$P_{JJ}$, after being subjected to a double enzymatic cleavage using the restriction endonucleases Hind III and BamH I, is recovered.

4. The enzymatically cleaved product of the PCR amplification product B1 obtained in step 2, after being subjected to a double enzymatic cleavage using the restriction endonucleases Hind III and BamH I, is recovered.

5. A recombinant plasmid pACYC184-$P_{JJ}$-pheL$^{3248}$A* is obtained by linking the vector backbone in step 3 and the enzymatically cleaved product in step 4. According to the sequencing result, a structural description for the recombinant plasmid pACYC184-$P_{JJ}$-pheL$^{3248}$A* is set forth as follows: a specific DNA molecule is inserted between the enzymatic cleavage sites of Xba I and BamH I of the plasmid pACYC184; and the specific DNA molecule sequentially consists, from upstream to downstream, of the following elements: the promoter $P_{JJ}$ shown by SEQ ID No: 39 of the sequence listing, a recognition sequence for enzymatic cleavage by restriction endonuclease Hind III, the RBS sequence "AGTCACTTAAGGAAACAAAC" (SEQ ID NO: 256), and the DNA molecule shown by SEQ ID No: 62 of the sequence listing.

6. The enzymatically cleaved product of the PCR amplification product B2 obtained in step 2, after being subjected to a double enzymatic cleavage using the restriction endonucleases Hind III and BamH I, is recovered.

7. A recombinant plasmid pACYC184-$P_{JJ}$-pheL$^{3250}$A* is obtained by linking the vector backbone in step 3 and the enzymatically cleaved product in step 6. According to the sequencing result, a structural description for the recombinant plasmid pACYC184-$P_{JJ}$-pheL$^{3250}$A* is set forth as follows: a specific DNA molecule is inserted between the enzymatic cleavage sites of Xba I and BamH I of the plasmid pACYC184; and the specific DNA molecule sequentially consists, from upstream to downstream, of the following elements: the promoter $P_{JJ}$ shown by SEQ ID No: 39 of the sequence listing, a recognition sequence for enzymatic cleavage by restriction endonuclease Hind III, and the DNA molecule shown by the nucleotides at positions 117-1413 of SEQ ID No: 62 of the sequence listing.

8. The enzymatically cleaved product of the PCR amplification product B3 obtained in step 2, after being subjected to a double enzymatic cleavage using the restriction endonucleases Hind III and BamH I, is recovered. 9. A recombinant plasmid pACYC184-$P_{JJ}$-pheL$^{3251}$A* is obtained by linking the vector backbone in step 3 and the enzymatically cleaved product in step 8. According to the sequencing result, a structural description for the recombinant plasmid pACYC184-$P_{JJ}$-pheL$^{3251}$A* is set forth as follows: a specific DNA molecule is inserted between the enzymatic cleavage sites of Xba I and BamH I of the plasmid pACYC184; and the specific DNA molecule sequentially consists, from upstream to downstream, of the following elements: the promoter $P_{JJ}$ shown by SEQ ID No: 39 of the sequence listing, a recognition sequence for enzymatic cleavage by restriction endonuclease Hind III, and the DNA molecule shown by the nucleotides at positions 127-1413 of SEQ ID No: 62 of the sequence listing.

III. Construction of Three Recombinant Plasmids

1. A PCR amplification product is obtained by performing a PCR amplification using the genome of the E. coli K12 MG1655 as a template and using a primer pair comprised of WY4023 and WY4024.

```
WY4023:
ACATGCATGC CAAAGCATAGCGGATTGTTTTC

WY4024:
CGCGGATCC TTAAGCCACGCGAGCCGTCA
```

After a sequencing, in the PCR amplification product, the nucleotide sequence between the enzymatic cleavage sites of Sph I and BamH I is shown by SEQ ID No: 65 of the sequence listing, coding for the protein shown by SEQ ID No: 66 of the sequence listing. The protein shown by SEQ ID No: 66 is 3-deoxy-D-arabino-heptulosonate-7-phosphate synthetase (AroF protein). In SEQ ID No: 65 of the sequence listing, the open reading frame is the nucleotides at positions 195-1265.

2. The enzymatically cleaved product of the PCR amplification product obtained in step 1, after being subjected to a double enzymatic cleavage using the restriction endonucleases Sph I and BamH I, is recovered.

3. The vector backbone of the recombinant plasmid pACYC184-$P_{JJ}$-pheL$^{3248}$A*, after being subjected to a double enzymatic cleavage using the restriction endonucleases Sph I and BamH I, is recovered.

4. A recombinant plasmid pACYC184-$P_{JJ}$-pheL$^{3248}$A*-aroF is obtained by linking the enzymatically cleaved product in step 2 and the vector backbone in step 3. According to the sequencing result, a structural description for the recombinant plasmid pACYC184-$P_{JJ}$-pheL$^{3248}$A*-aroF is set forth as follows: said specific DNA molecule in 5 of step II is inserted between the enzymatic cleavage sites of Xba I and BamH I of the plasmid pACYC184; the aroF gene shown by SEQ ID No: 65 of the sequence listing is inserted between the enzymatic cleavage sites of Sph I and BamH I (in the recombinant plasmid, the specific DNA molecule and the aroF gene are present in reverse).

5. The vector backbone of the recombinant plasmid pACYC184-$P_{JJ}$-pheL$^{3250}$A*, after being subjected to a double enzymatic cleavage using the restriction endonucleases Sph I and BamH I, is recovered.

6. A recombinant plasmid pACYC184-$P_{JJ}$-pheL$^{3250}$A*-aroF is obtained by linking the enzymatically cleaved product in step 2 and the vector backbone in step 5. According to the sequencing result, a structural description for the recombinant plasmid pACYC184-$P_{JJ}$-pheL$^{3250}$A*-aroF is set forth as follows: said specific DNA molecule in 7 of step II is inserted between the enzymatic cleavage sites of Xba I and BamH I of the plasmid pACYC184; the aroF gene shown by SEQ ID No: 65 of the sequence listing is inserted between the enzymatic cleavage sites of Sph I and BamH I (in the recombinant plasmid, the specific DNA molecule and the aroF gene are present in reverse). 7. The vector backbone of the recombinant plasmid pACYC184-$P_{JJ}$-pheL$^{3251}$A* after being subjected to a double enzymatic cleavage using the restriction endonucleases Sph I and BamH I, is recovered.

8. A recombinant plasmid pACYC184-$P_{JJ}$-pheL$^{3251}$A*-aroF is obtained by linking the enzymatically cleaved product in step 2 and the vector backbone in step 7. According to the sequencing result, a structural description for the recombinant plasmid pACYC184-$P_{JJ}$-pheL$^{3251}$A*-aroF is set forth as follows: said specific DNA molecule in 9 of step II is inserted between the enzymatic cleavage sites of Xba I and BamH I of the plasmid pACYC184; the aroF gene shown by SEQ ID No: 65 of the sequence listing is inserted between the enzymatic cleavage sites of Sph I and BamH I (in the recombinant plasmid, the specific DNA molecule and the aroF gene are present in reverse).

IV. Construction of Recombinant Bacteria

Recombinant bacteria is obtained by introducing the recombinant plasmid pACYC184-$P_{JJ}$-pheL$^{3248}$A*-aroF into the *E. coli* K12 MG1655, and named as engineered bacteria Phe3248.

Recombinant bacteria is obtained by introducing the recombinant plasmid pACYC184-$P_{JJ}$-pheL$^{3250}$A*-aroF into the *E. coli* K12 MG1655, and named as engineered bacteria Phe3250.

Recombinant bacteria is obtained by introducing the recombinant plasmid pACYC184-$P_{JJ}$-pheL$^{3251}$A*-aroF into the *E. coli* K12 MG1655, and named as engineered bacteria Phe3251.

V. Fermentation Test of Engineered Bacteria for Phenylalanine in a Shake Flask

The test strain is: the engineered bacteria Phe3248, the engineered bacteria Phe3250 or the engineered bacteria Phe3251.

1. The test strain is streaked onto a solid LB medium plate, followed by static culture for 12 h at 37° C.

2. After completion of step 1, a bacterial lawn on the plate is picked and seeded into a liquid LB medium, followed by shaking culture for 8 h at 37° C., 220 rpm, and a seed solution is obtained (OD$_{600nm}$ value=5.0).

3. After completion of step 2, the seed solution is seeded into a fermentation medium in a seeding amount of 3%, followed by shaking culture at 37° C., 220 rpm.

The fermentation medium is: glucose 20.0 g/L, ammonium sulfate 15.0 g/L, potassium dihydrogen phosphate 2.0 g/L, magnesium sulfate heptahydrate 2.0 g/L, yeast powders 2.0 g/L, calcium carbonate 15.0 g/L, microelement mixture 5 mL/L, and water as the remainder.

The microelement mixture is: FeSO$_4$.7H$_2$O 10 g/L, CaCl$_2$ 1.35 g/L, ZnSO$_4$.7H$_2$O 2.25 g/L, MnSO$_4$.4H$_2$O 0.5 g/L, CuSO$_4$.5H$_2$O 1 g/L, (NH$_4$)$_6$Mo$_7$O$_{24}$.4H$_2$O 0.106 g/L, Na$_2$B$_4$O$_7$.10H$_2$O 0.23 g/L, CoCl$_2$.6H$_2$O 0.48 g/L, 35% HCl 10 mL/L, and water as the remainder.

During the culture, ammoniacal liquor is used to adjust the pH value of the reaction system to make it maintain at 6.8-7.0.

During the culture, sampling is made once every 3-4 h to detect the content of glucose by using a biosensor analyzer SBA-40D. When the content of glucose in the system is less than 5 g/L, glucose is supplemented to make the concentration of glucose in the system up to 10 g/L.

Sampling is made after culture for 36 h, followed by centrifugation at 12,000 g for 2 min. The supernatant (the fermented supernatant) is taken for detection of the concentration of L-phenylalanine.

The results are shown in Table 21 (by a mean±standard deviation from repeated tests in triplicate). As compared with the engineered bacteria Phe3248 and the engineered bacteria Phe3251, the yield of L-phenylalanine produced in fermentation by the engineered bacteria Phe3250 is significantly improved.

TABLE 21

| | Content of L-phenylalanine in fermented supernatant (g/L) |
|---|---|
| Engineered bacteria Phe3248 | 0.82 ± 0.07 |
| Engineered bacteria Phe3250 | 1.55 ± 0.25 |
| Engineered bacteria Phe3251 | 0.77 ± 0.15 |

A method for detecting the concentration of L-phenylalanine is: HPLC, which is optimized based on the method for detecting amino acids in a reference (Amino Acids & Biotic Resources, 2000, 22, 59-60), and the method is particularly presented as follows (HPLC coupled to pre-column derivatization with 2, 4-dinitrofluorobenzene (FDBN)):

First, 10 μL of the supernatant is taken into a 2 mL centrifuge tube, into which 200 μL of 0.5M NaHCO$_3$ aqueous solution and 100 μL of 1% (v/v) FDBN-acetonitrile solution are added. Next, the centrifuge tube is placed in a water bath to be heated at a constant temperature of 60° C. for 60 min in the dark, then cooled to the room temperature, into which 700 μL of 0.04 mol/L KH$_2$PO$_4$ aqueous solution (pH=7.2±0.05; the pH is adjusted with 40 g/L KOH aqueous solution) is added, and shaken well. After being static for 15 min, filtration is performed and filtrates are collected. The filtrates are for injection, and injection volume is 15 μL.

C18 column (ZORBAX Eclipse XDB-C18, 4.6*150 mm, Agilent, USA) is used as the chromatographic column; column temperature: 40° C.; UV detection wavelength: 360 nm; mobile phase A: 0.04 mol/L KH$_2$PO$_4$ aqueous solution (pH=7.2±0.05; the pH is adjusted with 40 g/100 mL KOH aqueous solution), mobile phase B: 55% (v/v) acetonitrile aqueous solution, and total flux of the mobile phases: 1 mL/min.

The process of elution is presented as follows: at the starting time of elution (0 min), the mobile phase A accounts for 86% by volume of the total flux of the mobile phases, and mobile phase B for 14%; the process of elution is divided into 4 stages, and in each stage, parts by volume of the mobile phase A and the mobile phase B accounting for the total flux of the mobile phases appear a linear variation; when the first stage (a total duration of 2 min from the starting time) ends, the mobile phase A accounts for 88% by volume of the total flux of the mobile phases, and mobile phase B for 12%; when the second stage (a total duration of 2 min from the ending time for the first stage) ends, the mobile phase A accounts for 86% by volume of the total flux of the mobile phases, and mobile phase B for 14%; when the third stage (a total duration of 6 min from the ending time for the second stage) ends, the mobile phase A accounts for 70% by volume of the total flux of the mobile phases, and the mobile phase B for 30%; when the fourth stage (a total duration of 10 min from the ending time for the third stage) ends, the mobile phase A accounts for 30% by volume of the total flux of the mobile phases, and mobile phase B for 70%.

A standard curve is depicted by using the commercially available L-phenylalanine as the standard, and the concentration of phenylalanine in a sample is calculated.

At last, it should be noted that the above examples obviously are only an illustration for clearly describing the present invention rather than a limitation to the embodiments thereof. For the ordinarily skilled in the art, other variations or alterations in different forms can be made based on the above description. There is no need or probability illustrating all the embodiments herein, but the obvious variations or alterations derived therefrom are still within the protection scope of the present invention.

INDUSTRIAL APPLICATIONS

The present invention provides a method for modification by truncating the functional sequence of a threonine attenuator from the 5'end step by step, and an expressing element of the 5'-untranslated region (5'-UTR) enhancing a gene expression is screened and obtained. Applying the 5'-UTR element optimized and obtained by the present invention to regulate the expression of the alanine dehydrogenase gene ald can improve the yield of L-alanine from engineered bacteria. The present invention obtains a nucleic acid sequence with efficiently enhanced gene expression, and constructs a strain for producing L-alanine, providing a novel method for improving the production of L-alanine in fermentation.

The present invention obtains a threonine attenuator mutant for efficiently relieving feedback repression, which significantly improves the efficiency for removal of the repression, thereby improving a gene expression level. The engineered bacteria overexpressing the threonine operon comprising the mutant can significantly improve the yield of threonine. Mutants in the present invention practically can be used for production of threonine in fermentation by bacteria. The present invention obtains a method for efficiently relieving transcriptive repression of a threonine operon by truncating the functional sequence of a threonine attenuator from the 5'end step by step. Applying the method provided by the present invention for modifying a threonine attenuator can significantly improve the expression level of a threonine operon, thereby improving the performance for fermentation of threonine by engineered bacteria. The present invention obtains a nucleic acid sequence with efficiently relieved feedback repression, and constructs a strain for efficiently producing threonine, providing a novel method for improving the production of threonine in fermentation.

The present invention can be applied to produce isoleucine. Thus, it is obvious that the present invention also can be used for the biosynthesis of the compounds downstream of the metabolic pathway of isoleucine as well as the synthesis of the derivatives of isoleucine. Applying the solutions provided by the present invention can significantly improve the yields of isoleucine and derivatives thereof, possessing an extremely significant value for application and promotion in the field of producing isoleucine and derivatives thereof.

The present invention can be applied to produce valine. Thus, it is obvious that the present invention also can be used for the biosynthesis of the compounds downstream of the metabolic pathway of valine. Applying the solutions provided by the present invention can significantly improve the yields of valine and derivatives thereof, possessing an extremely significant value for application and promotion in the field of producing valine and derivatives thereof.

The present invention can be used for the biosynthesis of the compounds downstream of the metabolic pathway of tryptophan, such as hydroxytryptamine, niacin, coenzymes, indoleacetic acid, pigments, alkaloid and etc. Obviously, the method for relieving a tryptophan attenuator of E. coli in the present invention can likewise be applied for tryptophan attenuators of other genuses. Applying the solutions provided by the present invention can significantly improve the yields of tryptophan and derivatives thereof, possessing an extremely significant value for application and promotion in the field of producing tryptophan and derivatives thereof.

Applying the method provided by the present invention for modifying a histidine attenuator significantly improves the performance for fermentation of histidine by engineered bacteria. The present invention practically can be used for the production of histidine in fermentation by bacteria. It is obvious that the present invention can also be applied for the biosynthesis of the compounds like histamine downstream of the metabolic pathway of histidine. Applying the solutions provided by the present invention can significantly improve the yields of histidine and derivatives thereof, possessing an extremely significant value for application and promotion in the field of producing histidine and derivatives thereof.

Applying the method provided by the present invention for modifying a phenylalanine attenuator significantly improves the performance for fermentation of phenylalanine by engineered bacteria. The present invention practically can be used for the production of phenylalanine in fermentation by bacteria. It is obvious that the present invention can also be applied for the biosynthesis of the compounds downstream of the metabolic pathway of phenylalanine, such as D-phenylalanine, phenylpyruvic acid, mandelic acid, phenyl acetate, phenyl ethanol, phenethylamine, styrene, cinnamic acid and etc. Applying the method provided by the present invention for modifying a phenylalanine attenuator significantly improves the expression levels of a phenylalanine operon or other genes, thereby improving the performance for fermentation of phenylalanine and derivatives thereof by engineered bacteria. The present invention obtains a nucleic acid sequence with efficiently relieved feedback repression, and constructs a strain for producing phenylalanine, providing a novel method for improving the production of phenylalanine in fermentation. Applying the solutions provided by the present invention can significantly improve the yields of phenylalanine and derivatives thereof, possessing an extremely significant value for application and promotion in the field of producing phenylalanine and derivatives thereof.

The invention claimed is:

1. A modified attenuator nucleic acid sequence encoding a bacterial amino acid biosynthetic enzyme, wherein:
the modified attenuator nucleic acid sequence is an attenuator of biosynthesis of L-alanine, wherein the modified attenuator nucleic acid sequence is a DNA molecule represented by nucleotides at positions 294 to n1 of SEQ ID NO: 14, wherein n1 is a natural number greater than or equal to 310 but smaller than or equal to 606;
the modified attenuator nucleic acid sequence is an attenuator of biosynthesis of threonine, wherein the modified attenuator nucleic acid sequence is a DNA molecule represented by nucleotides at positions 294 to n1 of SEQ ID NO: 20, wherein n1 is a natural number greater than or equal to 310 but smaller than or equal to 336;
the modified attenuator nucleic acid sequence is an attenuator of biosynthesis of valine, wherein the modified attenuator nucleic acid sequence is a DNA molecule represented by nucleotides at positions n1 to n2 of SEQ ID NO: 38, wherein n1 is a natural number greater than or equal to 129 but smaller than or equal to 148, and n2 is a natural number greater than or equal to 155 but smaller than or equal to 215;
the modified attenuator nucleic acid sequence is an attenuator of biosynthesis of tryptophan, wherein the modified attenuator nucleic acid sequence is a DNA molecule represented by nucleotides at positions n1 to n2 of SEQ ID NO: 40, wherein n1 is a natural number greater than or equal to 115 but smaller than or equal to 122, and n2 is a natural number greater than or equal to 135 but smaller than or equal to 186;

the modified attenuator nucleic acid sequence is an attenuator of biosynthesis of histidine, wherein the modified attenuator nucleic acid sequence is a DNA molecule represented by nucleotides at positions n1 to n2 of SEQ ID NO: 51, wherein n1 is a natural number greater than or equal to 126 but smaller than or equal to 143, and n2 is a natural number greater than or equal to 148 but smaller than or equal to 286; or the modified attenuator nucleic acid sequence is an attenuator of biosynthesis of phenylalanine, wherein the modified attenuator nucleic acid sequence is a DNA molecule represented by nucleotides at positions n1 to n2 of SEQ ID NO: 62, wherein n1 is a natural number greater than or equal to 105 but smaller than or equal to 118, and n2 is a natural number greater than or equal to 123 but smaller than or equal to 176; and wherein the modified attenuator nucleic acid sequence forms an anterior reverse complementary palindromic sequence and a loop sequence in a terminator stem-loop structure, and a preceding sequence thereof, wherein a posterior reverse complementary palindromic sequence in the terminator stem-loop structure remains, so that the remaining sequence is unable to form a stable terminator stem-loop structure.

2. The modified attenuator of claim 1, wherein when the attenuator nucleic acid sequence is an attenuator of biosynthesis of L-alanine, the modified attenuator nucleic acid sequence is represented by nucleotides at positions 294 to n1 of SEQ ID NO: 14, wherein n1 is a natural number greater than or equal to 310 but smaller than or equal to 336.

3. An operon, a recombinant vector, or a recombinant bacterium, comprising the modified attenuator nucleic acid sequence of claim 1.

4. The operon, recombinant vector, or recombinant bacterium of claim 3, wherein the operon, recombinant vector, or recombinant bacterium comprises a target gene that is regulated by a regulator sequence comprising the modified attenuator nucleic acid sequence.

5. The operon, recombinant vector, or recombinant bacterium of claim 4, wherein the target gene is a gene related to amino acid expression.

6. The operon, recombinant vector, or recombinant bacterium of claim 4, wherein the target gene is any one of:
  (1) a gene coding for alanine dehydrogenase,
  (2) a gene coding for aspartokinase I-homoserine dehydrogenase complex, a gene coding for homoserine dehydrogenase and a gene coding for threonine synthetase,
  (3) a gene coding for ATP phosphoribosyltransferase mutated from a gene coding for a wild-type protein to a gene coding for a mutant protein with relieved feedback repression, and
  (4) a gene coding for a bifunctional enzyme of chorismate mutase-prephenate dehydratase mutated from a gene coding for a wild-type protein to a gene coding for a mutant protein with relieved feedback repression.

7. The operon, recombinant vector, or recombinant bacterium of claim 6, wherein the bacterium is *E. coli*.

8. A method for improving the capability of a bacterium producing a target protein or a target compound, comprising the step of: including in the bacterium a relevant gene coding for the target protein or a protein coding gene relevant to synthesis of the target compound, wherein the coding gene is regulated by a regulator sequence comprising a modified attenuator nucleic acid sequence according to claim 1.

9. The method of claim 8, wherein, the attenuator is an attenuator of L-alanine, the modified attenuator nucleic acid sequence is represented by nucleotides at positions 294 to n1 of SEQ ID NO: 14, and wherein n1 is a natural number greater than or equal to 310 but smaller than or equal to 336.

10. The method of claim 8, wherein the bacterium is *E. coli*.

* * * * *